(12) United States Patent
Arasappan et al.

(10) Patent No.: US 7,399,749 B2
(45) Date of Patent: Jul. 15, 2008

(54) SUBSTITUTED PROLINES AS INHIBITORS OF HEPATITIS C VIRUS NS3 SERINE PROTEASE

(75) Inventors: Ashok Arasappan, Bridgewater, NJ (US); F. George Njoroge, Warren, NJ (US); Viyyoor M. Girijavallabhan, Parsippany, NJ (US)

(73) Assignee: Schering Corporation, Kenilworth, NJ (US)

(*) Notice: Subject to any disclaimer, the term of this patent is extended or adjusted under 35 U.S.C. 154(b) by 260 days.

(21) Appl. No.: 11/132,083

(22) Filed: May 18, 2005

(65) Prior Publication Data

US 2005/0272663 A1    Dec. 8, 2005

Related U.S. Application Data

(60) Provisional application No. 60/573,191, filed on May 20, 2004.

(51) Int. Cl.
*A61K 38/00* (2006.01)
(52) U.S. Cl. .......................... 514/18; 514/299; 514/43; 530/300; 530/331
(58) Field of Classification Search ............... None
See application file for complete search history.

(56) References Cited

U.S. PATENT DOCUMENTS

| | | | |
|---|---|---|---|
| 5,712,145 | A | 1/1998 | Houghton et al. |
| 6,608,027 | B1 | 8/2003 | Tsantrizos et al. |
| 7,012,066 | B2 * | 3/2006 | Saksena et al. ............... 514/18 |

FOREIGN PATENT DOCUMENTS

| | | |
|---|---|---|
| EP | 0 381 216 B1 | 12/1995 |
| WO | WO 89/04669 | 6/1989 |
| WO | WO 98/14181 | 4/1998 |
| WO | WO 98/17679 | 4/1998 |
| WO | WO 98/22496 | 5/1998 |
| WO | WO 99/07734 | 2/1999 |
| WO | WO 00/09543 | 2/2000 |
| WO | WO 00/09558 | 2/2000 |
| WO | WO 00/59929 | 10/2000 |
| WO | WO 01/74768 A2 | 10/2001 |
| WO | WO 01/77113 A2 | 10/2001 |
| WO | WO 01/81325 A2 | 11/2001 |
| WO | WO 02/08187 A1 | 1/2002 |
| WO | WO 02/08198 A2 | 1/2002 |
| WO | WO 02/08244 A2 | 1/2002 |
| WO | WO 02/08251 A2 | 1/2002 |
| WO | WO 02/08256 A2 | 1/2002 |
| WO | WO 02/48172 A2 | 6/2002 |

OTHER PUBLICATIONS

Perni, R B et al., "Inhibitors of hepatitis C virus NS3.4A protease 2. Warhead SAR and optimization", Biorganic & Medicinal Chem Ltrs. (14); pp. 1441-1446 (2004).
International Search Report corresponding to PCT/US2005/017401 dated Oct. 4, 2005.
Berenguer, Marina, et al., "Hepatitis B and C ...," Proceedings of the Association of American Physicians 110(2):98-112 (1998).
Dimasi, Nazzareno, et al., "Characterization of Engineered ...," Journal of Virology 71(10):7461-69 (1997).
Elzouki, Abdul-Nasser, et al., "Serine protease inhibitors ...," Journal of Hepatology 27:42-48 (1997).
Failla, Cristina Maria, et al., "Redesigning the substrate...," Folding & Design 1(1):35-42 (Jan. 10, 1996).
Han, Wei, et al., "alpha-Ketoamides, alpha-Ketoesters ...," Bioorganic & Medicinal Chemistry Letters 10:711-713 (2000).
Hoofnagle, Jay H., et al., "The Treatment of ...," Drug Therapy 336(5):347-56 (1997).
Ingallinella, Paolo, et al., "Potent Peptide Inhibitors ...," Biochemistry 37:8906-14 (1998).
Kolykhalov, Alexander A., et al., "Specificity of the Hepatitis ...," Journal of Virology 68(11):7525-7533 (Nov. 1994).
Komoda, Yasumasa, et al., "Substrate Requirements of ...," Journal of Virology 68(11):7351-7357 (Nov. 1994).
Landro, James A., et al., "Mechanistic Role of an ...," Biochemistry 36:9340-48 (1997).
Llinas-Brunet, Montse, et al., "Peptide-Based Inhibitors ...," Bioorganic & Medicinal Chemistry Letters 8:1713-1718 (1998).
Marchetti, Antonella, et al., "Synthesis of Two Novel ...," Synlett S1:1000-1002 (1999).
Martin, F., et al., "Affinity selection of a ...," Protein Engineering 10(5):607-14 (1997).
Martin, Franck, et al., "Design of Selective ...," Biochemistry 37:11459-68 (1998).
Pizzi, Elisabetta, et al., "Molecular model of ...," Proc. Natl. Acad. Sci. USA 91:888-892 (Feb. 1994).
BioWorld Tody 9(217):4 (Nov. 10, 1998).
U.S. No. 10/052,386 filed Jan. 18, 2002.

* cited by examiner

*Primary Examiner*—Anish Gupta
(74) *Attorney, Agent, or Firm*—Palaiyur S. Kalyanaraman; Serena Farquharson-Torres

(57) ABSTRACT

The present invention discloses novel compounds which have HCV protease inhibitory activity as well as methods for preparing such compounds. In another embodiment, the invention discloses pharmaceutical compositions comprising such compounds as well as methods of using them to treat disorders associated with the HCV protease.

26 Claims, No Drawings

SUBSTITUTED PROLINES AS INHIBITORS OF HEPATITIS C VIRUS NS3 SERINE PROTEASE

FIELD OF THE INVENTION

The present invention relates to novel hepatitis C virus ("HCV") protease inhibitors, pharmaceutical compositions containing one or more such inhibitors, methods of preparing such inhibitors and methods of using such inhibitors to treat hepatitis C and related disorders. This invention additionally discloses compounds containing novel proline moieties in the P2 position as inhibitors of the HCV NS3/NS4a serine protease. This application claims priority from U.S. provisional patent application, Ser. No. 60/573,191 filed May 20, 2004.

BACKGROUND OF THE INVENTION

Hepatitis C virus (HCV) is a (+)-sense single-stranded RNA virus that has been implicated as the major causative agent in non-A, non-B hepatitis (NANBH), particularly in blood-associated NANBH (BB-NANBH) (see, International Patent Application Publication No. WO 89/04669 and European Patent Application Publication No. EP 381 216). NANBH is to be distinguished from other types of viral-induced liver disease, such as hepatitis A virus (HAV), hepatitis B virus (HBV), delta hepatitis virus (HDV), cytomegalovirus (CMV) and Epstein-Barr virus (EBV), as well as from other forms of liver disease such as alcoholism and primary biliar cirrhosis.

Recently, an HCV protease necessary for polypeptide processing and viral replication has been identified, cloned and expressed. (See, e.g., U.S. Pat. No. 5,712,145). This approximately 3000 amino acid polyprotein contains, from the amino terminus to the carboxy terminus, a nucleocapsid protein (C), envelope proteins (E1 and E2) and several non-structural proteins (NS1, 2, 3, 4a, 5a and 5b). NS3 is an approximately 68 kda protein, encoded by approximately 1893 nucleotides of the HCV genome, and has two distinct domains: (a) a serine protease domain consisting of approximately 200 of the N-terminal amino acids; and (b) an RNA-dependent ATPase domain at the C-terminus of the protein. The NS3 protease is considered a member of the chymotrypsin family because of similarities in protein sequence, overall three-dimensional structure and mechanism of catalysis. Other chymotrypsin-like enzymes are elastase, factor Xa, thrombin, trypsin, plasmin, urokinase, tPA and PSA. The HCV NS3 serine protease is responsible for proteolysis of the polypeptide (polyprotein) at the NS3/NS4a, NS4a/NS4b, NS4b/NS5a and NS5a/NS5b junctions and is thus responsible for generating four viral proteins during viral replication. This has made the HCV NS3 serine protease an attractive target for antiviral chemotherapy. The inventive compounds can inhibit such protease. They also can modulate the processing of hepatitis C virus (HCV) polypeptide.

It has been determined that the NS4a protein, an approximately 6 kda polypeptide, is a co-factor for the serine protease activity of NS3. Autocleavage of the NS3/NS4a junction by the NS3/NS4a serine protease occurs intramolecularly (i.e., cis) while the other cleavage sites are processed intermolecularly (i.e., trans).

Analysis of the natural cleavage sites for HCV protease revealed the presence of cysteine at P1 and serine at P1' and that these residues are strictly conserved in the NS4a/NS4b, NS4b/NS5a and NS5a/NS5b junctions. The NS3/NS4a junction contains a threonine at P1 and a serine at P1'. The Cys→Thr substitution at NS3/NS4a is postulated to account for the requirement of cis rather than trans processing at this junction. See, e.g., Pizzi et al. (1994) Proc. Natl. Acad. Sci (USA) 91:888-892, Failla et al. (1996) Folding & Design 1:35-42. The NS3/NS4a cleavage site is also more tolerant of mutagenesis than the other sites. See, e.g., Kollykhalov et al. (1994) J. Virol. 68:7525-7533. It has also been found that acidic residues in the region upstream of the cleavage site are required for efficient cleavage. See, e.g., Komoda et al. (1994) J. Virol. 68:7351-7357.

Inhibitors of HCV protease that have been reported include antioxidants (see, International Patent Application Publication No. WO 98/14181), certain peptides and peptide analogs (see, International Patent Application Publication No. WO 98/17679, Landro et al. (1997) Biochem. 36:9340-9348, Ingallinella et al. (1998) Biochem. 37:8906-8914, Llinàs-Brunet et al. (1998) Bioorg. Med. Chem. Lett. 8:1713-1718), inhibitors based on the 70-amino acid polypeptide eglin c (Martin et al. (1998) Biochem. 37:11459-11468, inhibitors affinity selected from human pancreatic secretory trypsin inhibitor (hPSTI-C3) and minibody repertoires (MBip) (Dimasi et al. (1997) J. Virol. 71:7461-7469), cV$_H$E2 (a "camelized" variable domain antibody fragment) (Martin et al. (1997) Protein Eng. 10:607-614), and α1-antichymotrypsin (ACT) (Elzouki et al.) (1997) J. Hepat. 27:42-28). A ribozyme designed to selectively destroy hepatitis C virus RNA has recently been disclosed (see, BioWorld Today 9(217): 4 (Nov. 10, 1998)).

Reference is also made to the PCT Publications, No. WO 98/17679, published Apr. 30, 1998 (Vertex Pharmaceuticals Incorporated); WO 98/22496, published May 28, 1998 (F. Hoffmann-La Roche AG); and WO 99/07734, published Feb. 18, 1999 (Boehringer Ingelheim Canada Ltd.).

HCV has been implicated in cirrhosis of the liver and in induction of hepatocellular carcinoma. The prognosis for patients suffering from HCV infection is currently poor. HCV infection is more difficult to treat than other forms of hepatitis due to the lack of immunity or remission associated with HCV infection. Current data indicates a less than 50% survival rate at four years post cirrhosis diagnosis. Patients diagnosed with localized resectable hepatocellular carcinoma have a five-year survival rate of 10-30%, whereas those with localized unresectable hepatocellular carcinoma have a five-year survival rate of less than 1%.

Reference is made to WO 00/59929 (U.S. Pat. No. 6,608,027, Assignee: Boehringer Ingelheim (Canada) Ltd.; Published Oct. 12, 2000) which discloses peptide derivatives of the formula:

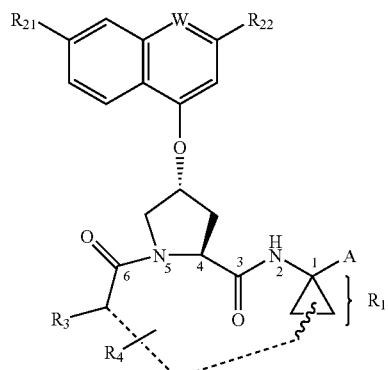

Reference is made to A. Marchetti et al, *Synlett*, S1, 1000-1002 (1999) describing the synthesis of bicylic analogs of an inhibitor of HCV NS3 protease. A compound disclosed therein has the formula:

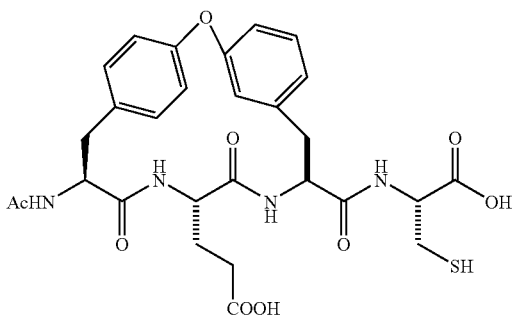

Reference is also made to W. Han et al, *Bioorganic & Medicinal Chem. Lett*, (2000) 10, 711-713, which describes the preparation of certain α-ketoamides, α-ketoesters and α-diketones containing allyl and ethyl functionalities.

Reference is also made to WO 00/09558 (Assignee: Boehringer Ingelheim Limited; Published Feb. 24, 2000) which discloses peptide derivatives of the formula:

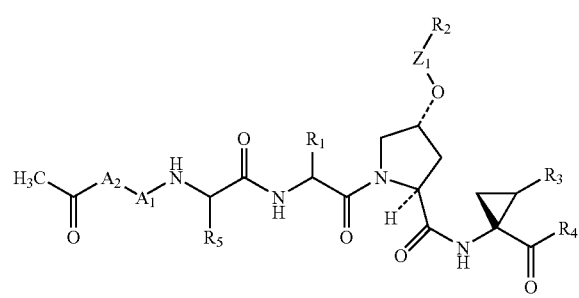

where the various elements are defined therein. An illustrative compound of that series is:

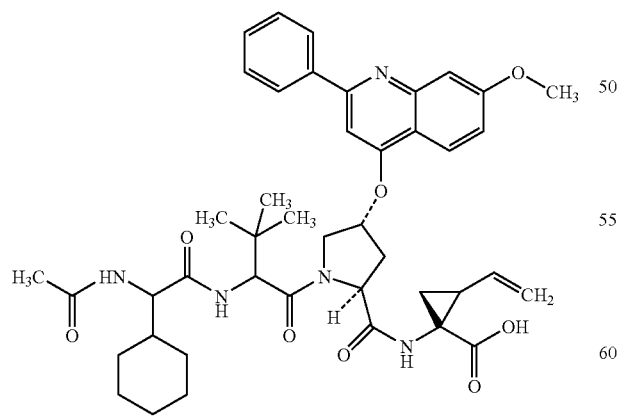

Reference is also made to WO 00/09543 (Assignee: Boehringer Ingelheim Limited; Published Feb. 24, 2000) which discloses peptide derivatives of the formula:

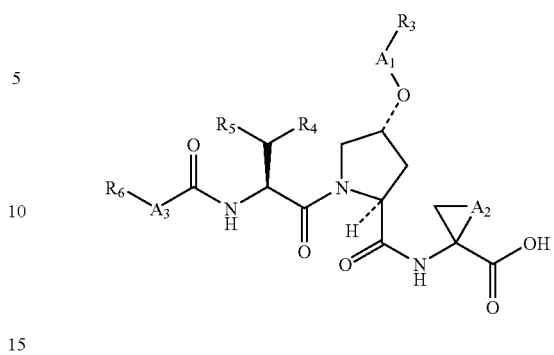

where the various elements are defined therein. An illustrative compound of that series is:

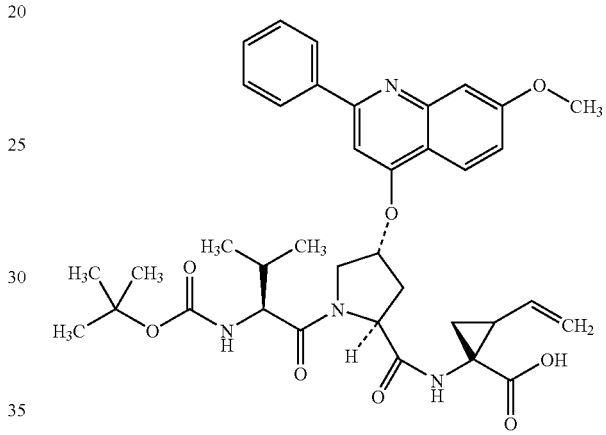

Reference is also made to U.S. Pat. No. 6,608,027 (Boehringer Ingelheim, Canada) which discloses NS3 protease inhibitors of the type:

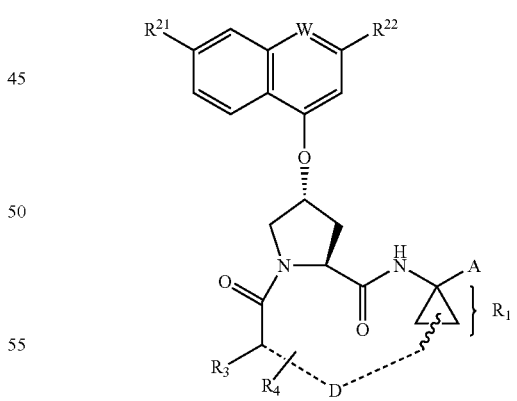

wherein the various are defined therein.

Current therapies for hepatitis C include interferon-α (INF$_\alpha$) and combination therapy with ribavirin and interferon. See, e.g., Beremguer et al. (1998) *Proc. Assoc. Am. Physicians* 110(2):98-112. These therapies suffer from a low sustained response rate and frequent side effects. See, e.g., Hoofnagle et al. (1997) *N. Engl. J. Med.* 336:347. Currently, no vaccine is available for HCV infection.

Reference is further made to WO 01/74768 (Assignee: Vertex Pharmaceuticals Inc) published Oct. 11, 2001, which discloses certain compounds of the following general formula (R is defined therein) as NS3-serine protease inhibitors of Hepatitis C virus:

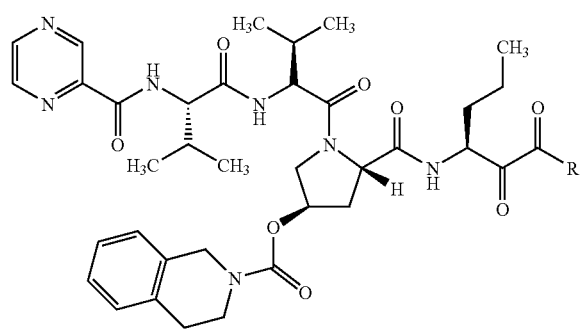

A specific compound disclosed in the afore-mentioned WO 01/74768 has the following formula:

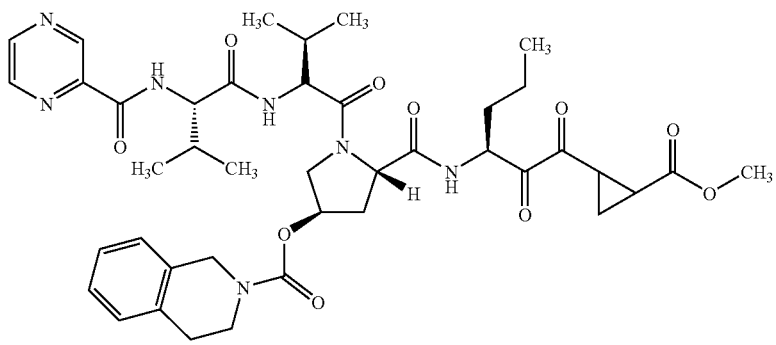

PCT Publications WO 01/77113; WO 01/081325; WO 02/08198; WO 02/08256; WO 02/08187; WO 02/08244; WO 02/48172; WO 02/08251; and pending U.S. patent application, Ser. No. 10/052,386, filed Jan. 18, 2002, disclose various types of peptides and/or other compounds as NS-3 serine protease inhibitors of hepatitis C virus. The disclosures of those applications are incorporated herein by reference thereto.

There is a need for new treatments and therapies for HCV infection. There is a need for compounds useful in the treatment or prevention or amelioration of one or more symptoms of hepatitis C.

There is a need for methods of treatment or prevention or amelioration of one or more symptoms of hepatitis C.

There is a need for methods for modulating the activity of serine proteases, particularly the HCV NS3/NS4a serine protease, using the compounds provided herein.

There is a need for methods of modulating the processing of the HCV polypeptide using the compounds provided herein.

SUMMARY OF THE INVENTION

In its many embodiments, the present invention provides a novel class of inhibitors of the HCV protease, pharmaceutical compositions containing one or more of the compounds, methods of preparing pharmaceutical formulations comprising one or more such compounds, and methods of treatment or prevention of HCV or amelioration of one or more of the symptoms of hepatitis C using one or more such compounds or one or more such formulations. Also provided are methods of modulating the interaction of an HCV polypeptide with HCV protease. Among the compounds provided herein, compounds that inhibit HCV NS3/NS4a serine protease activity are preferred. The present invention discloses compounds having the general structure shown in structural Formula 1:

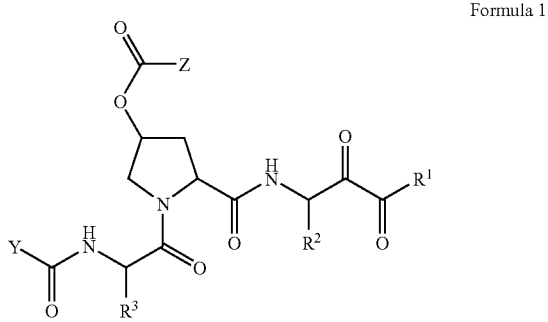

Formula 1 wherein:

Z is selected from the group consisting of a heterocyclyl moiety, —N(H)(alkyl), —N(alkyl)$_2$, —N(H)(cycloalkyl), —N(cycloalkyl)$_2$, —N(H)(aryl, —N(aryl)$_2$, —N(H)(heterocyclyl), —N(heterocyclyl)$_2$, —N(H)(heteroaryl), and —N(heteroaryl)$_2$;

$R^1$ is H, OR$^8$, NR$^9$R$^{10}$, or CHR$^9$R$^{10}$, wherein R$^8$, R$^9$ and R$^{10}$ can be the same or different, each being independently selected from the group consisting of H, alkyl-, alkenyl-, alkynyl-, aryl-, heteroalkyl-, heteroaryl-, cycloalkyl-, heterocyclyl-, arylalkyl-, and heteroarylalkyl, or alternately $R^9$ and $R^{10}$ in $NR^9R^{10}$ are connected to each other such that $NR^9R^{10}$ forms a four to eight-membered heterocyclyl, and likewise independently alternately $R^9$ and $R^{10}$ in $CHR^9R^{10}$ are connected to each other such that $CHR^9R^{10}$ forms a four to eight-membered cycloalkyl;

$R^2$ and $R^3$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl;

Y is selected from the following moieties:

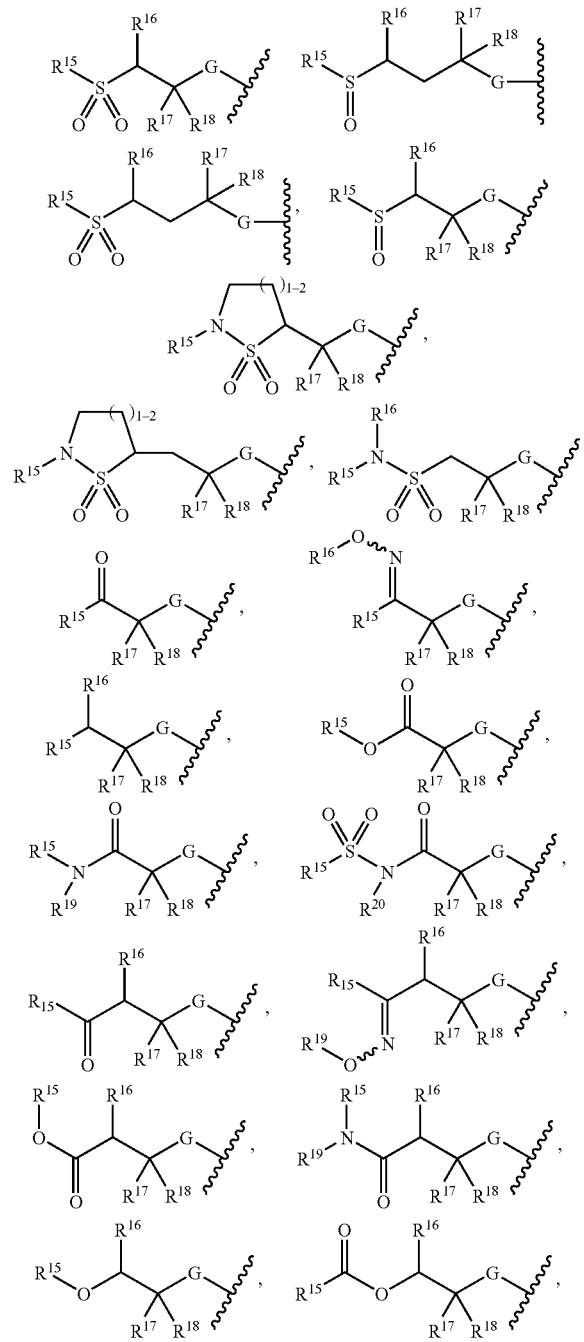

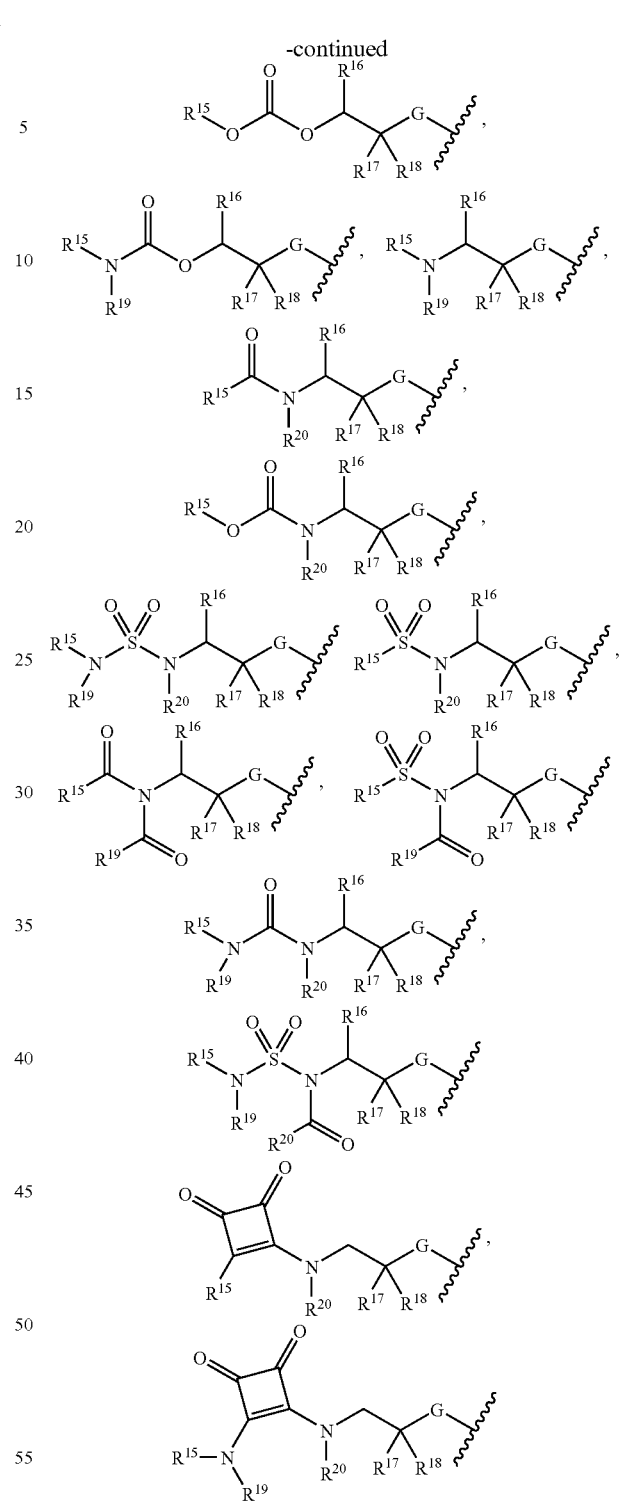

wherein G id NH or O; and $R^{15}$, $R^{16}$, $R^{17}$, $R^{18}$, $R^{19}$, $R^{20}$, $R^{21}$ can be the same or different, each being independently selected from the group consisting of H, alkyl, heteroalkenyl, alkynyl, heteroalkynyl, cycloalkyl, heterocyclyl, aryl, arylalkyl, heteroaryl, and heteroarylalkyl, or alternately (i) $R^{17}$ and $R^{18}$ are independently connected to each other to form a three to eight-membered cycloalkyl or heterocyclyl; (ii) likewise independently $R^{15}$ and $R^{19}$ are connected to each other to form a four to eight-membered heterocyclyl; (iii) likewise independently $R^{15}$ and $R^{16}$ are connected to each other to form a four to eight-membered heterocyclyl; and (iv) likewise independently $R^{15}$ and $R^{20}$ are connected to each other to form a four to eight-membered heterocyclyl;

wherein each of said alkyl, aryl, heteroaryl, cycloalkyl or heterocyclyl can be unsubstituted or optionally independently substituted with one or more moieties selected from the group consisting of hydroxy, alkoxy, aryloxy, thio, alkylthio, arylthio, amino, amido, alkylamino, arylamino, alkylsulfonyl, arylsulfonyl, sulfonamido, alkyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

In the above-noted definitions, preferred alkyl is made of one to ten carbon atoms, preferred alkenyl or alkynyl is made of two to ten carbon atoms, preferred cycloalkyl is made of three to eight carbon atoms, and preferred heteroalkyl, heteroaryl or heterocycloalkyl (heterocyclyl) has one to six oxygen, nitrogen, sulfur, or phosphorus atoms.

The compounds represented by Formula I, by themselves or in combination with one or more other suitable agents disclosed herein, can be useful for treating diseases such as, for example, HCV, HIV, AIDS (Acquired Immune Deficiency Syndrome), and related disorders, as well as for modulating the activity of hepatitis C virus (HCV) protease, preventing HCV, or ameliorating one or more symptoms of hepatitis C. Such modulation, treatment, prevention or amelioration can be done with the inventive compounds as well as with pharmaceutical compositions or formulations comprising such compounds. Without being limited to theory, it is believed that the HCV protease may be the NS3 or NS4a protease. The inventive compounds can inhibit such protease. They can also modulate the processing of hepatitis C virus (HCV) polypeptide.

DETAILED DESCRIPTION

In an embodiment, the present invention discloses compounds which are represented by structural Formula 1 or a pharmaceutically acceptable salt or solvate thereof, wherein the various moieties are as defined above.

In another embodiment, the compound of Formula 1 exists in the following stereomeric form:

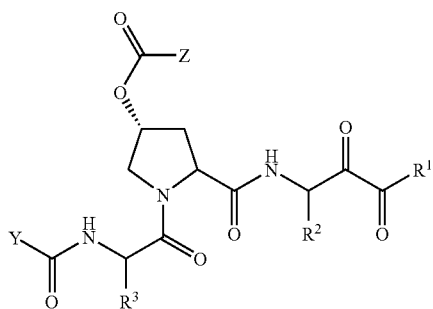

wherein the various moieties are as defined for Formula I.

In another embodiment, Z is selected from the group consisting of the following moieties:

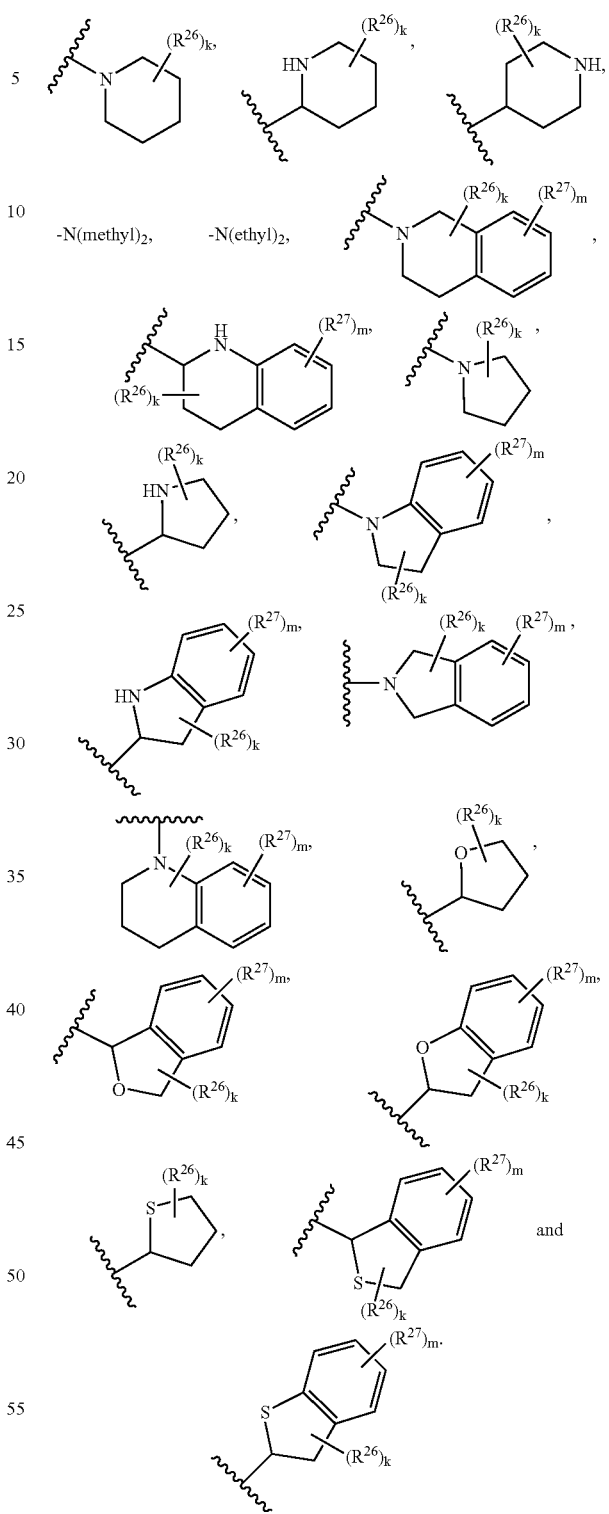

wherein k=0-4, m=0-4, k and m can be the same or different, $R^{26}$ and $R^{27}$ can be the same or different, each being independently selected from the group consisting of hydroxy, alkoxy, aryloxy, thio, alkylthio, arylthio, amino, amido, alkylamino, arylamino, alkylsulfonyl, arylsulfonyl, sulfonamido, alkyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

In another embodiment, $R^1$ is $NR^9R^{10}$, and $R^9$ is H, $R^{10}$ is H, or $R^{14}$ wherein $R^{14}$ is alkyl, aryl, heteroalkyl, heteroaryl, cycloalkyl, alkyl-aryl, alkyl-heteroaryl, aryl-alkyl, alkenyl, alkynyl or heteroaryl-alkyl.

In another embodiment, $R^{14}$ is selected from the group consisting of:

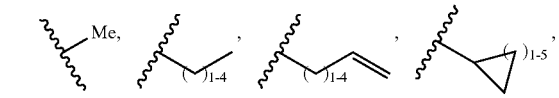
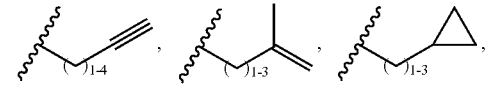
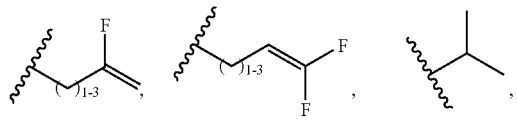
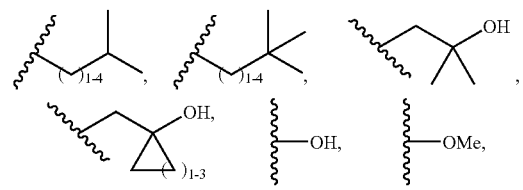
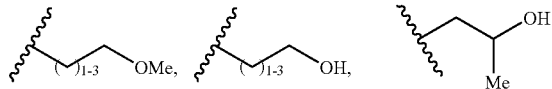
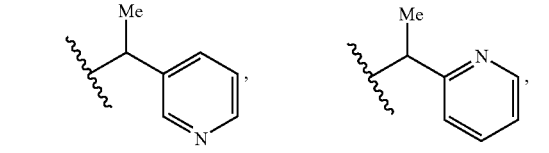
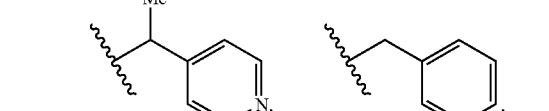
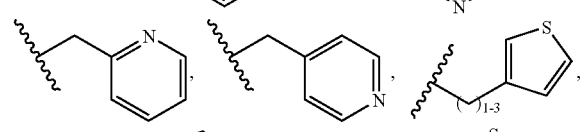
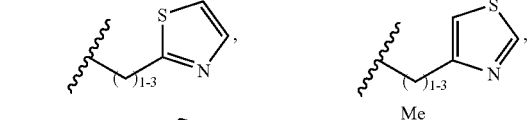
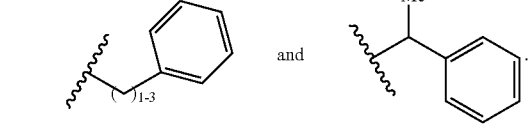

In another embodiment, $R^2$ is selected from the group consisting of the following moieties:

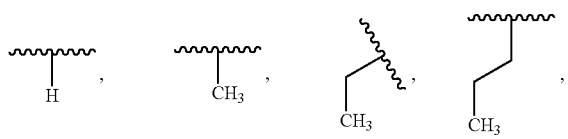
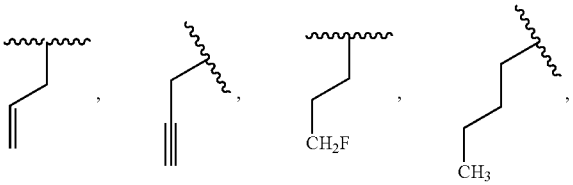
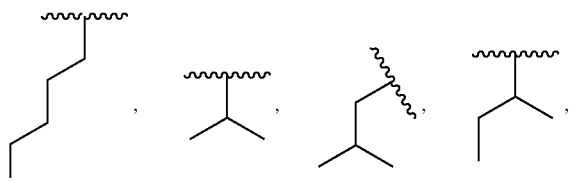
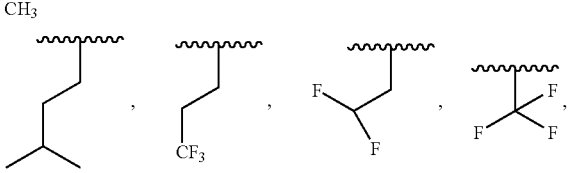
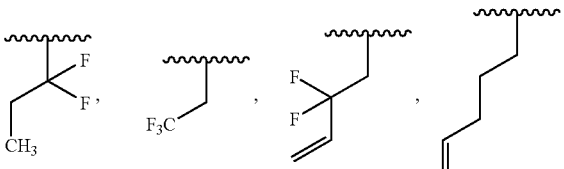
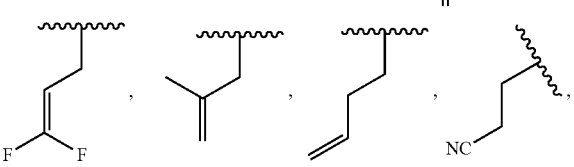
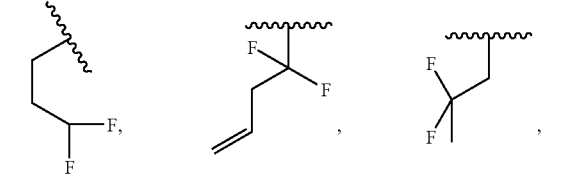
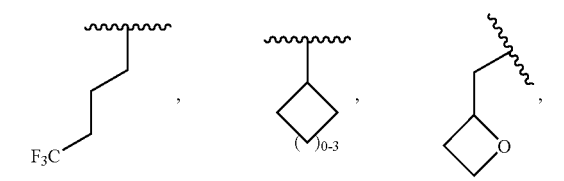
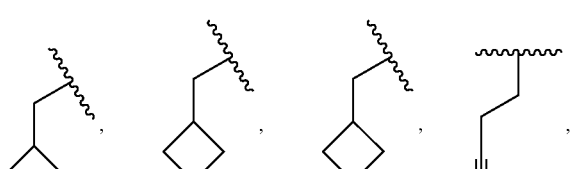

-continued
In a further embodiment, R³ is selected from the group consisting of:
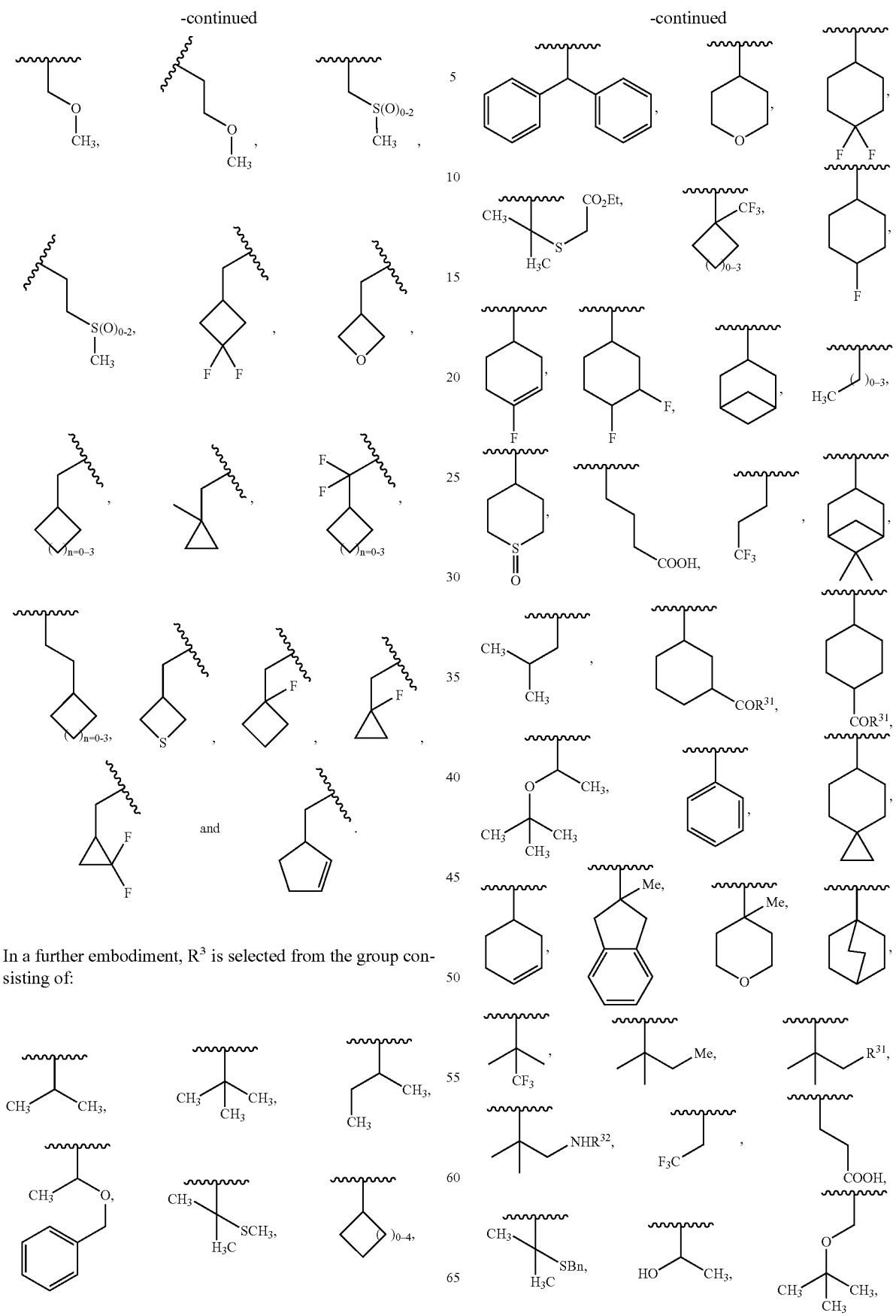

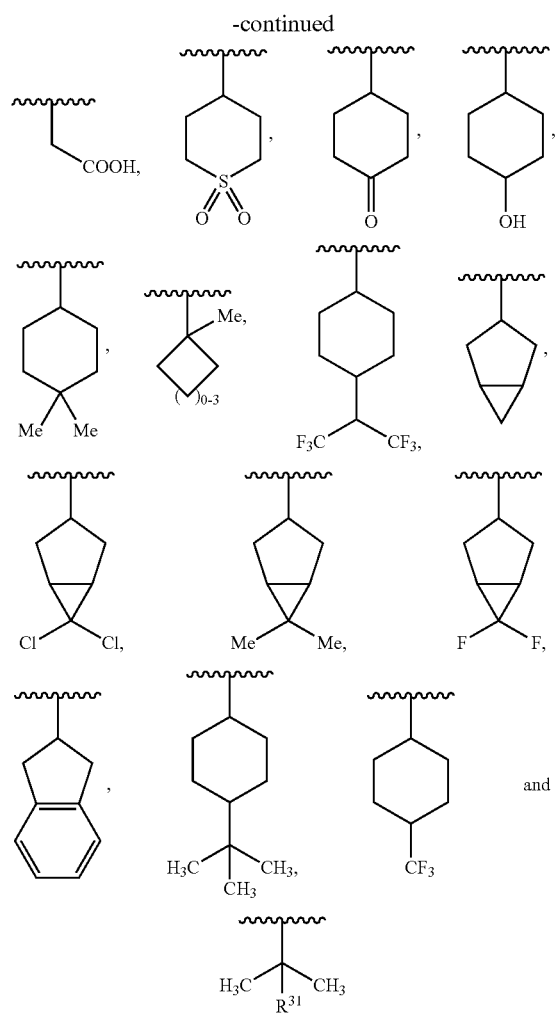
wherein R³¹ is OH or O-alkyl; and
R³² is H, C(O)CH₃, C(O)OtBu or C(O)N(H)tBu.
In an additional embodiment, R³ is selected from the group consisting of the following moieties:
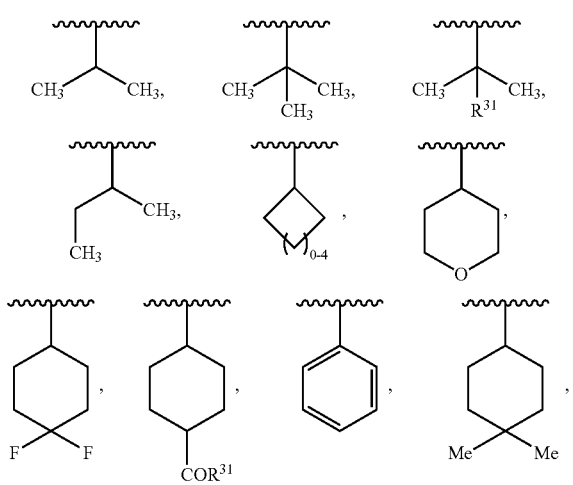
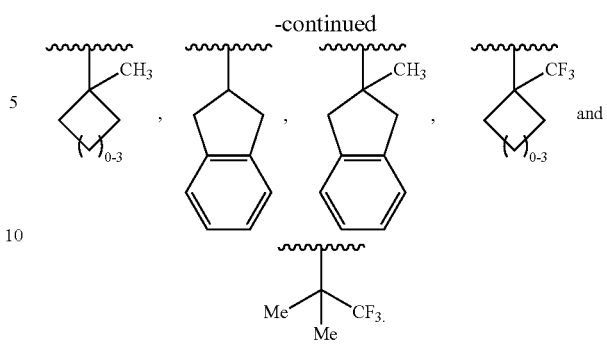
In an yet another embodiment, G is NH.
In a further embodiment, Y is selected from the following moieties:
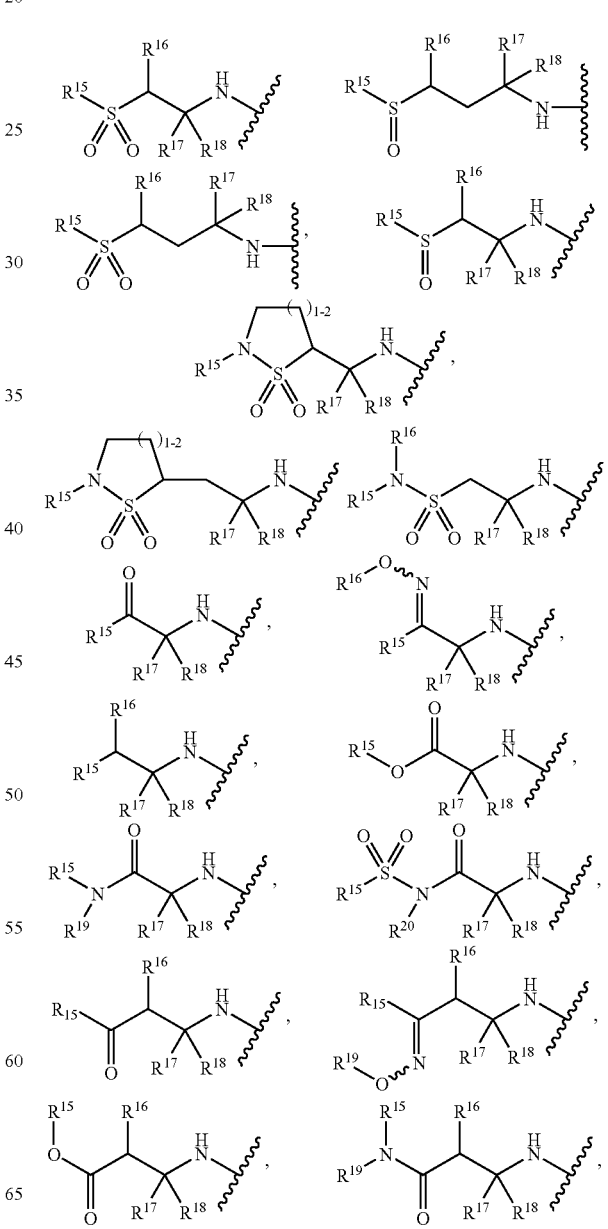

-continued

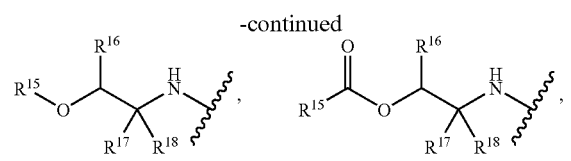

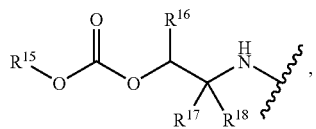

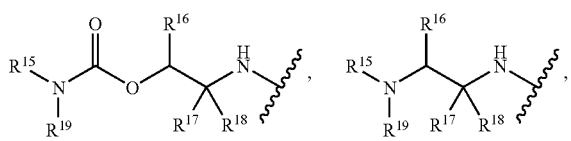

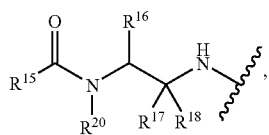

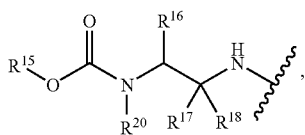

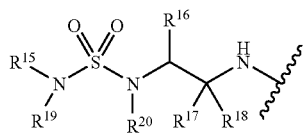

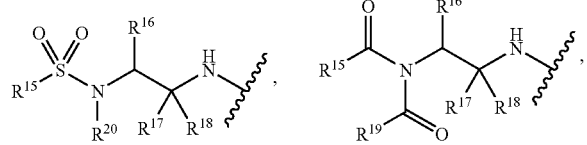

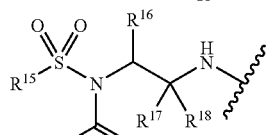

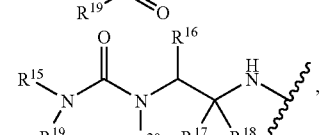

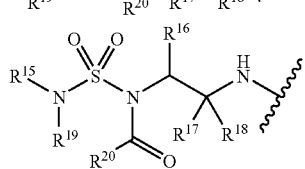

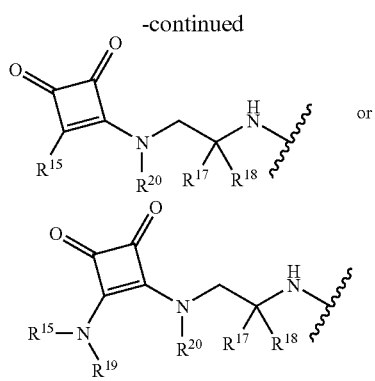 or wherein $R^{15}$, $R^{16}$, $R^{17}$, $R^{18}$, $R^{19}$, $R^{20}$ and $R^{21}$ each being independently selected from the group consisting of H, alkyl, heteroalkynyl, cycloalkyl, heterocyclyl aryl, alkenyl, heteroalkenyl, alkynyl, heteroalkynyl, cycloalkyl, heterocyclyl, aryl, arylalkyl, heteroaryl, and heteroarylalkyl, or alternately (i) $R^{17}$ and $R^{18}$ are independently connected to each other to form a three to eight-membered cycloalkyl or heterocyclyl; (ii) likewise independently $R^{15}$ and $R^{19}$ are connected to each other to form a four to eight-membered heterocyclyl; (iii) likewise independently $R^{15}$ and $R^{16}$ are connected to each other to form a four to eight-membered heterocyclyl; and (iv) likewise independently $R^{15}$ and $R^{20}$ are connected to each other to form a four to eight-membered heterocyclyl;

wherein each of said alkyl, aryl, heteroaryl, cycloalkyl or heterocyclyl can be unsubstituted or optionally independently substituted with one or more moieties selected from the group consisting of: hydroxy, alkoxy, aryloxy, thio, alkylthio, arylthio, amino, amido, alkylamino, arylamino, alkylsulfonyl, arylsulfonyl, sulfonamido, alkyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

In a still additional embodiment, the moiety:

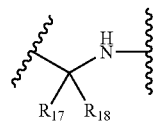

is selected from the following:

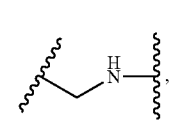 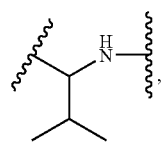 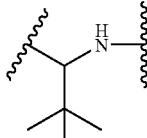

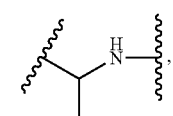 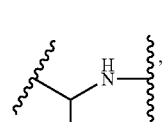 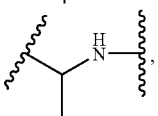

-continued
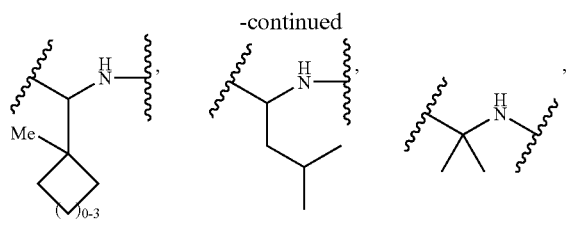
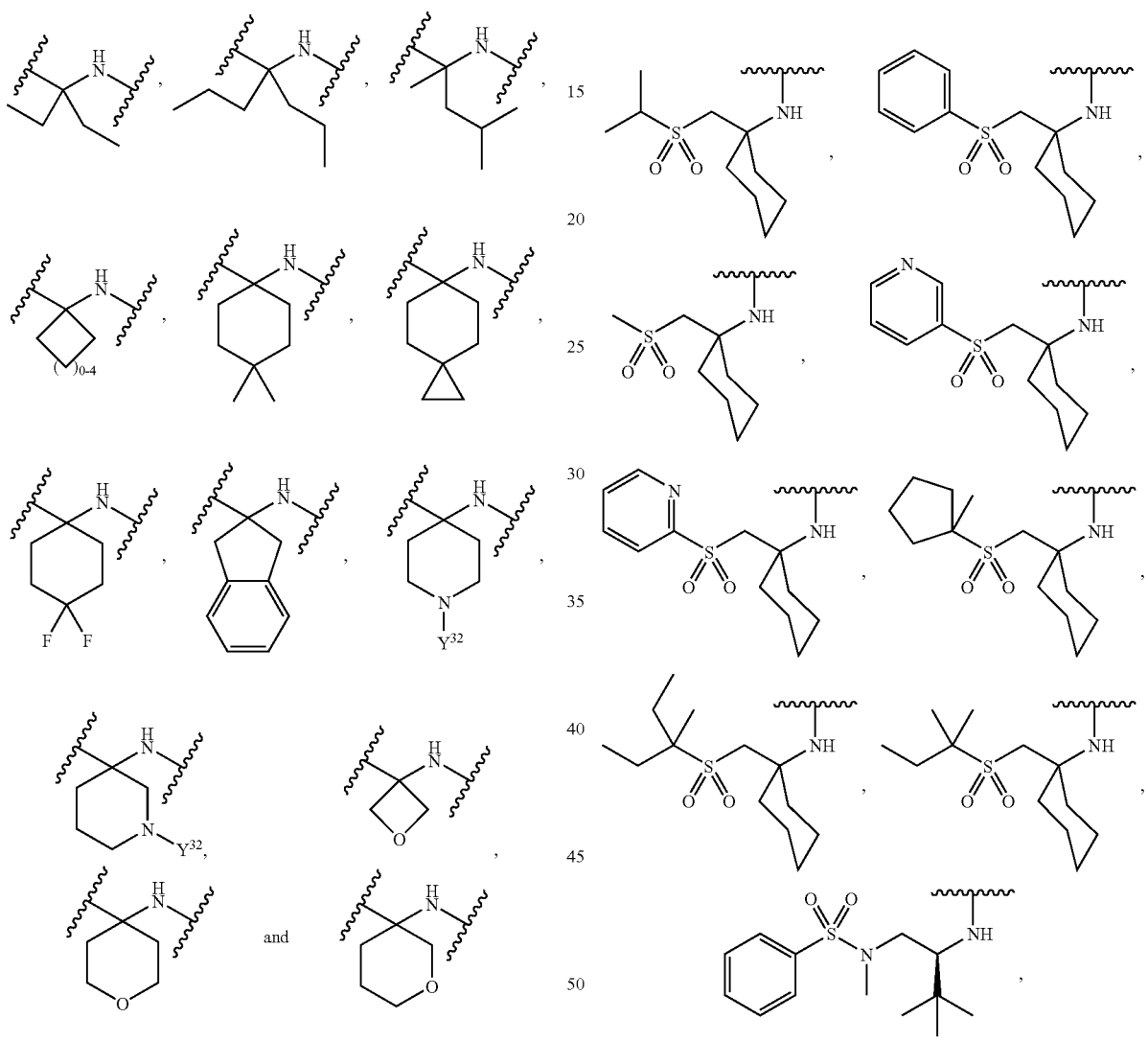
In a further embodiment, Y is selected from:
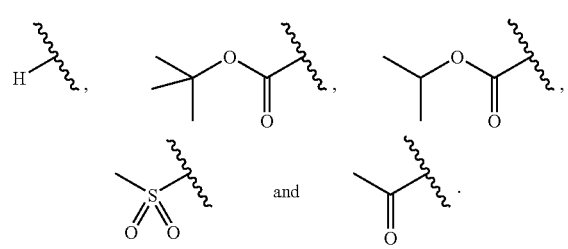
wherein $Y^{32}$ is selected from the group consisting of:
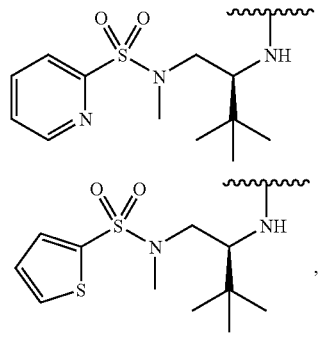

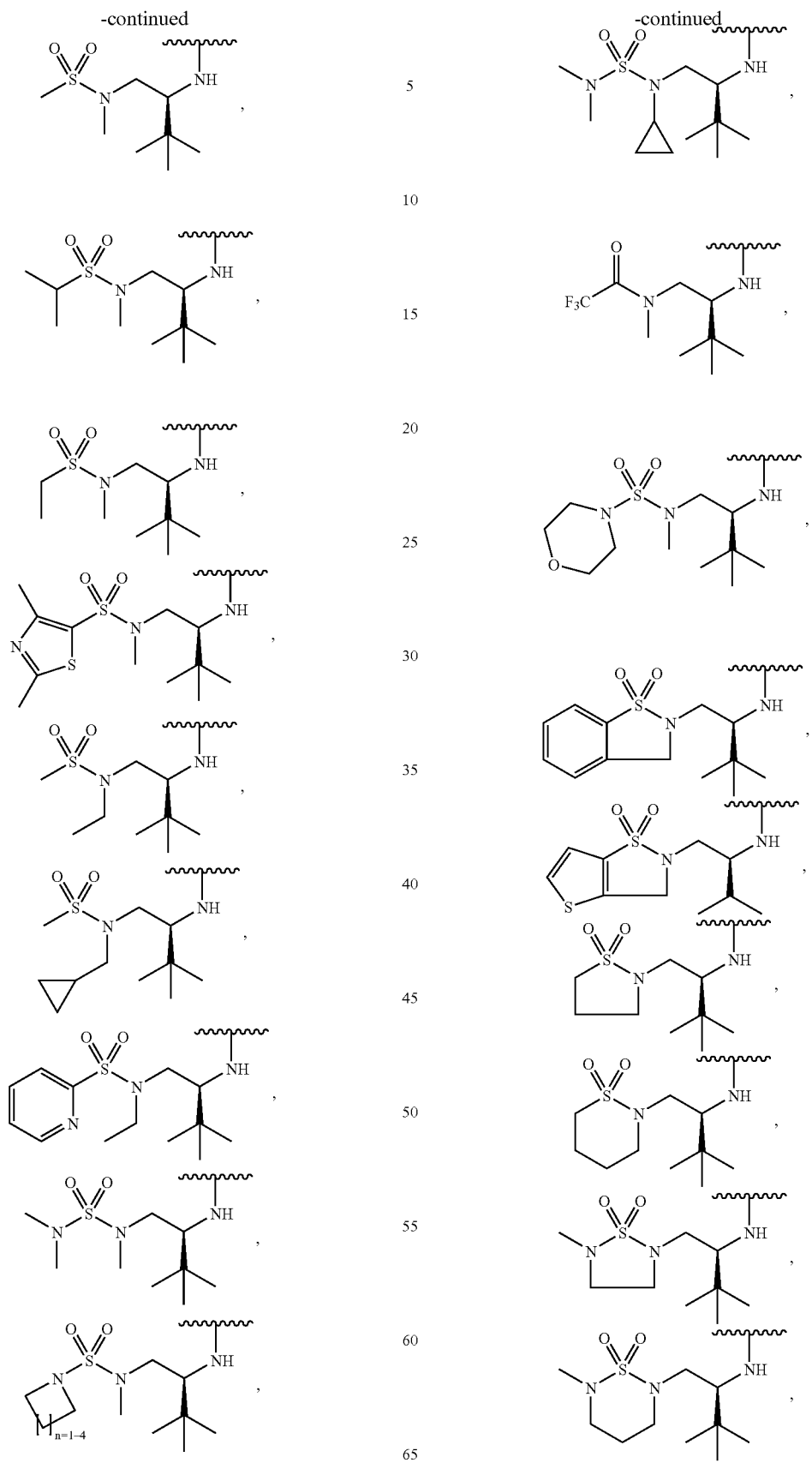

-continued
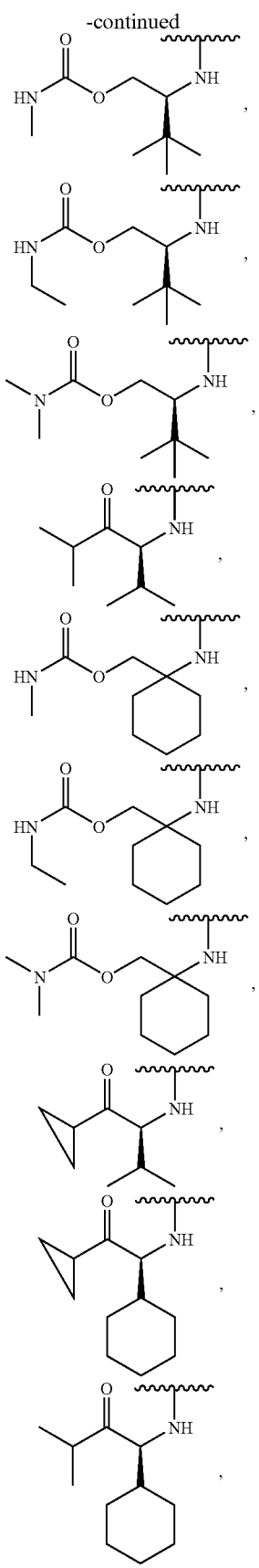
-continued
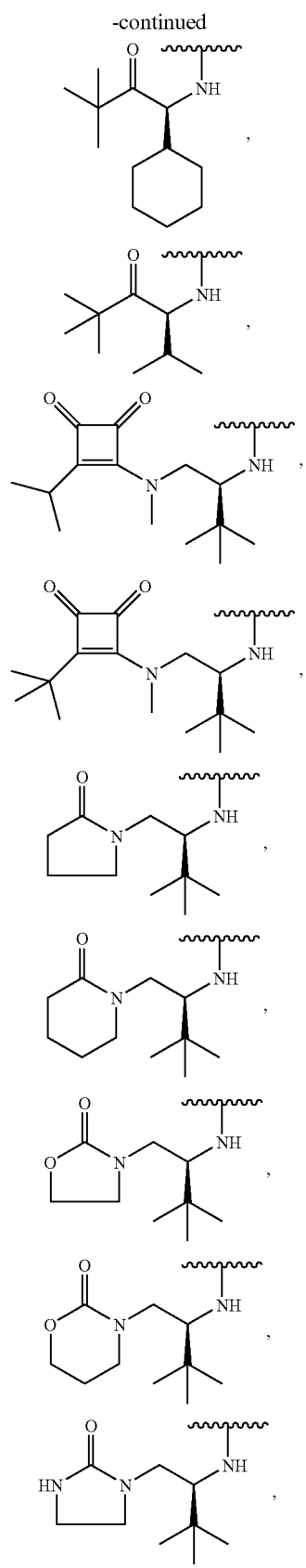

-continued
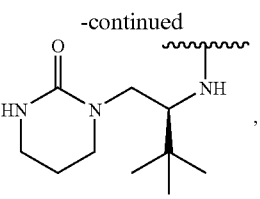
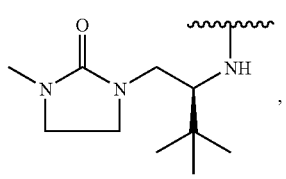
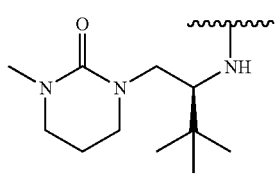
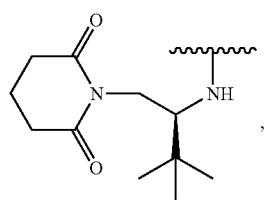
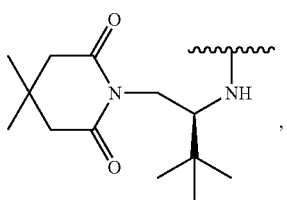
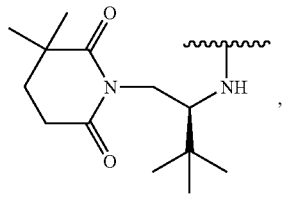
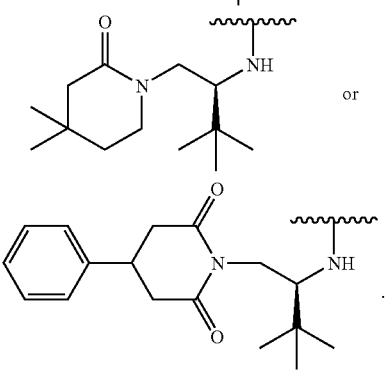
or
In an additional embodiment, Z is selected from the group consisting of the following structures:
-N(methyl)$_2$,   -N(ethyl)$_2$,
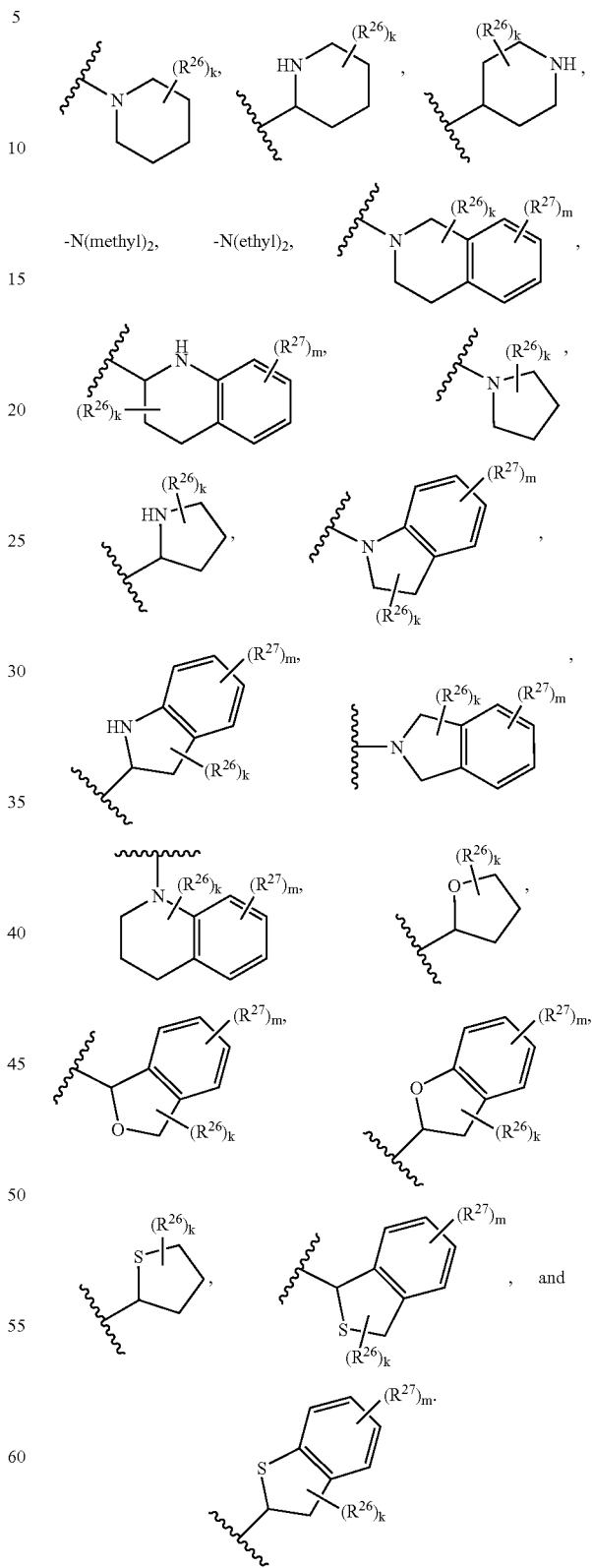
and wherein k=0-4, m=0-4, k and m can be the same or different, $R^{26}$ and $R^{27}$ can be the same or different, each being independently selected from the group consisting of hydroxy, alkoxy, aryloxy, thio, alkylthio, arylthio, amino, amido, alkylamino, arylamino, alkylsulfonyl, arylsulfonyl, sulfonamido, alkyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

In a still additional embodiment, Z is selected from the group consisting of the moieties:

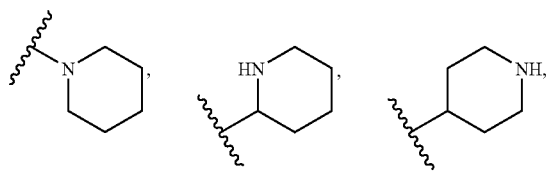

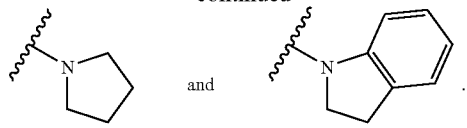

In a still additional embodiment, $R^1$ is $NH_2$ or $NHR^{14}$, where $R^{14}$ is selected from the group consisting of:

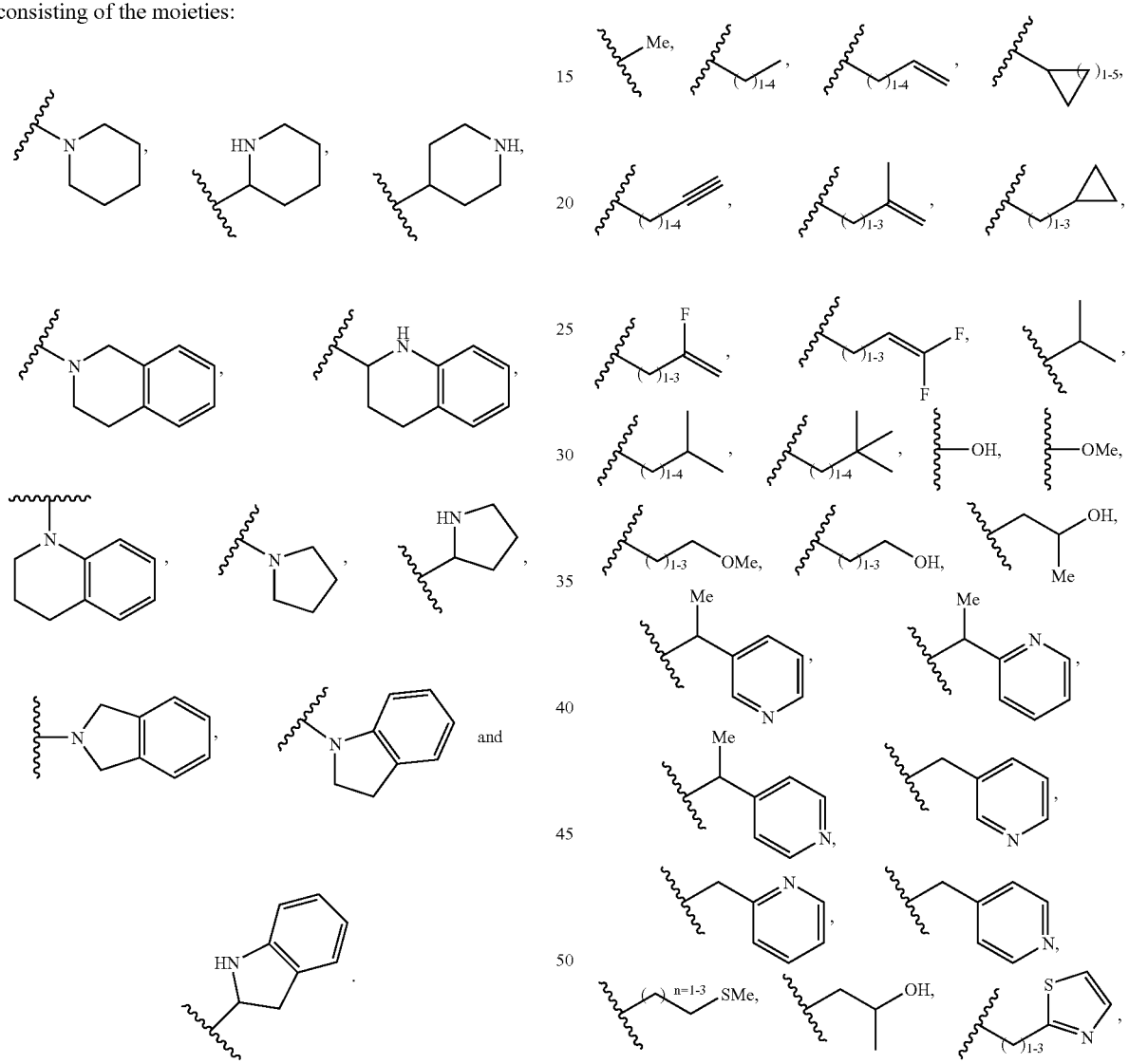

In a still additional embodiment, Z is selected from the following moieties:

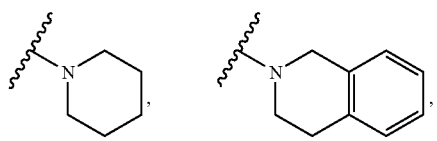

$R^2$ is selected from the group consisting of the following moieties:

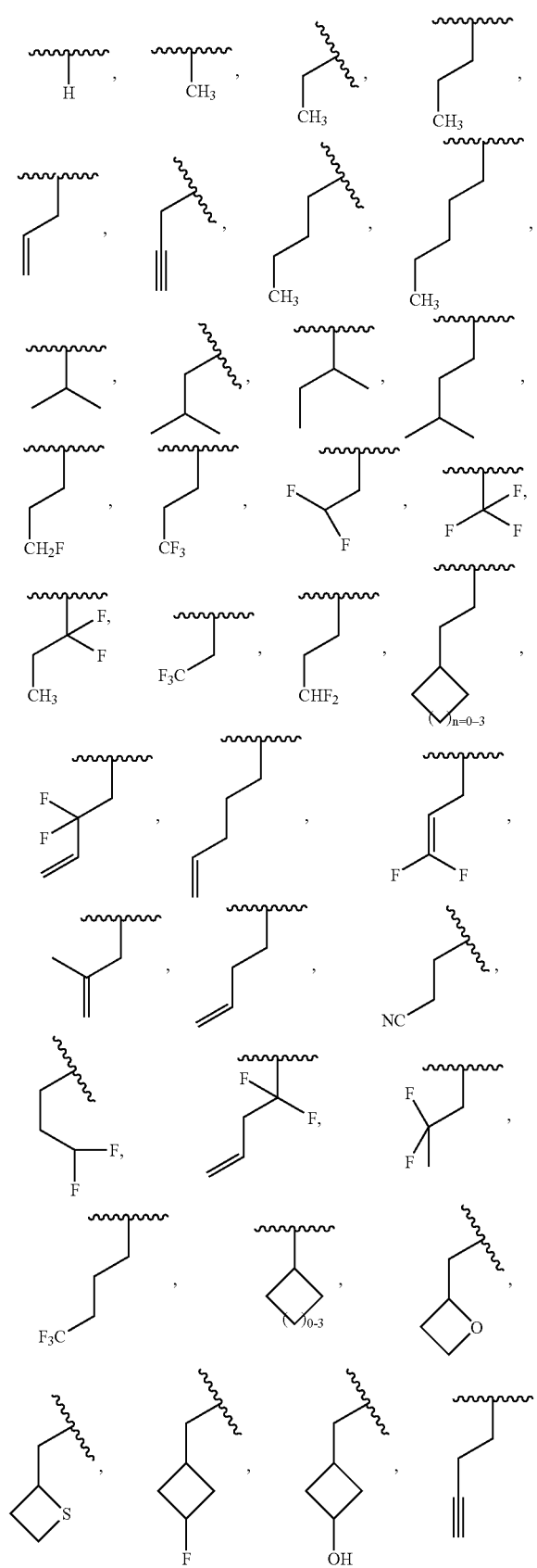
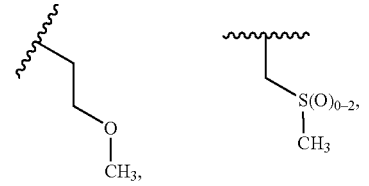
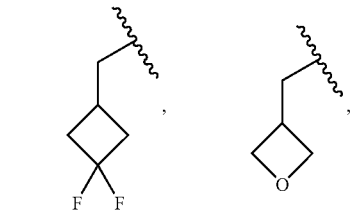
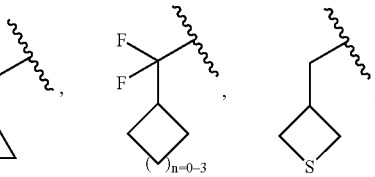
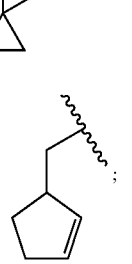
$R^3$ is selected from the group consisting of the following moieties:
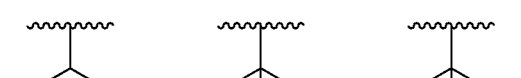
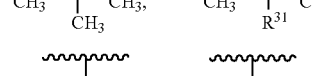
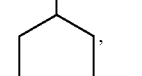
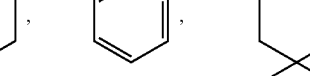
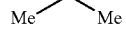

-continued

Z is selected from and Y is selected from:

-continued
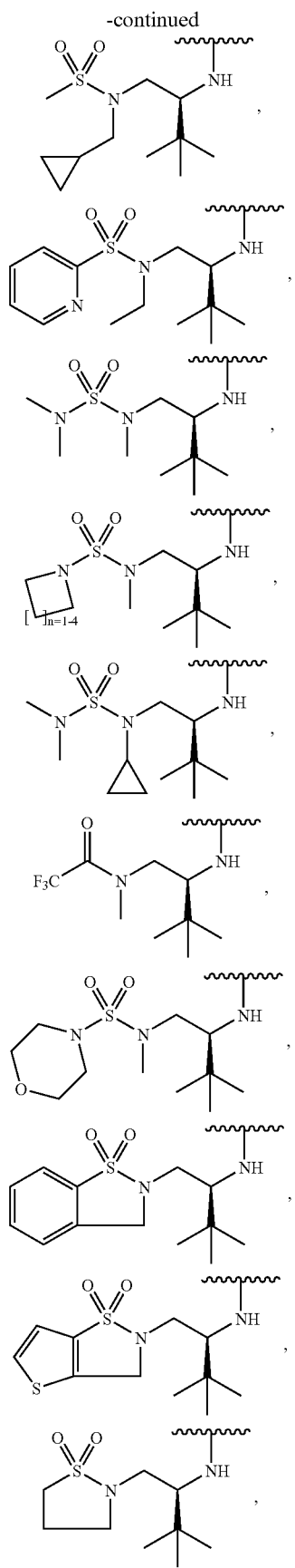
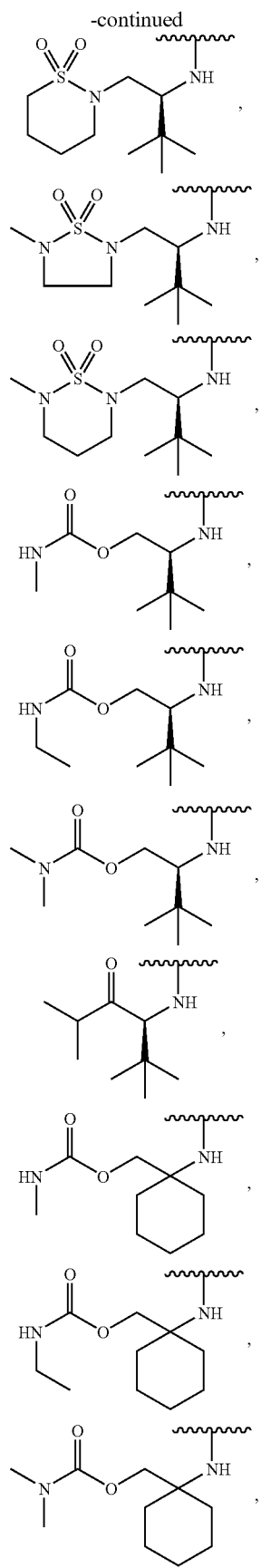

-continued
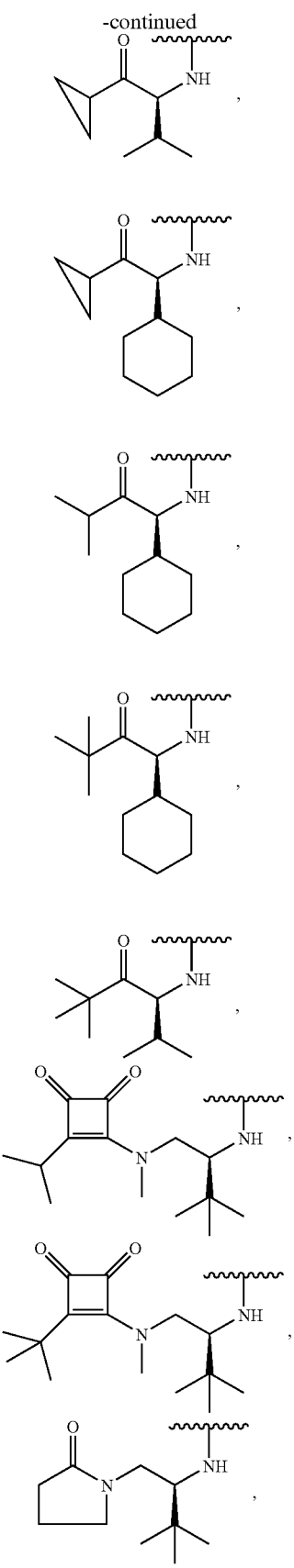
-continued
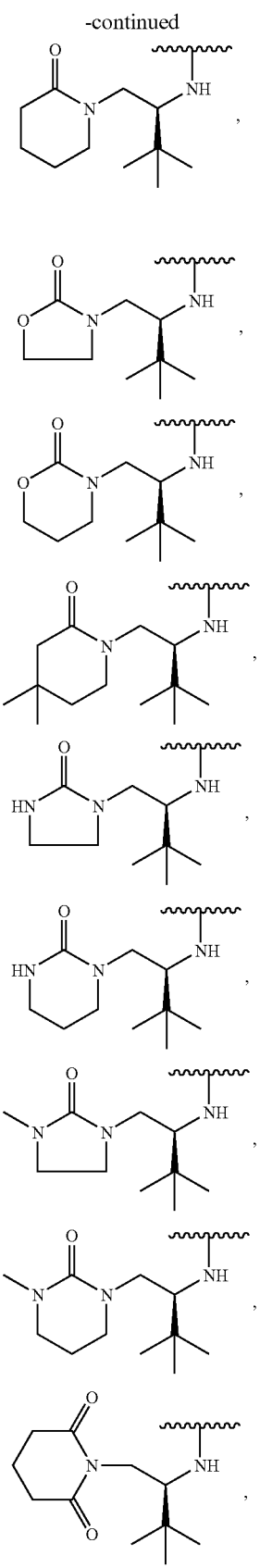

-continued
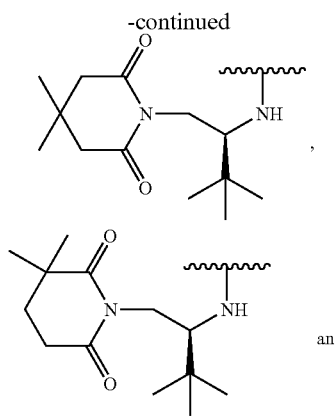
,
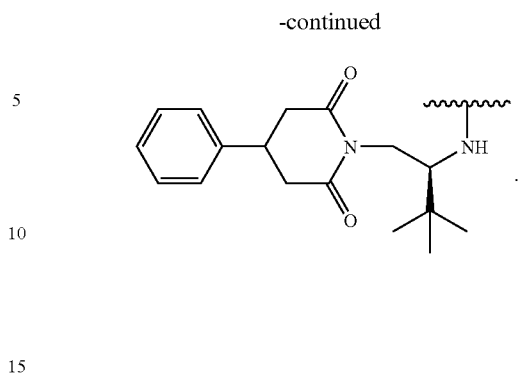
and
Yet another embodiment of the invention discloses compounds shown in Table 1.
TABLE 1
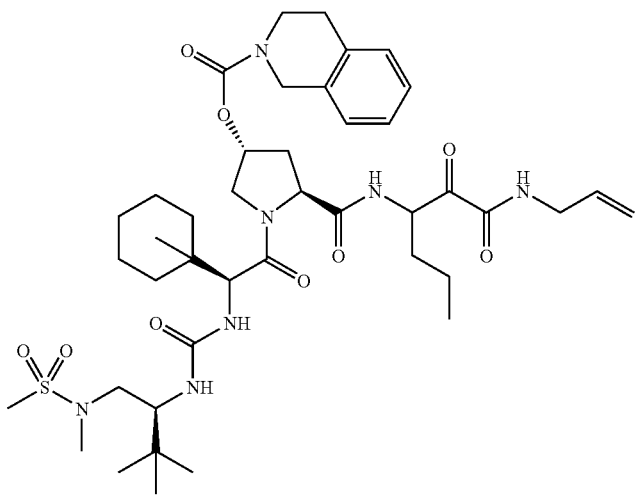
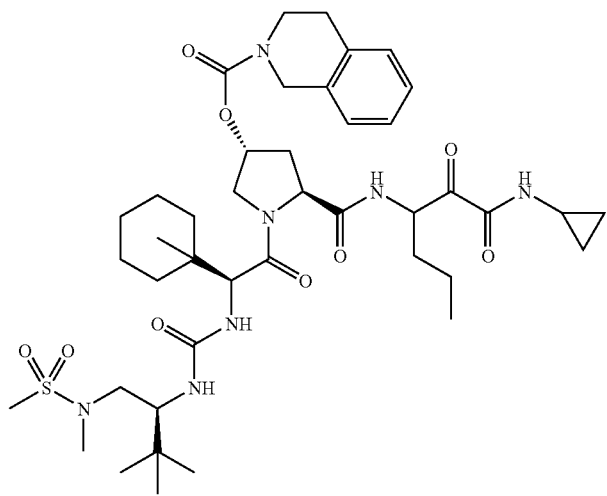

TABLE 1-continued
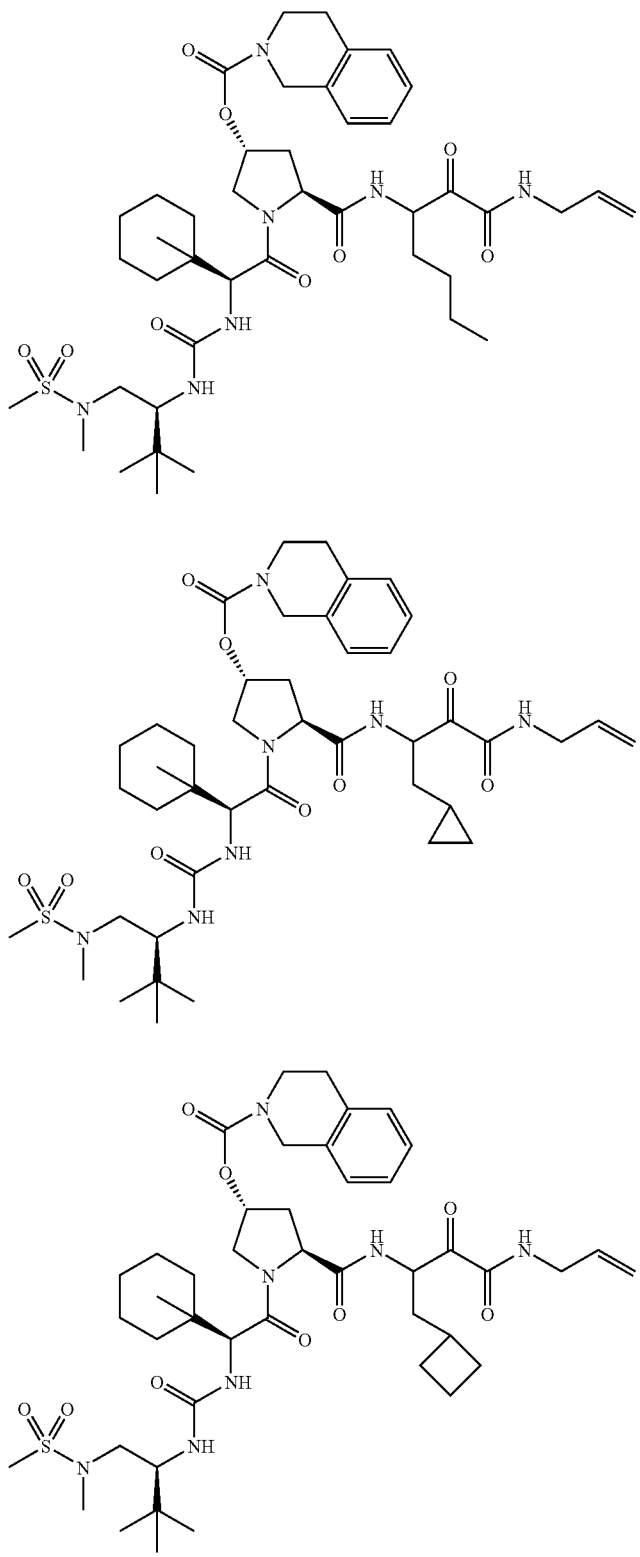

TABLE 1-continued
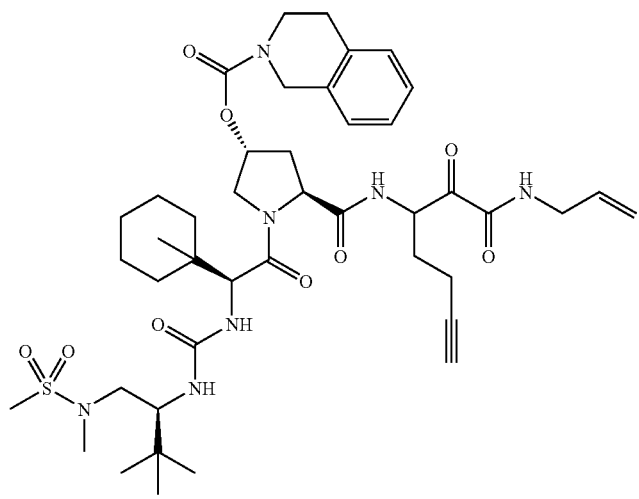
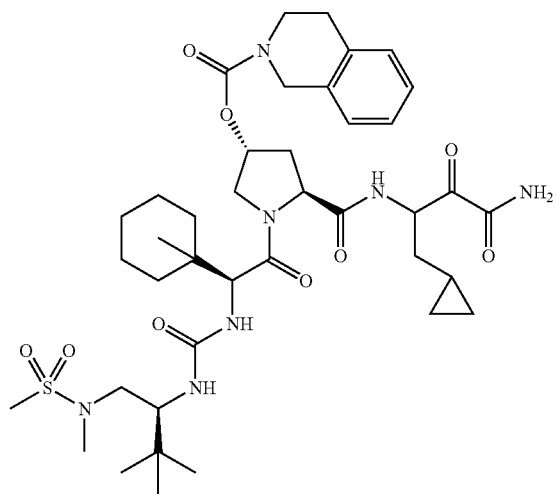
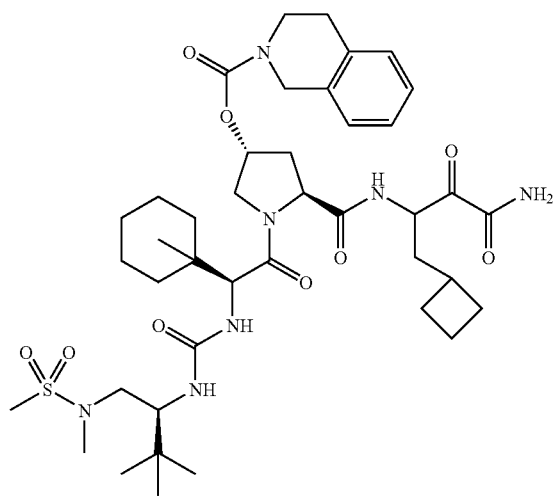

TABLE 1-continued
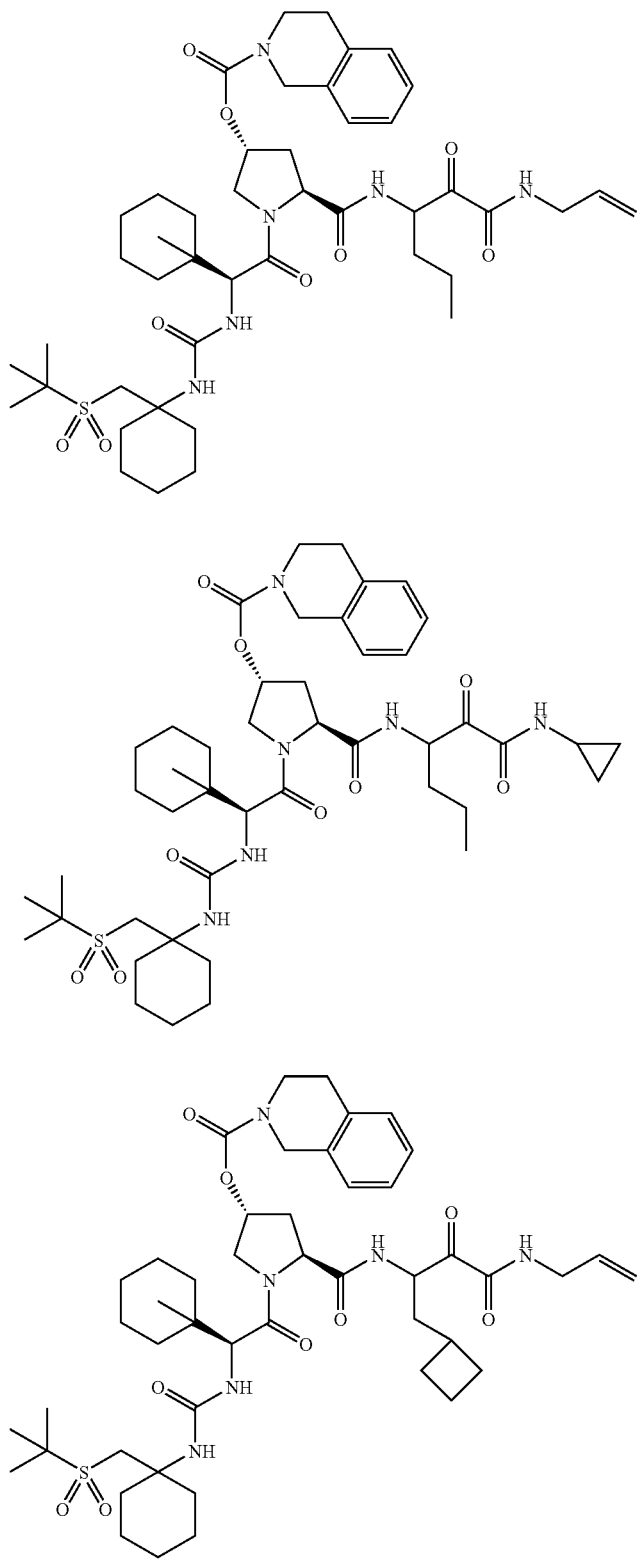

TABLE 1-continued
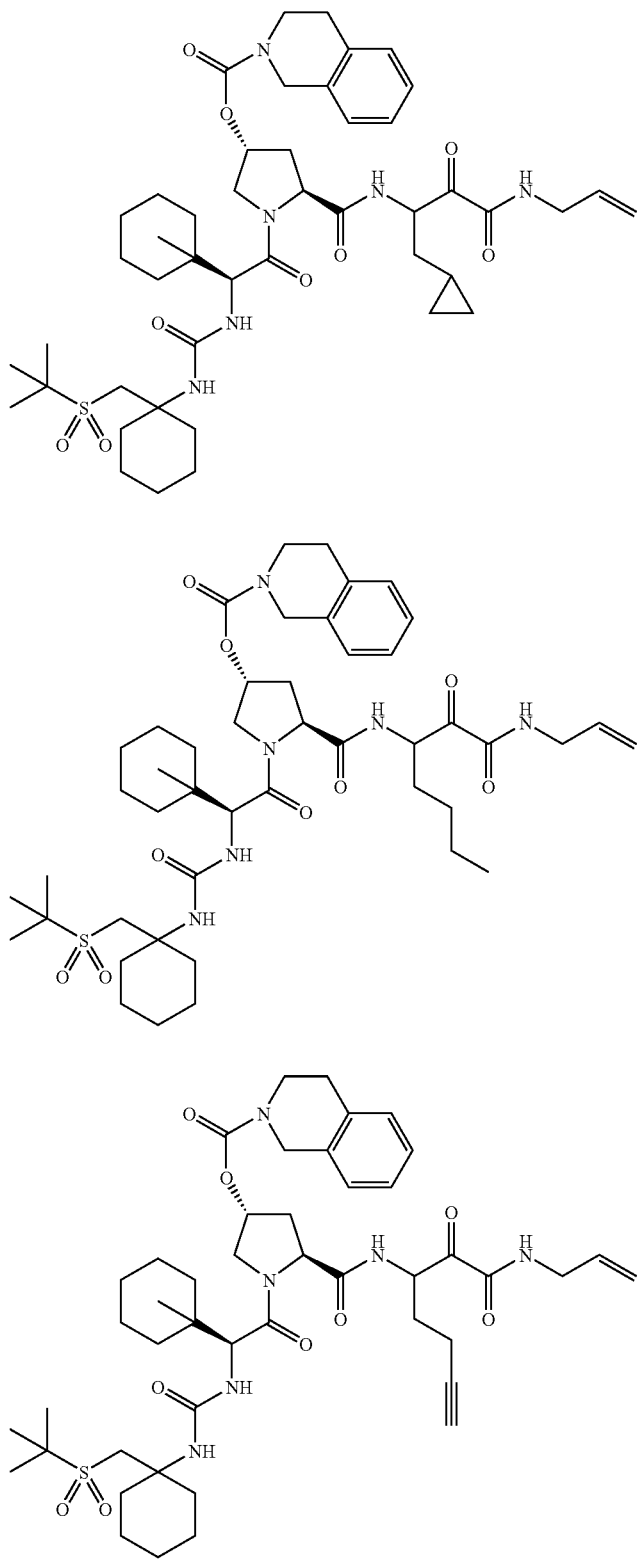

TABLE 1-continued
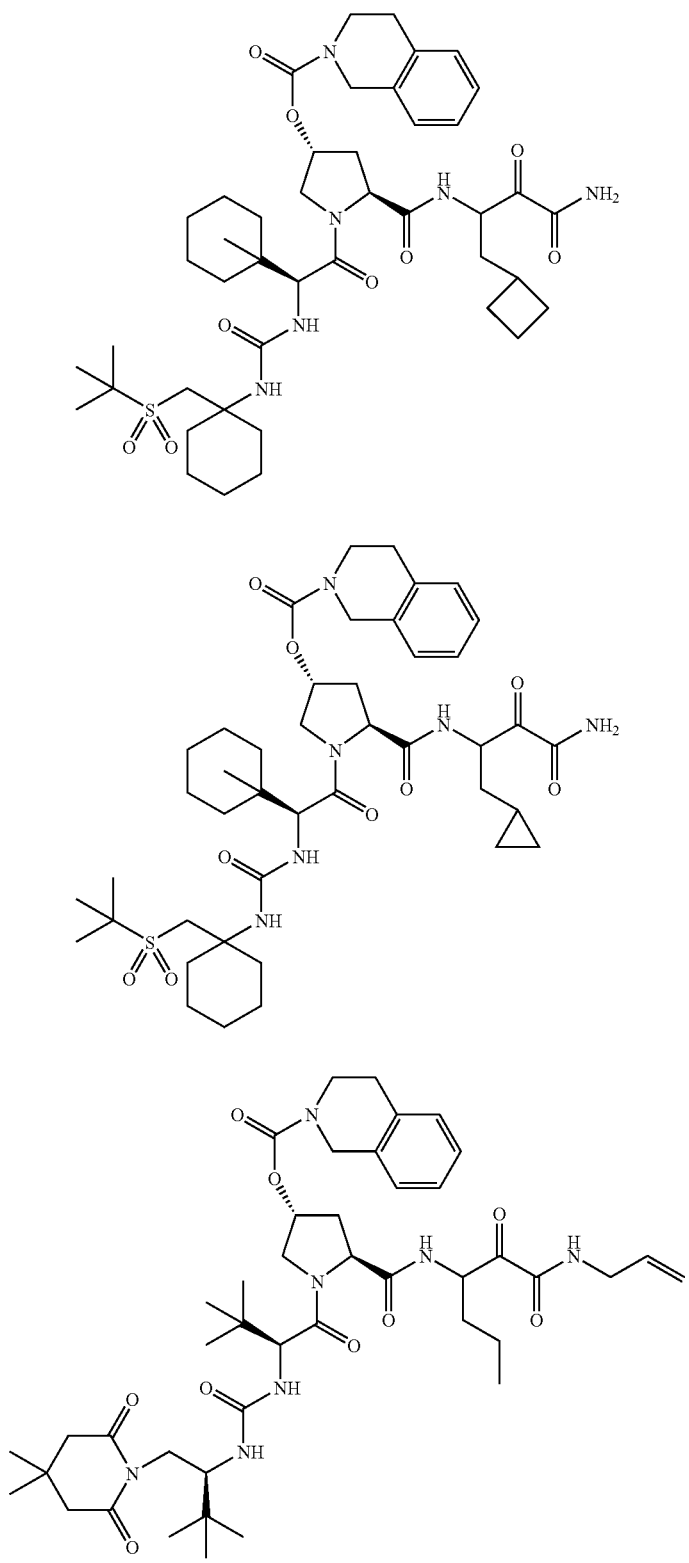

TABLE 1-continued
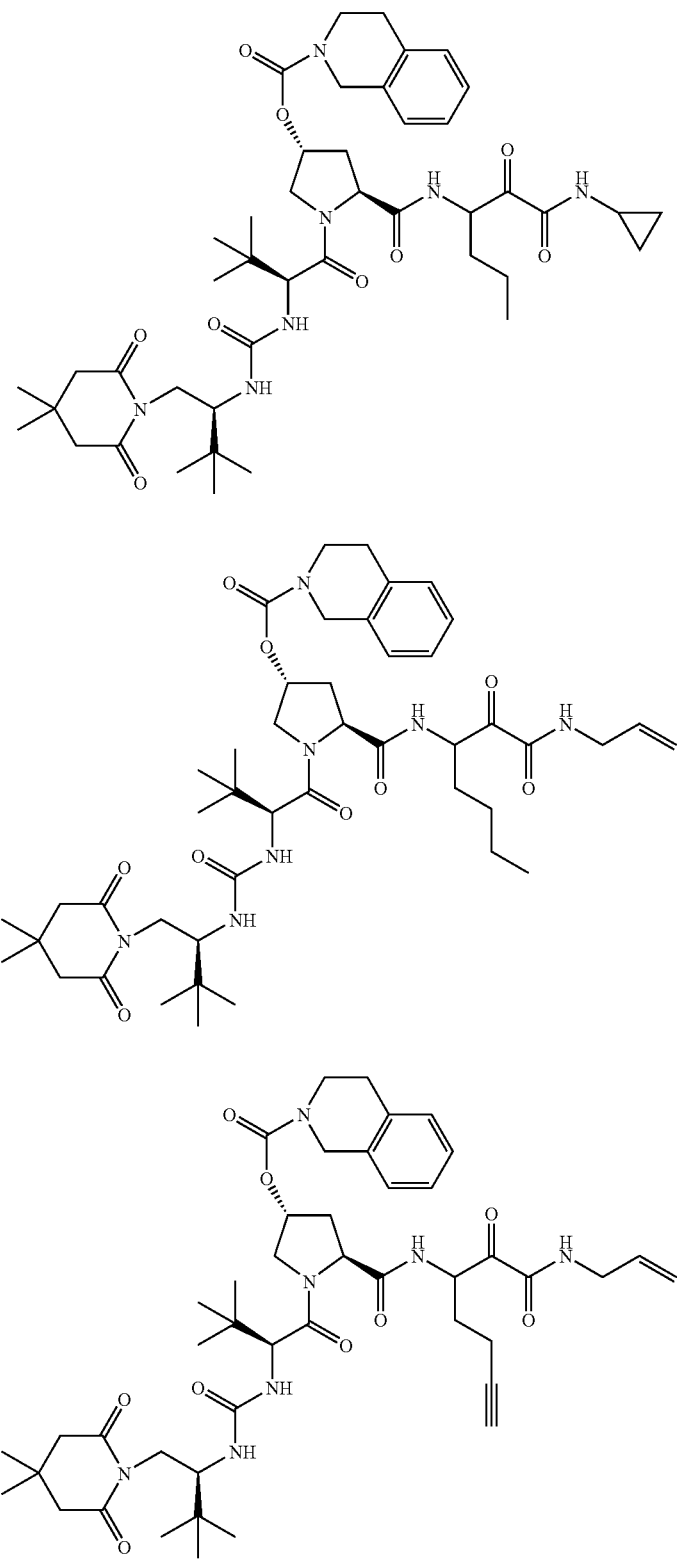

TABLE 1-continued
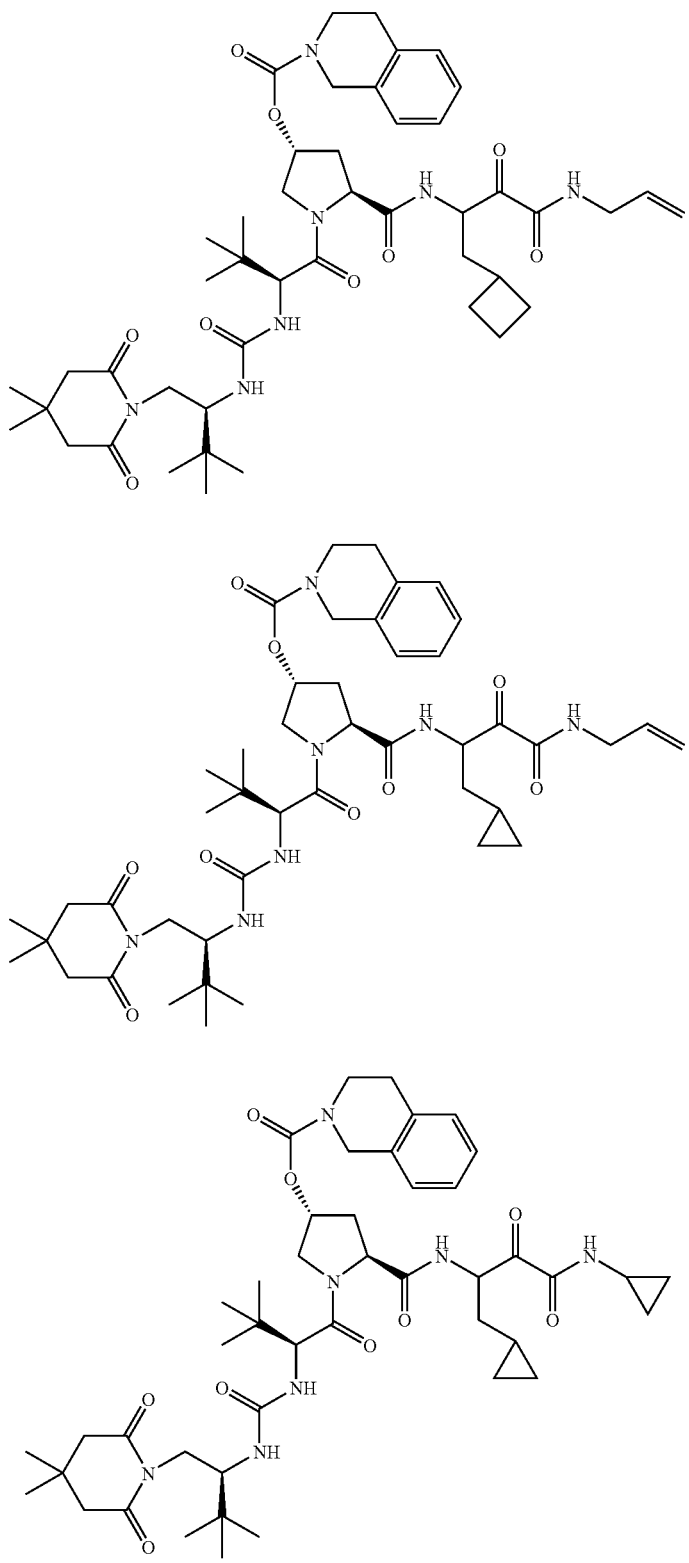

TABLE 1-continued
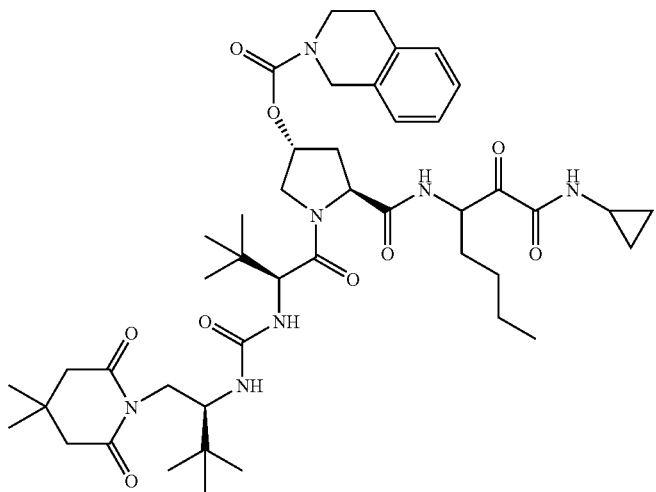
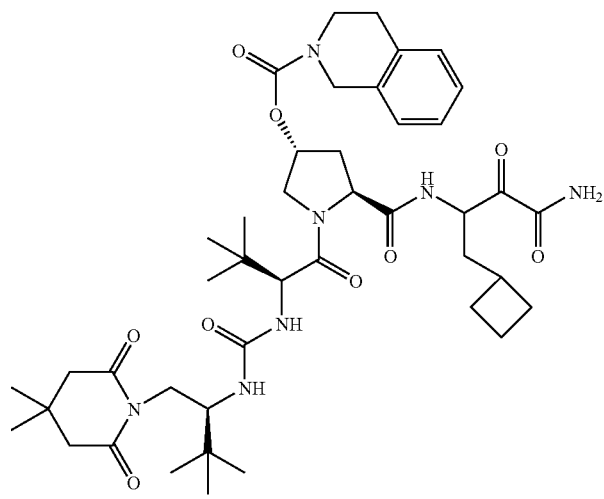
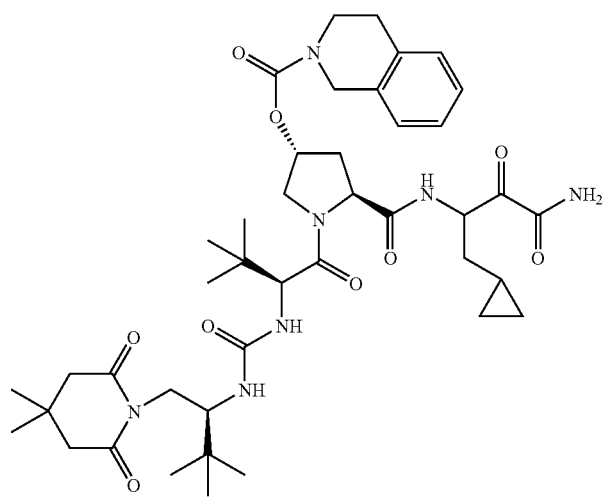

TABLE 1-continued
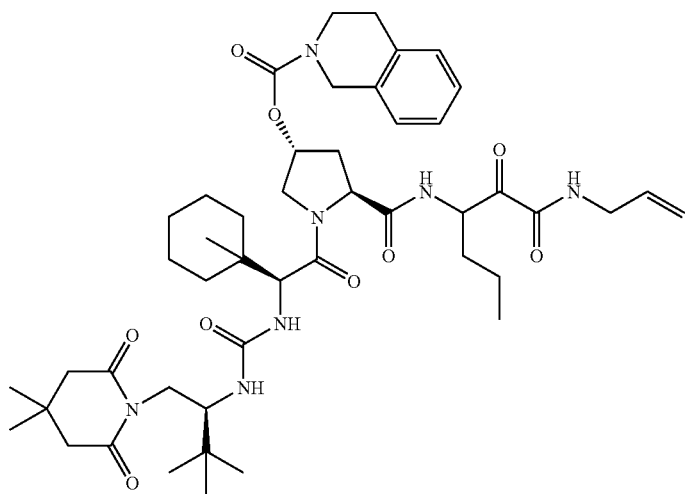
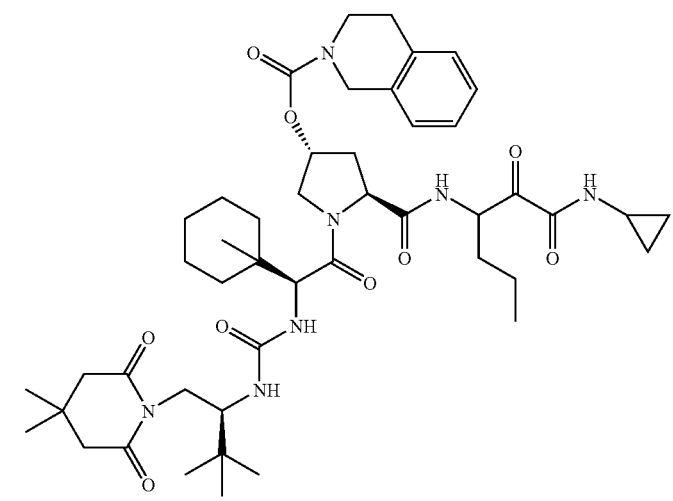
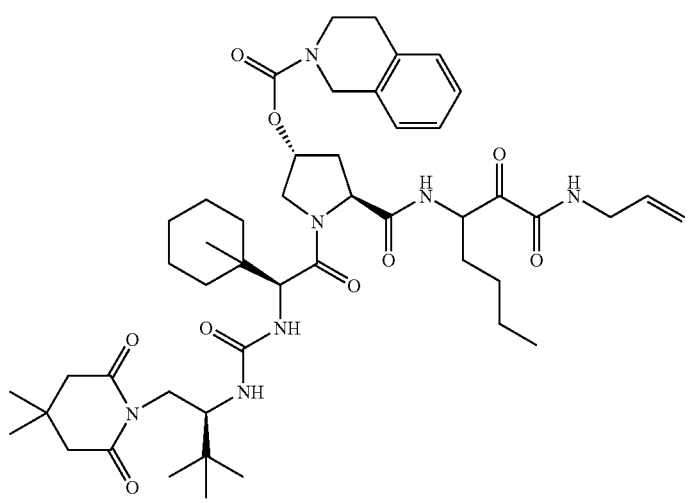

TABLE 1-continued
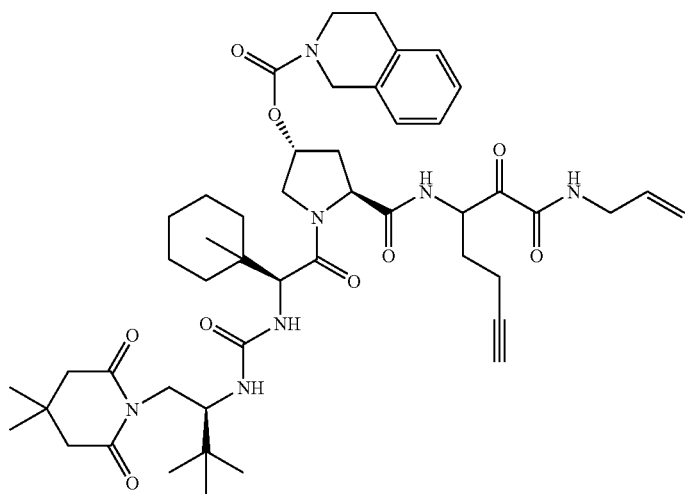
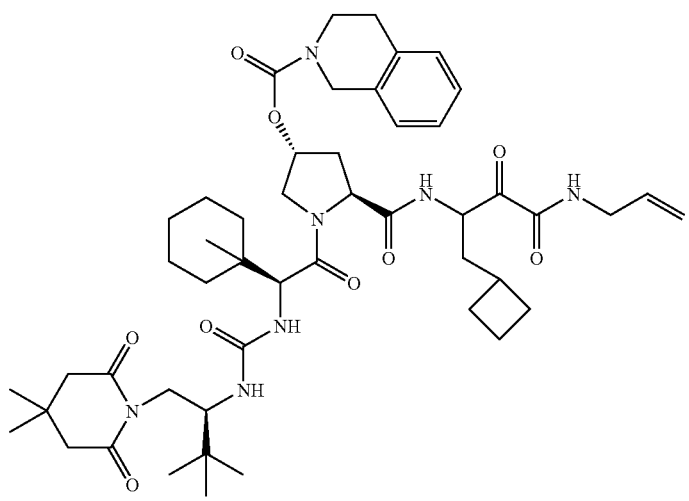
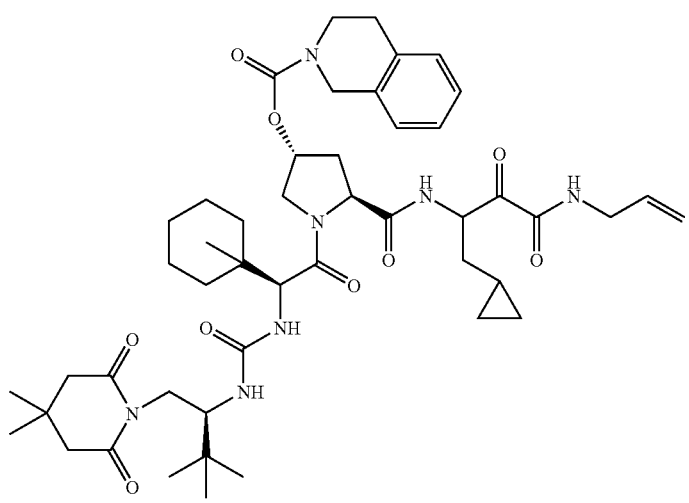

TABLE 1-continued
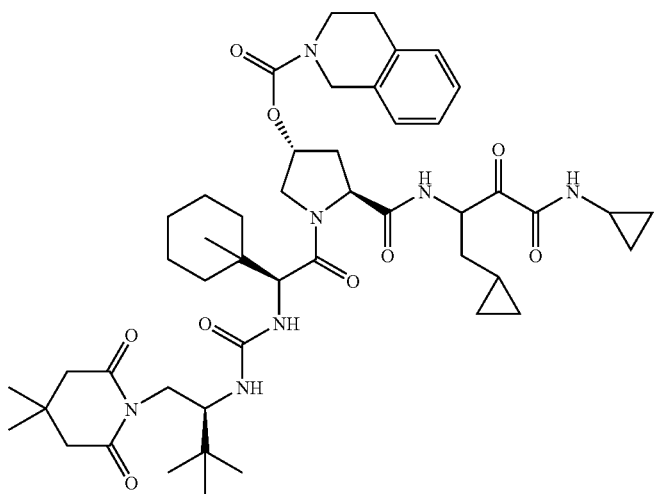
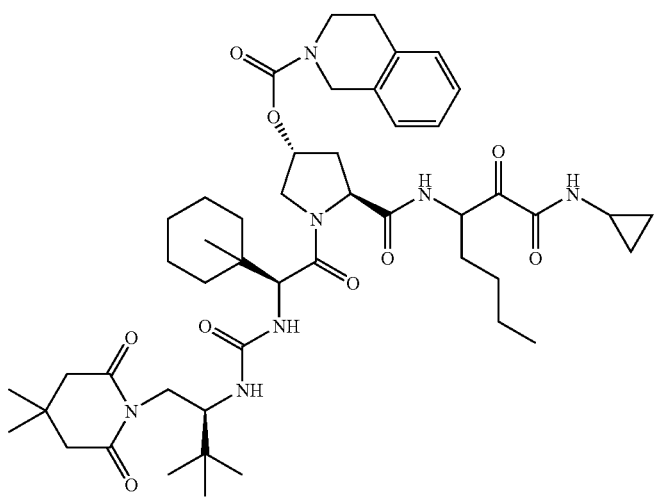
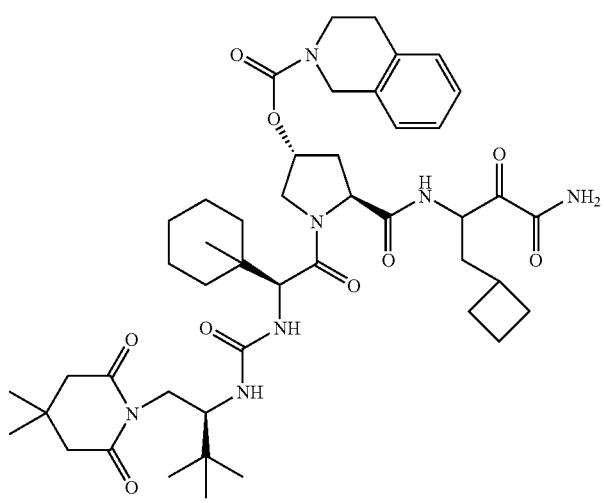

TABLE 1-continued
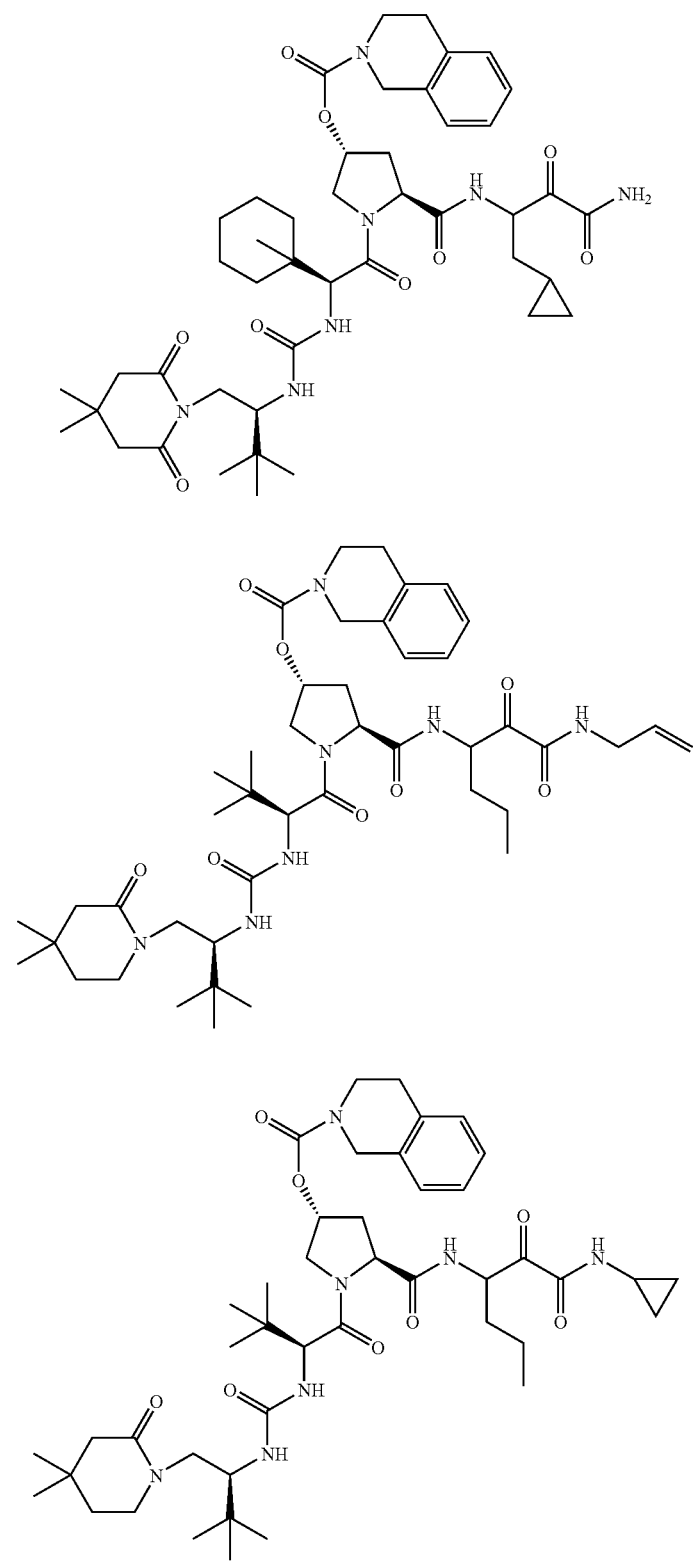

TABLE 1-continued
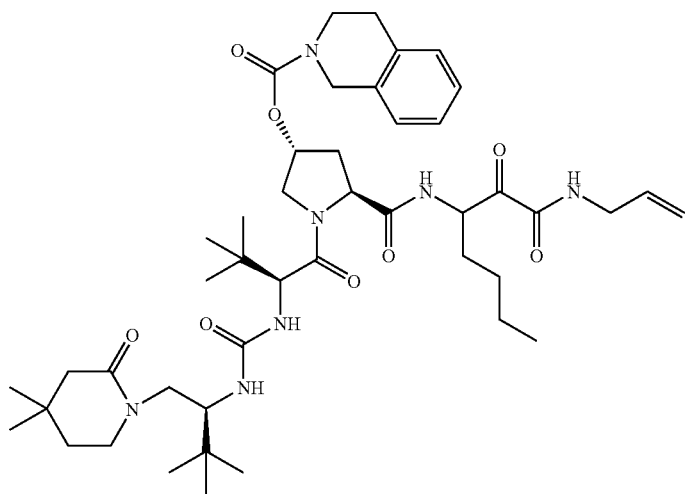
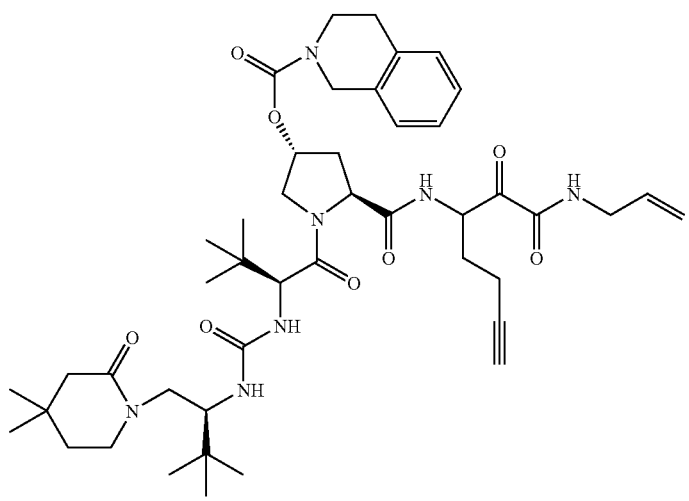
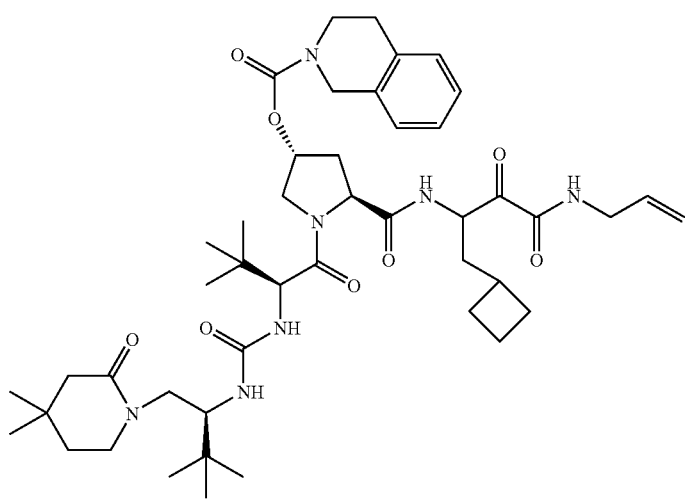

TABLE 1-continued
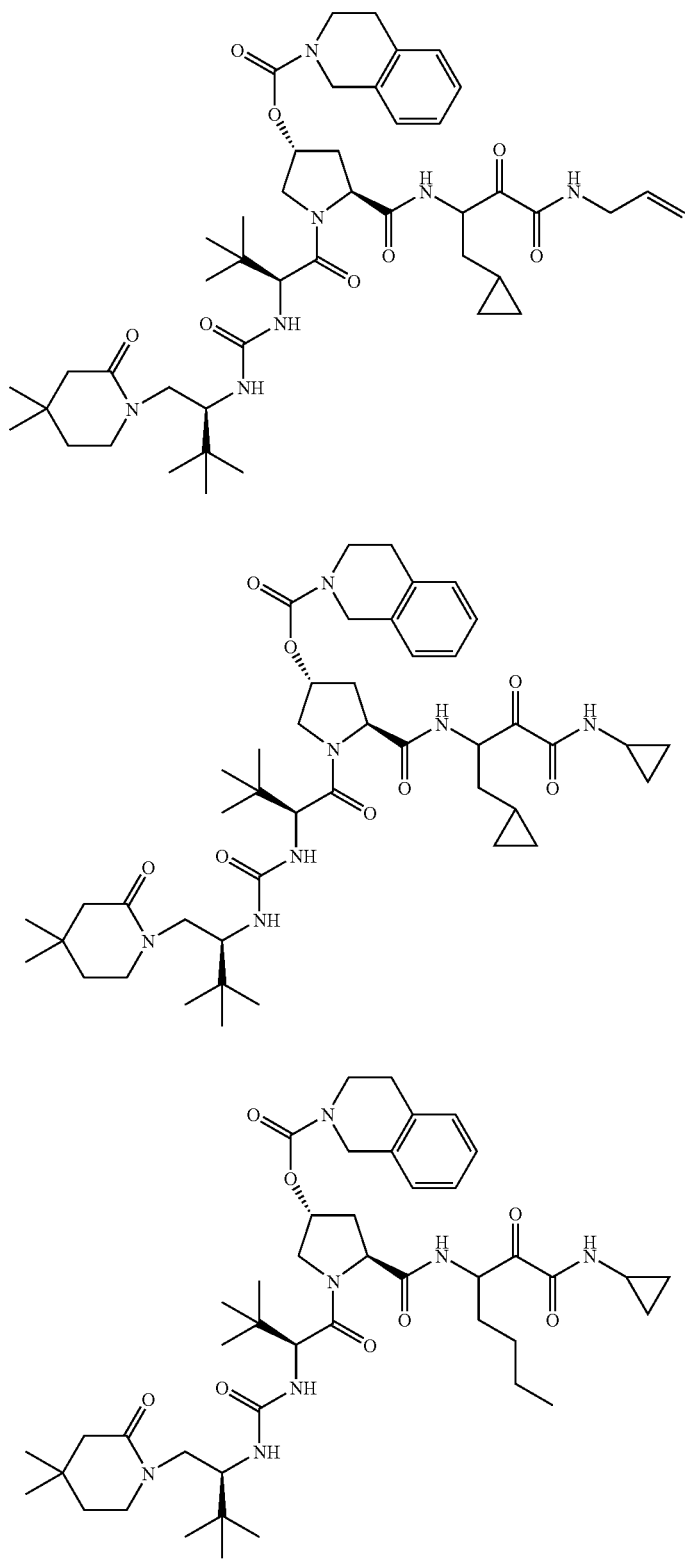

TABLE 1-continued
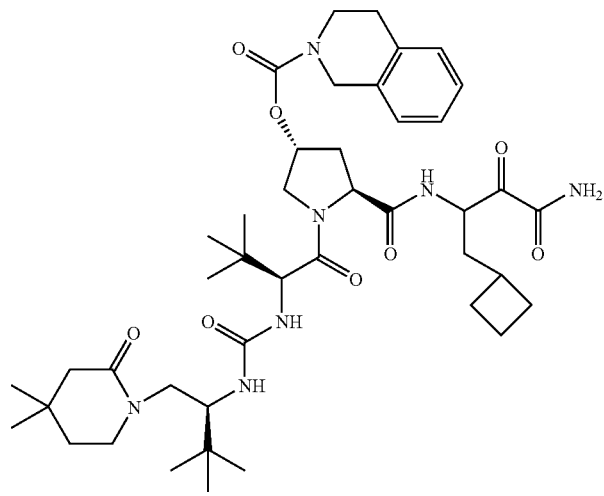
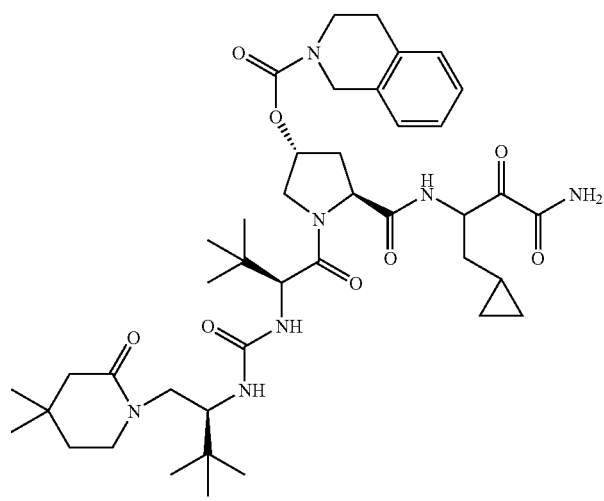
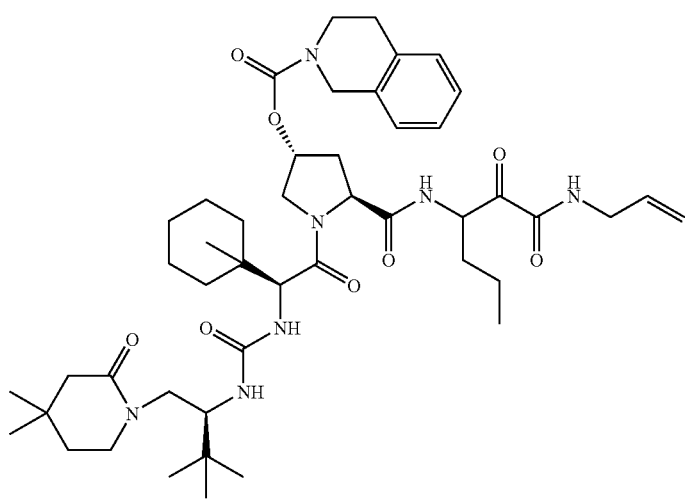

TABLE 1-continued
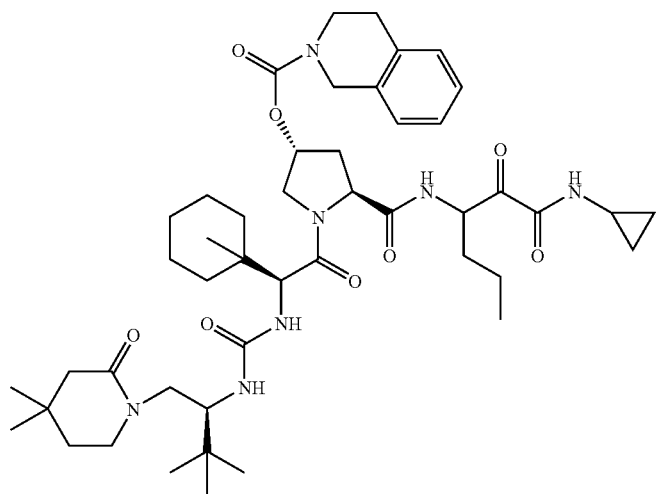
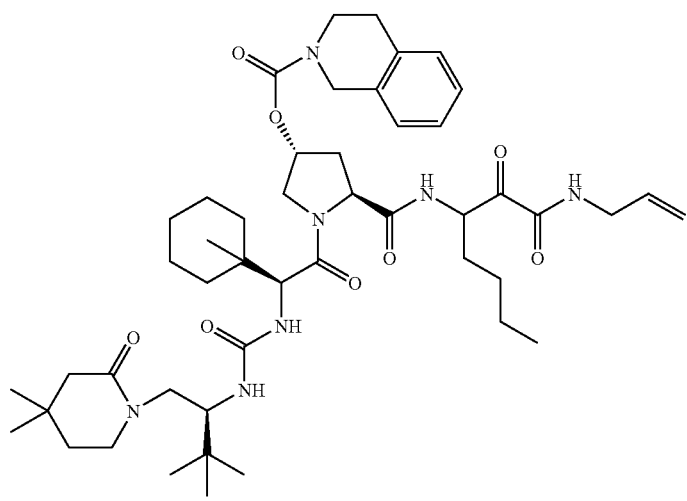
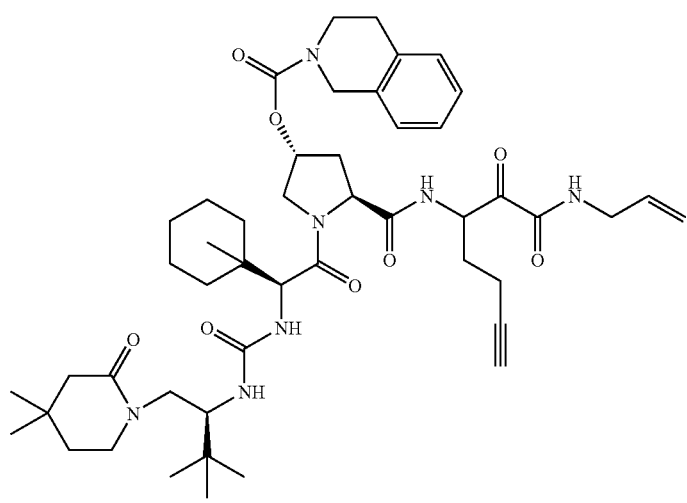

TABLE 1-continued
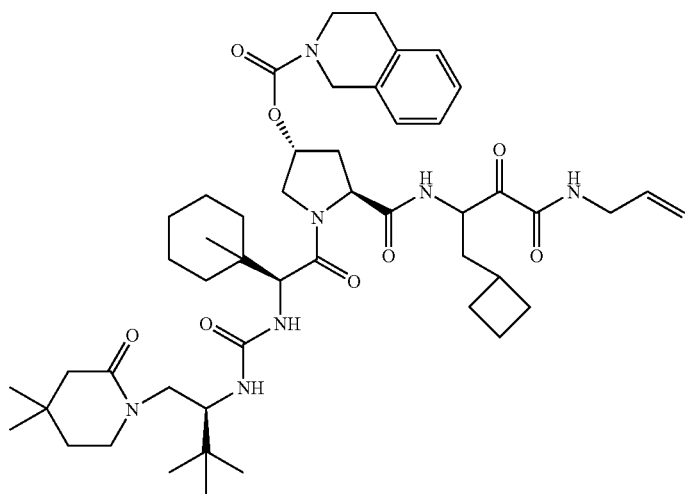
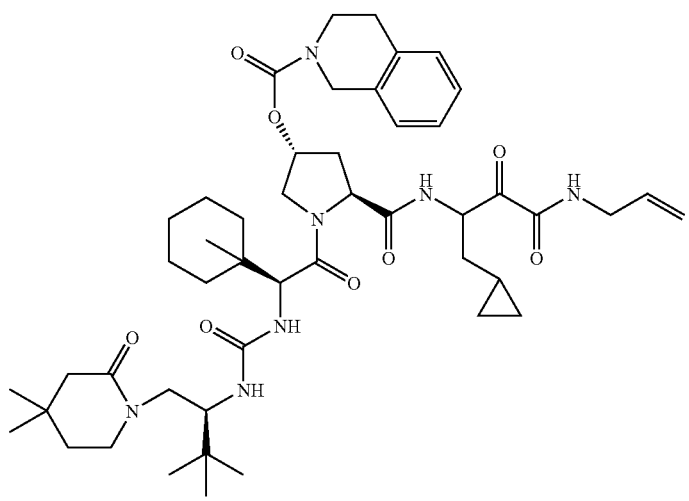
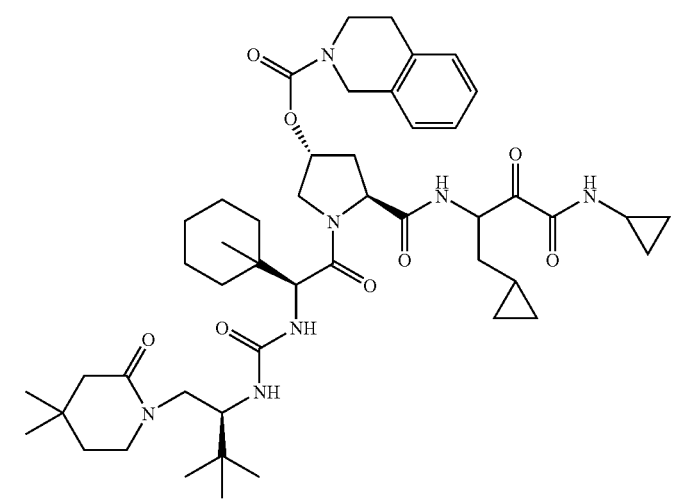

TABLE 1-continued
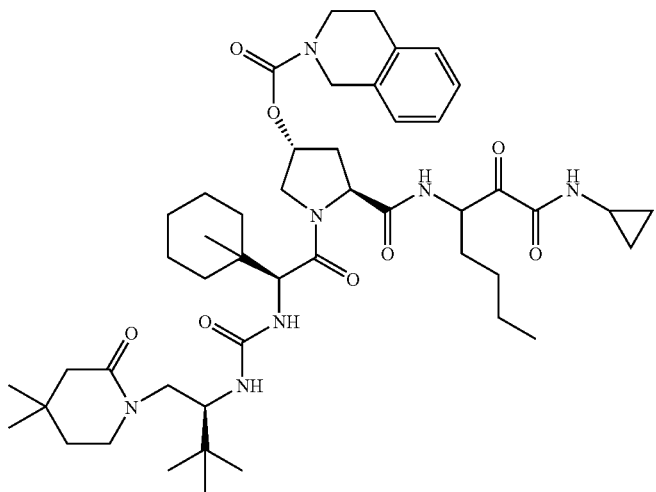
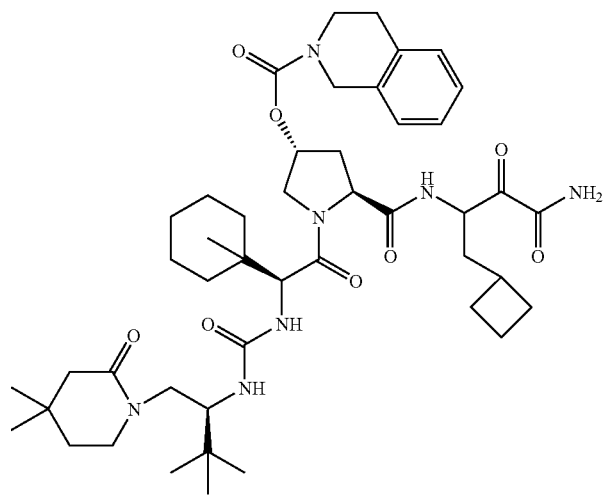
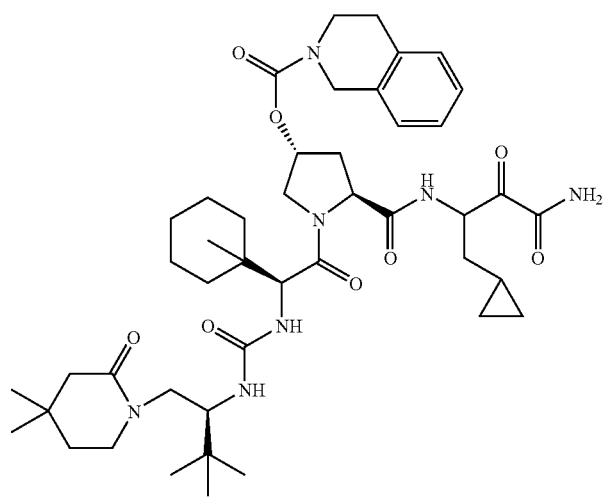

TABLE 1-continued
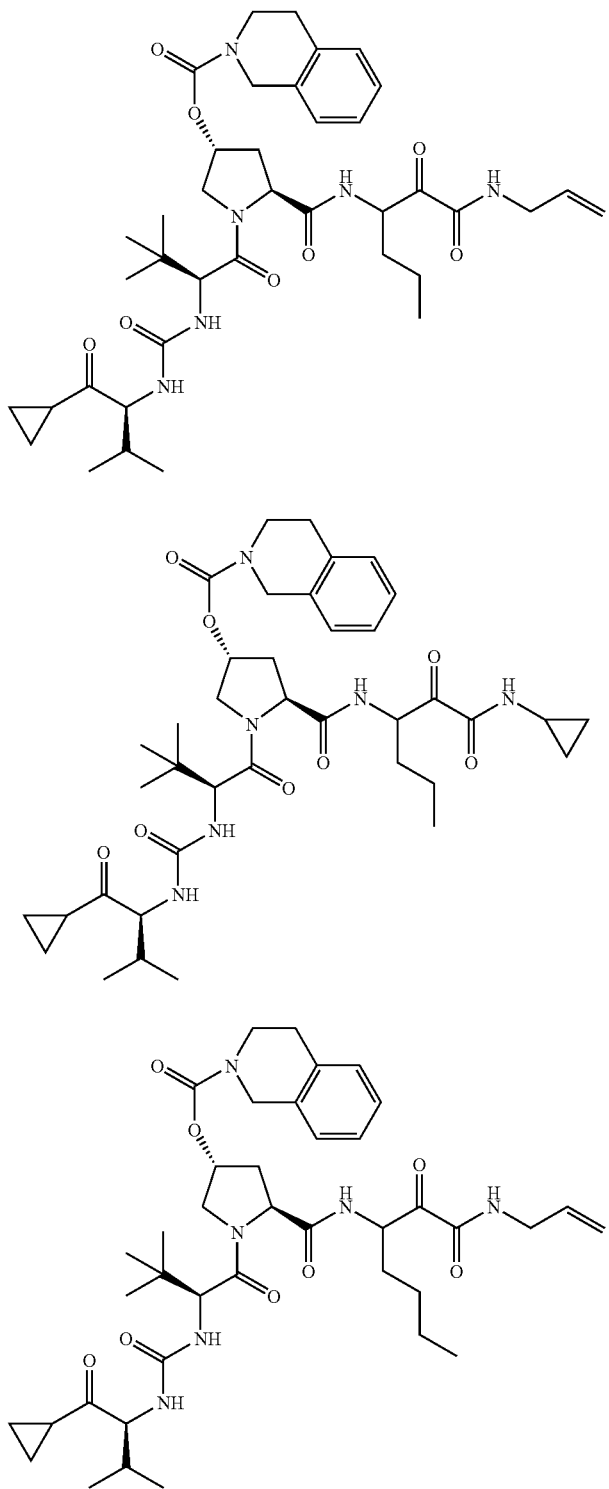

TABLE 1-continued
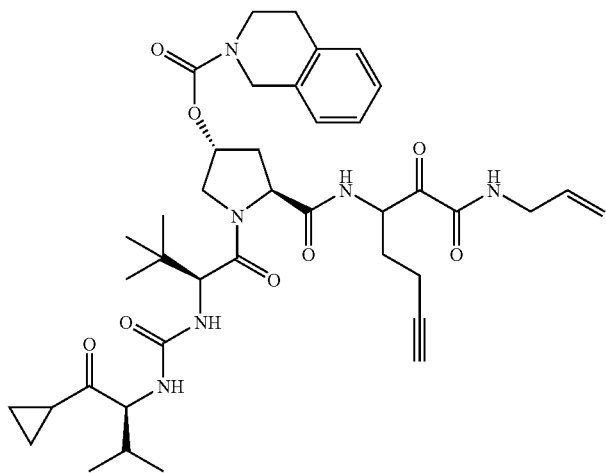
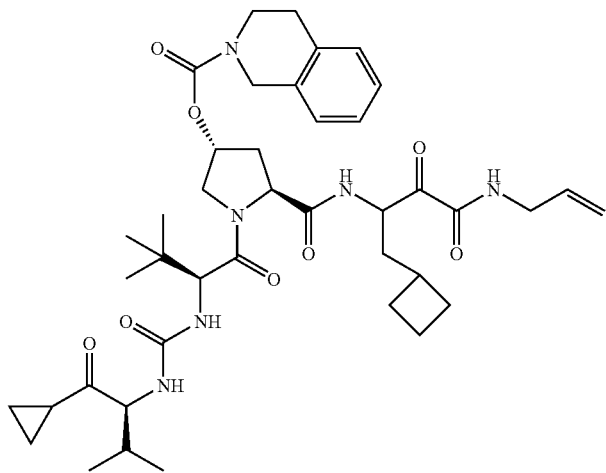
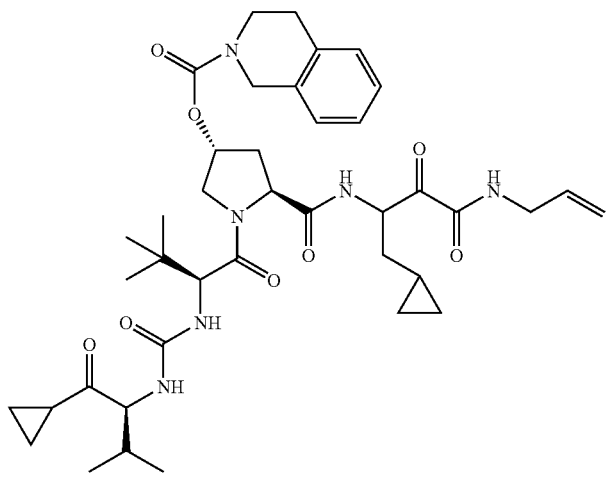

TABLE 1-continued
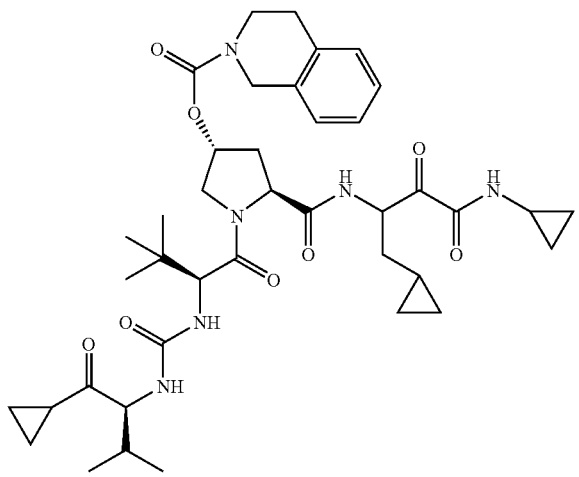
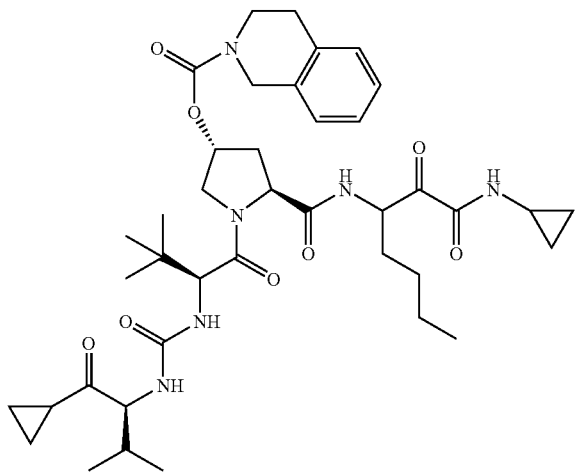
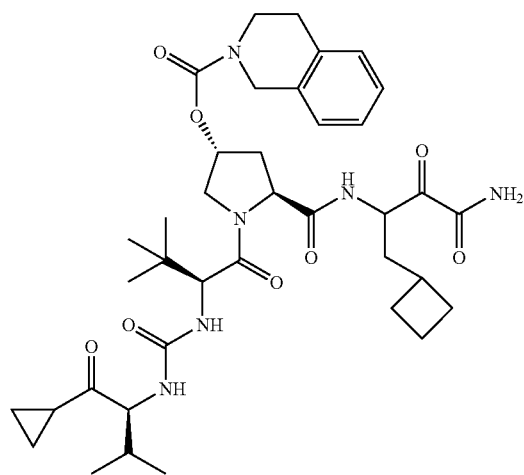

TABLE 1-continued
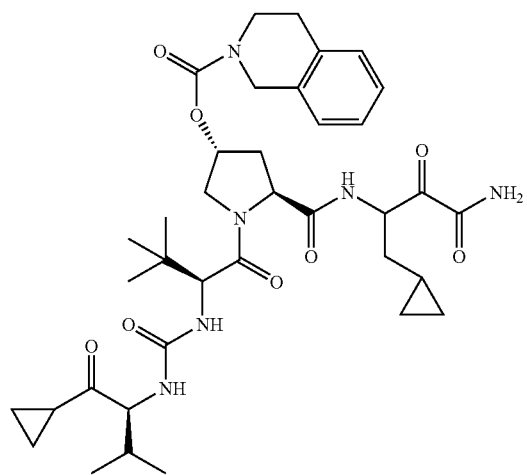
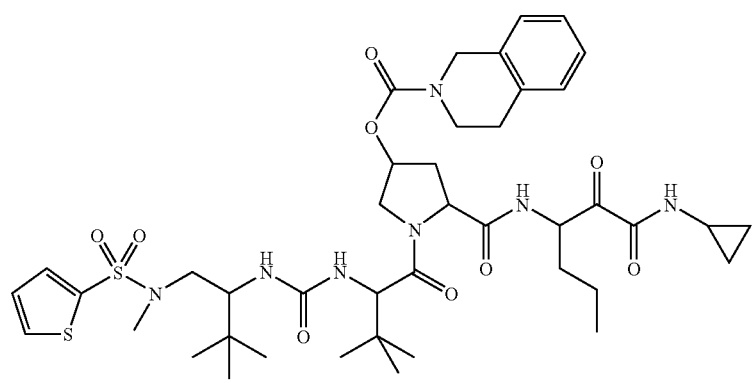
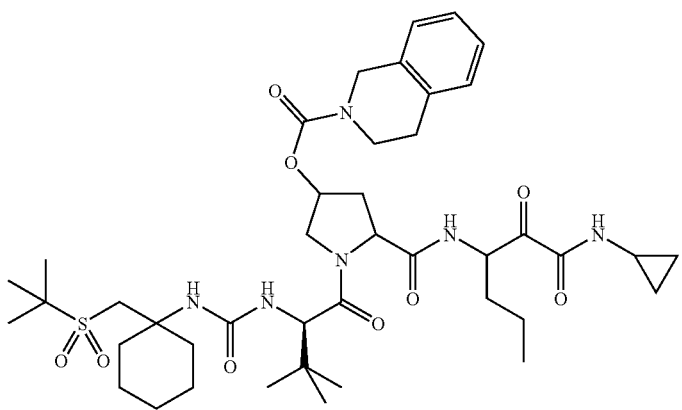

TABLE 1-continued
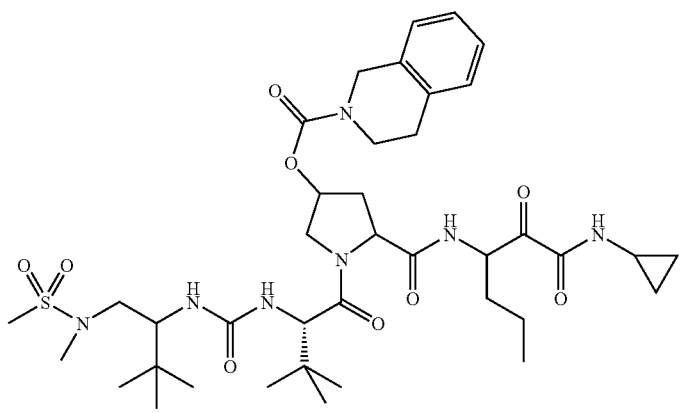
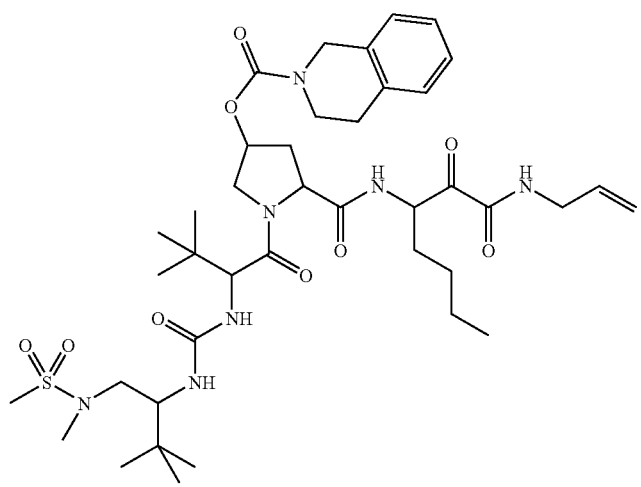
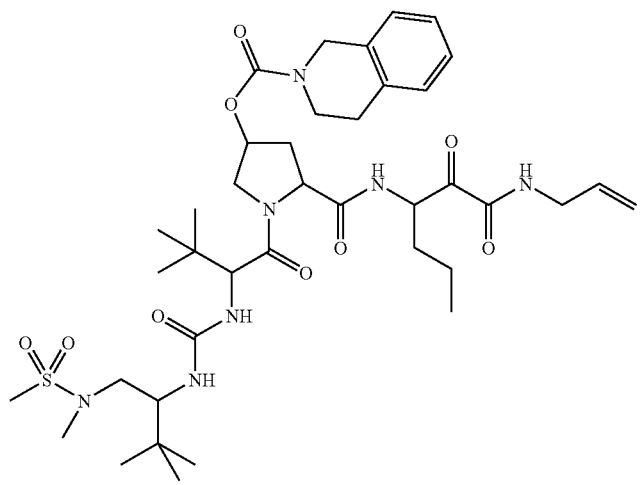

TABLE 1-continued
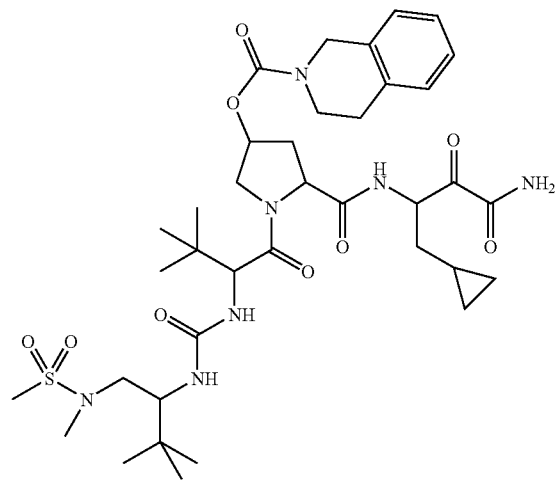
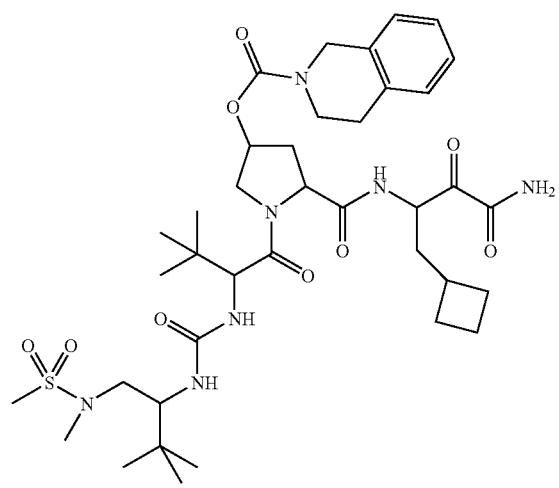
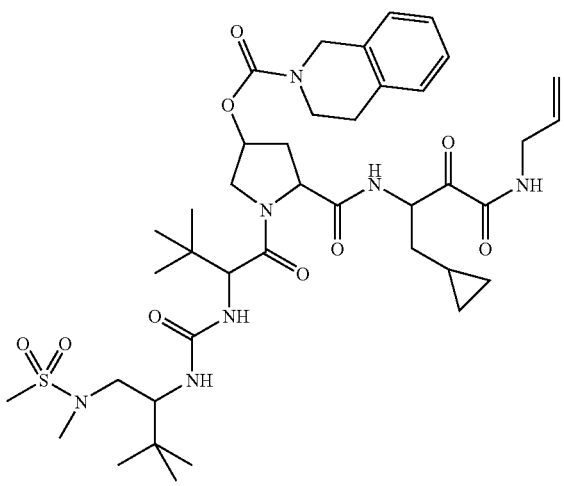

TABLE 1-continued
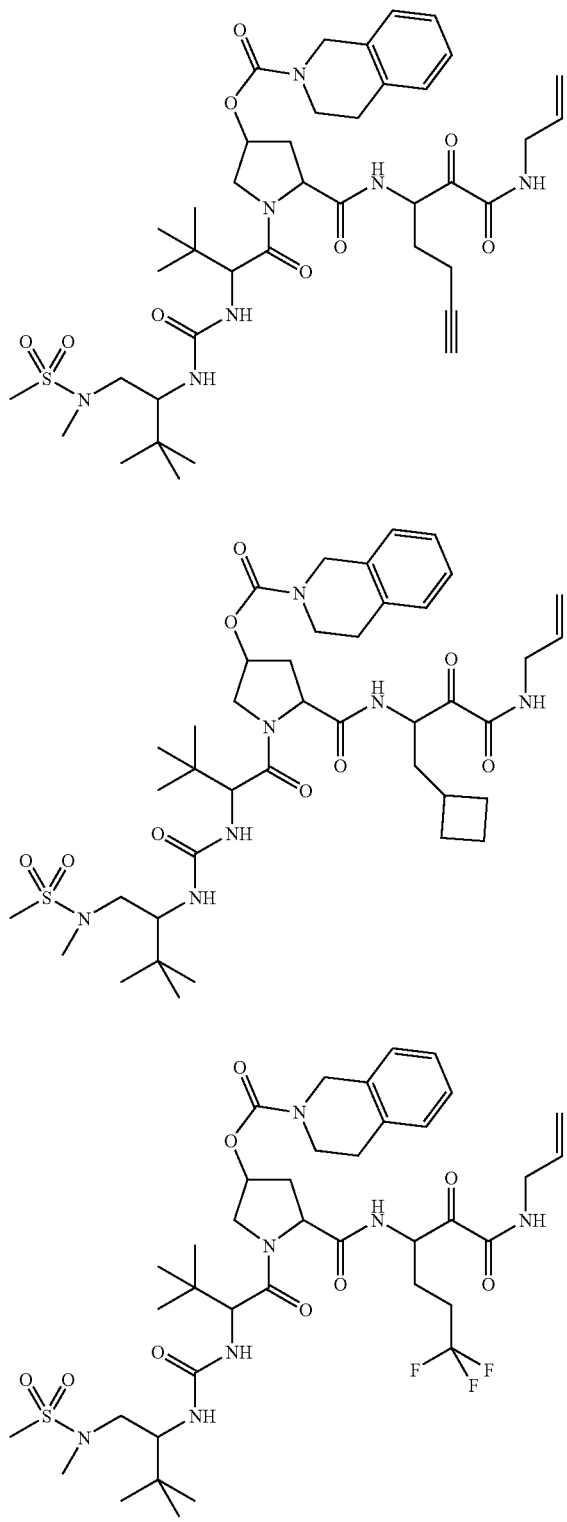

TABLE 1-continued
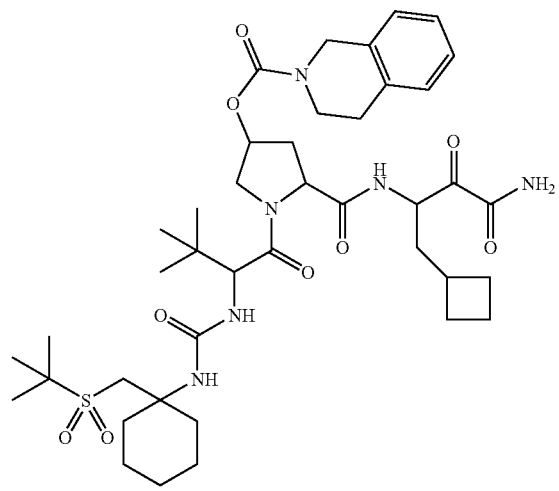
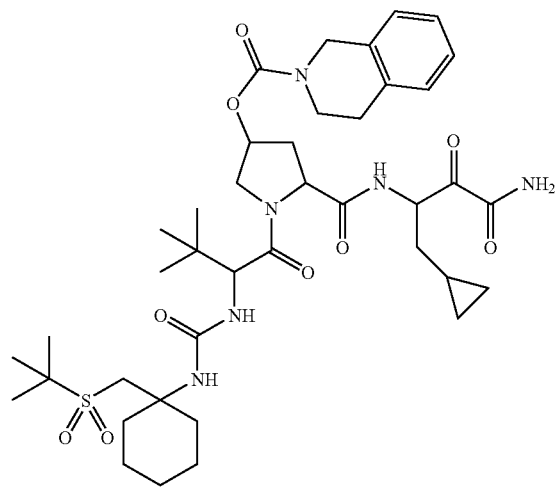
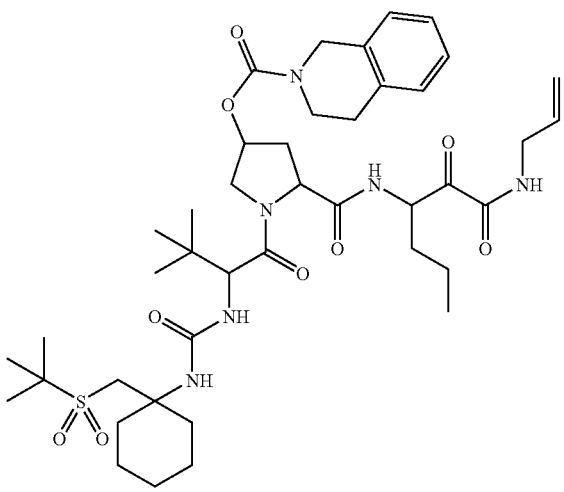

TABLE 1-continued
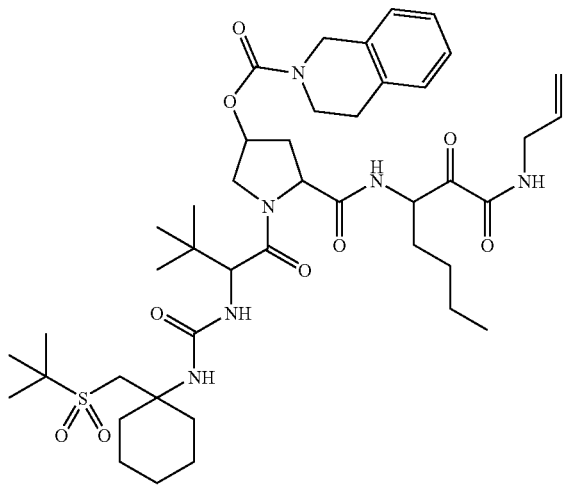
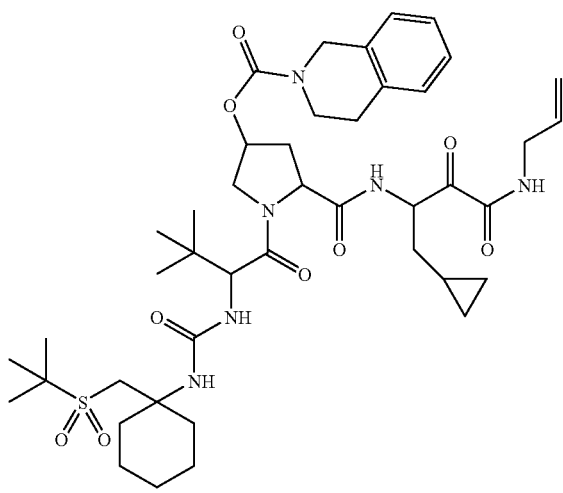
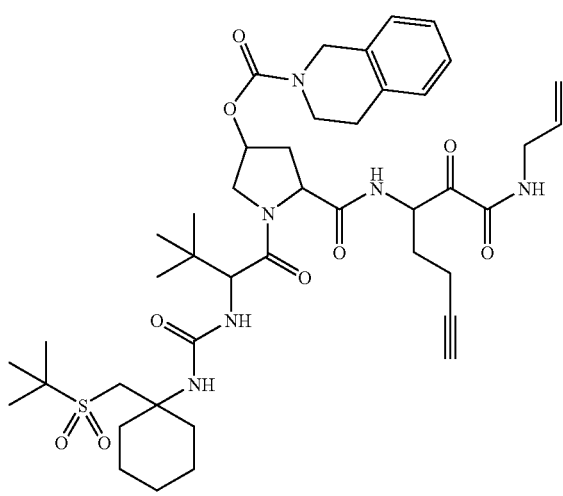

TABLE 1-continued

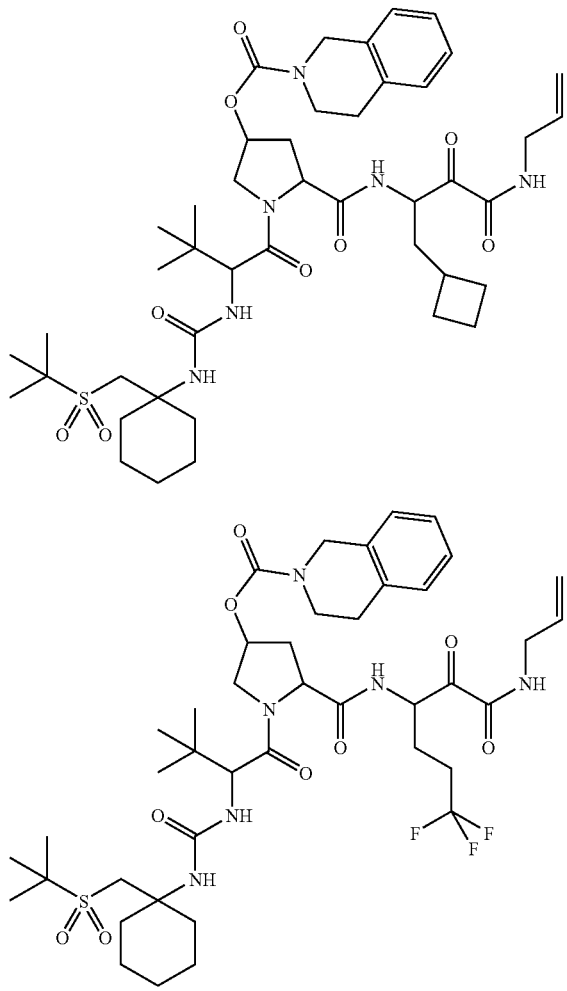

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, —N(alkyl)$_2$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. The term "substituted alkenyl" means that the alkenyl group may be substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like, as well as partially saturated species such as, for example, indanyl, tetrahydronaphthyl and the like.

"Halogen" or "halo" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

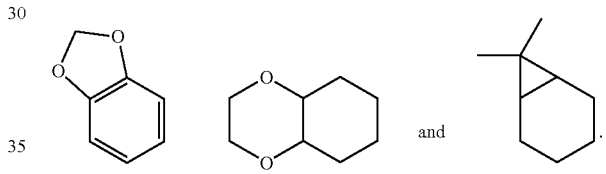

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-d ioxanyl, tetrahydrofuranyl, tetrahydrothiophenyl, lactam, lactone, and the like.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

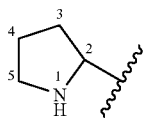

there is no —OH attached directly to carbons marked 2 and 5.

It should also be noted that tautomeric forms such as, for example, the moieties:

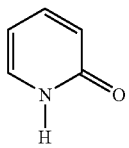 and 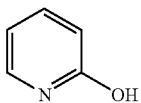

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-$S(O_2)$— group. Preferred groups are those in which the alkyl group is lower alkyl. The bond to the parent moiety is through the sulfonyl.

"Arylsulfonyl" means an aryl-$S(O_2)$— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "one or more" or "at least one", when indicating the number of substituents, compounds, combination agents and the like, refers to at least one, and up to the maximum number of chemically and physically permissible, substituents, compounds, combination agents and the like, that are present or added, depending on the context. Such techniques and knowledge are well known within the skills of the concerned artisan.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon or heteroatom with unsatisfied valences in the text, schemes, examples and Tables herein is assumed to have the hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula 1, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula 1 or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the serine protease and thus producing the desired therapeutic, ameliorative, inhibitory or preventative effect.

The compounds of Formula 1 can form salts which are also within the scope of this invention. Reference to a compound of Formula 1 herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula 1 contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula 1 may be formed, for example, by reacting a compound of Formula 1 with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula 1, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prod rug of enantiomers, stereoisomers, rotamers, tautomers, positional isomers, racemates or prodrugs of the inventive compounds.

Polymorphic forms of the compounds of Formula I, and of the salts, solvates and prodrugs of the compounds of Formula I, are intended to be included in the present invention.

It is to be understood that the utility of the compounds of Formula 1 for the therapeutic applications discussed herein is applicable to each compound by itself or to the combination or combinations of one or more compounds of Formula 1 as illustrated, for example, in the next immediate paragraph. The same understanding also applies to pharmaceutical composition(s) comprising such compound or compounds and method(s) of treatment involving such compound or compounds.

The compounds according to the invention can have pharmacological properties; in particular, the compounds of Formula 1 can be inhibitors of HCV protease, each compound by itself or one or more compounds of Formula 1 can be combined with one or more compounds selected from within Formula 1. The compound(s) can be useful for treating diseases such as, for example, HCV, HIV, (AIDS, Acquired Immune Deficiency Syndrome), and related disorders, as well as for modulating the activity of hepatitis C virus (HCV) protease, preventing HCV, or ameliorating one or more symptoms of hepatitis C.

The compounds of Formula 1 may be used for the manufacture of a medicament to treat disorders associated with the HCV protease, for example, the method comprising bringing into intimate contact a compound of Formula 1 and a pharmaceutically acceptable carrier.

In another embodiment, this invention provides pharmaceutical compositions comprising the inventive compound or compounds as an active ingredient. The pharmaceutical compositions generally additionally comprise at least one pharmaceutically acceptable carrier diluent, excipient or carrier (collectively referred to herein as carrier materials). Because of their HCV inhibitory activity, such pharmaceutical compositions possess utility in treating hepatitis C and related disorders.

In yet another embodiment, the present invention discloses methods for preparing pharmaceutical compositions comprising the inventive compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition.

Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like.

Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. HCV inhibitory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

The compounds of the invention may also be administered orally, intravenously, intrathecally, intranasally or subcutaneously.

The compounds of the invention may also comprise preparations which are in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gel—refers to the active ingredients dispersed or solubilized in a hydrophillic semi-solid matrix.

Powder for constitution refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrant—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binder—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glident—material that prevents caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Another embodiment of the invention discloses the use of the inventive compounds or pharmaceutical compositions disclosed above for treatment of diseases such as, for example, hepatitis C and the like. The method comprises administering a therapeutically effective amount of the inventive compound or pharmaceutical composition to a patient having such a disease or diseases and in need of such a treatment.

In yet another embodiment, the compounds of the invention may be used for the treatment of HCV in humans in monotherapy mode or in a combination therapy (e.g., dual combination, triple combination etc.) mode such as, for example, in combination with antiviral and/or immunomodulatory agents. Examples of such antiviral and/or immunomodulatory agents include Ribavirin (from Schering-Plough Corporation, Madison, N.J.) and Levovirin™ (from ICN Pharmaceuticals, Costa Mesa, Calif.), VP50406™ (from Viropharma, Incorporated, Exton, Pa.), ISIS 14803™ (from ISIS Pharmaceuticals, Carlsbad, Calif.), Heptazyme™ (from Ribozyme Pharmaceuticals, Boulder, Colo.), VX 497™ (from Vertex Pharmaceuticals, Cambridge, Mass.), Thymosin™ (from SciClone Pharmaceuticals, San Mateo, Calif.), Maxamine™ (Maxim Pharmaceuticals, San Diego, Calif.), mycophenolate mofetil (from Hoffman-LaRoche, Nutley, N.J.), interferon (such as, for example, interferon-alpha, PEG-interferon alpha conjugates) and the like. "PEG-interferon alpha conjugates" are interferon alpha molecules covalently attached to a PEG molecule. Illustrative PEG-interferon alpha conjugates include interferon alpha-2a (Roferon™, from Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron™), interferon alpha-2c (Berofor Alpha™, from Boehringer Ingelheim, Ingelheim, Germany) or consensus interferon as defined by determination of a consensus sequence of naturally occurring interferon alphas (Infergen™, from Amgen, Thousand Oaks, Calif.).

As stated earlier, the invention includes tautomers, rotamers, enantiomers and other stereoisomers of the inventive compounds also. Thus, as one skilled in the art appreciates, some of the inventive compounds may exist in suitable isomeric forms. Such variations are contemplated to be within the scope of the invention.

Another embodiment of the invention discloses a method of making the compounds disclosed herein. The compounds may be prepared by several techniques known in the art. Illustrative procedures are outlined in the following reaction schemes. The illustrations should not be construed to limit the scope of the invention which is defined in the appended claims. Alternative mechanistic pathways and analogous structures will be apparent to those skilled in the art.

It is to be understood that while the following illustrative schemes describe the preparation of a few representative inventive compounds, suitable substitution of any of both the natural and unnatural amino acids will result in the formation of the desired compounds based on such substitution. Such variations are contemplated to be within the scope of the invention.

Abbreviations:

Abbreviations which are used in the descriptions of the schemes, preparations and the examples that follow are:

THF: Tetrahydrofuran
DMF: N,N-Dimethylformamide
EtOAc: Ethyl acetate

AcOH: Acetic acid
HOOBt: 3-Hydroxy-1,2,3-benzotriazin4 (3H)-one
EDCl: 1-(3-dimethylaminopropyl)-3-ethylcarbodiimide hydrochloride
NMM: N-Methylmorpholine
ADDP: 1,1'-(Azodicarbobyl)dipiperidine
DEAD: Diethylazodicarboxylate
MeOH: Methanol
EtOH: Ethanol
Et2O: Diethyl ether
DMSO: Dimethylsulfoxide
HOBt: N-Hydroxybenzotriazole
PyBrOP: Bromo-tris-pyrrolidinophosphonium hexafluorophosphate
DCM: Dichloromethane
DCC: 1,3-Dicyclohexylcarbodiimide
TEMPO: 2,2,6,6-Tetramethyl-1-piperidinyloxy
Phg: Phenylglycine
Chg: Cyclohexylglycine
Bn: Benzyl
Bzl: Benzyl
Et: Ethyl
Ph: Phenyl
iBoc: isobutoxycarbonyl
iPr: isopropyl
$^t$Bu or Bu$^t$: tert-Butyl
Boc: tert-Butyloxycarbonyl
Cbz: Benzyloxycarbonyl
Cp: Cylcopentyldienyl
Ts: p-toluenesulfonyl
Me: Methyl
HATU: O-(7-azabenzotriazol-1-yl)-1,1,3,3-tetramethyluronium hexafluorophosphate
DMAP: 4-N,N-Dimethylaminopyridine
BOP: Benzotriazol-1-yl-oxy-tris(dimethylamino)hexafluorophosphate
PCC: Pyridiniumchlorochromate
KHMDS: Potassium Hexamethyldisilazide or Potassium bis(trimethylsilylamide)
NaHMDS: Sodium Hexamethyldisilazide or Sodium bis(trimethylsilylamide)
LiHMDS: Lithium Hexamethyldisilazide or Lithium bis(trimethylsilylamide)
10% Pd/C: 10% Palladium on carbon (by weight).
TG: Thioglycerol

EXAMPLES

Preparation of Intermediates:

Preparation of Intermediate 1.01:

Step 1:

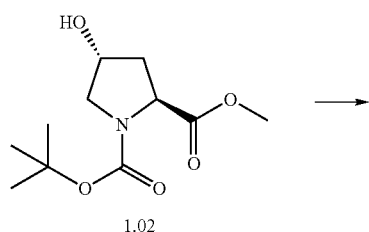

1.02

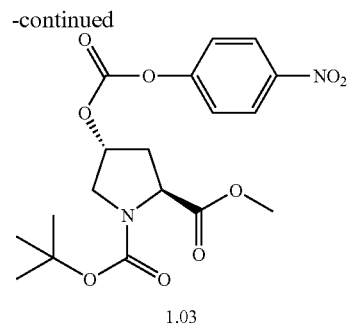

1.03

To a solution of the 4-hydroxyproline derivative 1.02 (1.0 g, 4.1 mmol) in g, 12.2 mmol) followed by pyridine (0.987 mL, 12.2 mmol). After 15 minutes at that temperature, the reaction flask was stored in the freezer (−20° C.), overnight (16 hr). The reaction mixture was diluted with dichloromethane (100 mL) and washed with saturated ammonium chloride solution (2×100 mL), brine (100 mL), dried (Na$_2$SO$_4$), filtered and concentrated. The crude material was purified by silica chromatography using 20/80 to 50/50 EtOAc/hexanes to provide 1.03 (1.5 g).

Step 2:

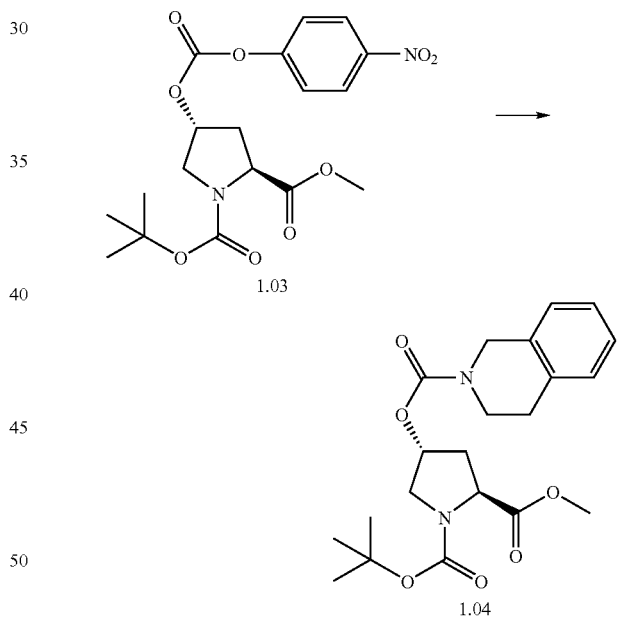

To a stirred solution of the proline derivative 1.03 (1.5 g, 3.66 mmol) in dichloromethane (30 mL) at 0° C. was added 1,2,3,4-tetrahydroisoquinoline (0.55 mL, 4.39 mmol) and DIPEA (2.02 mL, 10.98 mmol). After 15 minutes at that temperature, the reaction flask was stored in the freezer (−20° C.), overnight (16 hr). The reaction mixture was diluted with dichloromethane (70 mL) and washed with saturated ammonium chloride solution (100 mL), saturated sodium bicarbonate solution (3×100 mL), brine (100 mL), dried (Na$_2$SO$_4$), filtered and concentrated. The crude material was purified by silica chromatography using 5/95 to 25/75 EtOAc/dichloromethane to provide 1.4 g of the required material, 1.04. LC-MS: 405.1 (M+H)$^+$.

Step 3:

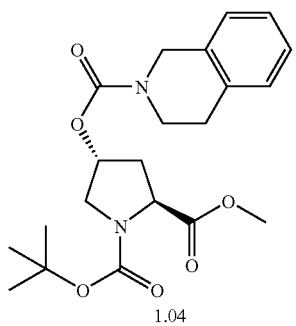

1.04

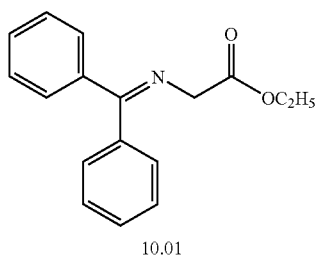

1.01

To the material obtained from above, 1.04 (1.4 g) was added 4M HCl in dioxane (25 mL). The reaction was maintained at RT for 1 h and then concentrated to afford the required intermediate 1.01 in quantitative yield which was used without purification.

Preparation of Intermediates 10.11 and 10.12:

Step 1:

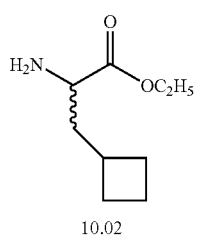

10.01

10.02

A stirred solution of ketimine 10.01 (50 g, 187.1 mmol) under $N_2$ in dry THF (400 mL) was cooled to −78° C. and treated with 1 M solution of K-$^t$BuO (220 mL, 1.15 equiv.) in THF. The reaction mixture was warmed to 0° C. and stirred for 1 h and treated with bromomethyl cyclobutane (28 mL, 249 mmol). The reaction mixture was stirred at room temperature for 48 h and concentrated in vacuo. The residue was dissolved in $Et_2O$ (300 mL) and treated with aq. HCl (2 M, 300 mL) The resulting solution was stirred at room temperature for 5 h and extracted with $Et_2O$ (1 L). The aqueous layer was made basic to pH~12-14 with NaOH (50% aq.) and extracted with $CH_2Cl_2$ (3×300 mL). The combined organic layers were dried ($MgSO_4$), filtered, and concentrated to give the pure amine (10.02, 18 g) as a colorless oil.

Step 2

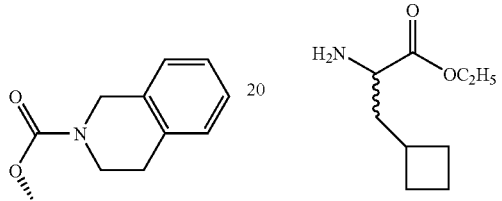

10.02　　　　　　　　　10.03

A solution of the amine 10.02 (18 g, 105.2 mmol) at 0° C. in $CH_2Cl_2$ (350 mL) was treated with di-tert-butyldicarbonate (23 g, 105.4 mmol) and stirred at rt. for 12 h. After the completion of the reaction (TLC), the reaction mixture was concentrated in vacuo and the residue was dissolved in THF/$H_2O$ (200 ml, 1:1) and treated with $LiOH \cdot H_2O$ (6.5 g, 158.5 mmol) and stirred at room temperature for 3 h. The reaction mixture was concentrated and the basic aqueous layer was extracted with $Et_2O$. The aqueous layer was acidified with conc. HCl to pH~1-2 and extracted with $CH_2Cl_2$. The combined organic layers were dried ($MgSO_4$), filtered, and concentrated in vacuo to yield 10.03 as a colorless viscous oil which was used for the next step without any further purification.

Step 3

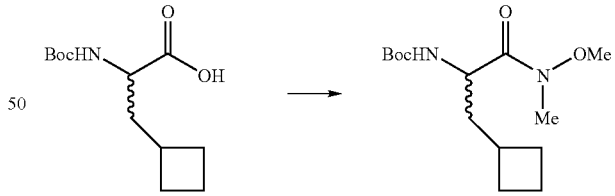

10.03　　　　　　　　　10.04

A solution of the acid 10.03 (15.0 g, 62 mmol) in $CH_2Cl_2$ (250 mL) was treated with BOP reagent (41.1 g, 93 mmol), N-methyl morpholine (27 mL), N,O-dimethyl hydroxylamine hydrochloride (9.07 g, 93 mmol) and stirred overnight at rt. The reaction mixture was diluted with 1 N aq. HCl (250 mL), and the layers were separated and the aqueous layer was extracted with $CH_2Cl_2$ (3×300 ml). The combined organic layers were dried ($MgSO_4$), filtered and concentrated in vacuo and purified by chromatography ($SiO_2$, EtOAc/Hex 2:3) to yield the amide 10.04 (15.0 g) as a colorless solid.

Step 4

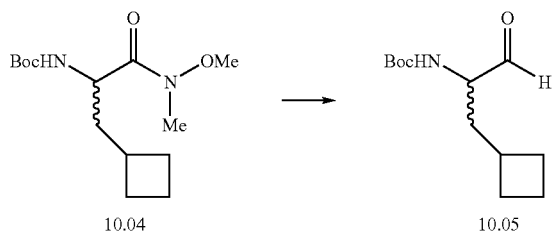

A solution of the amide 10.04 (15 g, 52.1 mmol) in dry THF (200 mL) was treated dropwise with a solution of LiAlH$_4$ (1M, 93 mL, 93 mmol) at 0° C. The reaction mixture was stirred at room temperature for 1 h and carefully quenched at 0° C. with a solution of KHSO$_4$ (10% aq.) and stirred for 0.5 h. The reaction mixture was diluted with aq. HCl (1 M, 150 mL) and extracted with CH$_2$Cl$_2$ (3×200 mL), The combined organic layers were washed with aq. HCl (1 M), saturated NaHCO$_3$, brine, and dried (MgSO$_4$). The mixture was filtered and concentrated in vacuo to yield 10.05 as a viscous colorless oil (14 g).

Step 5

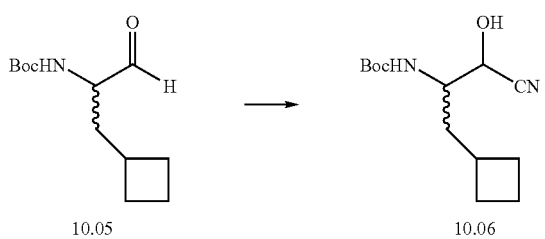

A solution of the aldehyde 10.05 (14 g, 61.6 mmol) in CH$_2$Cl$_2$ (50 mL), was treated with Et$_3$N (10.73 mL, 74.4 mmol), and acetone cyanohydrin (10.86 g, 127.57 mmol) and stirred at room temperature for 24 hrs. The reaction mixture was concentrated in vacuo and diluted with aq. HCl (1 M, 200 mL) and extracted into CH$_2$Cl$_2$ (3×200 mL). The combined organic layer were washed with H$_2$O, brine, dried (MgSO$_4$), filtered, concentrated in vacuo and purified by chromatography (SiO$_2$, EtOAc/Hex 1:4) to yield 10.06 (10.3 g) as a colorless liquid Step 6

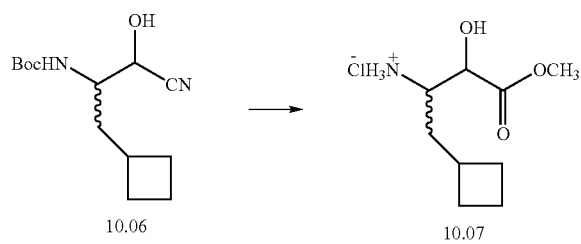

Methanol saturated with HCl*, prepared by bubbling HCl gas through CH$_3$OH (700 ml) at 0° C., was treated with the cyanohydrin 10.06 and heated to reflux for 24 h. The reaction was concentrated in vacuo to yield 10.07, which was used in the next step without purification.

*Alternatively 6M HCl prepared by addition of AcCl to dry methanol can also be used.

Step 7

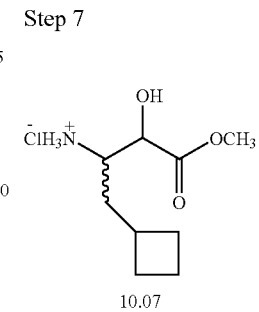

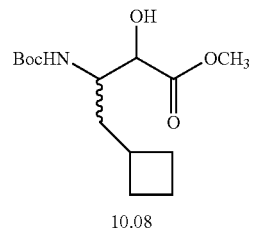

A solution of the amine hydrochloride 10.07 in CH$_2$Cl$_2$ (200 mL) was treated with Et$_3$N (45.0 mL, 315 mmol) and Boc$_2$O (45.7 g, 209 mmol) at −78° C. The reaction mixture was then stirred at room temperature overnight and diluted with HCl (2 M, 200 mL) and extracted into CH$_2$Cl$_2$. The combined organic layers were dried (MgSO$_4$) filtered, concentrated in vacuo and purified by chromatography (EtOAc/Hex 1:4) to yield hydroxy ester 10.08.

Step 8.

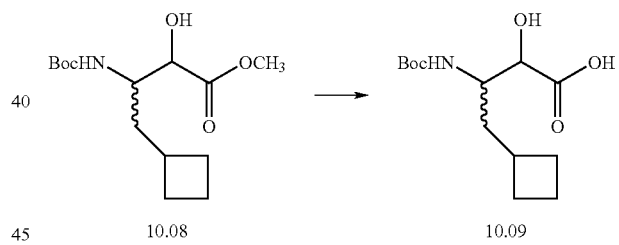

A solution of methyl ester 10.08 (3 g, 10.5 mmol) in THF/H$_2$O (1:1) was treated with LiOH.H$_2$O (645 mg, 15.75 mmol) and stirred at rt. for 2 h. The reaction mixture was acidified with aq HCl (1 M, 15 mL) and concentrated in vacuo. The residue was dried in vacuum to afford 10.09 in quantitative yield.

Step 9

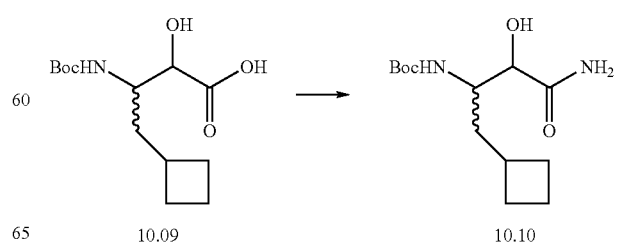

A solution of the acid 10.09 (from above) in CH$_2$Cl$_2$ (50 mL) and DMF (25 mL) was treated with NH$_4$Cl (2.94 g, 55.5 mmol), EDCI (3.15 g, 16.5 mmol), HOOBt (2.69 g, 16.5 mmol), and NMM (4.4 g, 44 mmol). The reaction mixture was stirred at room temperature for 3 d. The solvents were removed under vacuo and the residue was diluted with aq. HCl (250 mL) and extracted with CH$_2$Cl$_2$. The combined organic layers were washed with aq. saturated NaHCO$_3$, dried (MgSO$_4$) filtered concentrated in vacuo to obtain 10.10, which was used as it was in the following steps. (Alternatively 10.10 can also be obtained directly by the reaction of 10.06 (4.5 g, 17.7 mmol) with aq. H$_2$O$_2$ (10 mL), LiOH.H$_2$O (820 mg, 20.8 mmol) at 0° C. in 50 mL of CH$_3$OH for 0.5 h.)

Step 10

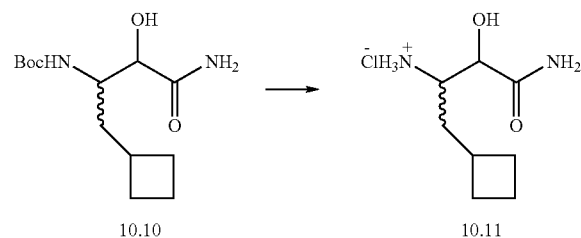

A solution of 10.10 obtained in the previous step was dissolved in 4 N HCl in dioxane and stirred at rt. for 2 h. The reaction mixture was concentrated in vacuo to give the intermediate 10.11 as a solid, which was used without further purification.

Step 11

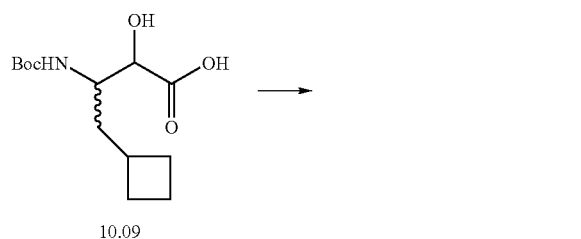

The required intermediate 10.12 was obtained from compound 10.09 using essentially the procedures described above in Steps 9, 10 with appropriate reagents.

Preparation of Intermediate 11.01

Step 1

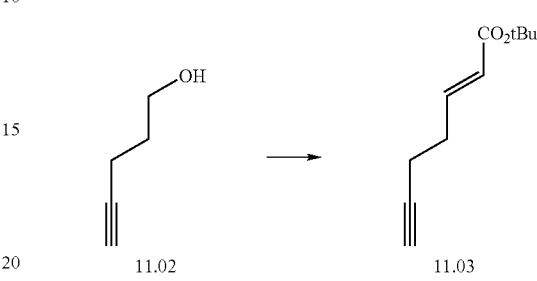

To a solution of 4-pentyn-1-ol, 11.02 (4.15 g; Aldrich) was added Dess-Martin Periodinane (30.25 g; Aldrich) and the resulting mixture was stirred for 45 min. before the addition of (tert-Butoxycarbonylmethylene)triphenylphosphorane (26.75 g; Aldrich). The resulting dark reaction was stirred overnight, diluted with EtOAc), washed with aq. sodium sulfite. sat. aq. NaHCO3, water, brine and dried. The volatiles were removed under reduced pressure and the residue was purified by silica gel column chromatography using 1% EtOAc in hexanes as eluent to give the desired compound, 11.03 (3.92 g). Some impure fractions were also obtained but set aside at this time.

Step 2

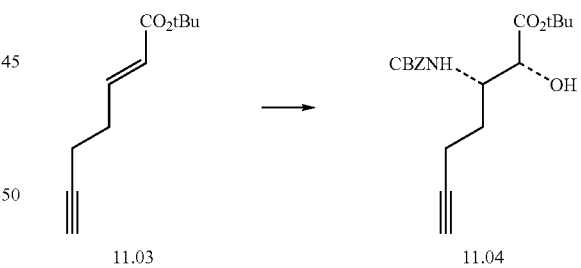

Using the alkene 11.03 (1.9 g) in n-propanol (20 ml; Aldrich)), benzyl carbamate (4.95 g; Aldrich) in n-propanol (40 ml), NaOH (1.29 g) in water (79 ml), tert-butyl hypochlorite (3.7 ml), (DHQ)$_2$PHAL (0.423 g; Aldrich)) in n-propanol (37.5 ml), and potassium osmate:dehydrate (0.1544 g; Aldrich) and the procedure set forth in Angew. Chem. Int. Ed. Engl (1998), 35, (23/24), pp. 2813-7, gave a crude product which was purified by silica gel column chromatography using EtOAc:Hexanes (1:5) to give the desired amino alcohol 11.04 (1.37 g, 37%) as a white solid.

113

Step 3

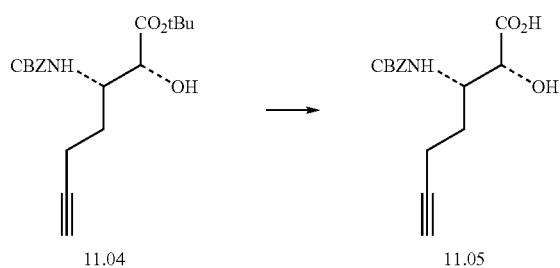

To the ester 11.04 (0.700 g) was added 4M HCl in dioxane (20 ml; Aldrich) and the resulting mixture was allowed to stand at room temperature overnight. The volatiles were removed under reduced pressure to give the acid 11.05 (0.621 g) as a white solid.

Step 4

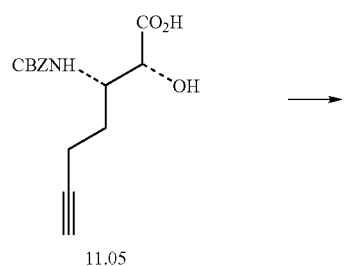

BOP reagent (3.65 g; Sigma) followed by triethylamine (3.45 ml) were added to a dichloromethane (20 ml) solution of the carboxylic acid 11.05 (2.00 g) and allyl amine (0.616 ml) at room temperature and the resulting mixture was stirred overnight. The reaction mixture was partitioned between EtOAc and 10% aq. HCl. The organic phase was separated, washed with sat. aq. sodium bicarbonate, water, dried (magnesium sulfate). The crude reaction product was purified by silica gel column chromatography using (EtOAc:Hexanes; 70:30) as eluent to provide the desired amide 11.01 (1.73 g) as a viscous yellow oil.

114

Preparation of Intermediates 12.03 and 12.04

Step 1

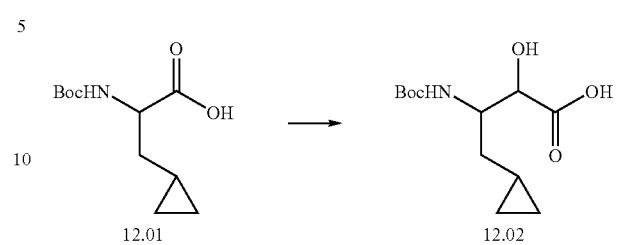

Compound 12.01 was converted to the required material 12.02 using essentially the procedures described for Intermediate 10.11, Steps 3-8.

Step 2

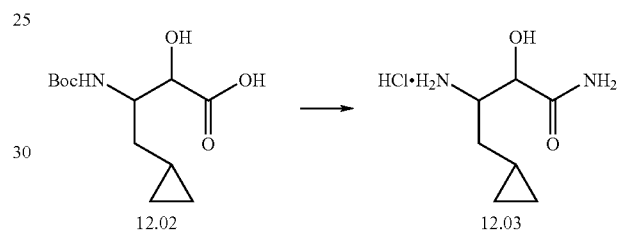

Compound 12.02 was converted to the required intermediate 12.03 using essentially the procedures described for Intermediate 10.11, Steps 9, 10.

Step 3

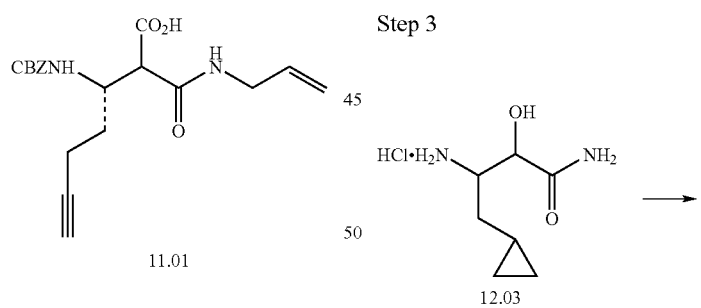

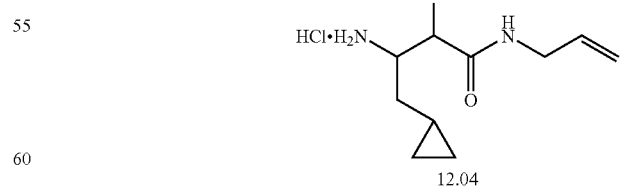

Compound 12.02 was converted to the required intermediate 12.03 using essentially the procedures described for Intermediate 10.12, Step 11.

Preparation of Intermediates 13.01 and 13.06

Step 1

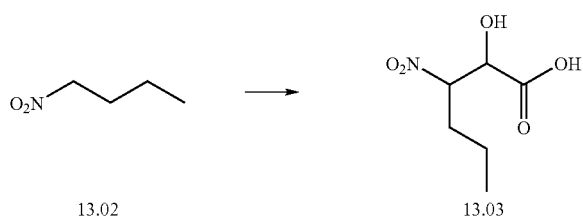

To a stirred solution of 1-nitrobutane, 13.02 (16.5 g, 0.16 mol) and glyoxylic acid in H$_2$O (28.1 g, 0.305 mol) and MeOH (122 mL) at 0° C.-5° C., was added dropwise triethylamine (93 mL, 0.667 mol) over 2 hrs. The solution was warmed to room temperature, stirred overnight and concentrated to dryness to give an oil. The oil was then dissolved in H$_2$O and acidified to pH=1 with 10% HCl, followed by extraction with EtOAc. The combined organic solution was washed with brine, dried over Na$_2$SO$_4$, filtered and concentrated to dryness to give the product 13.03 (28.1 g, 99% yield).

Step 2

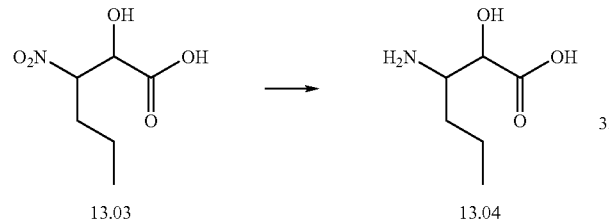

To a stirred solution of compound 13.03 (240 g, 1.35 mol) in acetic acid (1.25 L) was added 10% Pd/C (37 g). The resulting solution was hydrogenated at 59 psi for 3 hrs and then at 60 psi overnight. The acetic acid was then evaporated and azeotroped 3 times with toluene, then triturated with MeOH and ether. The solution was then filtered and azeotroped twice with toluene to afford 13.04 as an off white solid (131 g, 0.891 mol, 66%).

Step 3

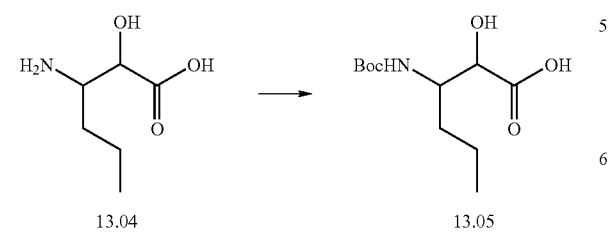

To a stirred solution of the amino acid 13.04 (2.0 g, 13.6 mmol) in dioxane (10 mL) and H$_2$O (5 mL) at 0° C., was added 1N NaOH solution (4.3 mL, 14.0 mmol). The resulting solution was stirred for 10 minutes, followed by addition of di-t-butyldicarbonate (0.110 g, 14.0 mmol) and stirred at 0° C. for 15 minutes. The solution was then warmed to room temperature, stirred for 45 minutes and kept at refrigerator overnight and concentrated to dryness to give a crude material. To the solution of this crude material in EtOAc (100 mL) and ice, was added KHSO$_4$ (3.36 g) and H$_2$O (32 mL) and stirred for 4-6 minutes. The organic layer was then separated and the aqueous layer was extracted twice with EtOAc and the combined organic layer was washed with water, brine, dried over Na$_2$SO$_4$, filtered and concentrated to dryness to give the product 13.05 as a clear gum (3.0 g, 89% yield).

Step 4

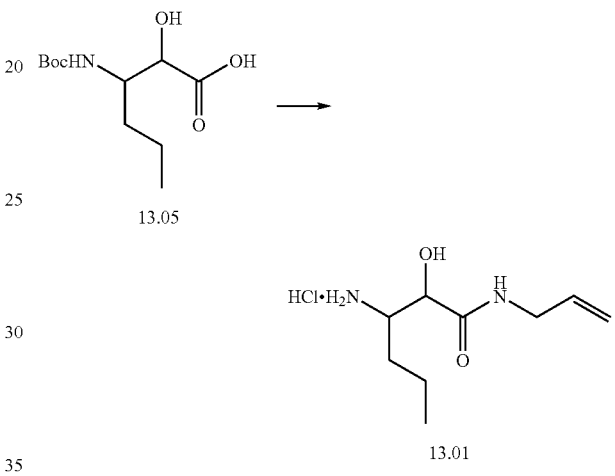

Compound 13.05 was converted to the required intermediate 13.01 using essentially the procedures described for Intermediate 10.12, Step 11.

Step 5

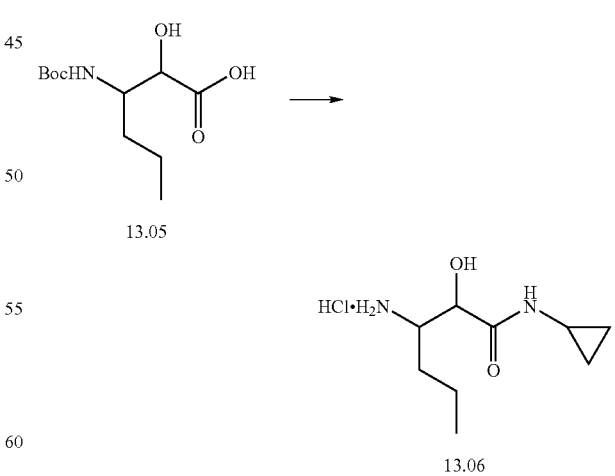

Compound 13.05 was converted to the required intermediate 13.06 following essentially the procedures described for Intermediate 10.12, Step 11, using cyclopropylamine (instead of allylamine) in the coupling reaction.

Preparation of Intermediate 14.01

Step 1

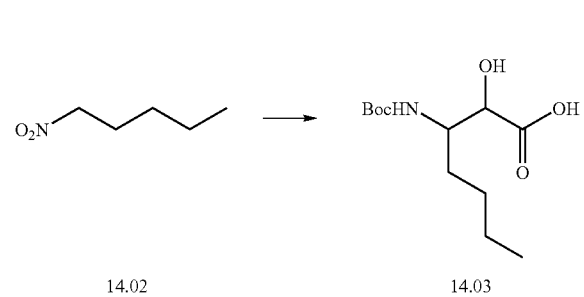

Compound 14.02 was converted to the required material 14.03 using essentially the procedures described for Intermediate 13.01, Steps 1-3.

Step 2

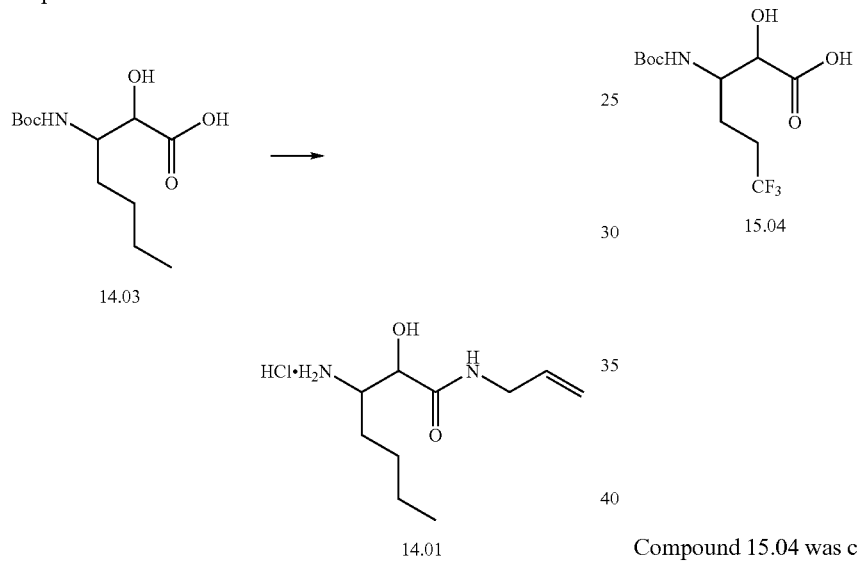

Compound 14.03 was converted to the required intermediate 14.01 using essentially the procedures described for Intermediate 10.12, Step 11.

Preparation of Intermediate 15.01

Step 1

To a suspension of silver nitrite (9 g, 58.5 mmol) in diethyl ether (25 mL) at 0° C. was added a solution of 4-iodo-1,1,1-trifluorobutane, 15.02 (10 g, 42.0 mmol) in diethyl ether (25 mL) slowly through an addition funnel (approx. 15 min). The resulting mixture was vigorously stirred at 0° C. and warmed to rt. After 50 h, the solid material was filtered off through a celite pad. The resulting diethyl ether solution was concentrated in vacuo to give 15.03 as colorless oil, which was used without further purification.

Step 2

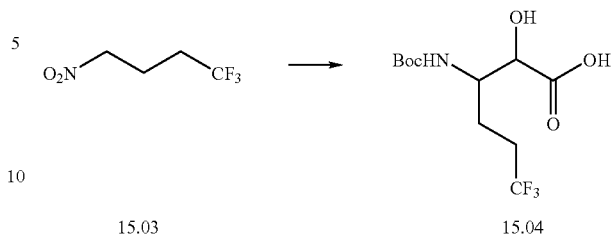

Compound 15.03 was converted to the required material 15.04 using essentially the procedures described for Intermediate 13.01, Steps 1-3.

Step 3

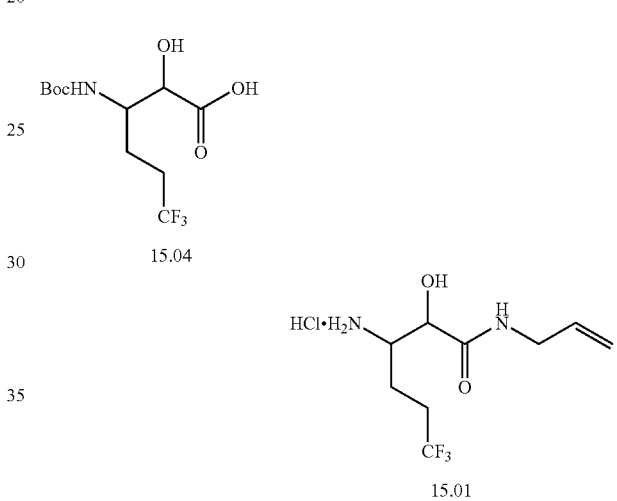

Compound 15.04 was converted to the required intermediate 15.01 using essentially the procedures described for Intermediate 10.12, Step 11.

Preparation of Intermediate 16.01

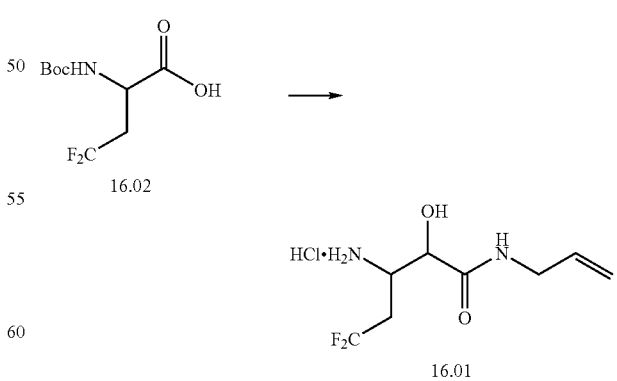

The acid 16.02 (Winkler, D.; Burger, K., *Synthesis*, 1996, 1419) is processed as described above (preparation of Intermediate 10.12) to give the expected intermediate 16.01.

Preparation of Intermediate 50.01

Step 1

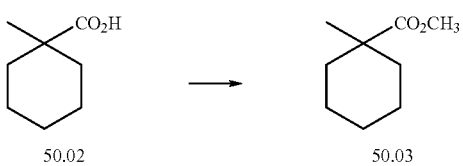

To a solution of 50.02 (15 g) in MeOH (150 mL) was added conc. HCl (3-4 mL) and the mixture was refluxed for 16 h. The reaction mixture was cooled to room temperature and concentrated. The residue was taken in diethyl ether (250 mL) and washed with cold saturated sodium bicarbonate solution, and brine. The organic layer was dried ($Na_2SO_4$) and concentrated to afford the methyl ester 50.03 (12.98 g) which was carried forward without further purification.

Step 2

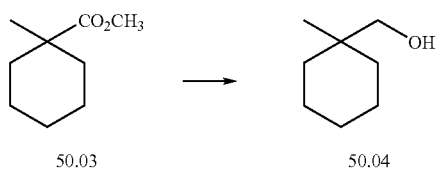

The methyl ester 50.03 from above was dissolved in methylene chloride (100 mL) and cooled to −78° C., under nitrogen atmosphere. DIBAL (1.0 M solution in methylene chloride, 200 mL) was added dropwise over 2 h period. The reaction mixture was warmed to room temperature over 16 h. The reaction mixture was cooled to 0° C. and MeOH (5-8 mL) was added dropwise. A solution of aqueous 10% sodium potassium tartarate (200 mL) was slowly added with stirring. Diluted with methylene chloride (100 mL) and separated the organic layer (along with some white precipitate). The organic layer was washed with 1 N HCl (250 mL), brine (200 mL), dried ($Na_2SO_4$) and concentrated to provide the alcohol 50.04 (11.00 g) as a clear oil.

Step 3

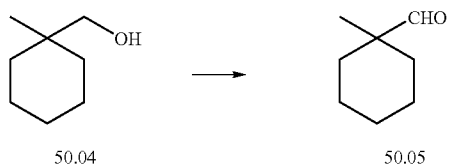

The alcohol 50.04 from above was dissolved in methylene chloride (400 mL) and cooled to 0° C. under nitrogen atmosphere. PCC (22.2 g) was added in portions and the reaction mixture was slowly warmed to room temperature over 16 h. The reaction mixture was diluted with diethyl ether (500 mL) and filtered through a pad of celite. The filtrate was concentrated and the residue was taken in diethyl ether (500 mL). This was passed through a pad of silica gel and the filtrate was concentrated to provide the aldehyde 50.05 which was carried forward without further purification.

Step 4

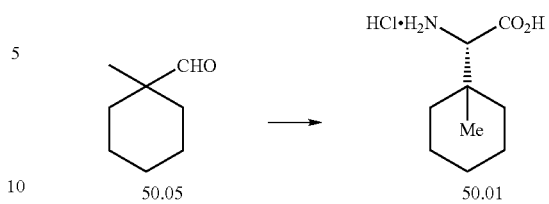

The aldehyde 50.05 from above was converted to the desired material 50.01 using essentially the method of Chakraborty et. al (Tetrahedron, 1995, 51(33), 9179-90).

Preparation of Intermediate 51.01

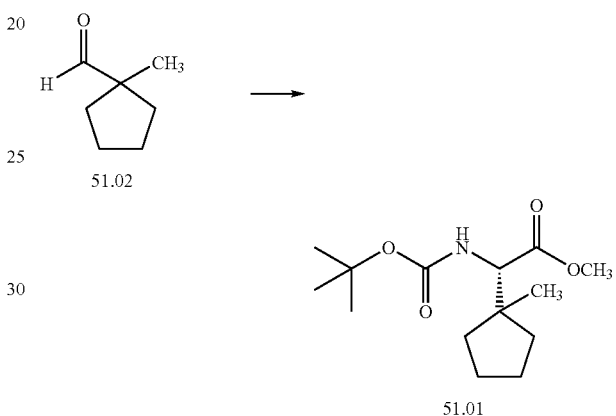

The required intermediate 51.01 was obtained from the aldehyde 51.02 using the literature described procedure (T. K. Chakraborty et al., *Tetrahedron*, 1995, 51 (33), 9179-90).

Preparation of Intermediate 60.01:

Step 1

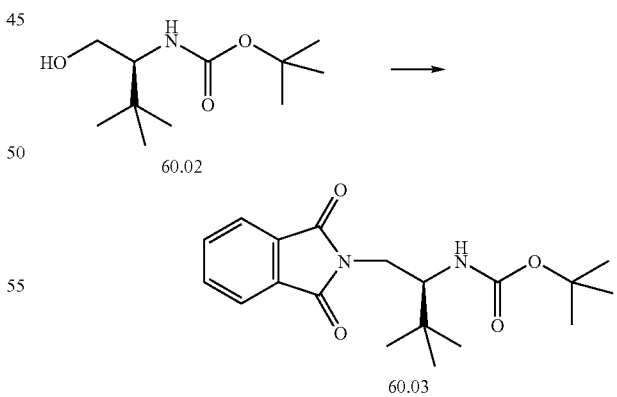

To a solution of phthalimide (1.01 g) in 50 mL of dry THF was added triphenylphosphine (3 eq) and N-t-boc-tert-leucinol 60.02 (1 eq). The mixture was cooled in an ice-water bath and diisopropyl azodicarboxylate (2.5 eq) was added dropwise. The resulting mixture was stirred at 0° C. for 10 min and warmed to room temp and stirred for approximately 2.5 h until no more starting material was detected by TLC (ethyl acetate/hexanes; 3:7). The mixture was concentrated under reduced pressure. The residue was suspended in 80 mL of dichloromethane. The solids were filtered off. The filtrate was concentrated to half its volume and hexanes (30 mL) were added. The solids were filtered off. The filtrate was concentrated under reduced pressure and the residue was chromatographed on silica gel (gradient: ethyl acetate/hexanes; 1:9 to 4:6) to give the product 60.03.

Step 2

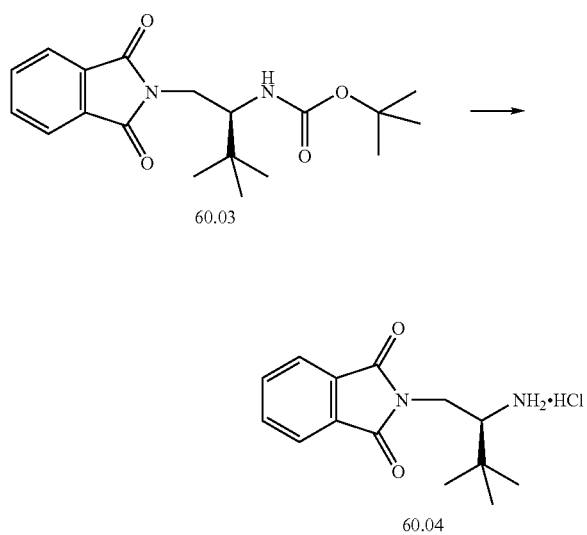

The N-Boc protected amine 60.03 (1.4 g) was dissolved in 20 mL of 4M HCl solution in dioxane. The mixture was stirred for 2 h. All the volatiles were removed under vacuum. No further purification was done and the required product 60.04 was used as is.

Step 3

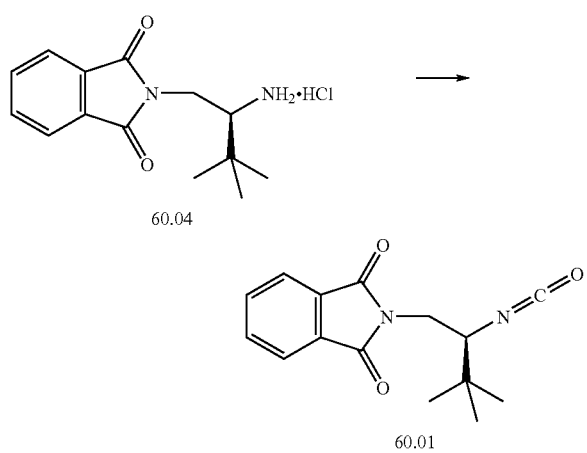

A mixture of amine hydrochloride 60.04 (1.14 g) in 20 mL of dichloromethane and 20 mL of aqueous saturated NaHCO3 solution at 0° C. was treated with phosgene (10 mL, 15% solution in toluene) and stirred for 2 h. The reaction mixture was diluted with 100 mL of dichloromethane and washed with 30 mL of cold aqueous saturated NaHCO3 solution. The organic layer was dried over magnesium sulfate, filtered, and further diluted with 10 mL of toluene. The mixture was concentrated and the product 60.01 was kept as a 0.2M solution in toluene.

Preparation of Intermediate 61.01:

Step 1

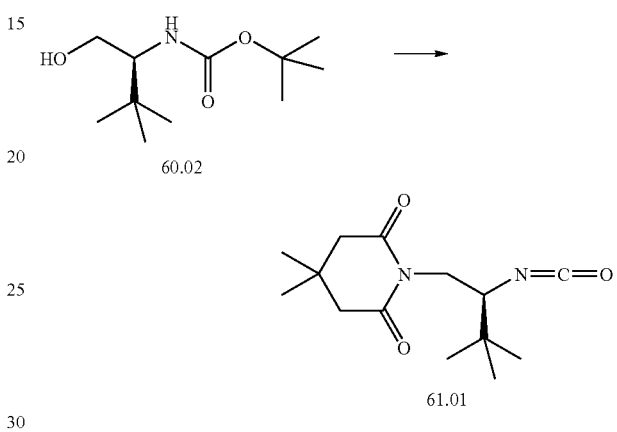

The required product 61.01 was obtained from 60.02 and 4,4-dimethylglutarimide using the procedures described above for intermediate 60.01.

Synthesis of Intermediate 62.01:

Step 1

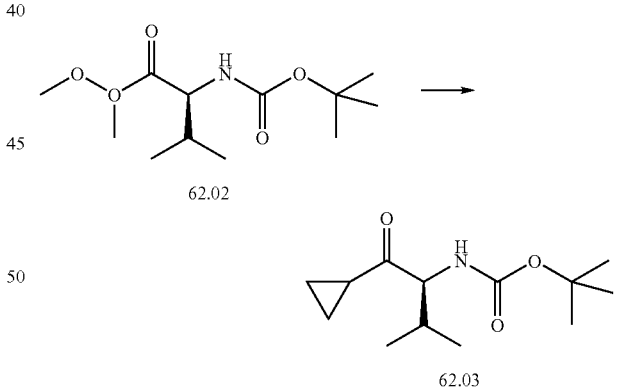

To amide 62.02 (0.5 g, 1 eq) in THF was added cyclopropylmagnesium bromide (4 eq, 7.68 mmol) at 0° C. The reaction was warmed up to RT after 15 min and the reaction was stirred at RT for 5 hrs, then it was quenched by the addition of 1N HCl. Reaction was diluted with EtOAc and washed with brine. The organic layer was dried over MgSO4, purified by column chromatography with 10% EtOAc in hexane to get 0.2 g of product 62.03.

Yield 43.1%.

Step 2

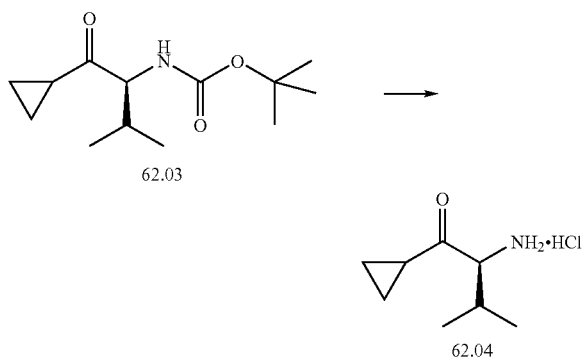

To N-Boc protected amine 62.03 (0.2 g) was added 4M HCl (in Dioxane). The reaction was stirred at RT for 50 min which TLC indicated the reaction had been completed. The mixture was concentrated to dryness to give 0.162 g of the required product 62.04.

Step 3

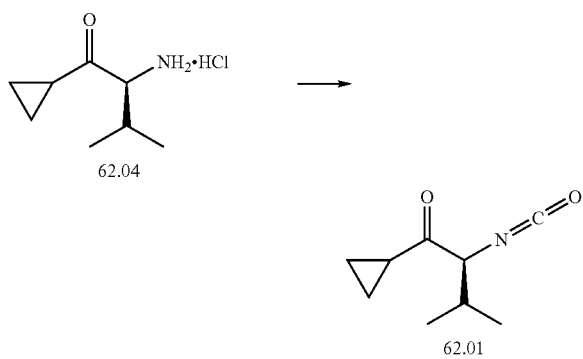

To a mixture of phosgene in $CH_2Cl_2$ (2 eq, 1.65 mmol), NaHCO3 (5 mL aq. sat. solution) was added 62.04 at 0° C. The mixture was stirred at RT for 2.5 h. Separated the organic layer and dried over $Na_2SO_4$ (anhydrous). Concentrated to half the volume with cooling bath. Diluted it to 10 mL to get desired isocyanate 62.01 as a 0.083M solution in dichloromethane.

Synthesis of Intermediate 63.01:

Step 1

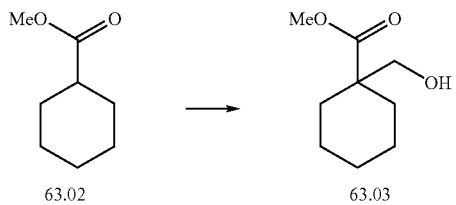

KHMDS (200 ml of a 0.5M solution in toluene) was added, dropwise to a stirred solution of methyl cyclohexanecarboxylate 63.02 (11.1 g; 78 mmol) in anhydrous THF (200 ml), at −78C under an atmosphere of nitrogen. When the addition was complete the reaction was maintained at this temperature for a further 0.5 h. before the addition of Benzyl chloromethyl ether (18.6 ml; 134 mmol). The reaction was allowed to warm to room temperature overnight and water (100 ml) was added. Aqueous work-up provided a residue which was purified by silica gel column chromatography using EtOAc; hexanes (1:10) as eluent to give the desired, impure, intermediate ether (14.98 g) as a colorless oil.

A black suspension of 10% Pd/C (0.5 g) and the aforementioned crude ether (4.1 g) in MeOH (80 ml) was exposed to an atmosphere of nitrogen (balloon) at room temp., overnight. The reaction was filtered through a pad of celite and the solid was washed thoroughly with methanol. The combined filtrate was concentrated under reduced pressure and the crude product was purified by silica gel column chromatography using EtOAc; hexanes (1:5) to give the primary alcohol (63.03; 0.62 g), a colorless oil.

Step 2

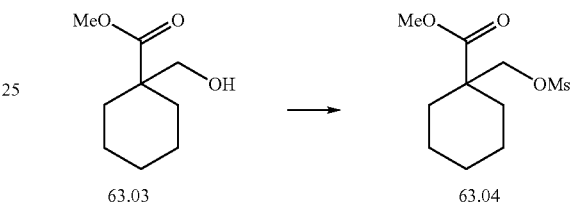

Methanesulfonyl Chloride (0.31 ml) followed by triethylamine (0.75 ml) were added to a stirred solution of the primary alcohol (63.03, 0.62 g) at 0° C., under an atmosphere of nitrogen. The resulting mixture was stirred at this temperature for 0.5 h. The reaction mixture was extracted into EtOAc and washed with 1M HCl, sat. aq. NaHCO3, water, dried (MgSO4) and concentrated. The residue (mesylate 63.04, 0.74 g), was obtained as a yellow oil, which was used in subsequent steps without purification.

Step 3

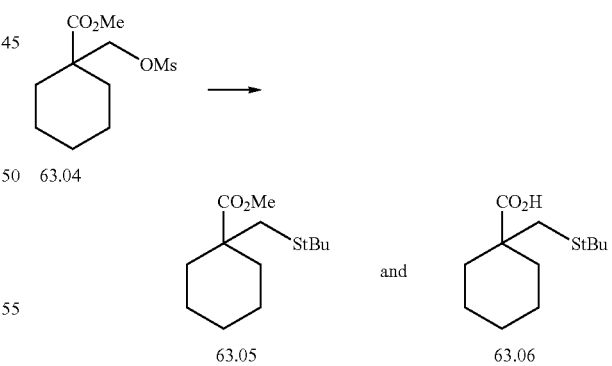

Dimethylformamide (20 ml; anhydrous; Aldrich) was added to sodium hydride (0.56 g; Aldrich) and tert-butyl mercaptan was added to the suspension while cooled in an ice bath under an atmosphere of nitrogen. Once the addition was complete the mesylate (63.04; prepared as above from 2.00 g of alcohol; 63.03) was added and the resulting mixture was stirred overnight at room temperature. The reaction was partitioned between EtOAc and water and the organic phase was separated, dried (MgSO4). Column chromatography on silica gel using EtOAc-Hexanes (2:98) provided the methyl ester-sulfide (63.05; 1.75 g).

EtOAc was added to the aqueous phase and 10% aq. HCl was added until the water layer pH=1. The organic layer was separated, washed with water, dried and concentrated under reduced pressure to give the sulfide-carboxylic acid (63.06; 0.747 g) as a white solid.

Step 4

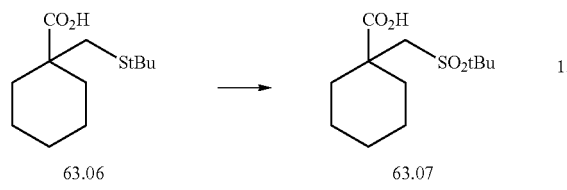

To the sulfide (63.06; 2.287 g) in methanol (75 ml) was added a solution of oxone (18.00 g; Aldrich) and the resulting white suspension was stirred overnight at room temperature. The volatiles were removed under reduced pressure and the white solid partitioned between EtOAc and water. The organic phase was separated, dried and concentrated to provide the sulfone (63.07; 2.52 g; contains some solvent).

Step 5

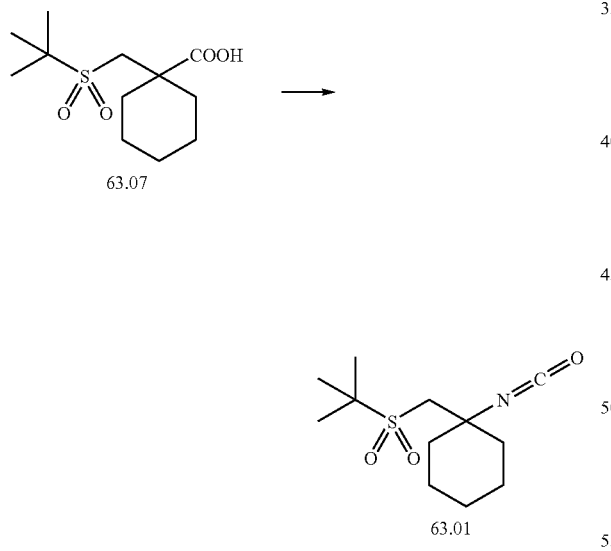

A solution of acid 63.07 (1.61 g) in 50 mL of toluene was treated with DPPA (1 eq, 1.33 mL, d 1.270) and triethylamine (1 eq, 0.85 mL, d 0.726). The mixture was heated to 100° C. for 2 h. The reaction mixture was diluted with aq sat NaHCO3 and extracted with dichloromethane (2×100 mL). The combined organic layers were washed with aq sat NaHCO3 and brine. The organic layer was dried over MgSO4, filtered and concentrated under reduced pressure until approximately 20 mL of solvent were left. The solution of the product 63.01 was adjusted to 0.2M concentration of isocyanate using toluene.

Synthesis of Intermediate 64.01:

Step 1

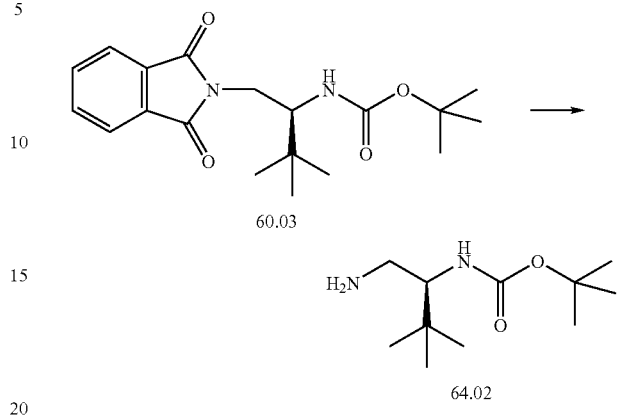

To a solution of phthalimide 60.03 (7 g) in 100 mL of MeOH was added hydrazine (0.9 mL, 28.68 mmol, 1.4 eq) and the mixture was refluxed (under N2) for 6 h. TLC showed some starting material present and more hydrazine was added (0.45 mL) and stirring was continued at room temperature overnight. A white precipitate was formed. The solids were filtered off and the filtrate was concentrated to yield the product 64.02 (4.48 g) as a white solid.

Step 2

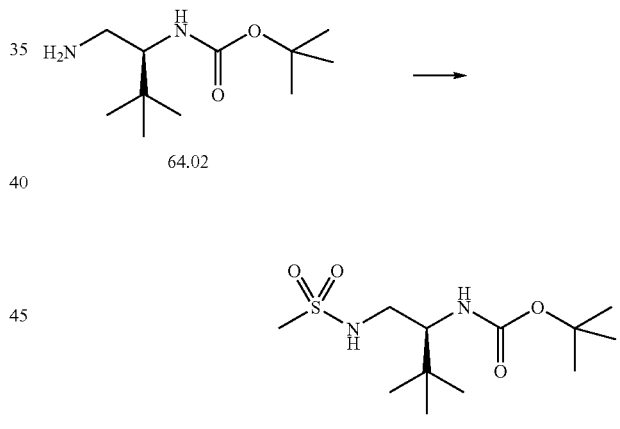

A solution of amine 64.02 (2.16 g, 10 mmol) in 100 mL of dichloromethane was cooled to 0° C. and treated with triethylamine (2 eq, 2.8 mL). Methanesulfonyl chloride (1.2 eq, 0.93 mL) was added dropwise. The heterogeneous mixture was stirred overnight (temp 0 to 25° C.). The solids were filtered off and the filtrate was washed with aqueous saturated ammonium chloride solution (100 mL), and brine (100 mL). The organic layer was dried over sodium sulfate, filtered and concentrated. The residue was taken in minimum amount of dichloromethane/ethyl acetate (approx 10 mL) and the insoluble white solid was filtered off. The filtrate was purified by column chromatography on silica gel to give the product 64.03 (2.7 g) as a thick semisolid.

Step 3

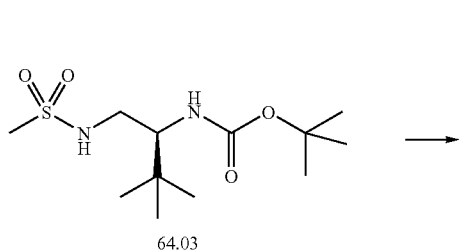
64.03

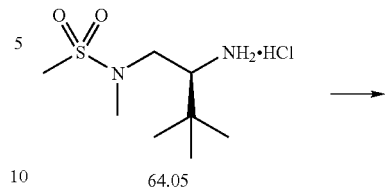
64.05

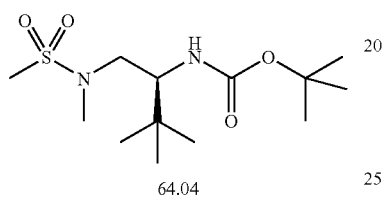
64.04

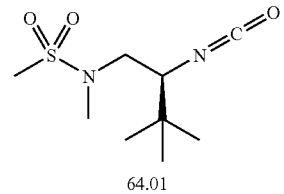
64.01

A solution of sulfonamide 64.03 (2.2 g, 7.5 mmol) in 50 mL of dry DMF was cooled to 0° C. and treated with cesium carbonate (3 eq, 7.34 g). Iodomethane (5 eq, 2.34 mL) was added dropwise and the mixture was stirred for 45 min. The cooling bath was removed and the mixture was stirred for further 4 h. The reaction was quenched by addition of aqueous saturated ammonium chloride solution (100 mL) and extracted with ethyl acetate (2×100 mL). The combined organic layers were washed with water (200 mL), brine (200 mL) and dried over sodium sulfate. The organic layer was filtered and concentrated. The residue was chromatographed on silica gel to afford the product 64.04 (2.16 g).

Step 4

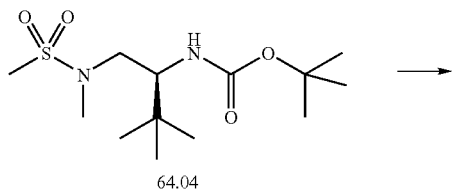
64.04

64.05

A mixture of amine hydrochloride 64.05 in dichloromethane and aqueous saturated NaHCO3 solution at 0° C. was treated with phosgene (15% solution in toluene) and stirred for 2 h. The reaction mixture was diluted with dichloromethane and washed with cold aqueous saturated NaHCO3 solution. The organic layer was dried over magnesium sulfate, filtered, and further diluted with toluene. The mixture was concentrated and the product 64.01 was adjusted and kept as a 0.2M solution in toluene.

Synthesis of Intermediate 65.01:

Step 1

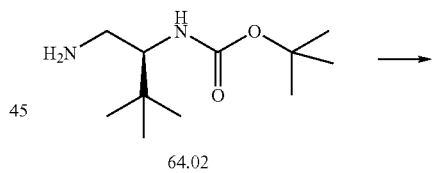
64.02

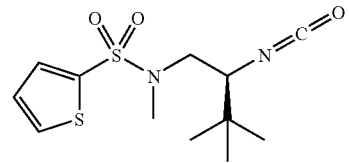
65.01

The N-Boc protected amine 64.04 (2.1 g, 6.82 mmol) was dissolved in 20 mL of 4M HCl in dioxane at room temperature. The reaction mixture was stirred for 1 h and then all the volatiles were removed under reduced pressure to afford the product 64.05 in quantitative yield.

The isocyanate 65.01 was prepared according to the procedure described for isocyanate 64.01 by employing 2-thiophenesulfonyl chloride instead of methanesulfonyl chloride in the sulfonamide synthesis step.

Synthesis of Preparative Examples

Synthesis of Example 101

Step 1

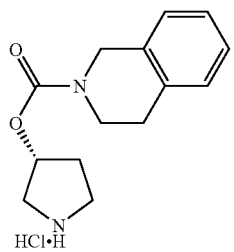
1.01

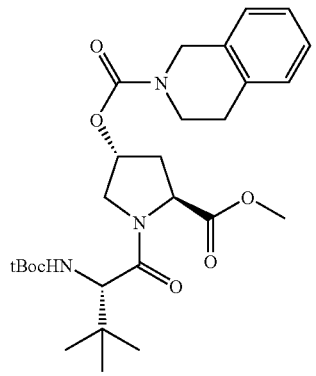
101a

To a stirred solution of the proline derivative 1.01 (3.66 mmol, prepared as described above) in dichloromethane (20 mL) and DMF (15 mL) at 0° C. was added L-boc-tert-leucine (930 mg, 4.03 mmol), DIPEA (2.02 mL, 10.98 mmol) and HATU (1.8 g, 4.76 mmol). After 15 minutes at that temperature, the reaction flask was stored in the freezer (−20° C.), overnight (16 hr). The reaction mixture was diluted with dichloromethane (80 mL) and washed with saturated sodium bicarbonate solution (80 mL), 10% aq. citric acid solution (80 mL), brine (80 mL), dried (Na$_2$SO$_4$), filtered and concentrated. The crude material was purified by silica chromatography using 25/75 to 50/50 EtOAc/hexanes to provide 1.77 g of the required material, 101 a. LC-MS: 518.1 (M+H)$^+$.

Step 2

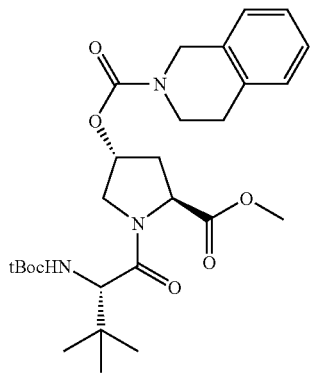
101a

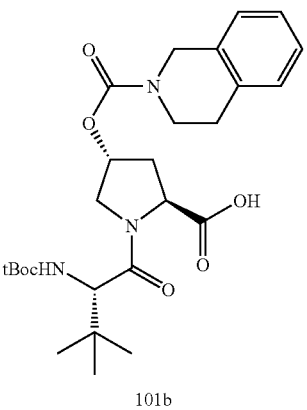
101b

To a solution of the methyl ester 101a (1.21 g, 2.34 mmol) in THF (10 mL) and MeOH (5 mL) was added aq. 1M LiOH solution (5 mL). The reaction mixture was stirred at RT for 4 h. It was then concentrated, diluted with water (50 mL) and acidified with solid citric acid (pH approximately 3) when white solid material crashed out. This solid was filtered off, washed with water and dried in vacuo to afford 970 mg of 101b. LC-MS: 504.1 (M+H)$^+$.

Step 3

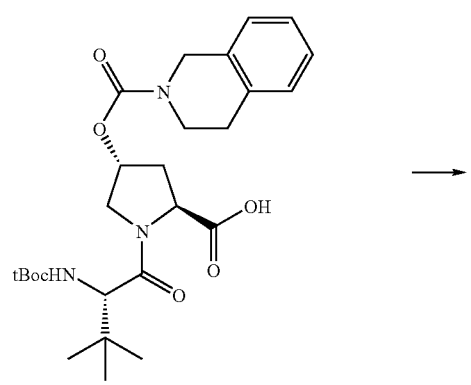
101b

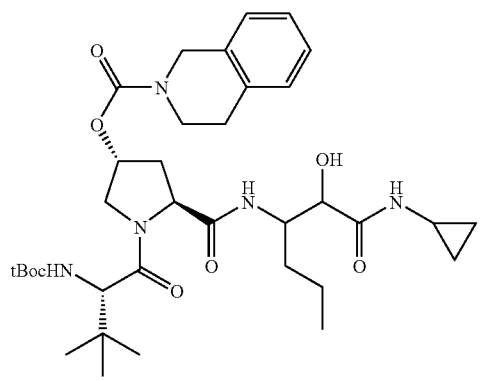
101c

The acid 101b (503 mg, 1 mmol) was coupled with intermediate 13.06 (334 mg, 1.5 mmol) using essentially procedure described above (Step 1, preparation of 101a) to provide 101c which was used without purification. MS: 672.37 (M+H)$^+$.

Step 4:

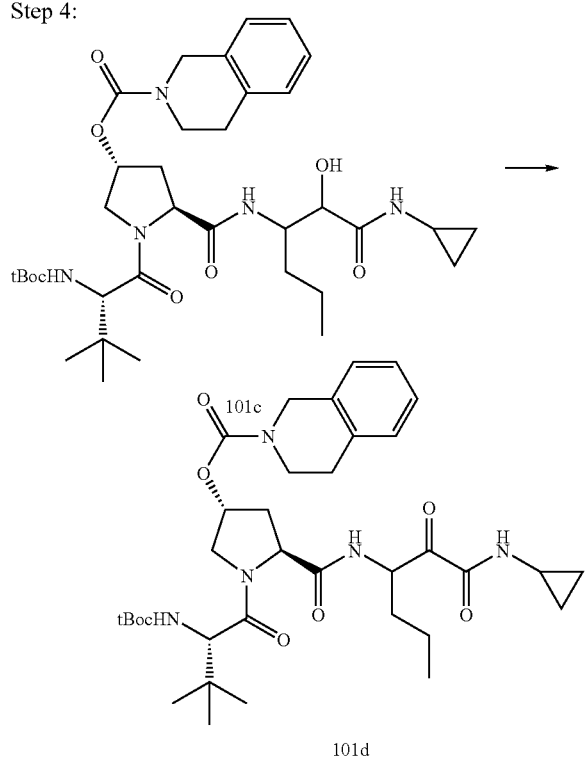

101d

To a solution of the hydroxyl compound 101c from above in dichloromethane (15 mL) was added Dess-Martin's periodinane (848 mg, 2 mmol) and the reaction mixture was stirred at RT for 5 h. At this time, the reaction mixture was diluted with dichloromethane (30 mL) and washed with 1:1 mixture of aq. 10% sodium thiosulfate solution and saturated sodium bicarbonate solution (2×25 mL each), brine (50 mL), dried (Na$_2$SO$_4$), filtered and concentrated. The crude material was purified by silica chromatography using 15/85 to 50/50 acetone/hexanes to provide 410 mg of the required material, 101d. LC-MS: 670.2 (M+H)$^+$.

Step 5:

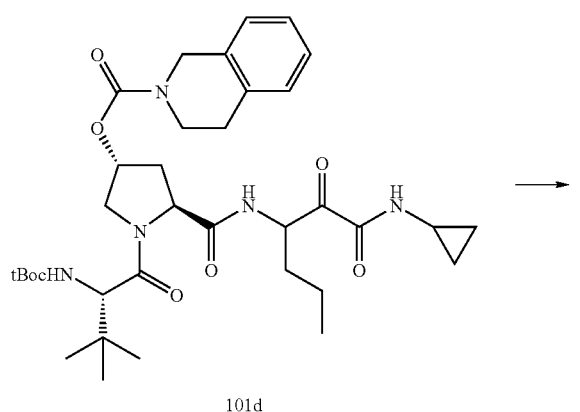

101d

-continued

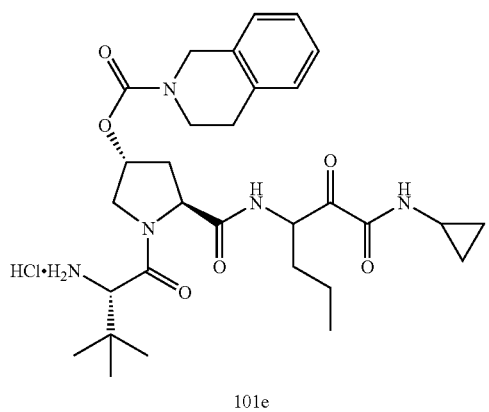

101e

Deprotection of the N-boc functionality of 101d to provide the required material 101e was carried out as described for intermediate 1.01, Step 3 (reaction time=2 h). LC-MS: 570.1 (M+H)$^+$.

Step 6:

101e 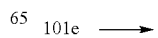

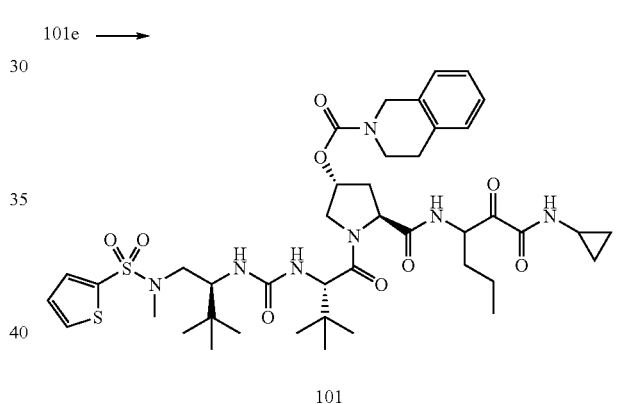

101

To a solution of the amine salt 101e (60 mg, 0.1 mmol) in dichloromethane (2 mL) at 0° C. was added DIPEA (0.06 mL, 0.3 mmol) followed by the isocyanate intermediate 65.01 (0.25 M solution in toluene, 0.8 mL, 0.2 mmol). After 15 minutes at that temperature, the reaction flask was stored in the freezer (−20° C.), overnight (16 hr). The reaction mixture was diluted with dichloromethane (20 mL) and washed with saturated ammonium chloride solution (20 mL), brine (20 mL), dried (Na$_2$SO$_4$), filtered and concentrated. The crude material was purified by silica chromatography using 15/85 to 50/50 acetone/hexanes to provide the required compound 101 (53 mg); LC–MS: 872.2 (M+H)$^+$.

Synthesis of Example 102

Step 1

101e ⟶

-continued

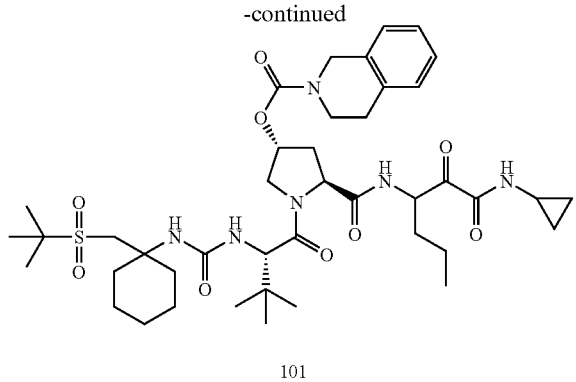

101

The required compound 102 was prepared from 101e and intermediate 63.01 using procedure described above for Example 101, Step 6. LC-MS of 102: 829.2 (M+H)$^+$.

Synthesis of Example 103

Step 1

101e ⟶

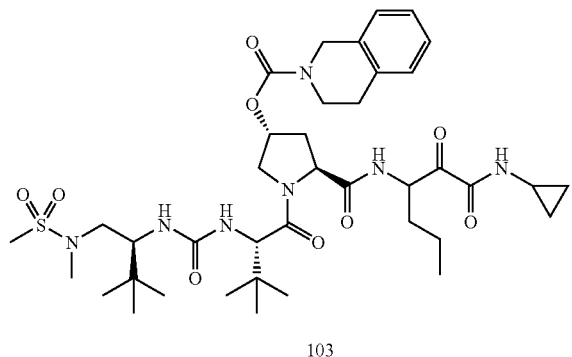

103

The required compound 103 was prepared from 101e and intermediate 64.01 using procedure described above for Example 101, Step 6. LC-MS of 103: 804.2 (M+H)$^+$.

In procedures similar to those described above, the other compounds in Table 2 were prepared. Additionally, the compounds in Table 1 can also be prepared similarly.

The present invention relates to novel HCV protease inhibitors. This utility can be manifested in their ability to inhibit the HCV NS3/NS4a serine protease. A general procedure for such demonstration is illustrated by the following in vitro assay.

Assay for HCV Protease Inhibitory Activity:

Spectrophotometric Assay: Spectrophotometric assay for the HCV serine protease can be performed on the inventive compounds by following the procedure described by R. Zhang et al, *Analytical Biochemistry*, 270 (1999) 268-275, the disclosure of which is incorporated herein by reference. The assay based on the proteolysis of chromogenic ester substrates is suitable for the continuous monitoring of HCV NS3 protease activity. The substrates are derived from the P side of the NS5A-NS5B junction sequence (Ac-DTEDVVX(Nva), where X=A or P) whose C-terminal carboxyl groups are esterified with one of four different chromophoric alcohols (3- or 4-nitrophenol, 7-hydroxy-4-methyl-coumarin, or 4-phenylazophenol). Illustrated below are the synthesis, characterization and application of these novel spectrophotometric ester substrates to high throughput screening and detailed kinetic evaluation of HCV NS3 protease inhibitors.

Materials and Methods:

Materials: Chemical reagents for assay related buffers are obtained from Sigma Chemical Company (St. Louis, Mo.). Reagents for peptide synthesis were from Aldrich Chemicals, Novabiochem (San Diego, Calif.), Applied Biosystems (Foster City, Calif.) and Perspective Biosystems (Framingham, Mass.). Peptides are synthesized manually or on an automated ABI model 431A synthesizer (from Applied Biosystems). UV/VIS Spectrometer model LAMBDA 12 was from Perkin Elmer (Norwalk, Conn.) and 96-well UV plates were obtained from Corning (Corning, N.Y.). The prewarming block can be from USA Scientific (Ocala, Fla.) and the 96-well plate vortexer is from Labline Instruments (Melrose Park, Ill.). A Spectramax Plus microtiter plate reader with monochrometer is obtained from Molecular Devices (Sunnyvale, Calif.).

Enzyme Preparation: Recombinant heterodimeric HCV NS3/NS4A protease (strain 1a) is prepared by using the procedures published previously (D. L. Sali et al, *Biochemistry*, 37 (1998) 3392-3401). Protein concentrations are determined by the Biorad dye method using recombinant HCV protease standards previously quantified by amino acid analysis. Prior to assay initiation, the enzyme storage buffer (50 mM sodium phosphate pH 8.0, 300 mM NaCl, 10% glycerol, 0.05% lauryl maltoside and 10 mM DTT) is exchanged for the assay buffer (25 mM MOPS pH 6.5, 300 mM NaCl, 10% glycerol, 0.05% lauryl maltoside, 5 μM EDTA and 5 μM DTT) utilizing a Biorad Bio-Spin P-6 prepacked column.

Substrate Synthesis and Purification: The synthesis of the substrates is done as reported by R. Zhang et al, (ibid.) and is initiated by anchoring Fmoc-Nva-OH to 2-chlorotrityl chloride resin using a standard protocol (K. Barlos et al, *Int. J. Pept. Protein Res.*, 37 (1991), 513-520). The peptides are subsequently assembled, using Fmoc chemistry, either manually or on an automatic ABI model 431 peptide synthesizer. The N-acetylated and fully protected peptide fragments are cleaved from the resin either by 10% acetic acid (HOAc) and 10% trifluoroethanol (TFE) in dichloromethane (DCM) for 30 min, or by 2% trifluoroacetic acid (TFA) in DCM for 10 min. The combined filtrate and DCM wash is evaporated azeotropically (or repeatedly extracted by aqueous Na$_2$CO$_3$ solution) to remove the acid used in cleavage. The DCM phase is dried over Na$_2$SO$_4$ and evaporated.

The ester substrates are assembled using standard acid-alcohol coupling procedures (K. Holmber et al, *Acta Chem. Scand.*, B33 (1979) 410-412). Peptide fragments are dissolved in anhydrous pyridine (30-60 mg/ml) to which 10 molar equivalents of chromophore and a catalytic amount (0.1 eq.) of para-toluenesulfonic acid (pTSA) were added. Dicyclohexylcarbodiimide (DCC, 3 eq.) is added to initiate the coupling reactions. Product formation is monitored by HPLC and can be found to be complete following 12-72 hour reaction at room temperature. Pyridine solvent is evaporated under vacuum and further removed by azeotropic evaporation with toluene. The peptide ester is deprotected with 95% TFA in DCM for two hours and extracted three times with anhydrous ethyl ether to remove excess chromophore. The deprotected substrate is purified by reversed phase HPLC on a C3 or C8 column with a 30% to 60% acetonitrile gradient (using six column volumes). The overall yield following HPLC purification can be approximately 20-30%. The molecular mass can be confirmed by electrospray ionization mass spectroscopy. The substrates are stored in dry powder form under desiccation.

Spectra of Substrates and Products: Spectra of substrates and the corresponding chromophore products are obtained in the pH 6.5 assay buffer. Extinction coefficients are determined at the optimal off-peak wavelength in 1-cm cuvettes (340 nm for 3-Np and HMC, 370 nm for PAP and 400 nm for 4-Np) using multiple dilutions. The optimal off-peak wavelength is defined as that wavelength yielding the maximum fractional difference in absorbance between substrate and product (product OD—substrate OD)/substrate OD).

Protease Assay: HCV protease assays are performed at 30° C. using a 200 µl reaction mix in a 96-well microtiter plate. Assay buffer conditions (25 mM MOPS pH 6.5, 300 mM NaCl, 10% glycerol, 0.05% lauryl maltoside, 5 µM EDTA and 5 µM DTT) are optimized for the NS3/NS4A heterodimer (D. L. Sali et al, ibid.)). Typically, 150 µl mixtures of buffer, substrate and inhibitor are placed in wells (final concentration of DMSO ≦4% v/v) and allowed to preincubate at 30° C. for approximately 3 minutes. Fifty µls of prewarmed protease (12 nM, 30° C.) in assay buffer, is then used to initiate the reaction (final volume 200 µl). The plates are monitored over the length of the assay (60 minutes) for change in absorbance at the appropriate wavelength (340 nm for 3-Np and HMC, 370 nm for PAP, and 400 nm for 4-Np) using a Spectromax Plus microtiter plate reader equipped with a monochrometer (acceptable results can be obtained with plate readers that utilize cutoff filters). Proteolytic cleavage of the ester linkage between the Nva and the chromophore is monitored at the appropriate wavelength against a no enzyme blank as a control for non-enzymatic hydrolysis. The evaluation of substrate kinetic parameters is performed over a 30-fold substrate concentration range (~6-200 µM). Initial velocities are determined using linear regression and kinetic constants are obtained by fitting the data to the Michaelis-Menten equation using non-linear regression analysis (Mac Curve Fit 1.1, K. Raner). Turnover numbers (kcat) are calculated assuming the enzyme is fully active. Evaluation of Inhibitors and Inactivators: The inhibition constants ($K_i$) for the competitive inhibitors Ac-D-(D-Gla)-L—I-(Cha)-C—OH (27), Ac-DTEDVVA(Nva)-OH and Ac-DTEDVVP(Nva)-OH are determined experimentally at fixed concentrations of enzyme and substrate by plotting vo/vi vs. inhibitor concentration ($[I]_o$) according to the rearranged Michaelis-Menten equation for competitive inhibition kinetics: $v_o/v_i = 1+[I]_o/(K_i(1+[S]_o/K_m))$, where $v_o$ is the uninhibited initial velocity, $v_i$ is the initial velocity in the presence of inhibitor at any given inhibitor concentration ($[I]_o$) and $[S]_o$ is the substrate concentration used. The resulting data are fitted using linear regression and the resulting slope, $1/(K_i(1+[S]_o/K_m))$, is used to calculate the $K_i$ value. The obtained Ki* values (in nanoMolar) for some of the inventive compounds are shown below in Table 2.

TABLE 2

| Example | Structure | LC-MS (M + H)+ | Ki* (nM) |
|---------|-----------|----------------|----------|
| 101 | 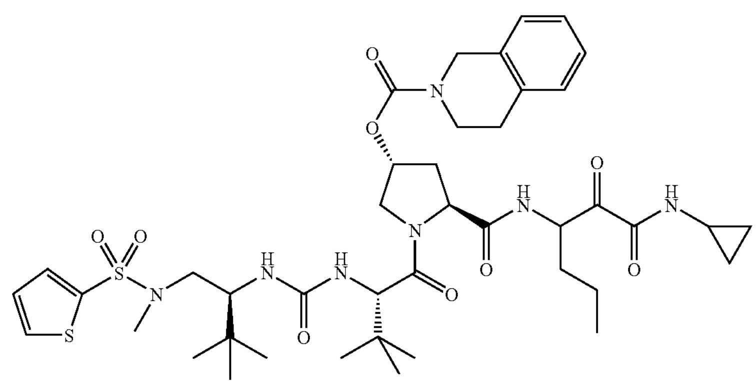 | 872.2 | 36 |
| 102 | 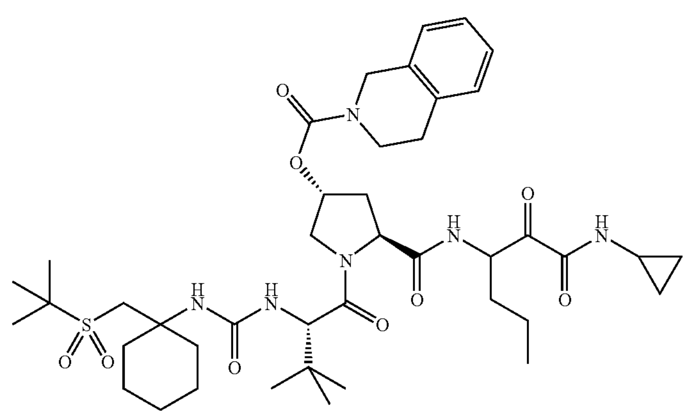 | 829.2 | 15 |

TABLE 2-continued

| Example | Structure | LC-MS (M + H)+ | Ki* (nM) |
|---------|-----------|----------------|----------|
| 103 | 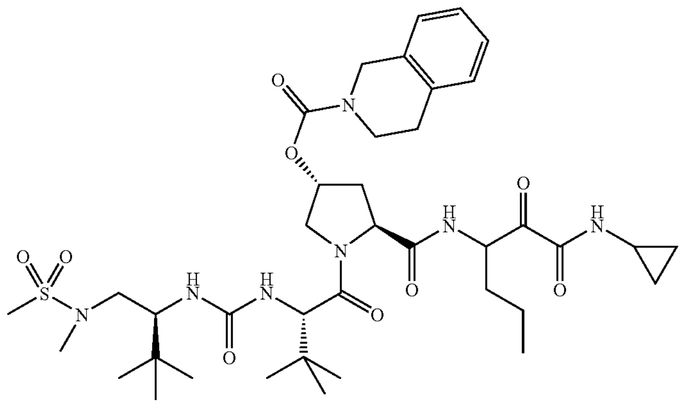 | 804.2 | 13 |
| 104 | 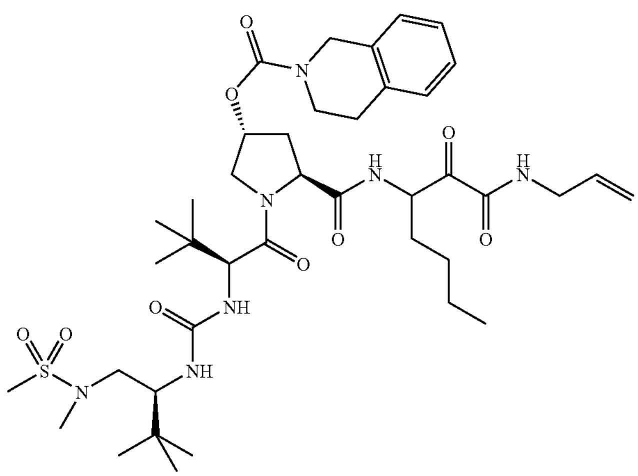 | 818.2 | 16 |
| 105 | 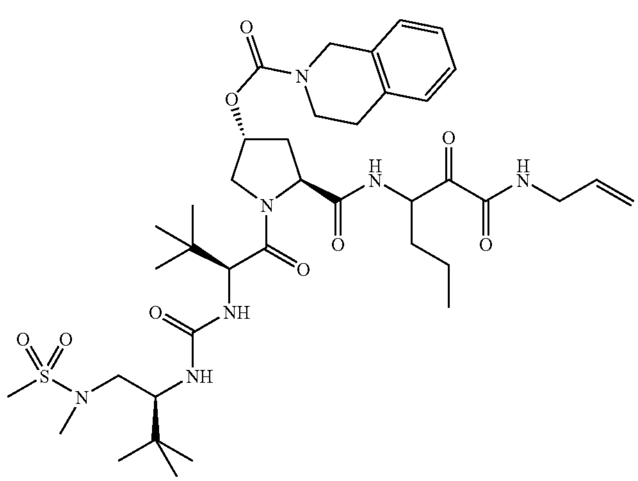 | 804.2 | 9 |

TABLE 2-continued

| Example | Structure | LC-MS (M + H)+ | Ki* (nM) |
|---|---|---|---|
| 106 | 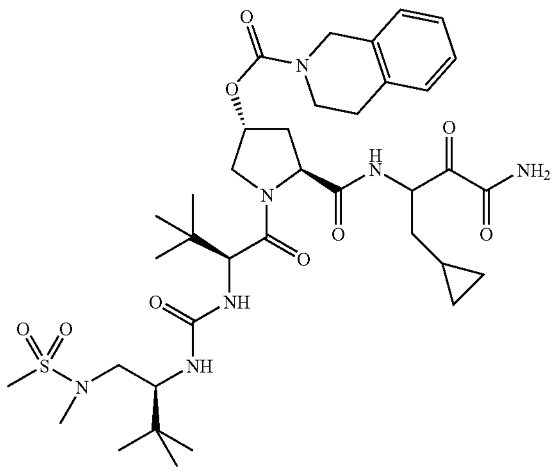 | 776.2 | 6 |
| 107 | 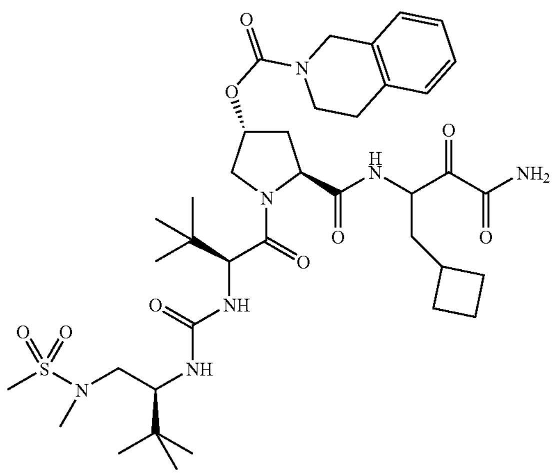 | 790.2 | 5 |
| 108 | 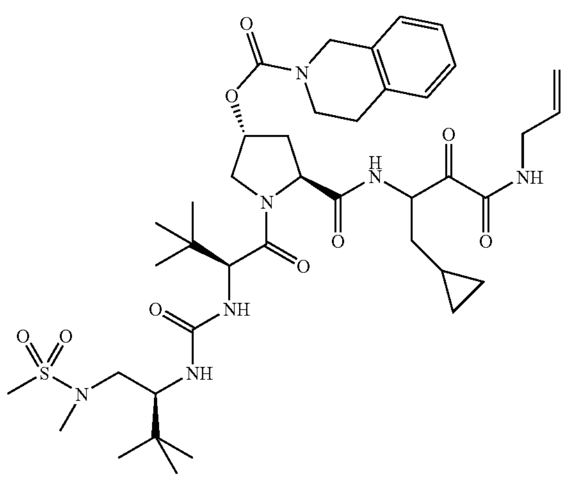 | 816.2 | 7 |

TABLE 2-continued

| Example | Structure | LC-MS (M + H)+ | Ki* (nM) |
|---------|-----------|----------------|----------|
| 109 | 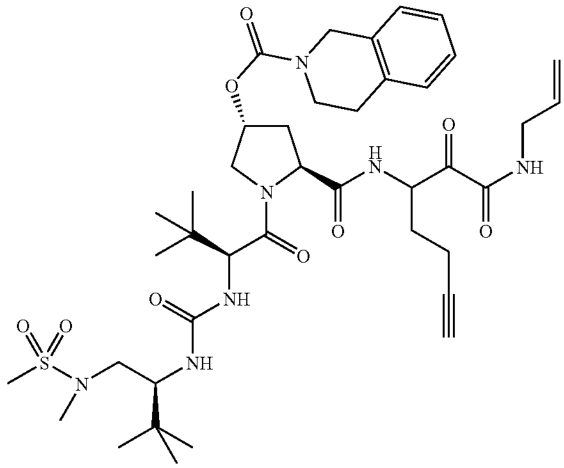 | 814.2 | 7 |
| 110 | 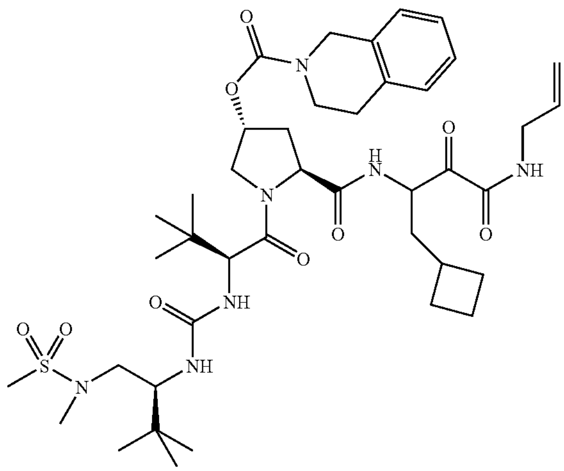 | 830.2 | 6 |
| 111 | 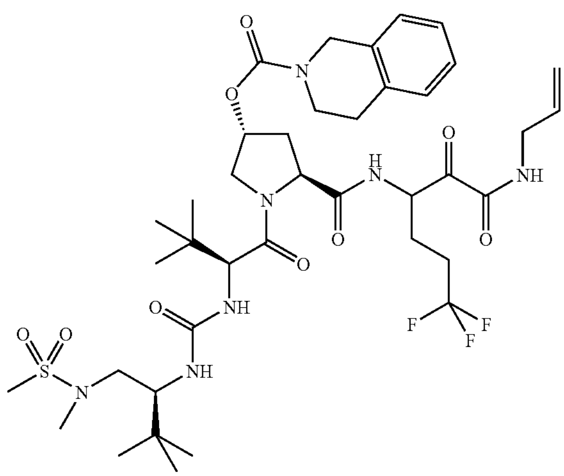 | 858.2 | 6 |

TABLE 2-continued

| Example | Structure | LC-MS (M + H)+ | Ki* (nM) |
|---|---|---|---|
| 112 | 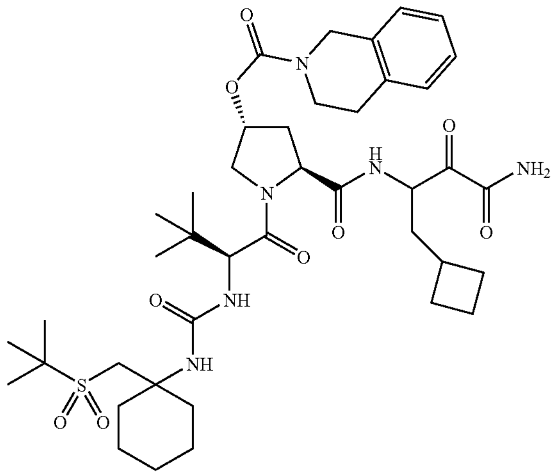 | 815.2 | 5.8 |
| 113 | 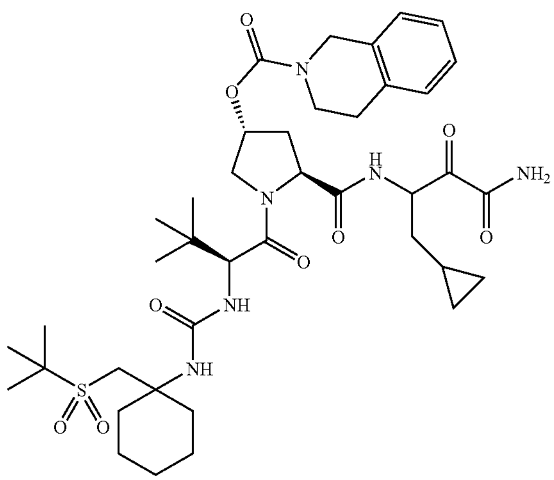 | 801.2 | 5.2 |
| 114 | 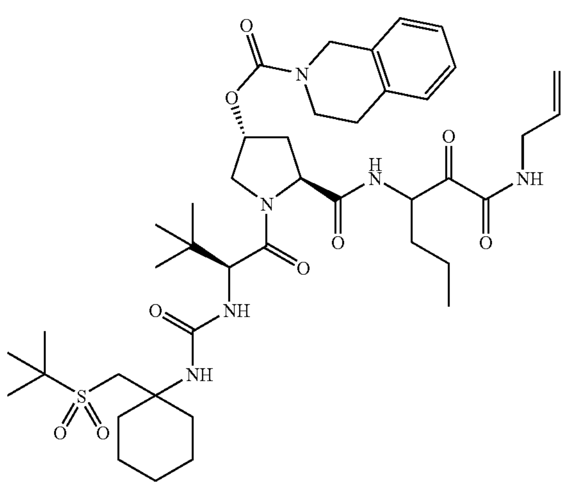 | 829.2 | 18 |

TABLE 2-continued

| Example | Structure | LC-MS (M + H)+ | Ki* (nM) |
|---|---|---|---|
| 115 | 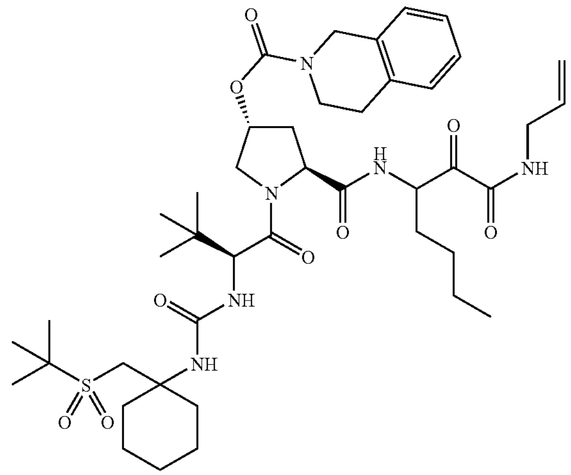 | 843.2 | 25 |
| 116 | 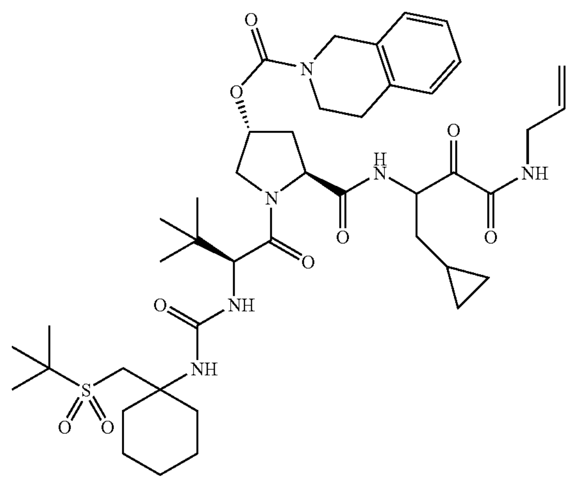 | 841.2 | 11 |
| 117 | 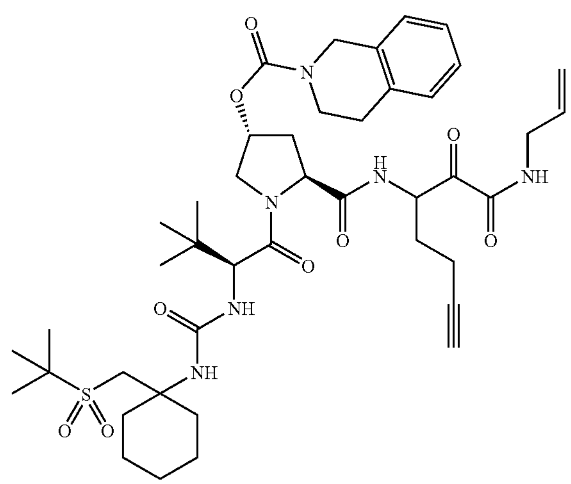 | 839.2 | 8 |

TABLE 2-continued

| Example | Structure | LC-MS (M + H)+ | Ki* (nM) |
|---|---|---|---|
| 118 | 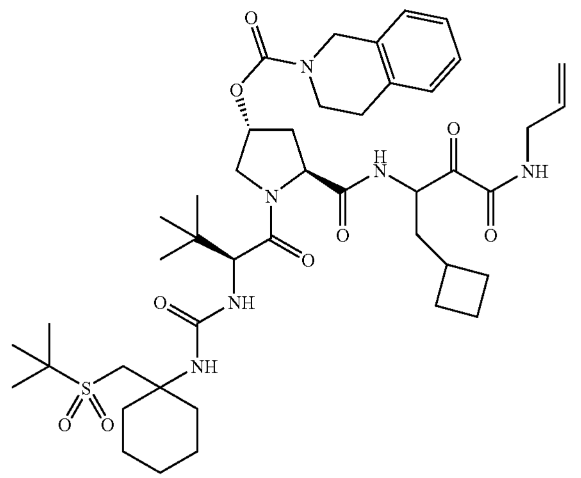 | 855.2 | 16 |
| 119 | 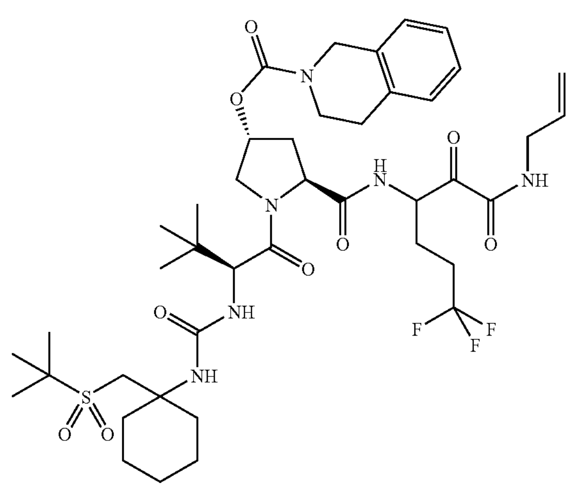 | 883.2 | 12 |

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound, or enantiomer, stereoisomer, rotamer, tautomer, and racemate of said compound, or a pharmaceutically acceptable salt of said compound, said compound having the general structure shown in Formula I:

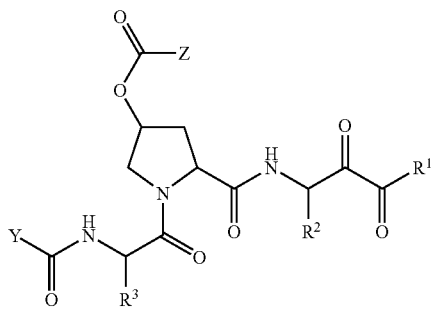

Formula 1 wherein:
Z is selected from the group consisting of a hetero-bicyclic ring system;
$R^1$ is $NR^9R^{10}$, wherein $R^9$ and $R^{10}$ can be the same or different, each being independently selected from the group consisting of H, alkyl-, alkenyl-, alkynyl-, aryl-, heteroalkyl-, heteroaryl-, cycloalkyl-, heterocyclyl-, arylalkyl-, and heteroarylalkyl, or alternately $R^9$ and $R^{10}$ in $NR^9R^{10}$ are connected to each other such that $NR^9R^{10}$ forms a four to eight-membered heterocyclyl, and likewise independently alternately $R^9$ and $R^{10}$ in $CHR^9R^{10}$ are connected to each other such that $CHR^9R^{10}$ forms a four to eight-membered cycloalkyl;
$R^2$ and $R^3$ can be the same or different, each being independently selected from the group consisting of H, alkyl, heteroalkyl, alkenyl, heteroalkenyl, alkynyl, heteroalkynyl, cycloalkyl, heterocyclyl, aryl, heteroaryl-;
Y is selected from the following moieties:

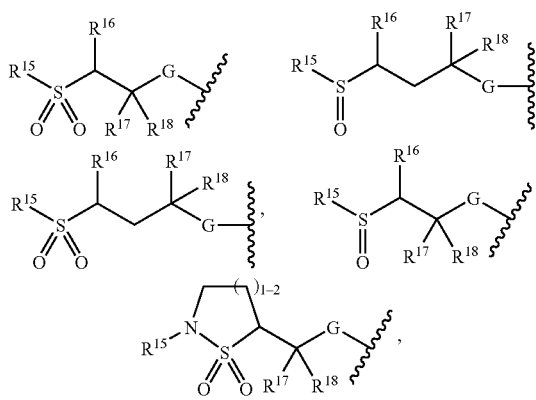

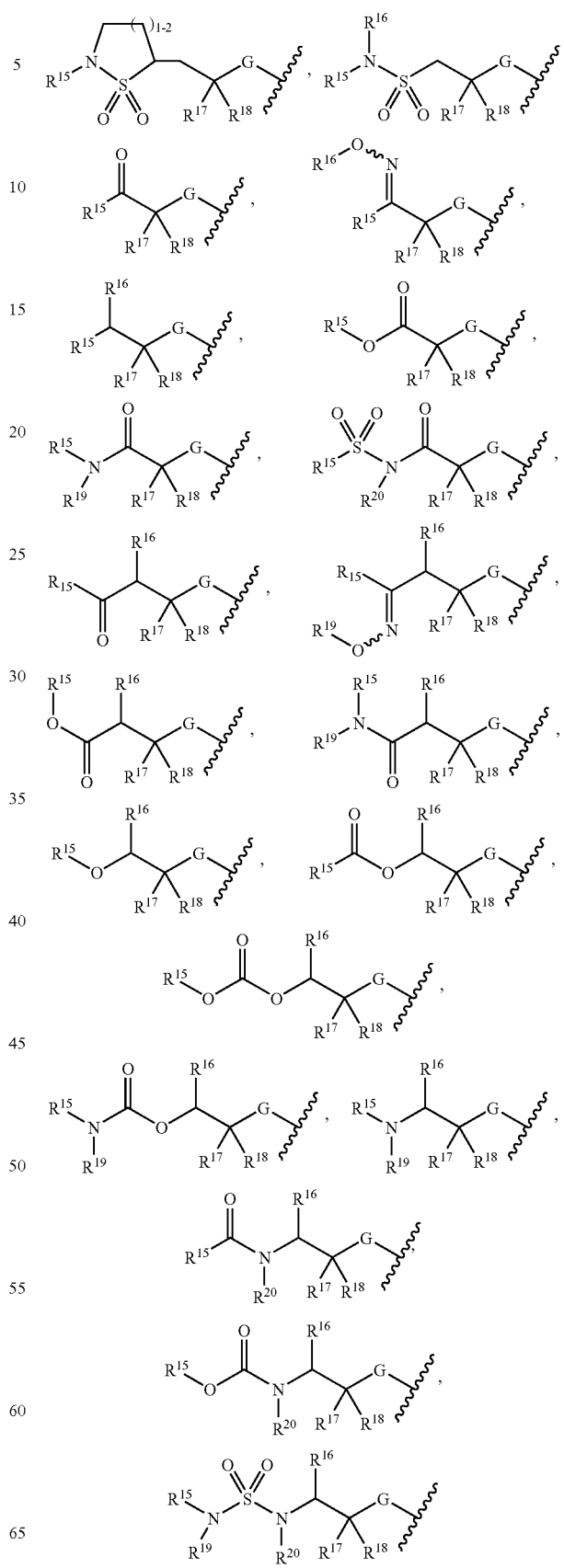

-continued

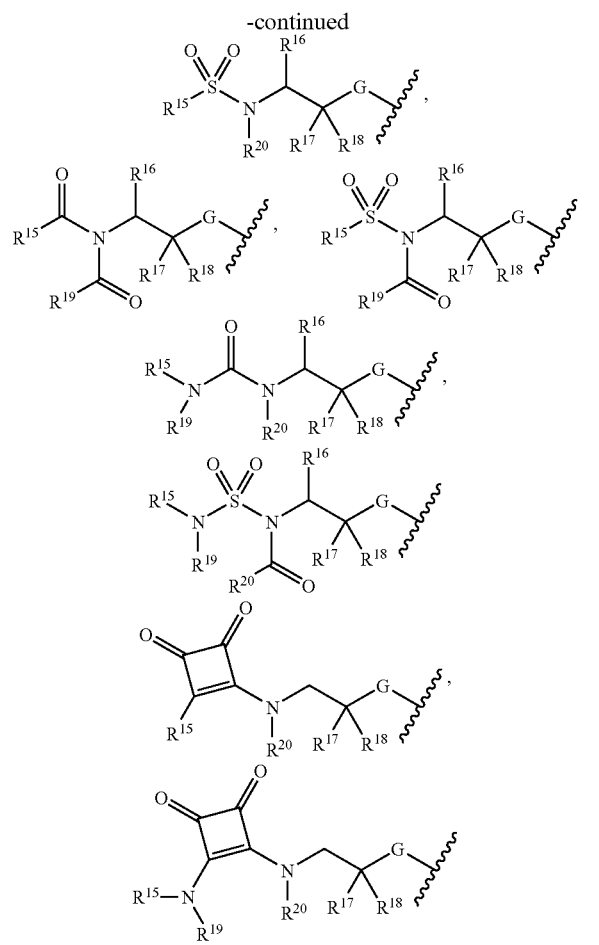

wherein G is NH or O; and $R^{15}$, $R^{16}$, $R^{17}$, $R^{18}$, $R^{19}$, $R^{20}$ and $R^{21}$ can be the same or different, each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately (i) $R^{17}$ and $R^{18}$ are independently connected to each other to form a three to eight-membered cycloalkyl or heterocyclyl; (ii) likewise independently $R^{15}$ and $R^{19}$ are connected to each other to form a four to eight-membered heterocyclyl; (iii) likewise independently $R^{15}$ and $R^{16}$ are connected to each other to form a four to sight-membered heterocyclyl; and (iv) likewise independently $R^{15}$ and $R^{20}$ are connected to each other to form a four to eight-membered heterocyclyl;

wherein each of said alkyl, aryl, heteroaryl, cycloalkyl or heterocyclyl can be unsubstituted or optionally independently substituted with one or more moieties selected from the group consisting of hydroxy, alkoxy, aryloxy, thio, alkylthio, arylthio, amino, amido, alkylamino, arylamino, alkylsulfonyl, arylsulfonyl, sulfonamido, alkyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

2. The compound of claim 1, wherein said compound has the formula:

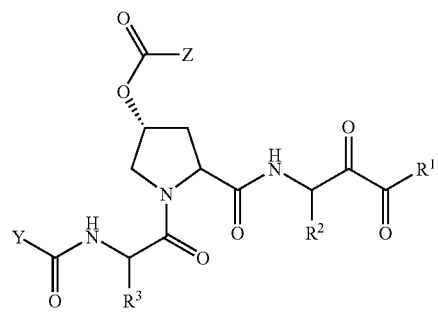

wherein the various moieties are as defined in claim 1.

3. The compound of claim 1, wherein $R^1$ is $NR^9R^{10}$, and $R^9$ is H, $R^{10}$ is H, or $R^{14}$ wherein $R^{14}$ is alkyl, aryl, heteroalkyl, heteroaryl, cycloalkyl, alkyl-aryl, alkyl-heteroaryl, aryl-alkyl, alkenyl, alkynyl or heteroaryl-alkyl.

4. The compound of claim 3, wherein $R^{14}$ is selected from the group consisting of:

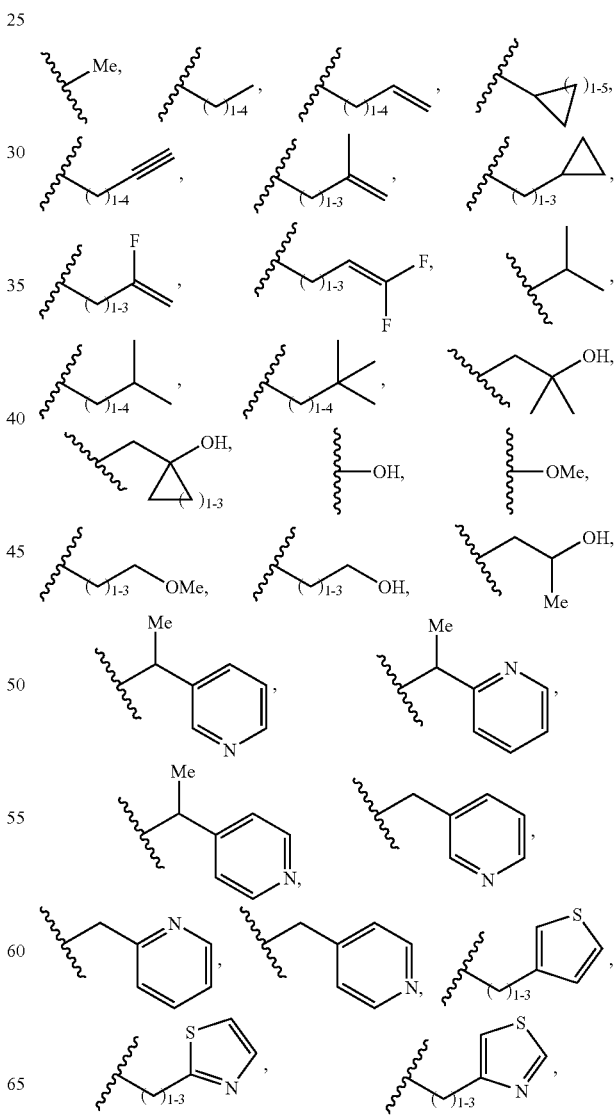

-continued
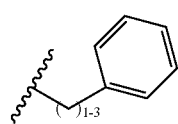 and 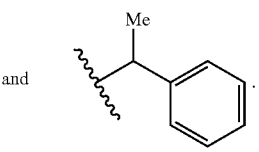
5. The compound of claim 1, wherein $R^2$ is selected from the group consisting of the following moieties:
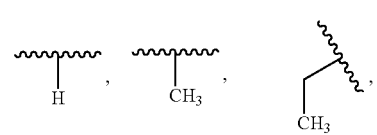 , 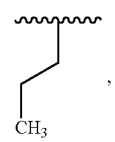 ,
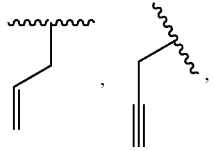 , 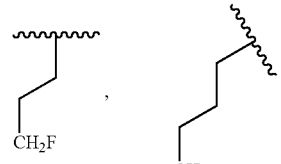 ,
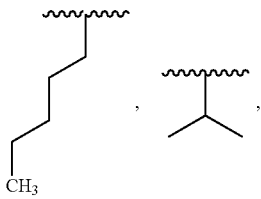 , 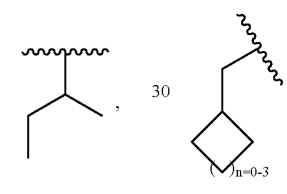 ,
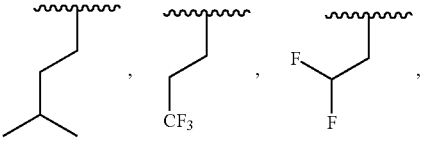 , 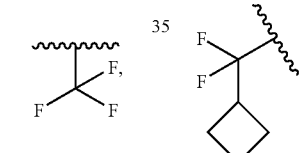 ,
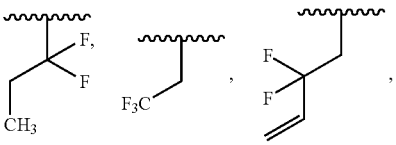 , 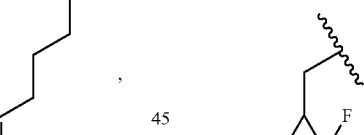 ,
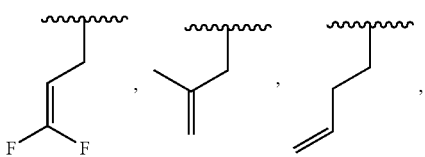 , 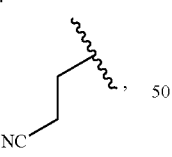 ,
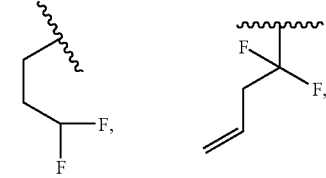 , 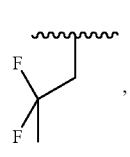 ,
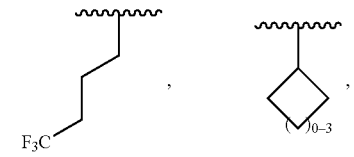 , 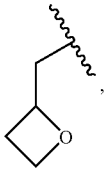 ,
-continued
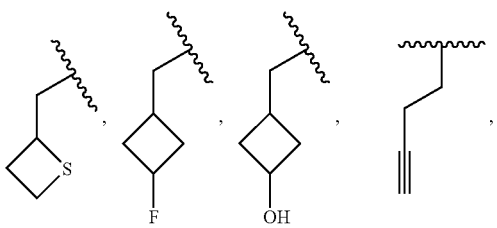
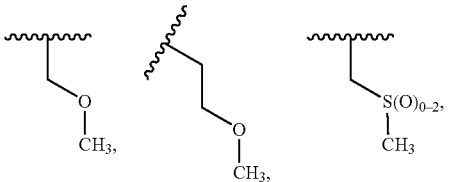
6. The compound of claim 1, wherein $R^3$ is selected from the group consisting of:
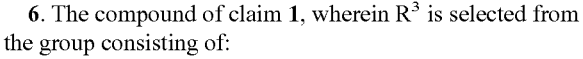
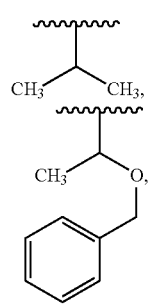 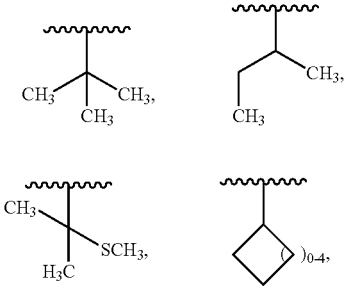

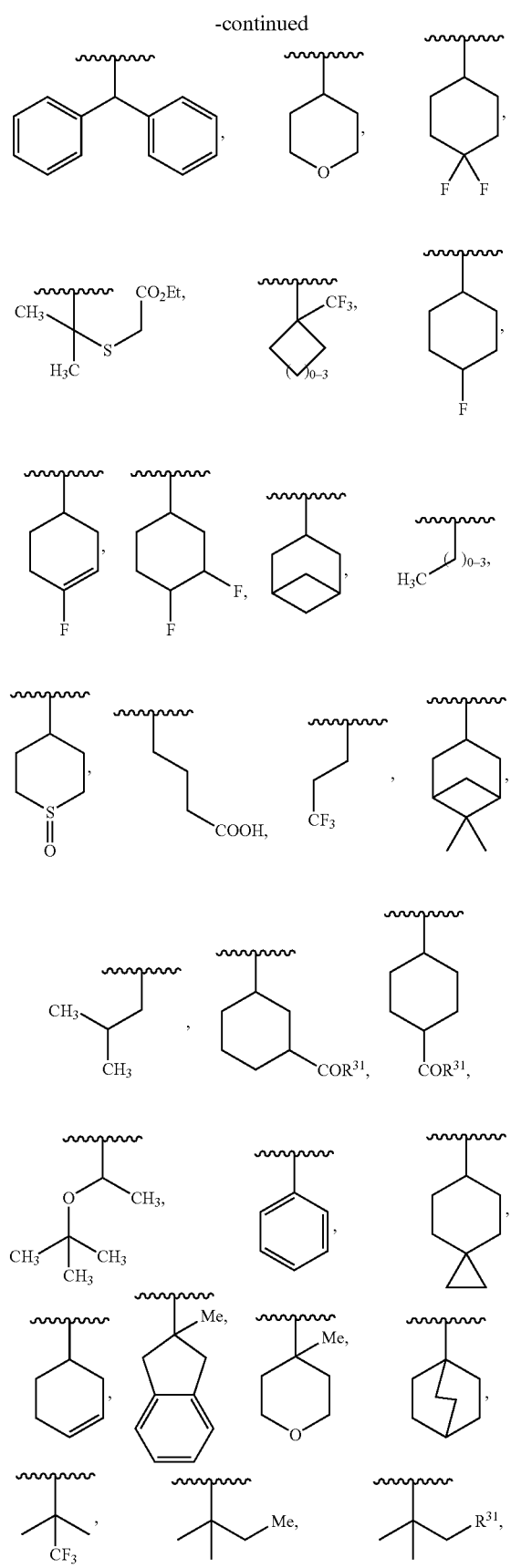
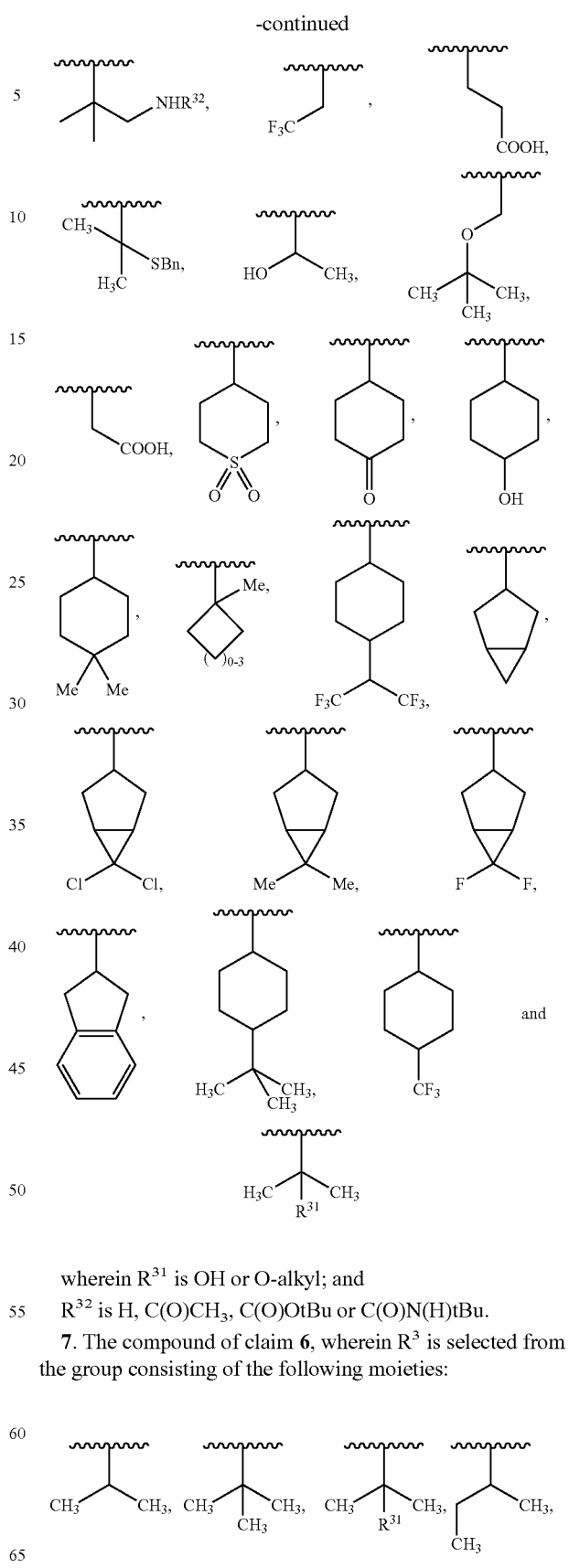
wherein $R^{31}$ is OH or O-alkyl; and
$R^{32}$ is H, C(O)CH$_3$, C(O)OtBu or C(O)N(H)tBu.
7. The compound of claim 6, wherein $R^3$ is selected from the group consisting of the following moieties:
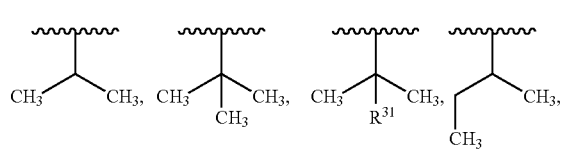

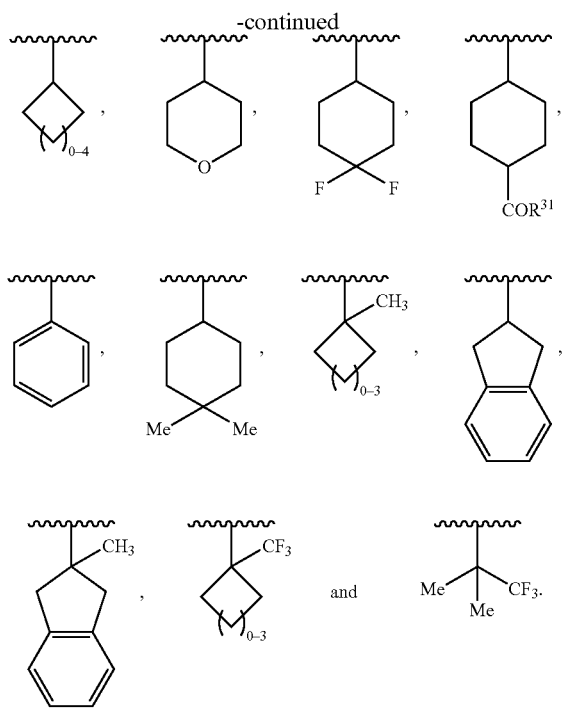
8. The compound of claim 1, wherein G is NH.
9. The compound of claim 8, wherein Y is selected from the following moieties:
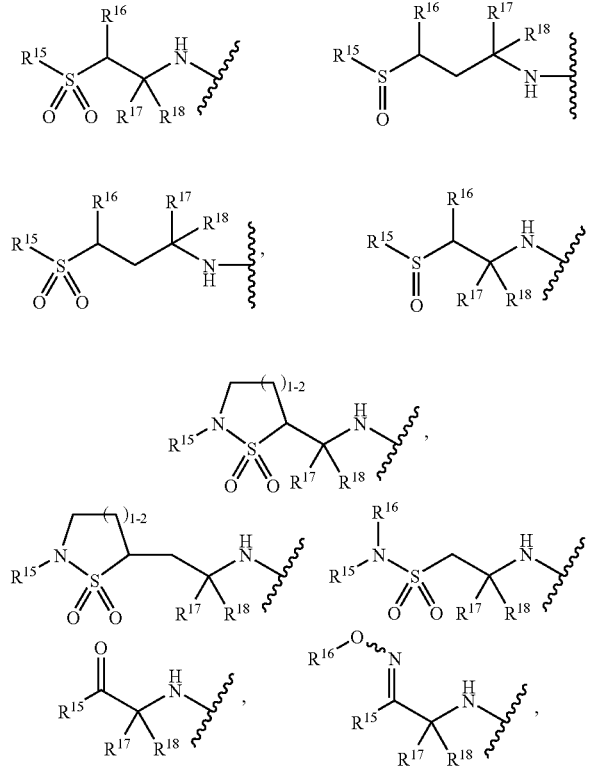
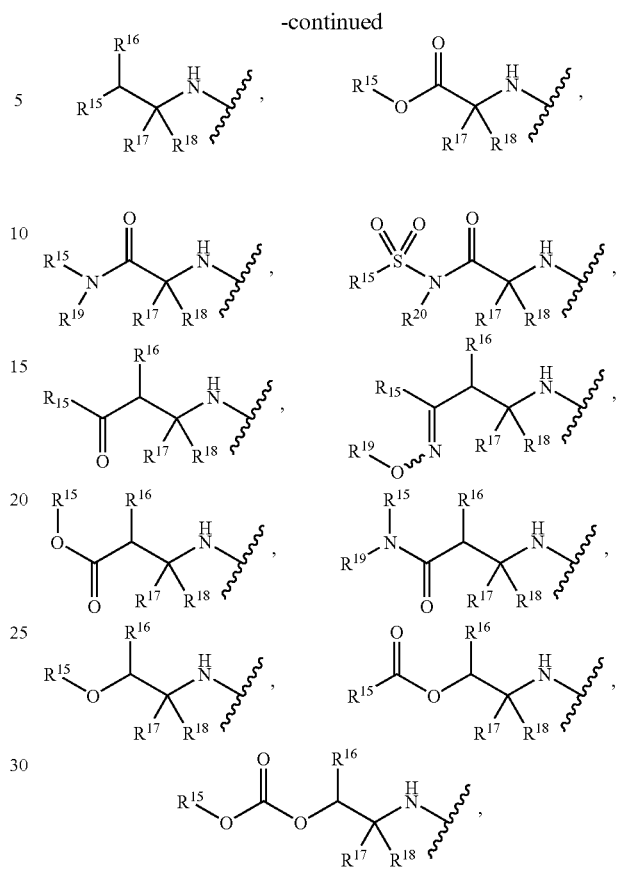
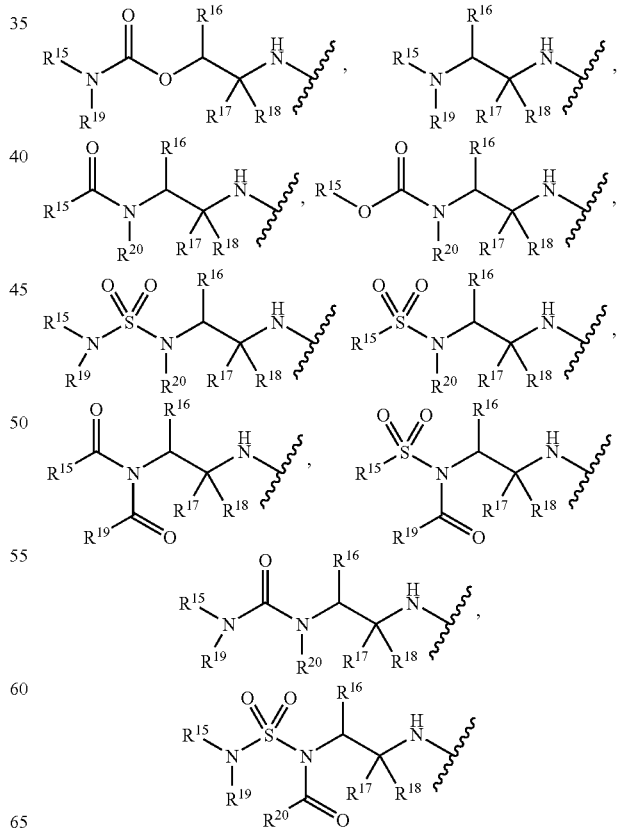

-continued

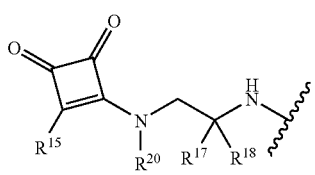 or

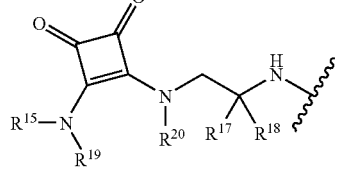

wherein $R^{15}$, $R^{16}$, $R^{17}$, $R^{18}$, $R^{19}$, $R^{20}$, $R^{21}$, $R^{22}$, $R^{23}$, $R^{24}$, and $R^{25}$ each being independently selected from the group consisting of H, alkyl, heteroalkyl, alkenyl, heteroalkenyl, alkynyl, heteroalkynyl, cycloalkyl, heterocyclyl, aryl, arylalkyl, heteroaryl, and heteroarylalkyl, or alternately (i) $R^{17}$ and $R^{18}$ are independently connected to each other to form a three to eight-membered cycloalkyl or heterocyclyl; (ii) likewise independently $R^{15}$ and $R^{19}$ are connected to each other to form a four to eight-membered heterocyclyl; (iii) likewise independent $R^{15}$ and $R^{16}$ are connected to each other to form a four to eight-membered heterocyclyl; and (iv) likewise independently $R^{15}$ and $R^{20}$ are connected to each other to form a four to eight-membered heterocyclyl;

wherein each of said alkyl, aryl, heteroaryl, cycloalkyl or heterocyclyl can be unsubstituted or optionally independently substituted with one or more moieties selected from the group consisting of: hydroxy, alkoxy, aryloxy, thio, alkylthio, arylthio, amino, amido, alkylamino, arylamino, alkylsulfonyl, arylsulfonyl, sulfonamido, alkyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

10. The compound of claim 9, wherein the moiety:

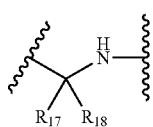

is selected from the following:

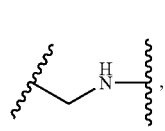, 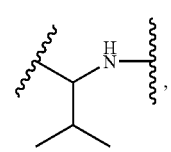, 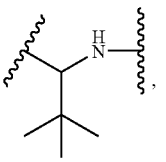,

-continued

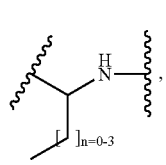, 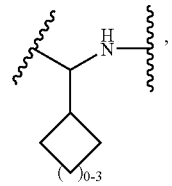,

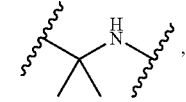,

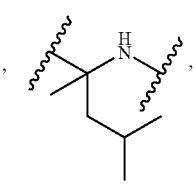,

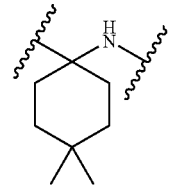, 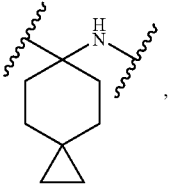,

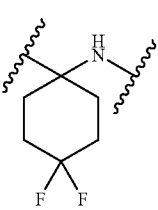, 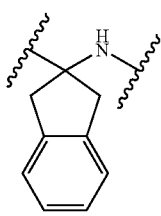, 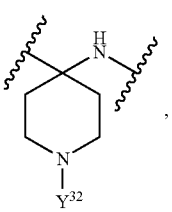,

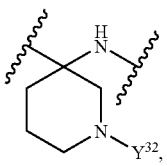, 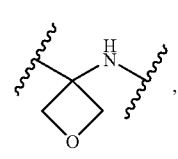,

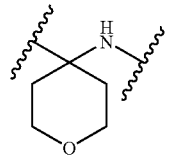 and 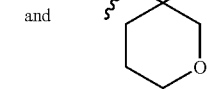

wherein $Y^{32}$ is selected from the group consisting of:

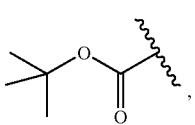, 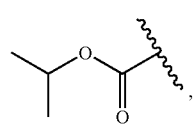,

-continued
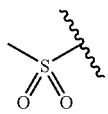 and 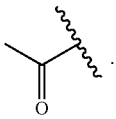
11. The compound of claim 9, wherein Y is selected from.:
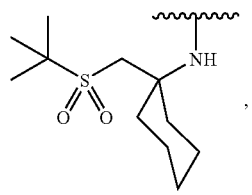 , 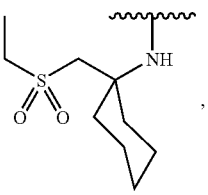 ,
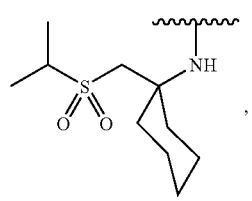 , 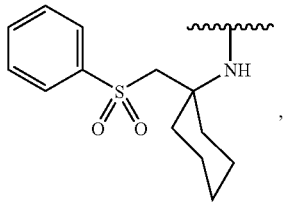 ,
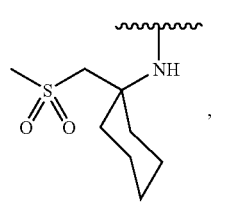 , 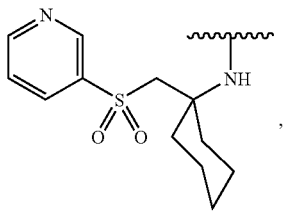 ,
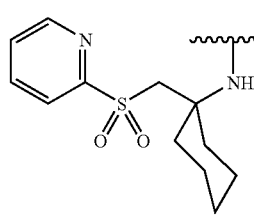 , 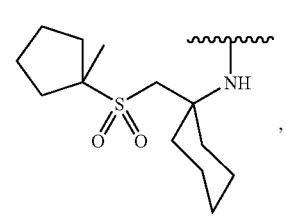 ,
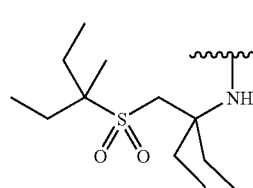 , 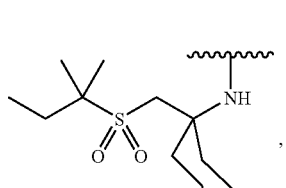 ,
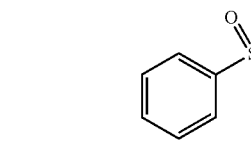
-continued
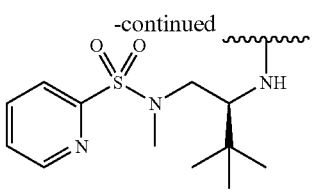 ,
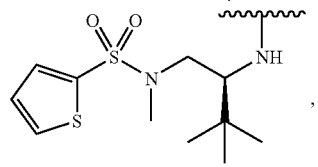 ,
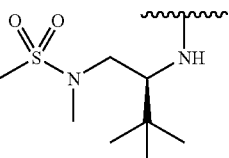 ,
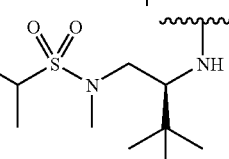 ,
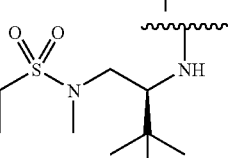 ,
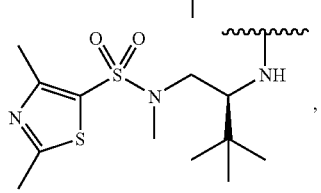 ,
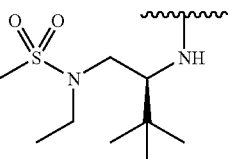 ,
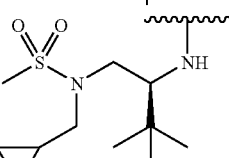 ,
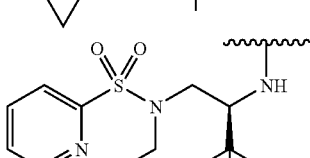 ,
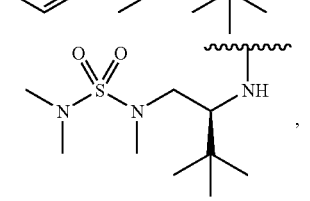 , -continued
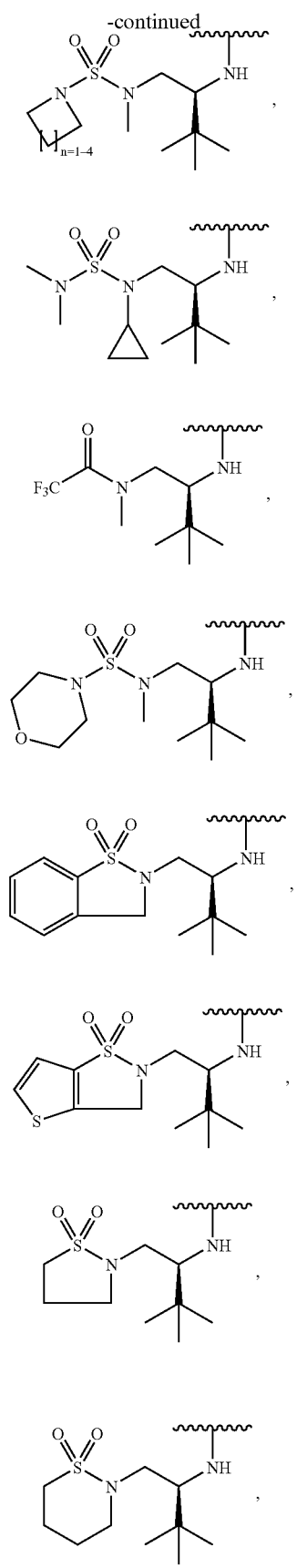
-continued
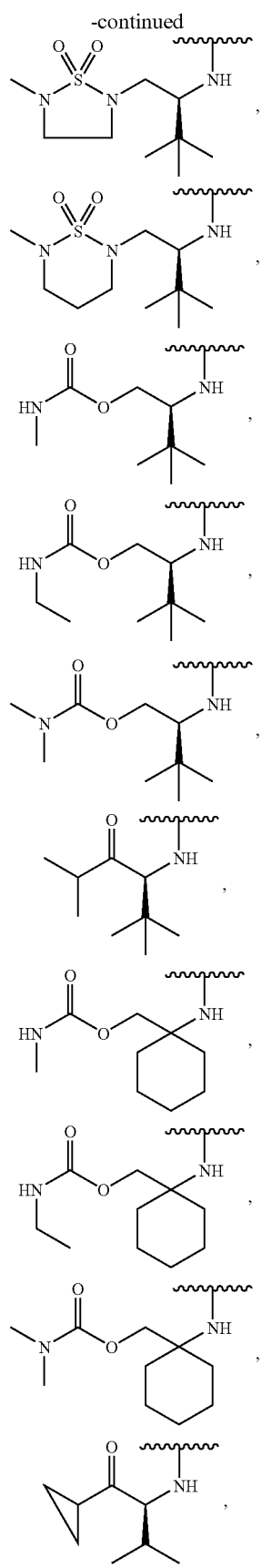

-continued
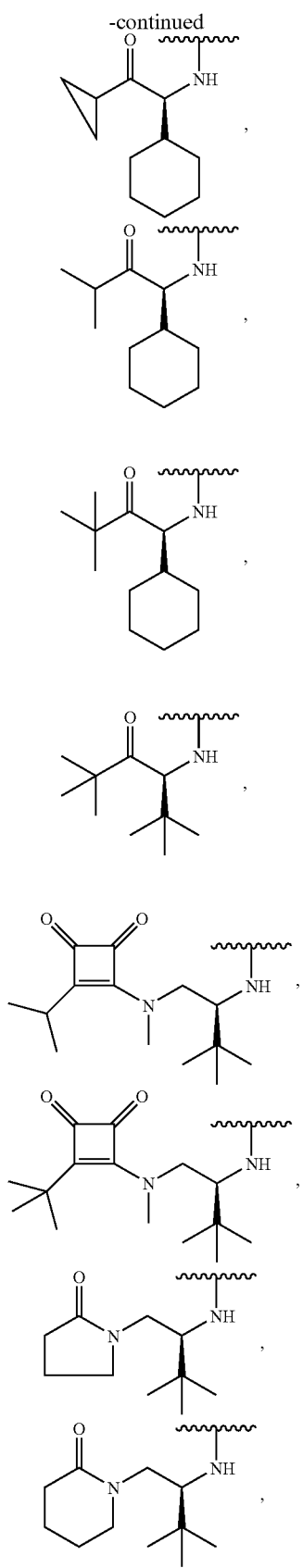
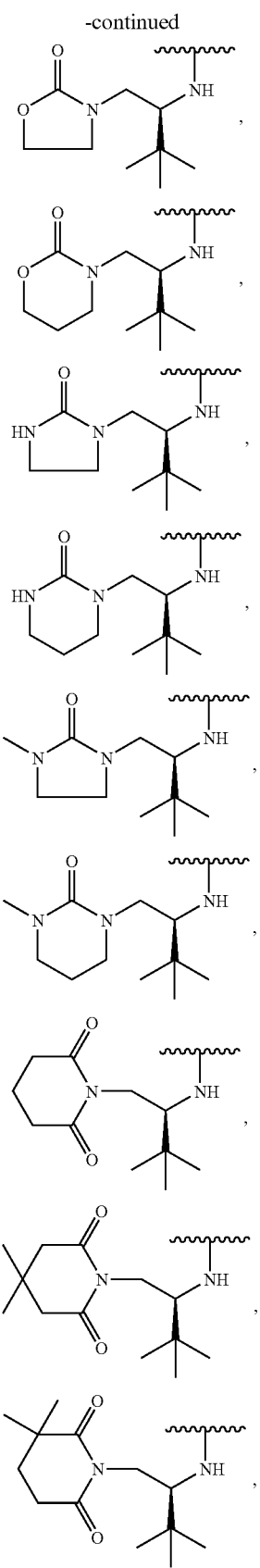

-continued

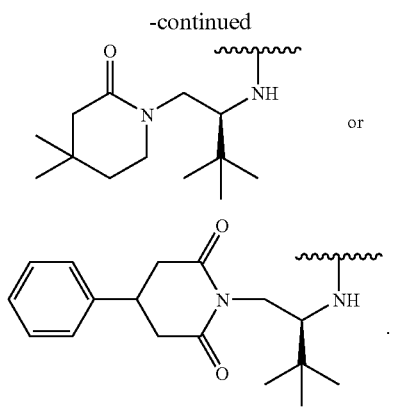

or

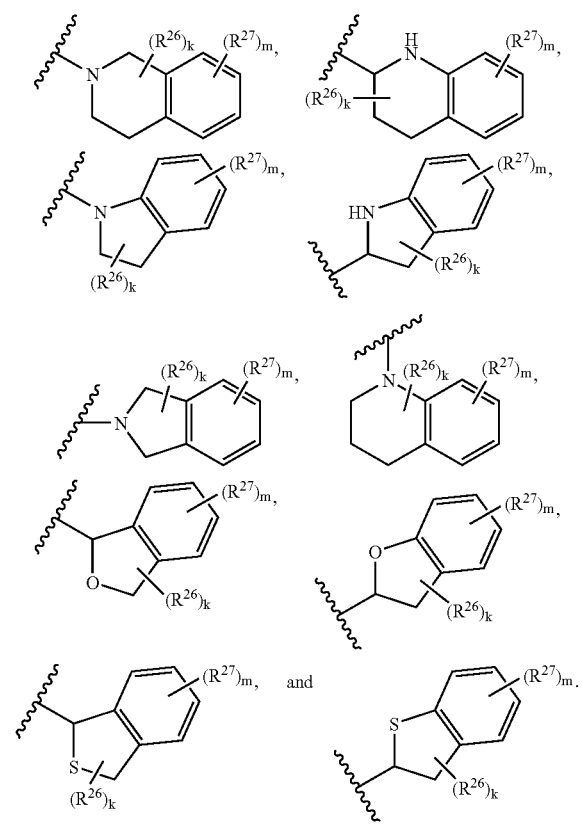

12. The compound of claim 1, wherein Z is selected from the group consisting of the following moieties:

wherein k=0-4, m=0-4, k and m can be the same or different, $R^{26}$ and $R^{27}$ can be the same or different, each being independently selected from the group consisting of hydroxy, alkoxy, aryloxy, thio, alkylthio, arylthio, amino, amido, alkylamino, arylamino, alkylsulfonyl, arylsulfonyl, sulfonamido, alkyl, aryl, heteroaryl, alkylsulfonamido, arylsulfonamido, keto, carboxy, carbalkoxy, carboxamido, alkoxycarbonylamino, alkoxycarbonyloxy, alkylureido, arylureido, halo, cyano, and nitro.

13. The compound of claim 12, wherein Z is selected from the group consisting of the moieties:

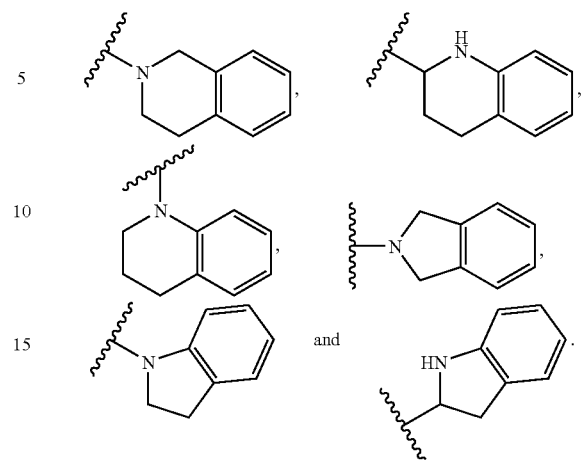

14. The compound of claim 13, wherein Z is selected from the group consisting of:

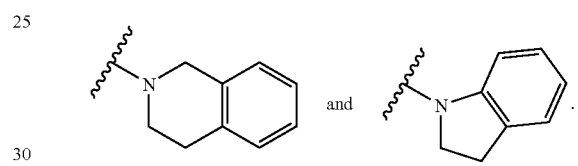

15. The compound of claim 1, wherein $R^1$ is $NH_2$ or $NHR^{14}$, where $R^{14}$ is selected from the group consisting of:

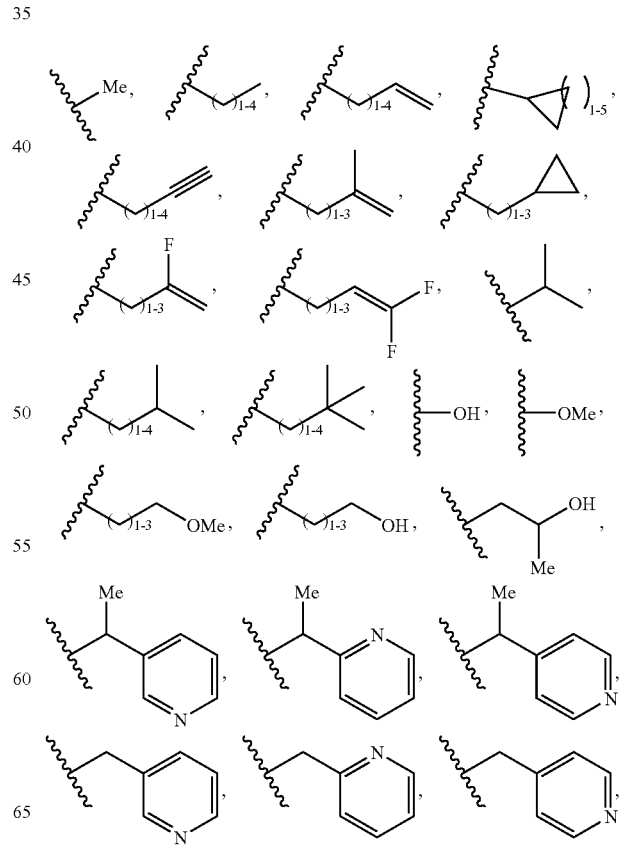

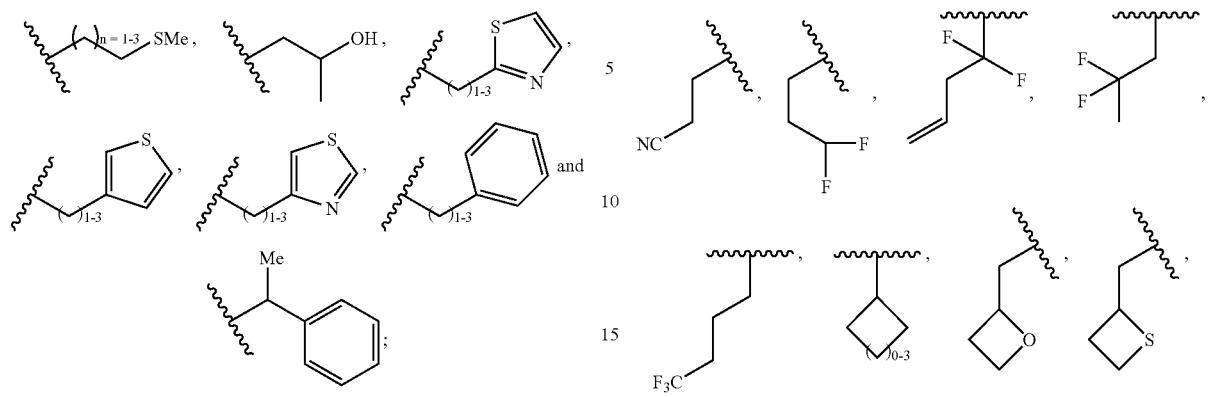
R² is selected from the group consisting of the following moieties:
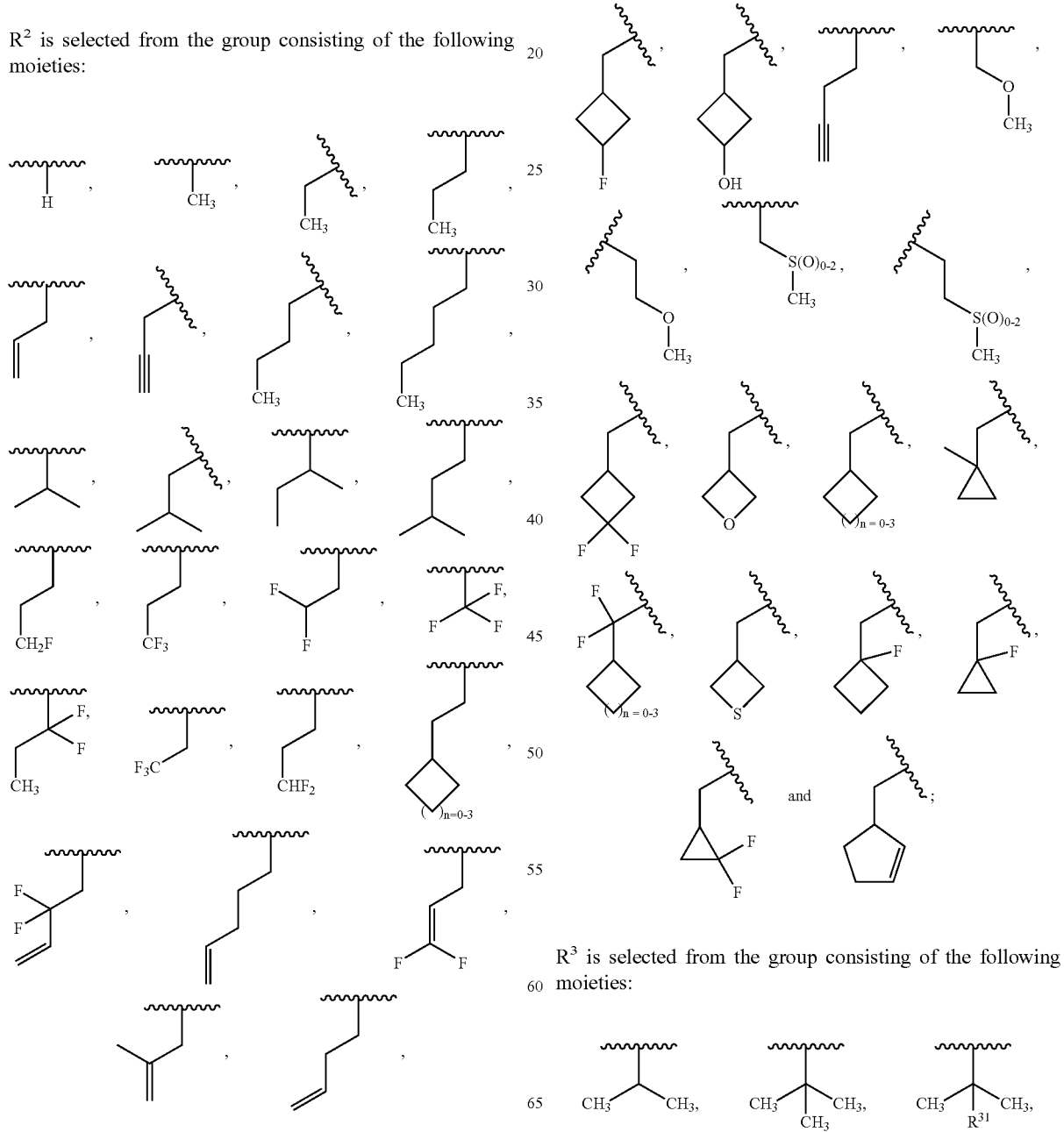
R³ is selected from the group consisting of the following moieties:

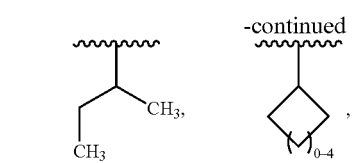 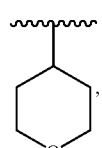 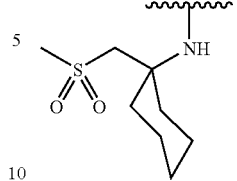
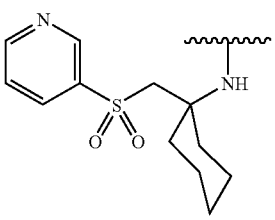
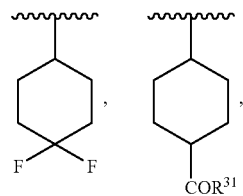 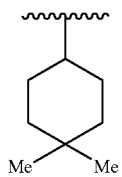
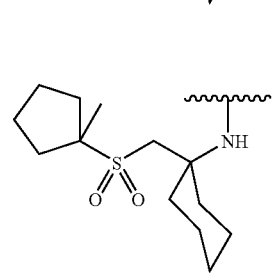
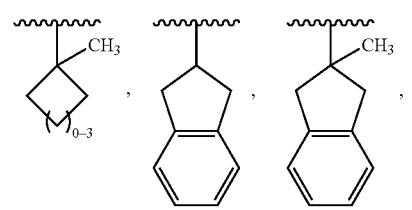 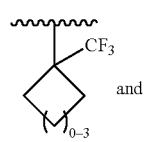
and
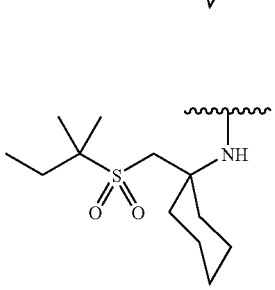
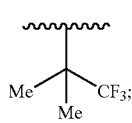
Z is selected from
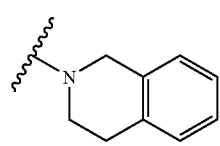 and 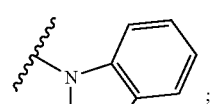 ;
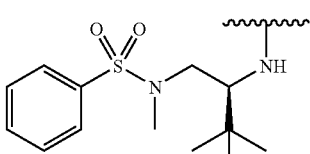
and Y is selected from:
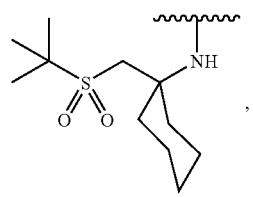 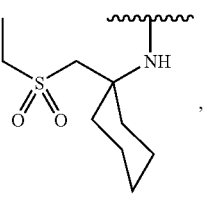
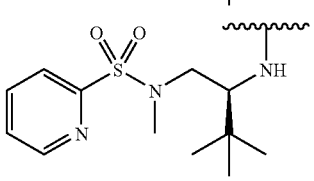
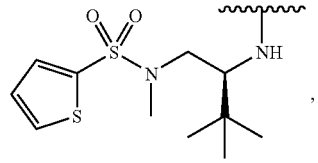
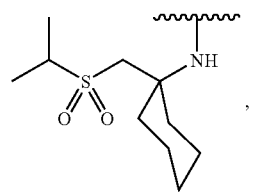 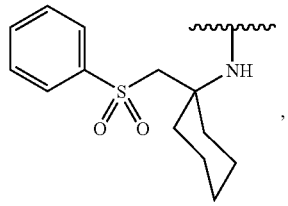
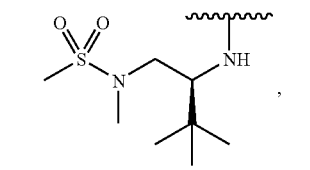
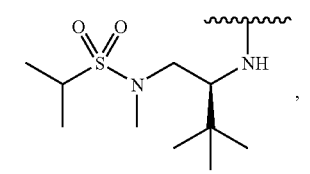

-continued
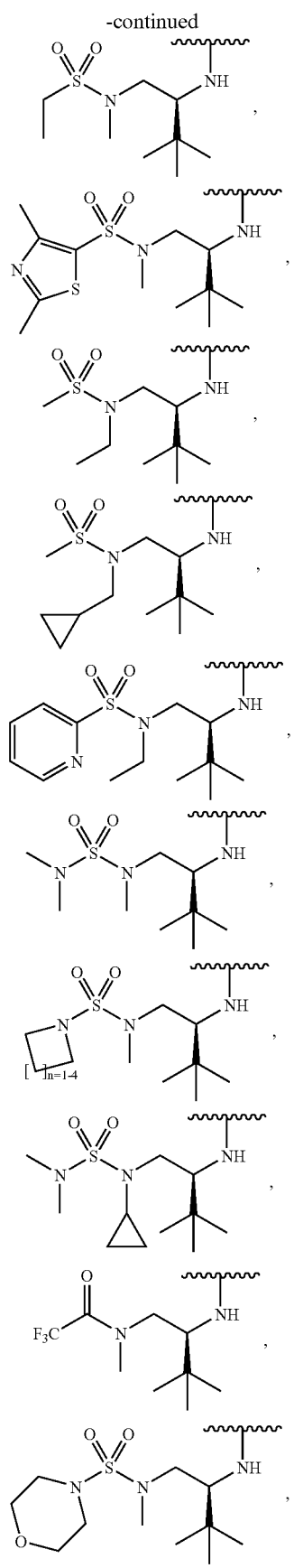
-continued
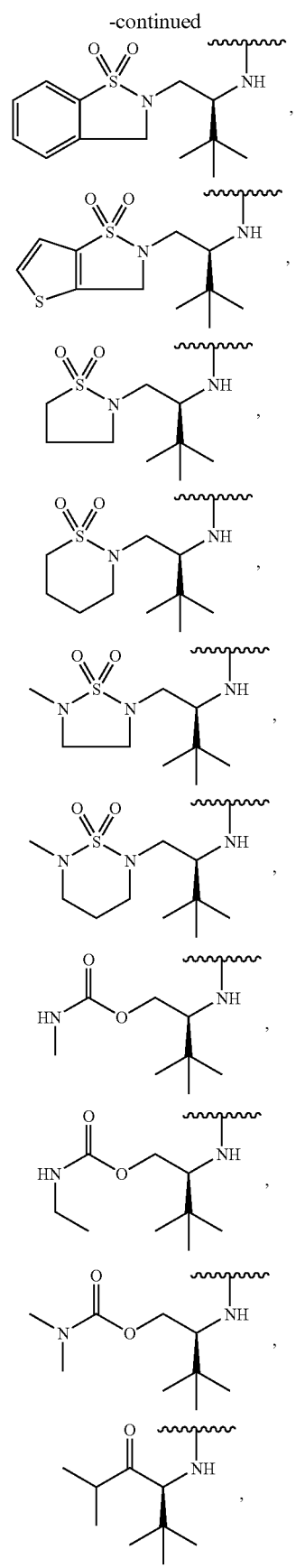

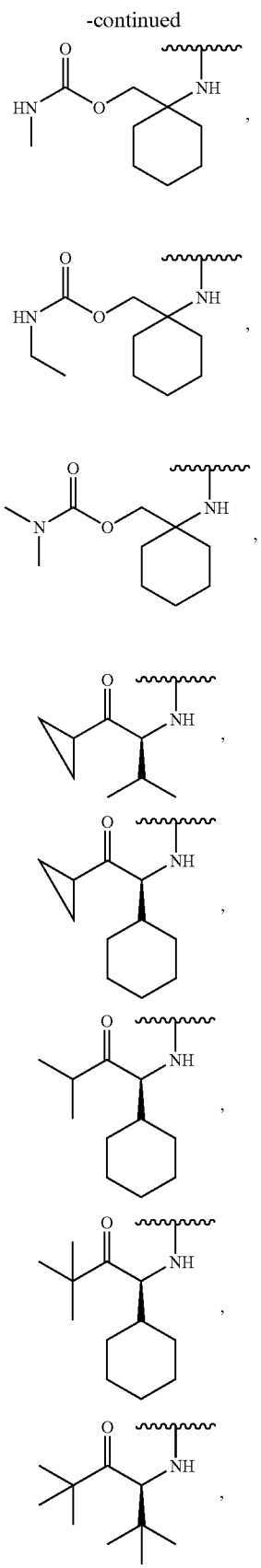
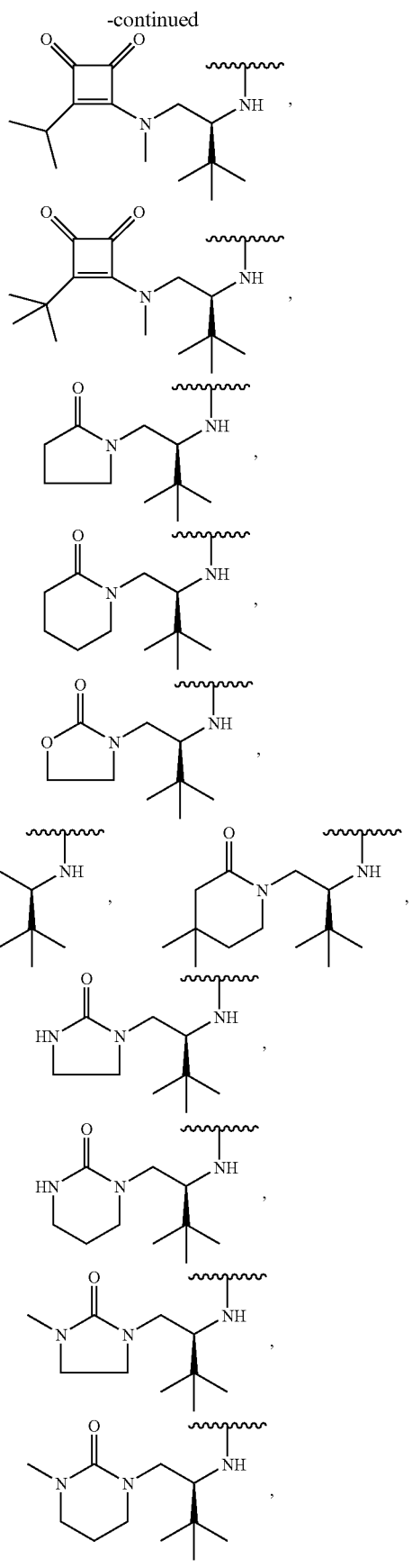

-continued

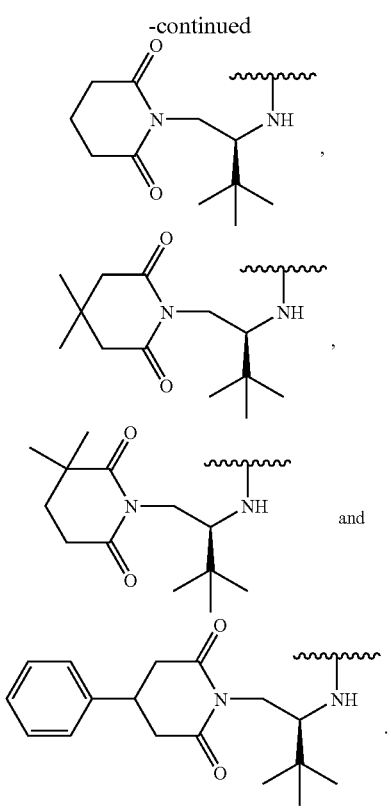

16. A pharmaceutical composition comprising as an active ingredient at least one compound of claim 1.

17. The pharmaceutical composition of claim 16 additionally comprising at least one pharmaceutically acceptable carrier.

18. The pharmaceutical composition of claim 17, additionally containing at least one antiviral agent.

19. The pharmaceutical composition of claim 18, additionally containing at least one interferon.

20. The pharmaceutical composition of claim 19, wherein said at least one antiviral agent is ribavirin and said at least one interferon is α-interferon or pegylated interferon.

21. A compound, or enantiomers, stereoisomers, rotamers, tautomers, and racemates of said compound, or a pharmaceutically acceptable salt or solvate of said compound, said compound being selected from the compounds of structures listed below:

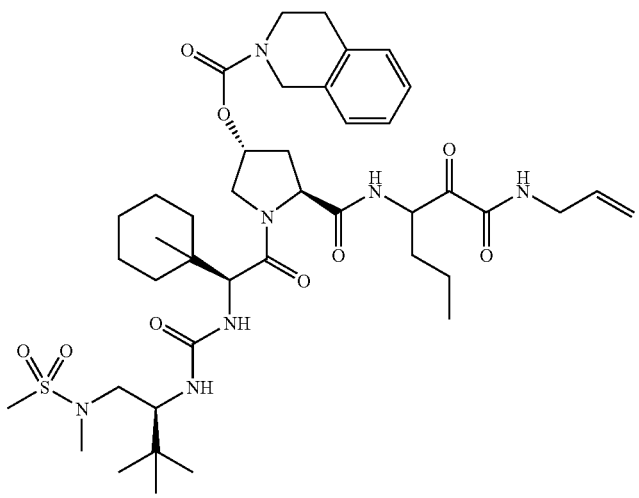

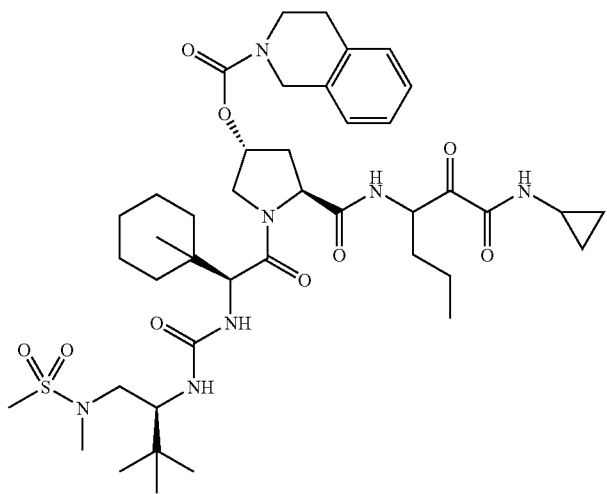
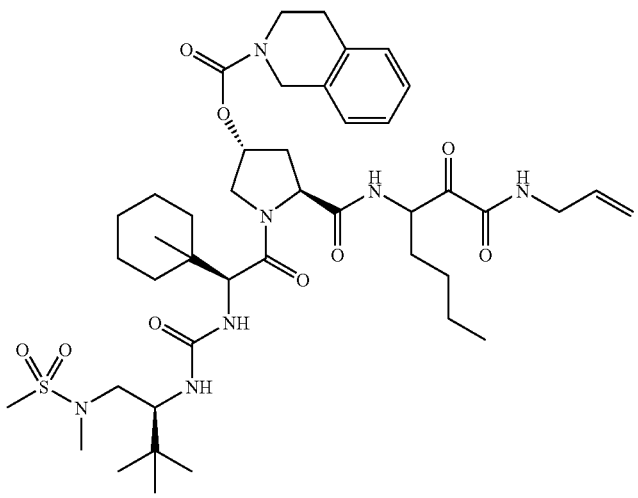
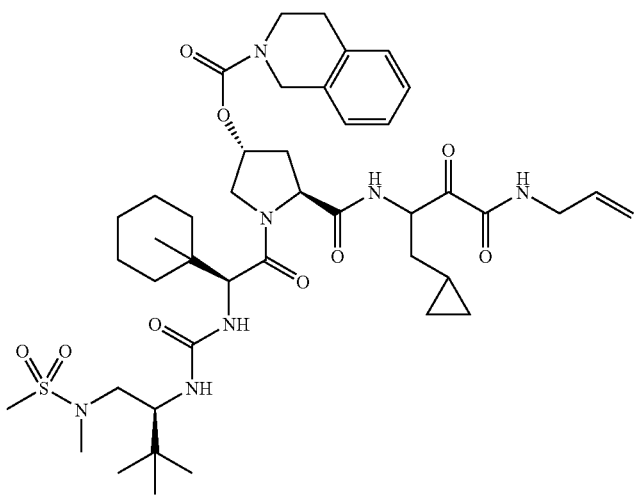

-continued
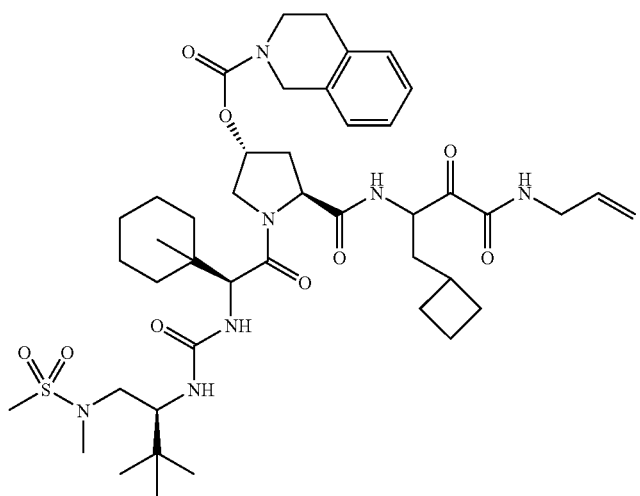
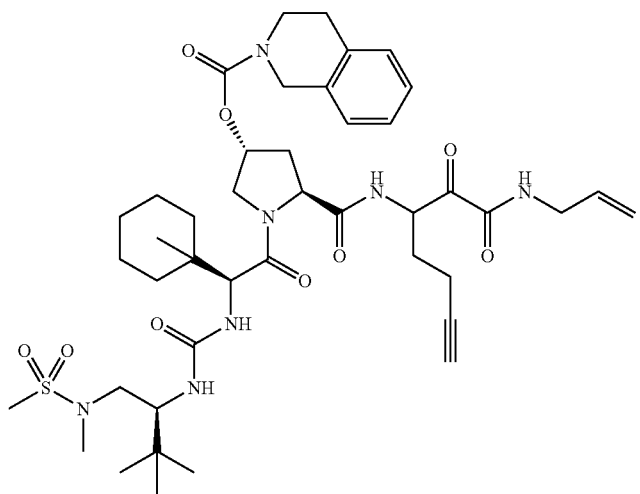
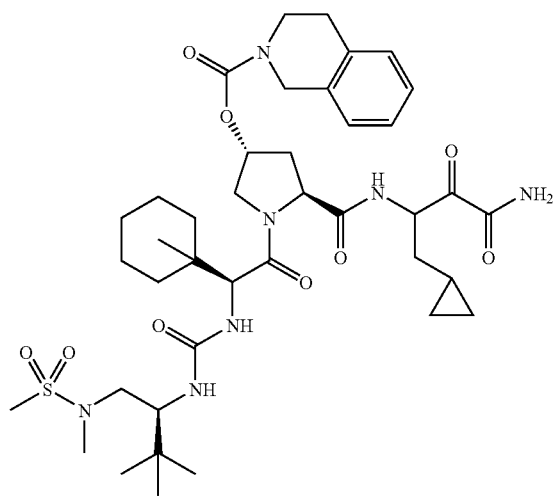

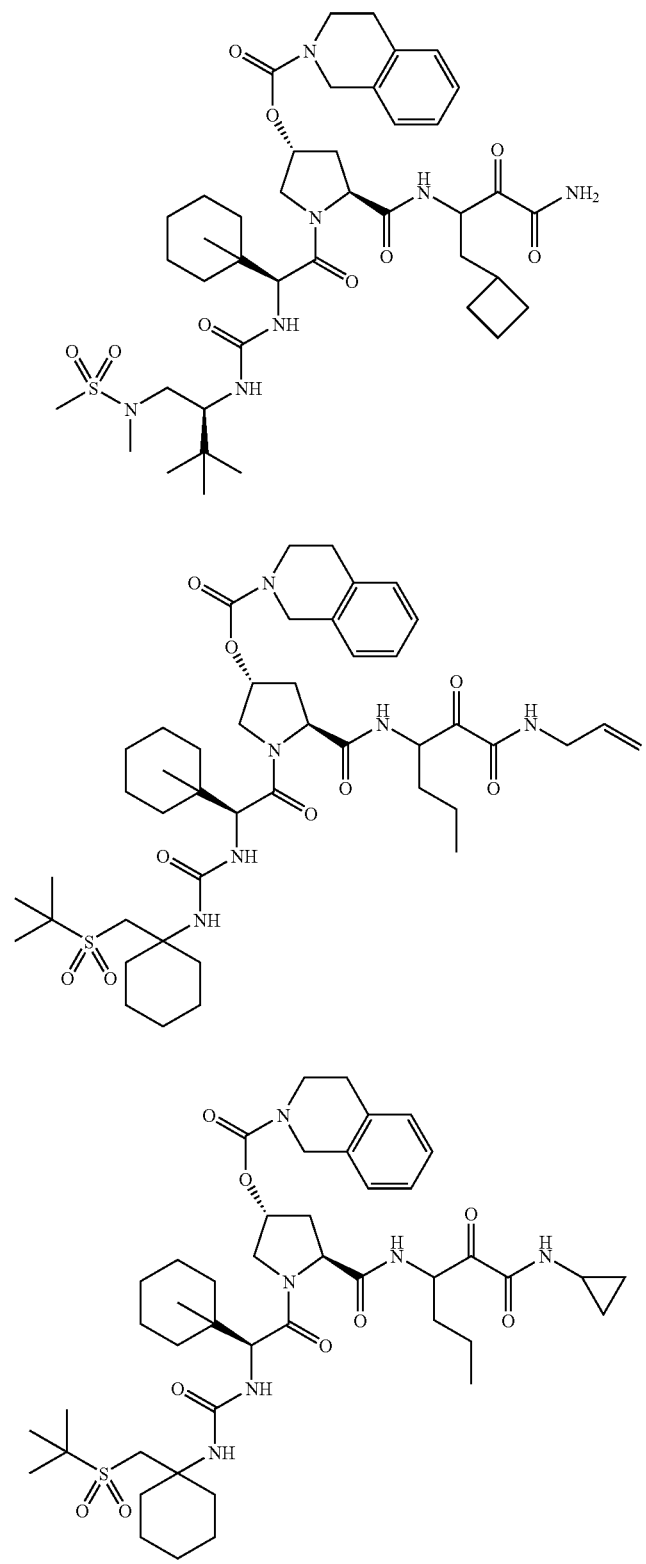

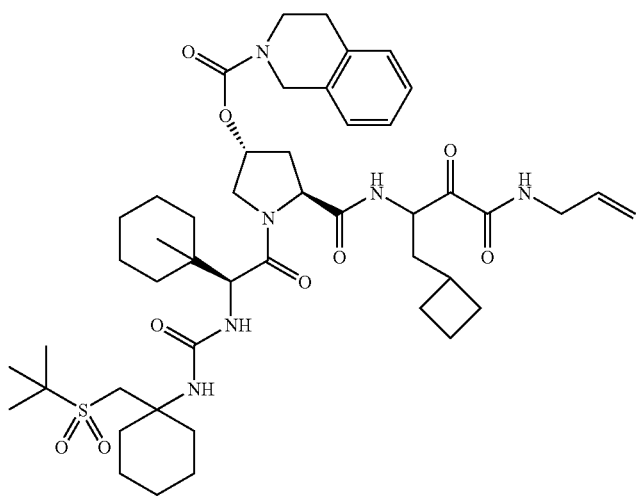
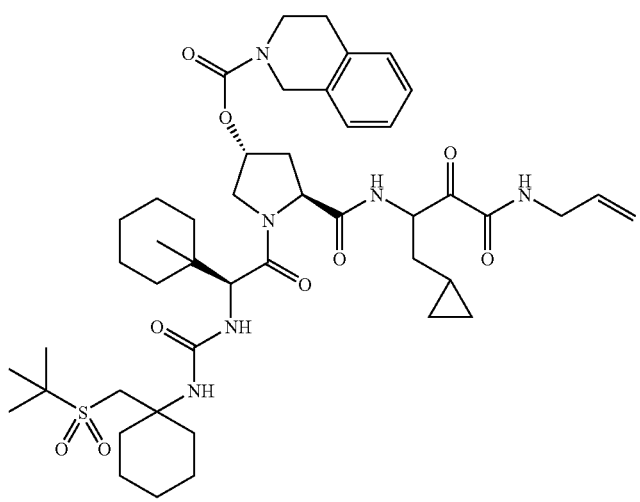
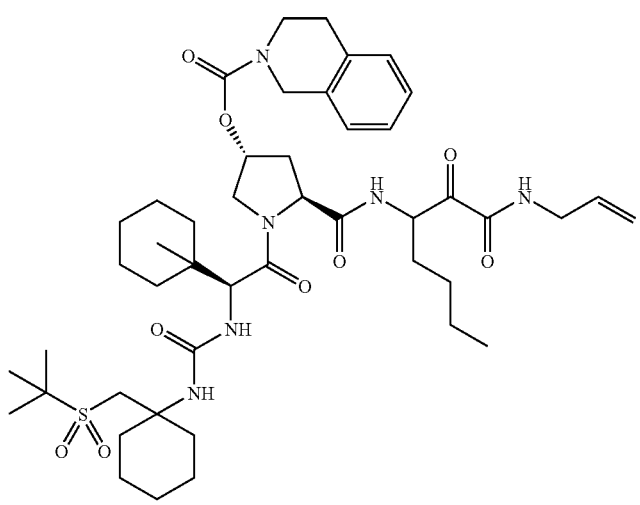

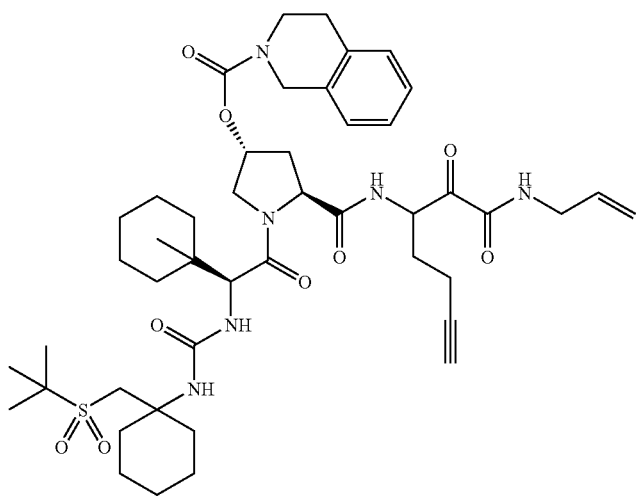
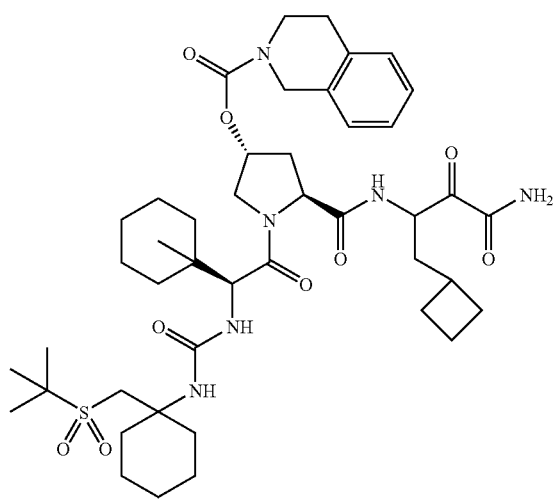
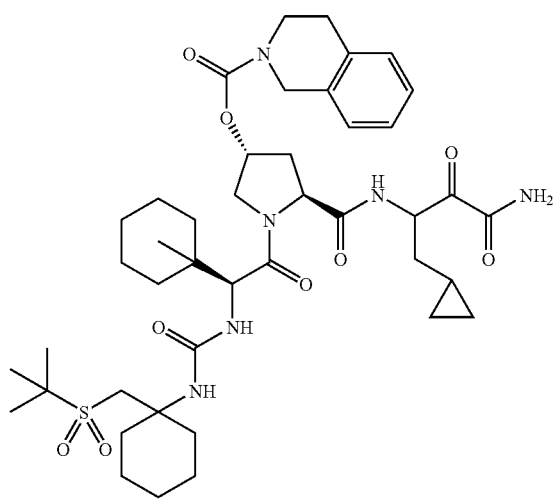

-continued
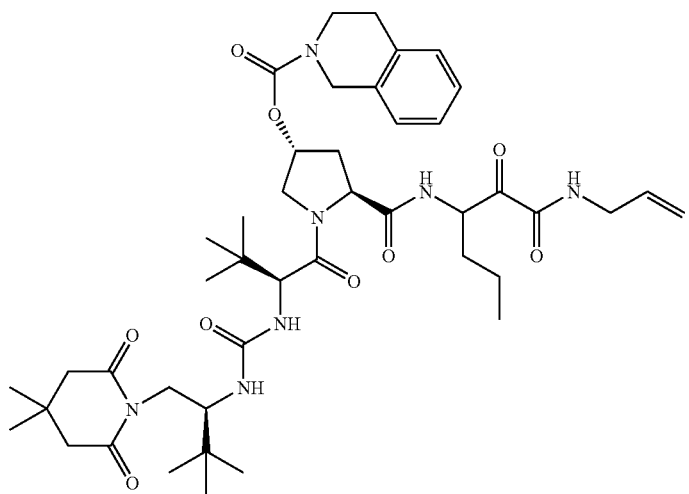
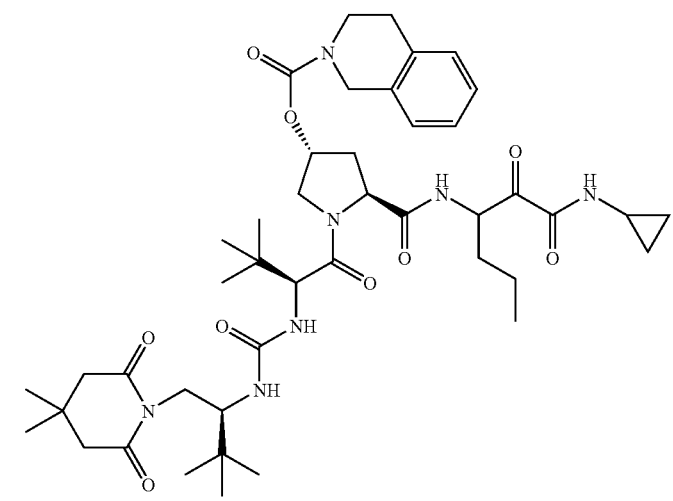
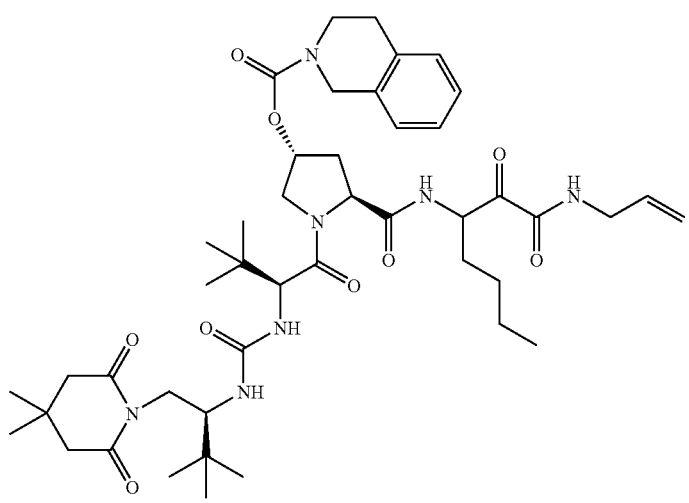

-continued
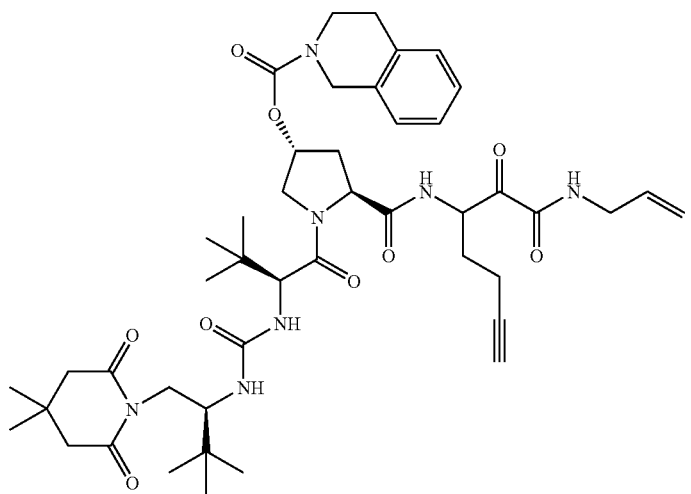
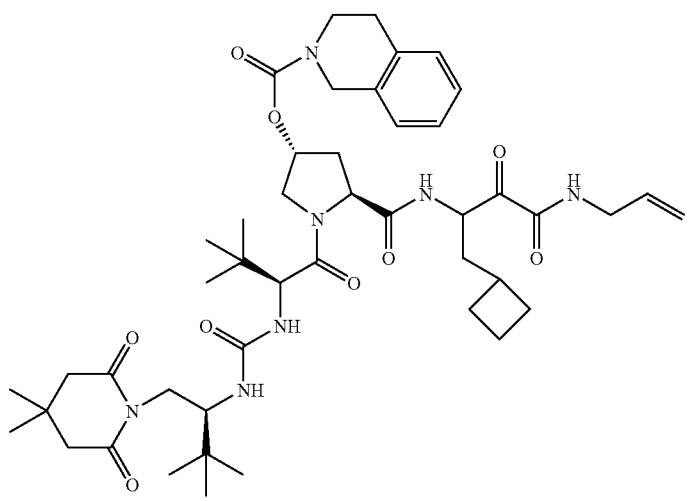
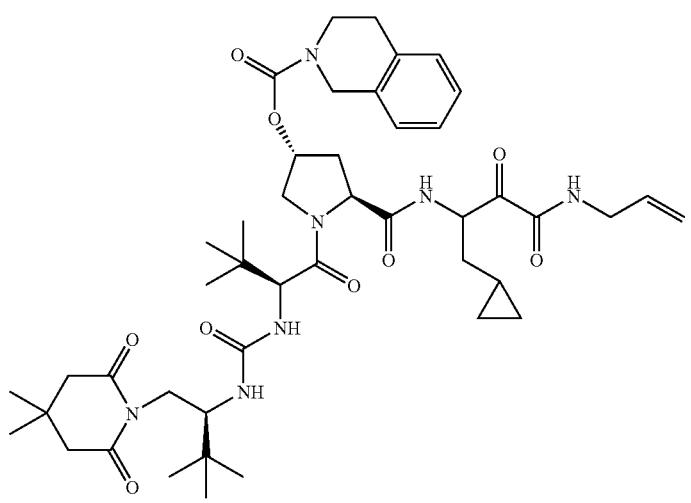

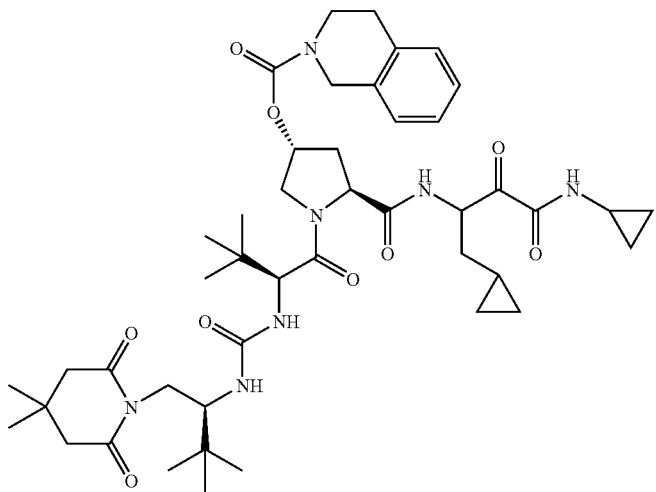
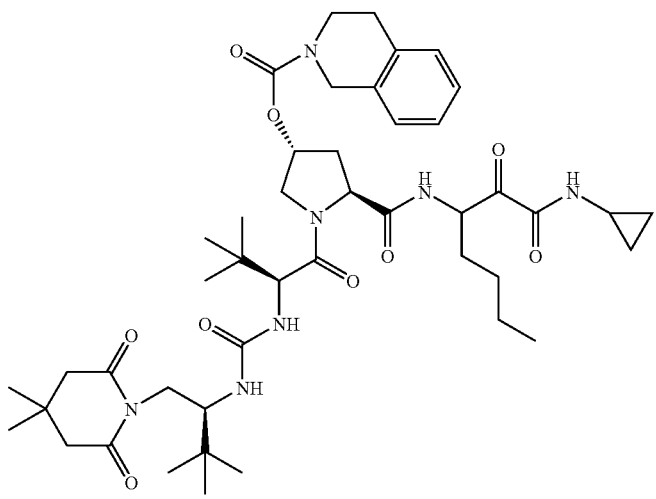
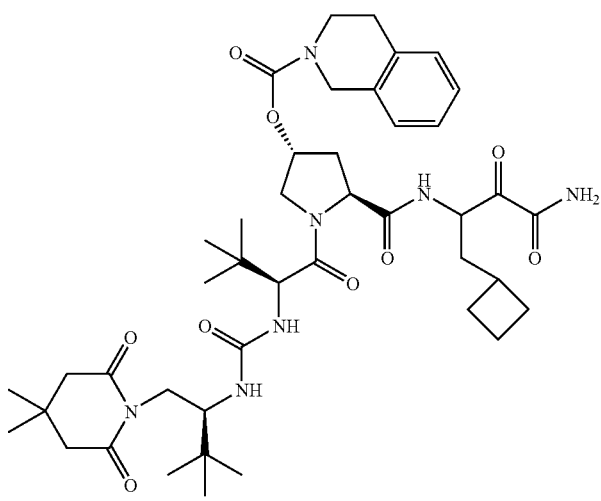

-continued
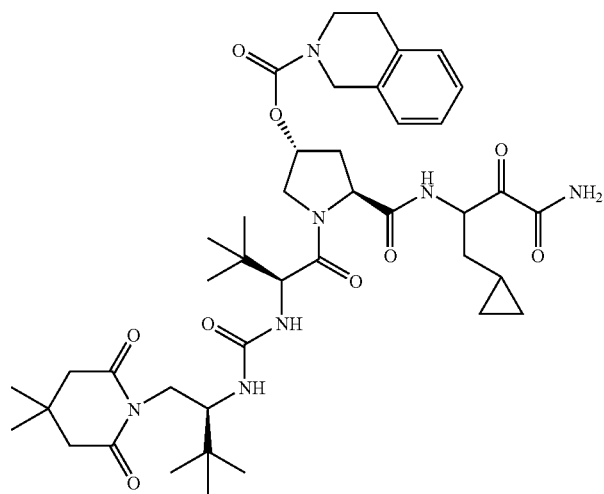
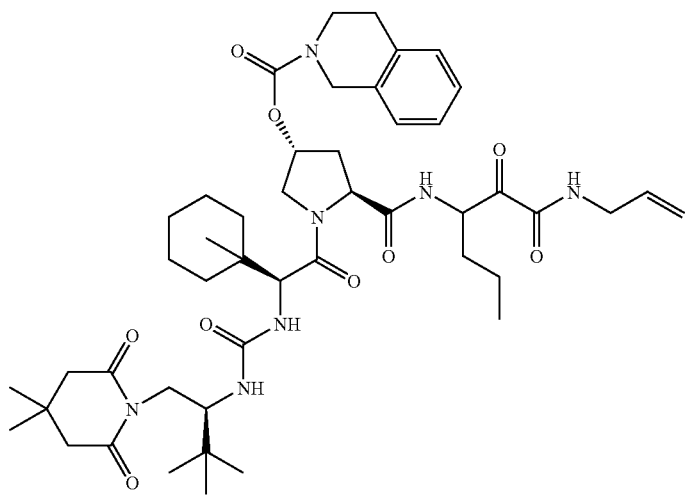
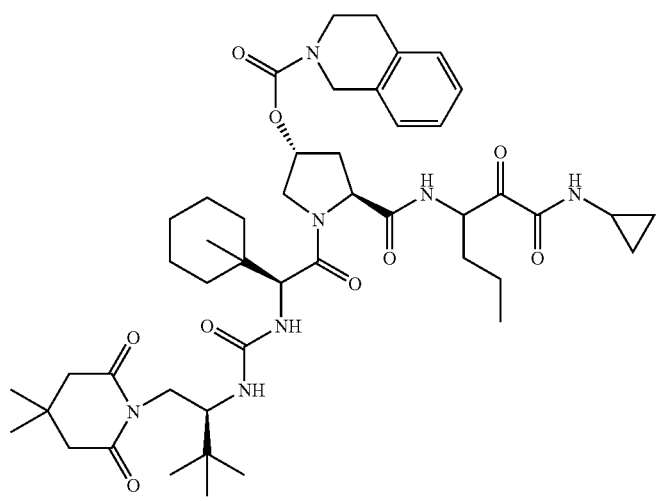

-continued
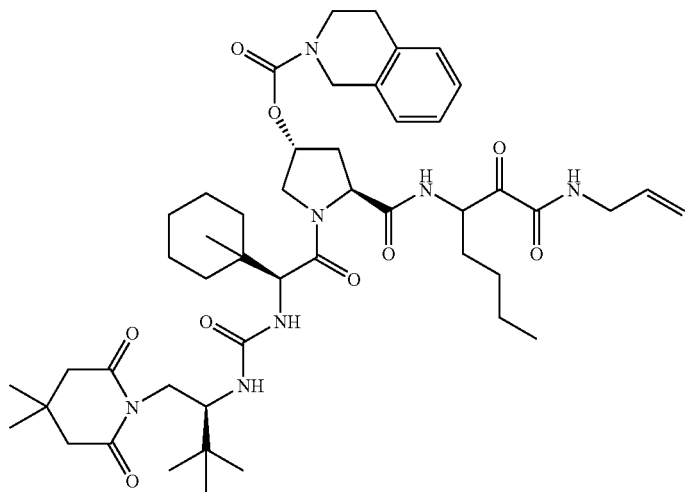
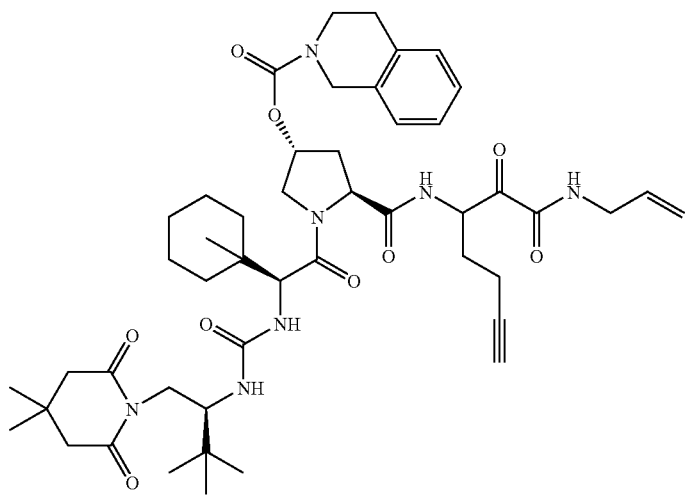
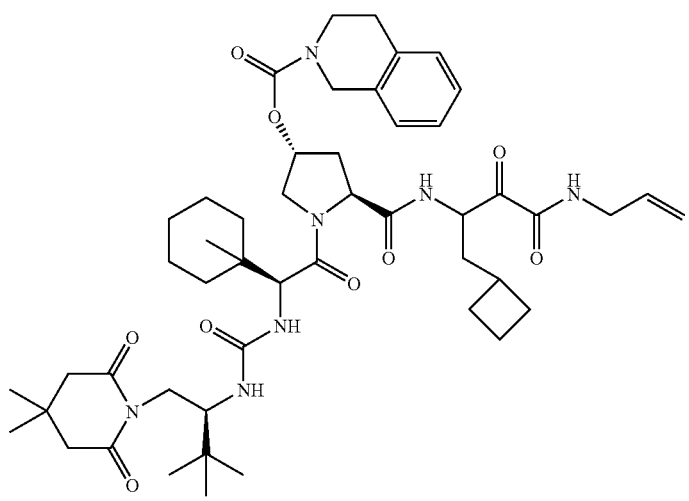

-continued
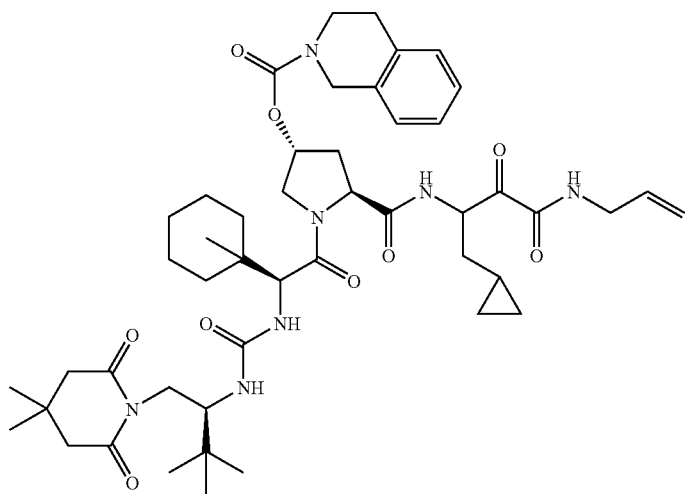
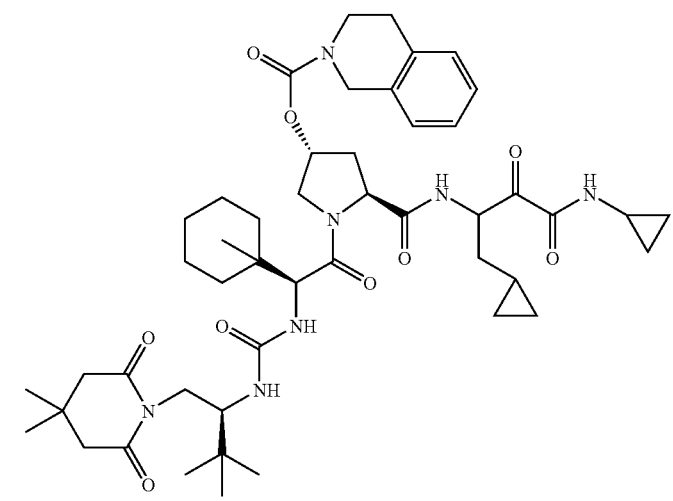
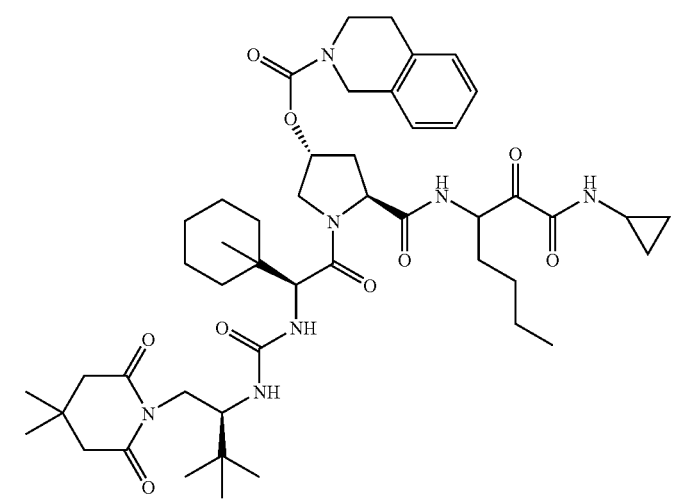

-continued
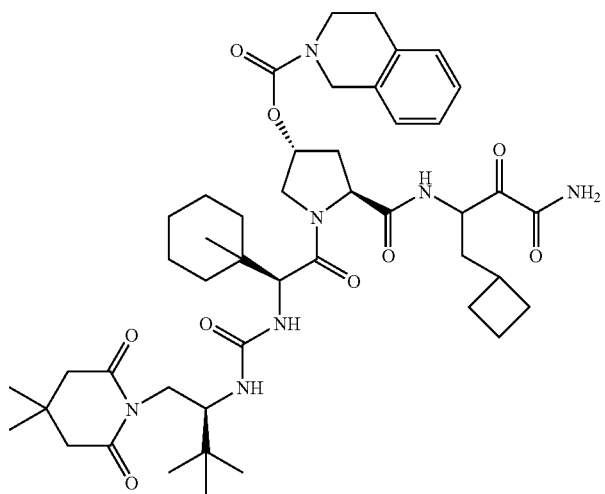
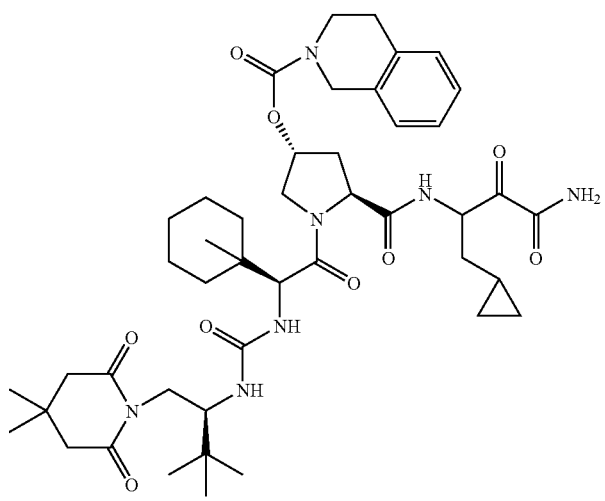
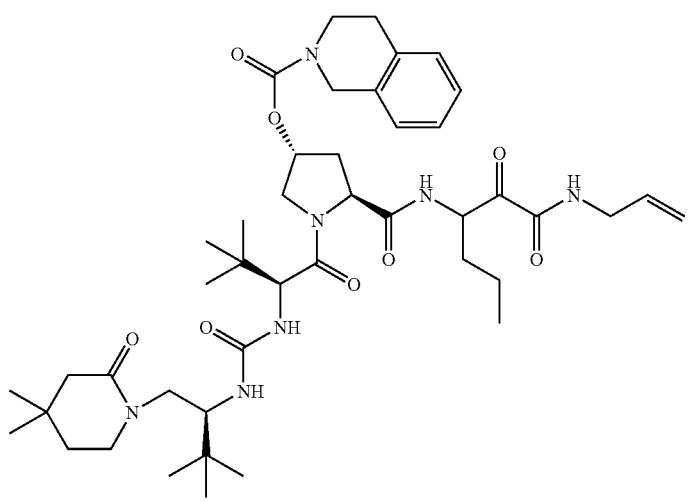

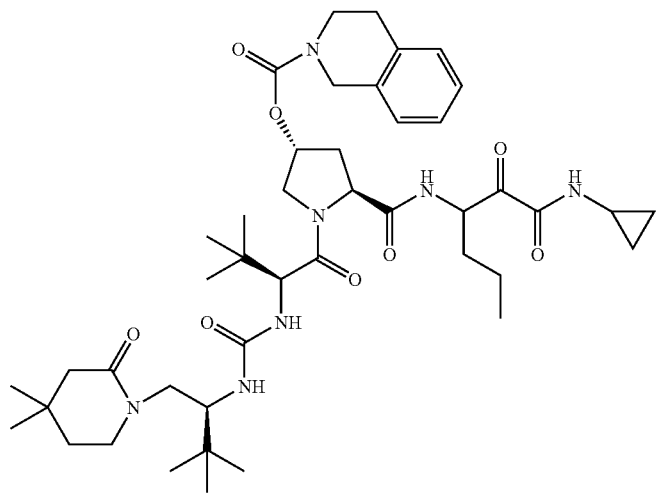
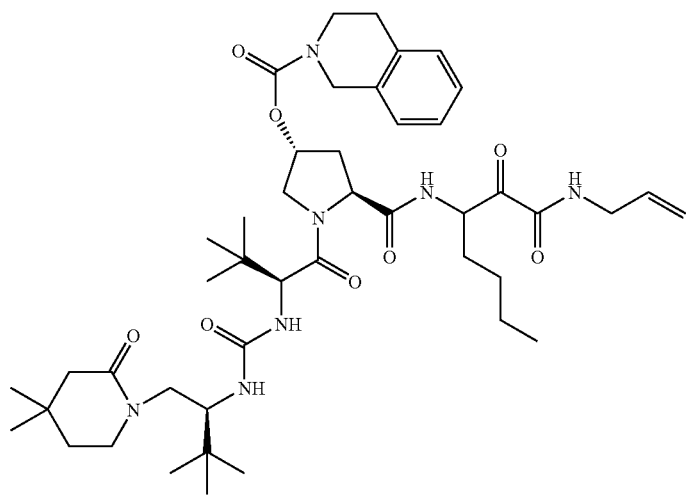
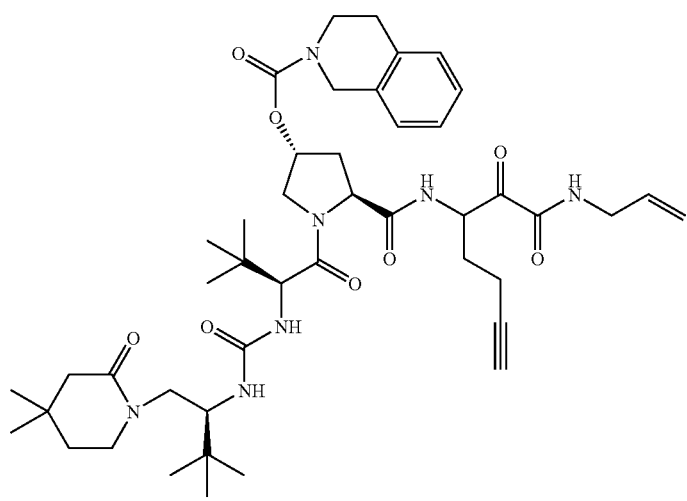

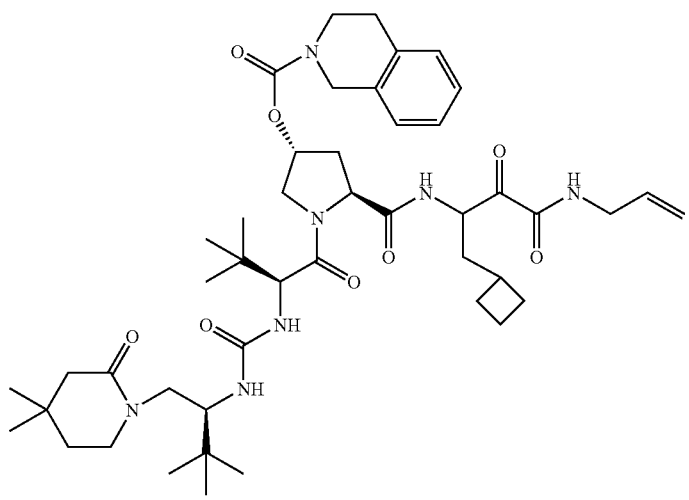
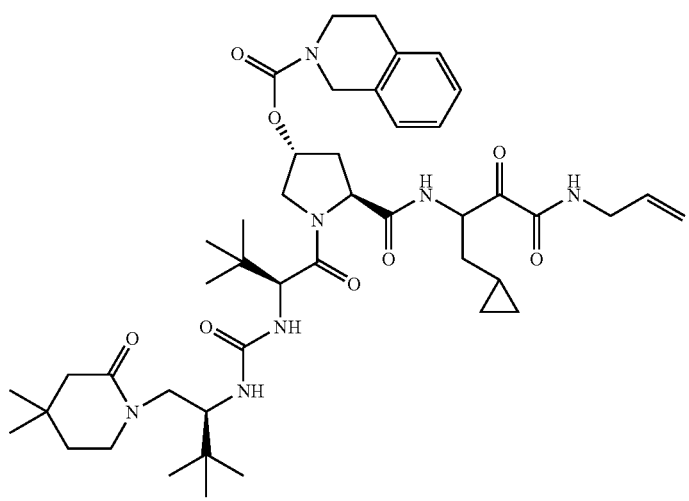
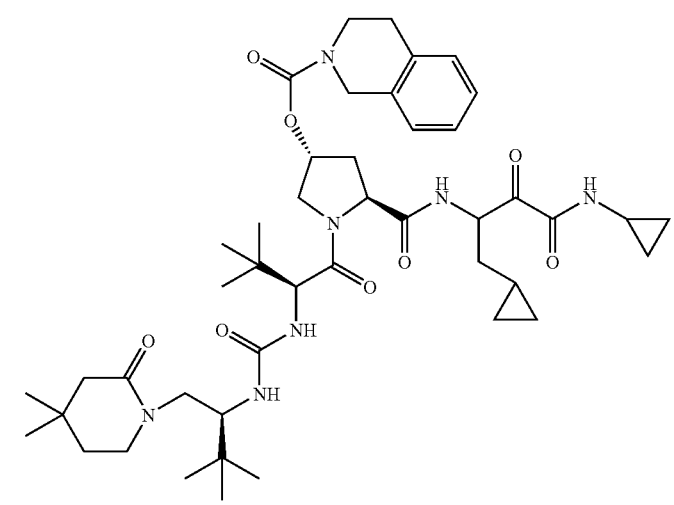

-continued
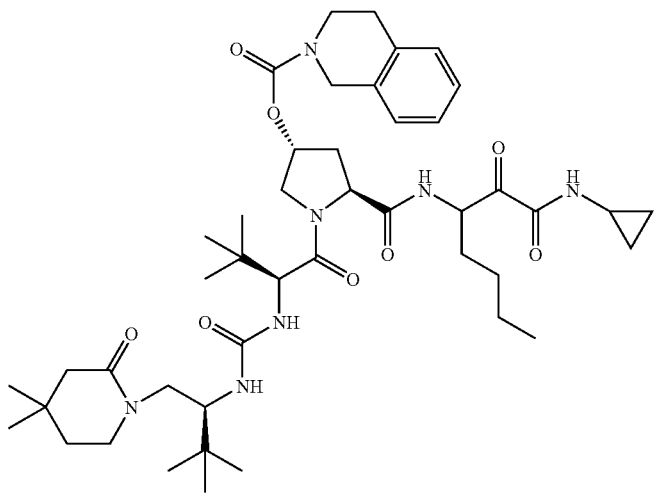
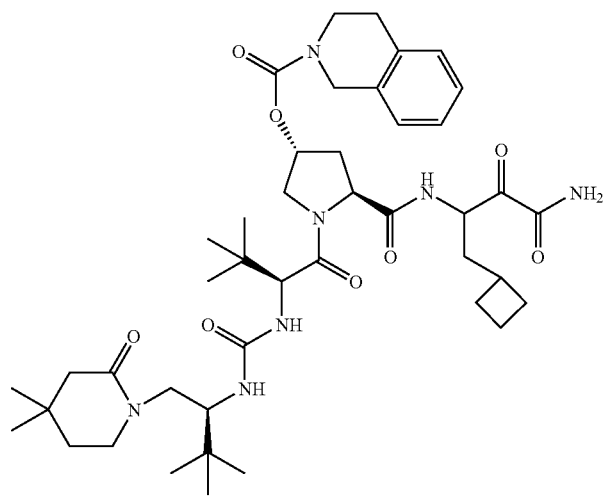
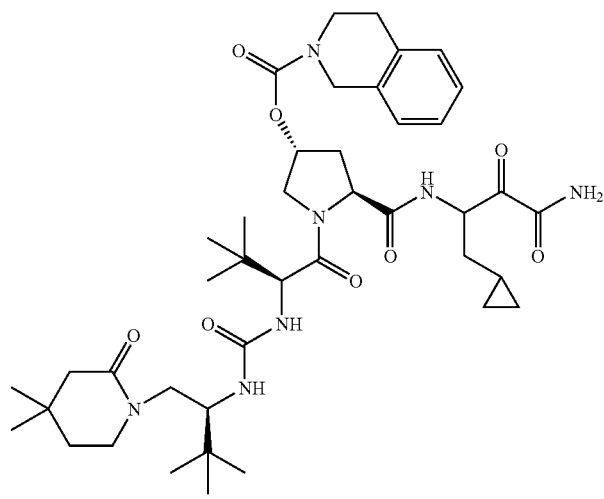

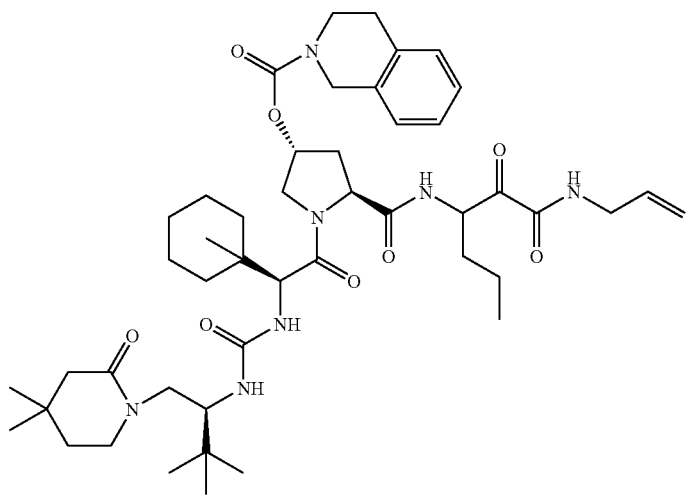
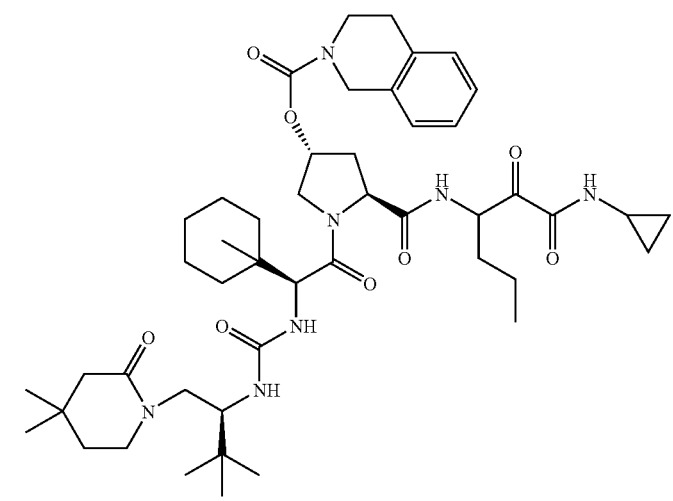
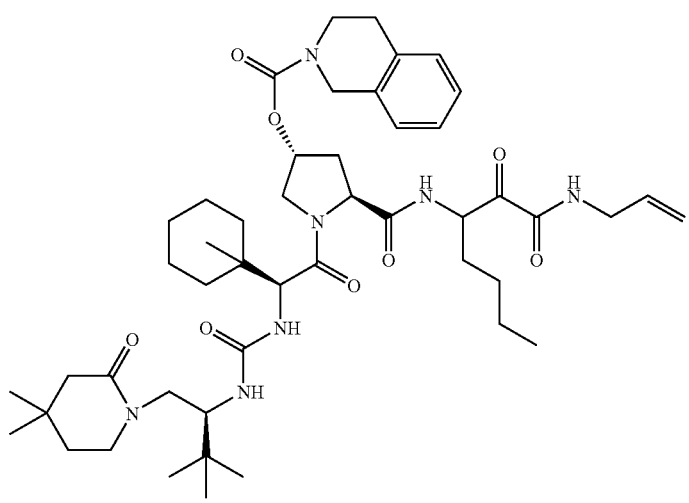

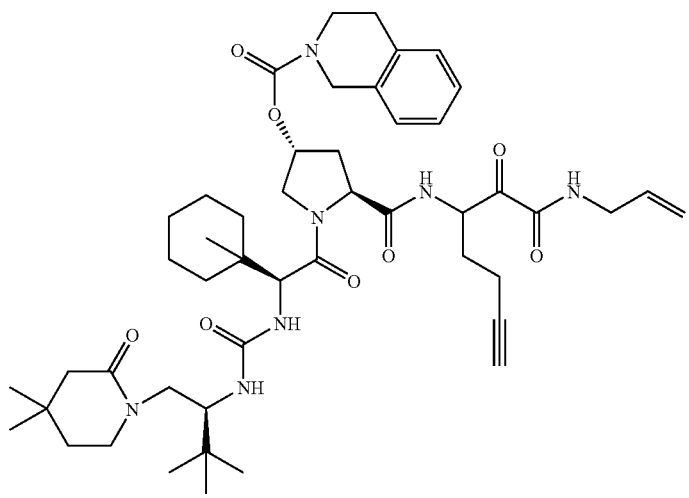
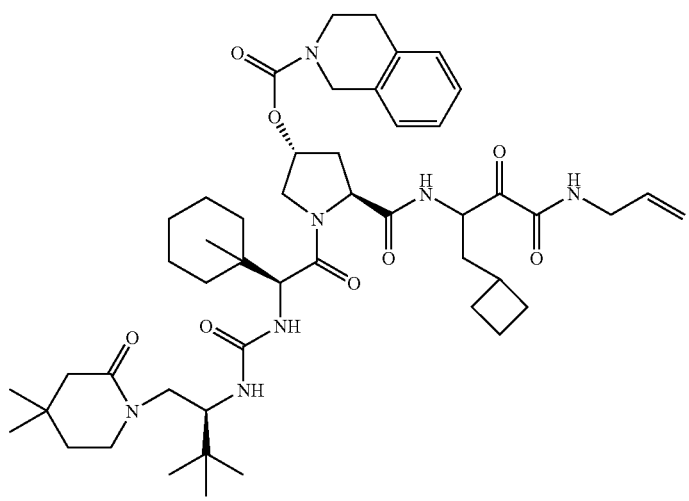
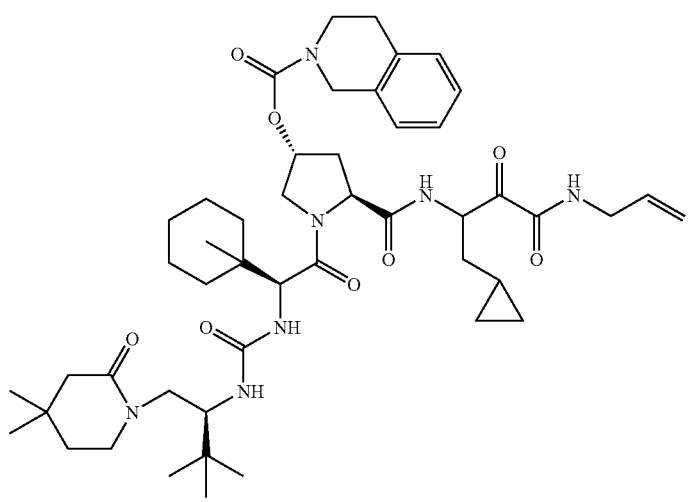

-continued
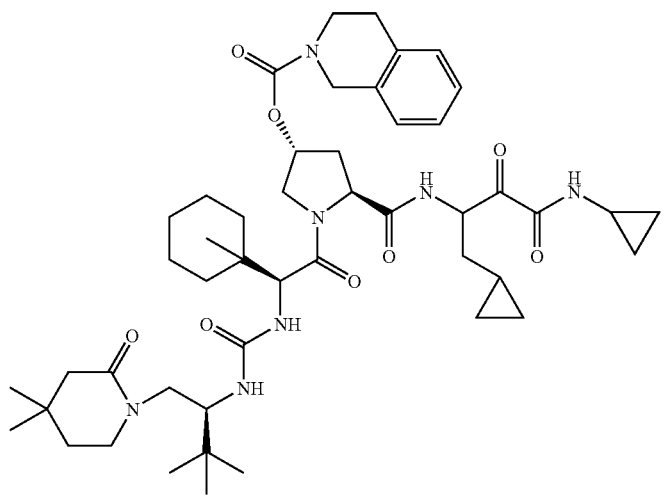
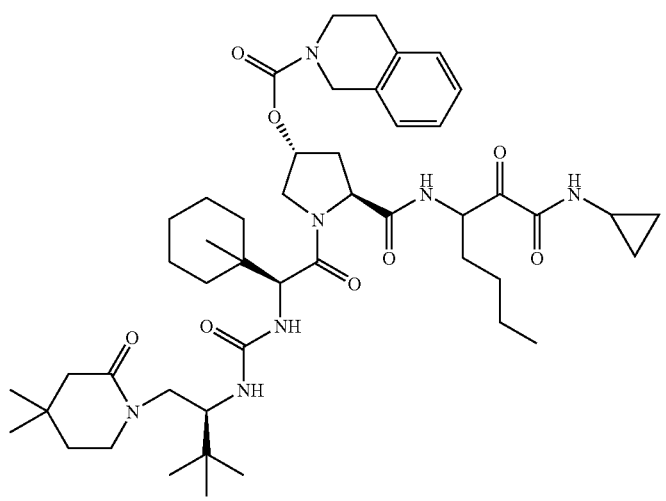
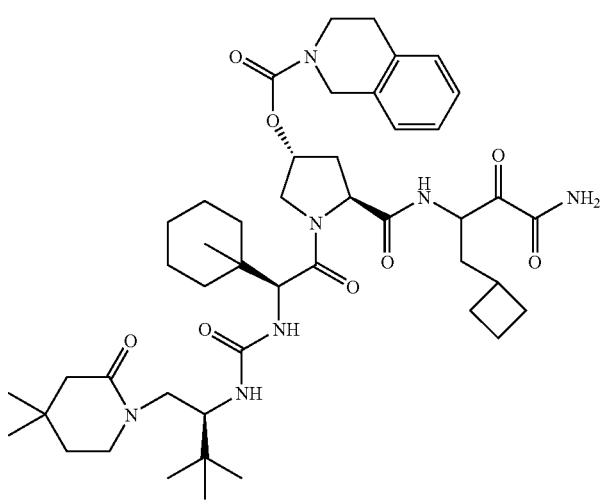

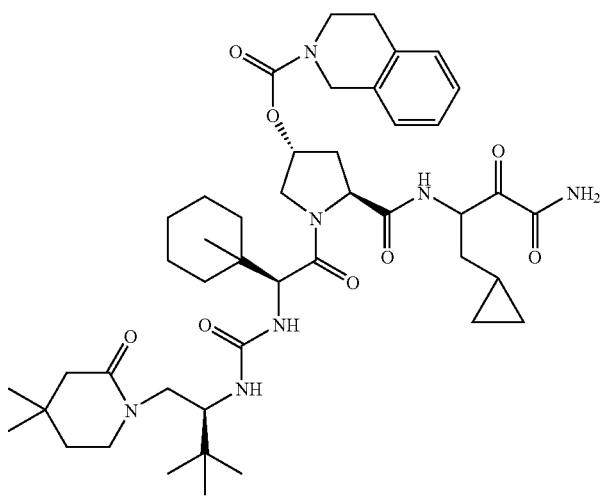
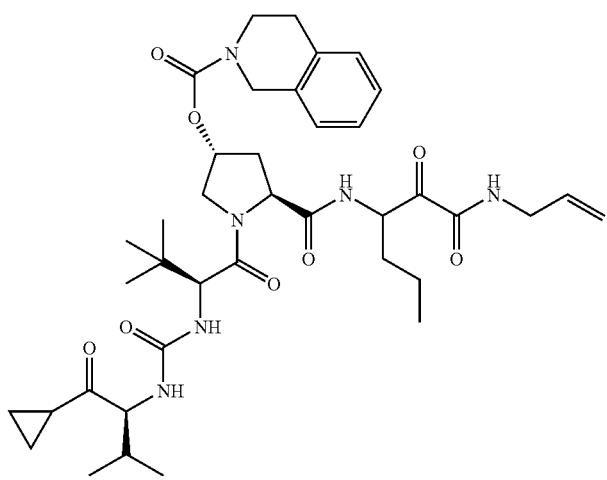
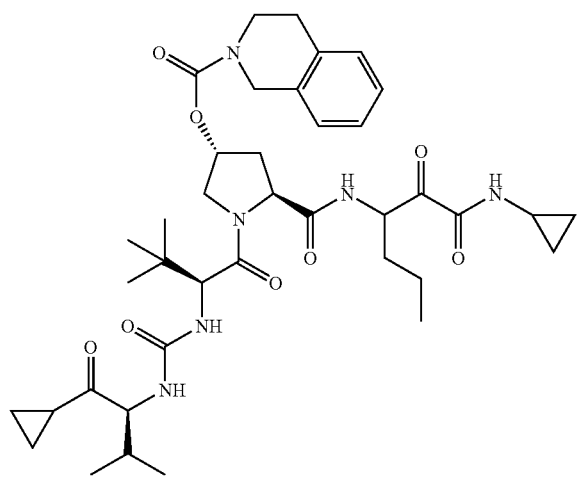

-continued
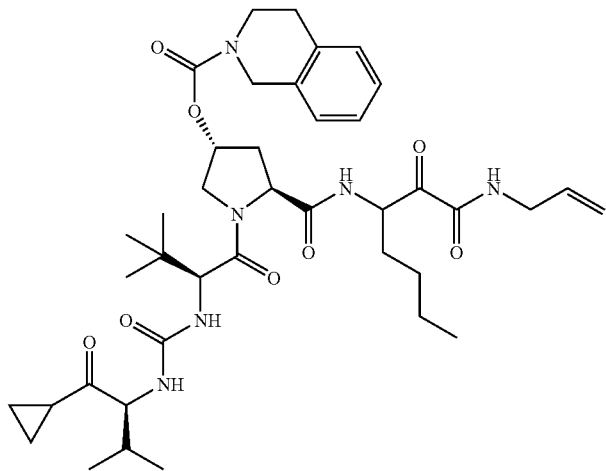
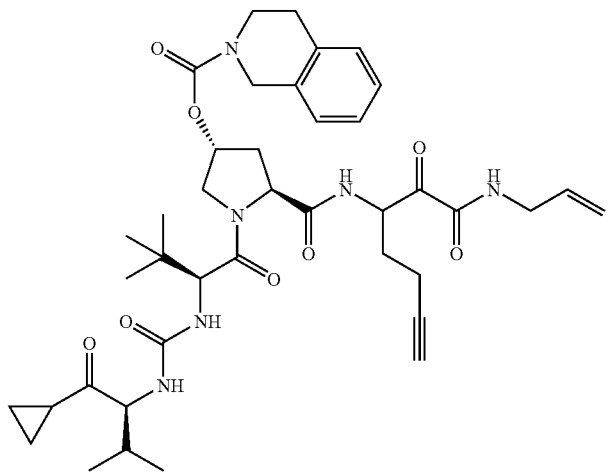
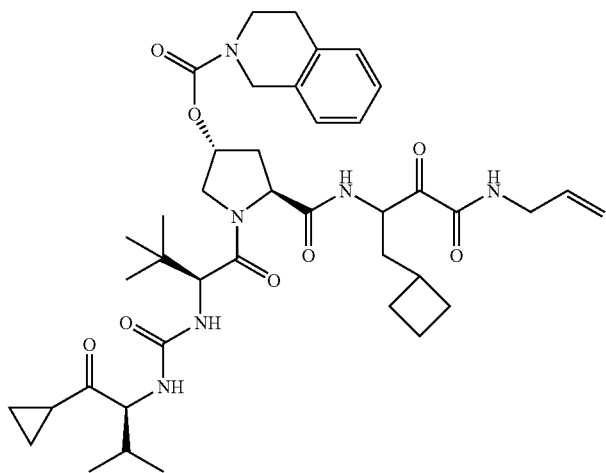

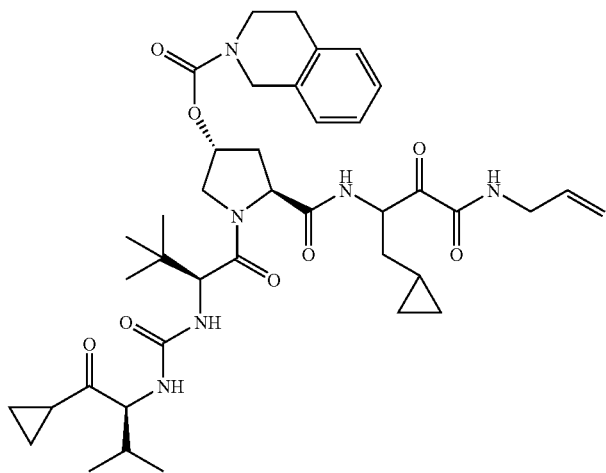
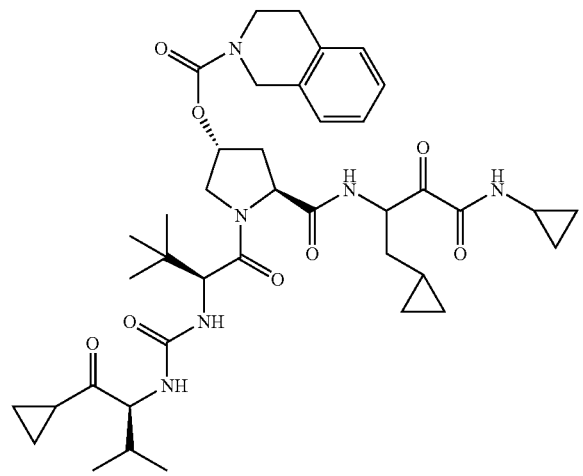
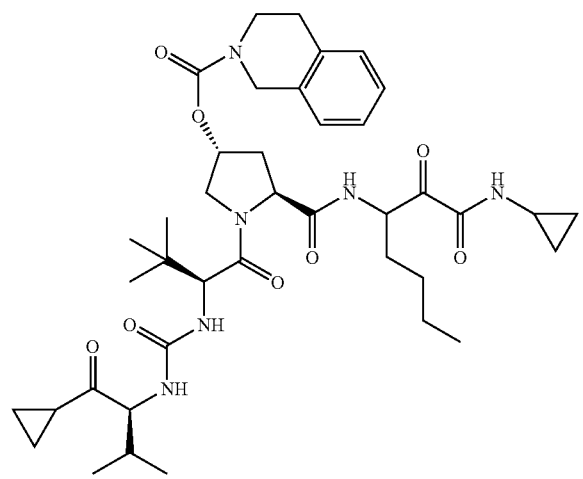

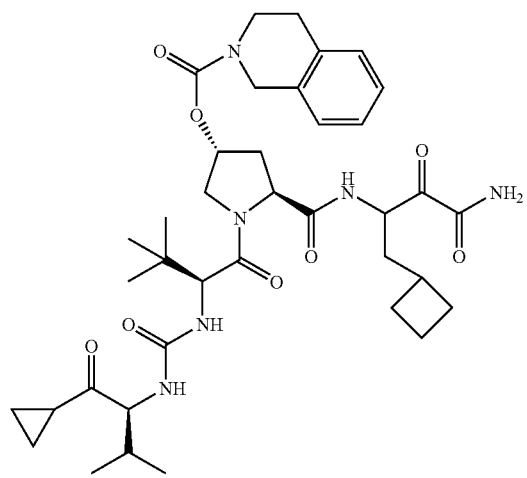
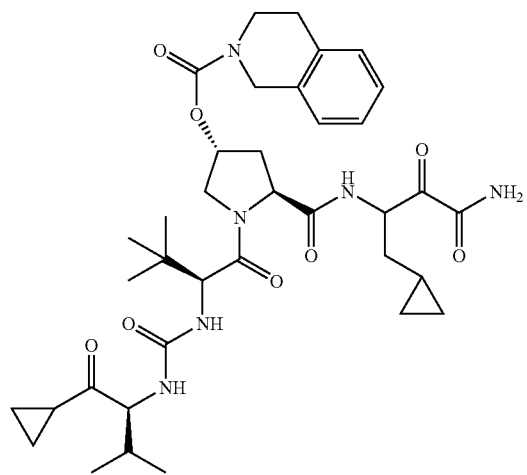
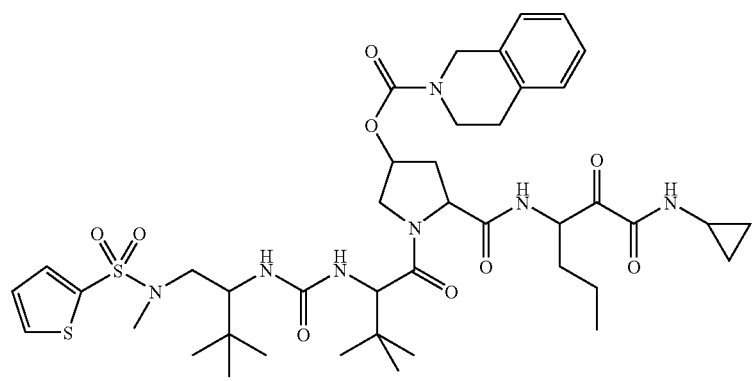

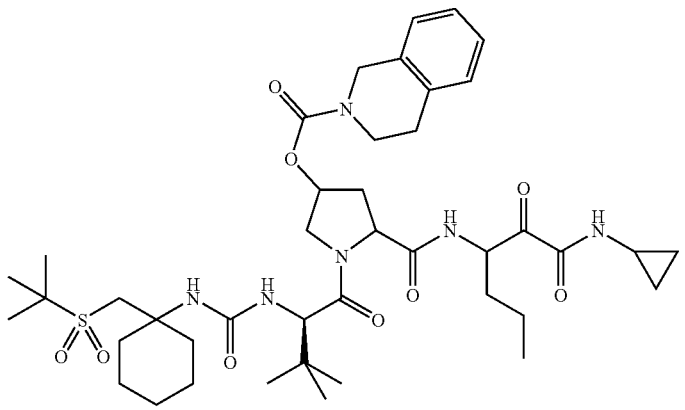
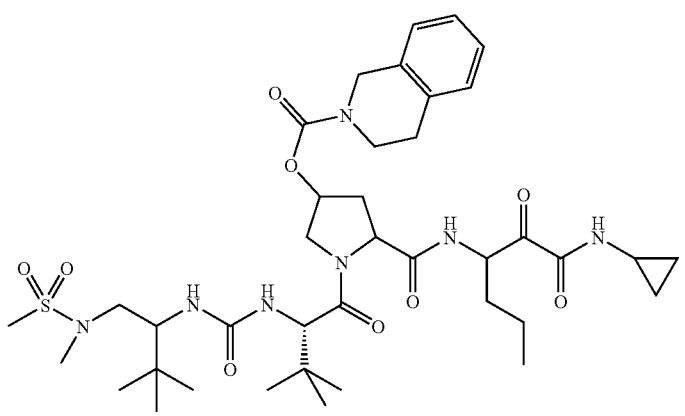
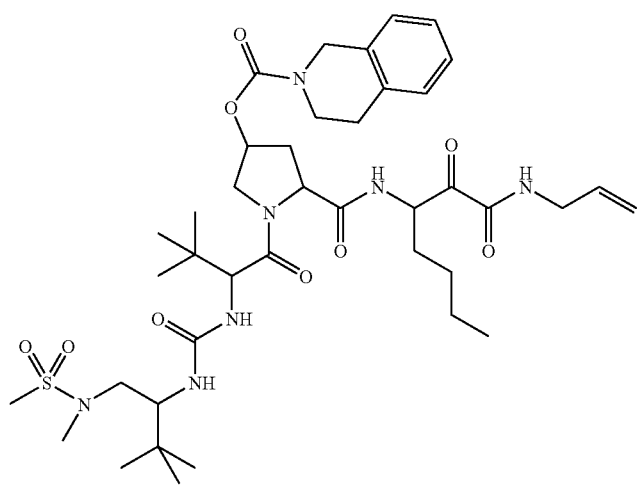

-continued
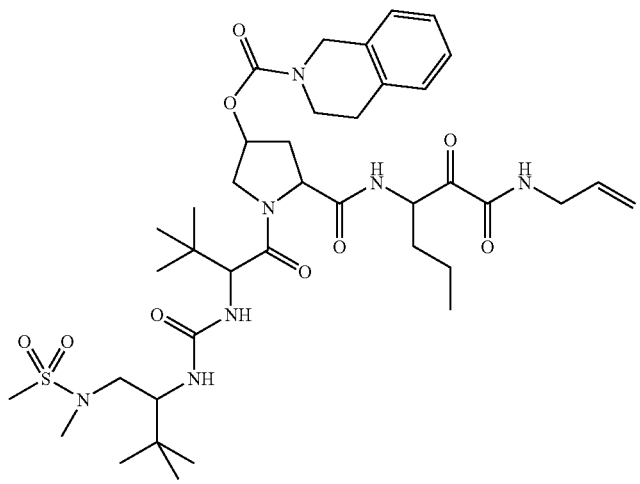
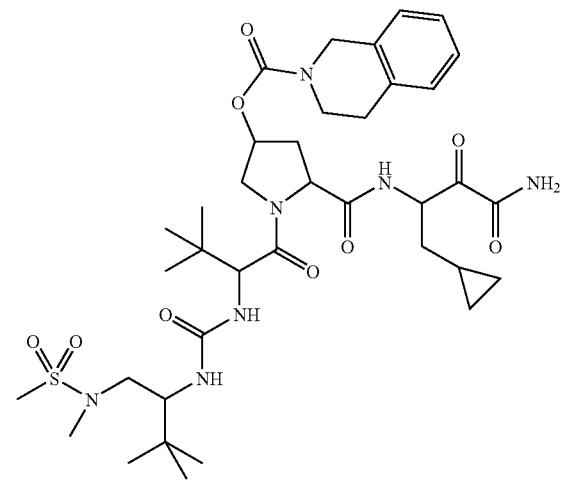
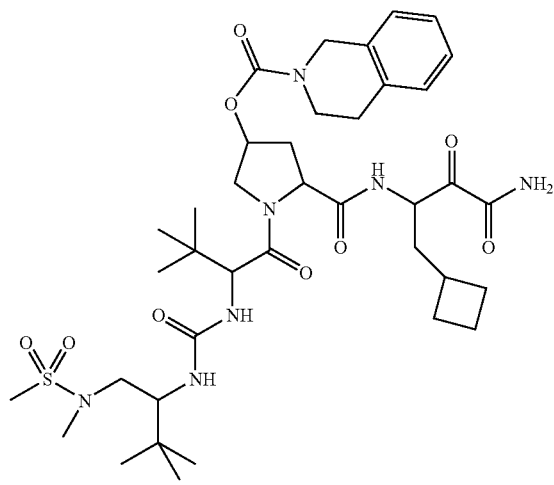

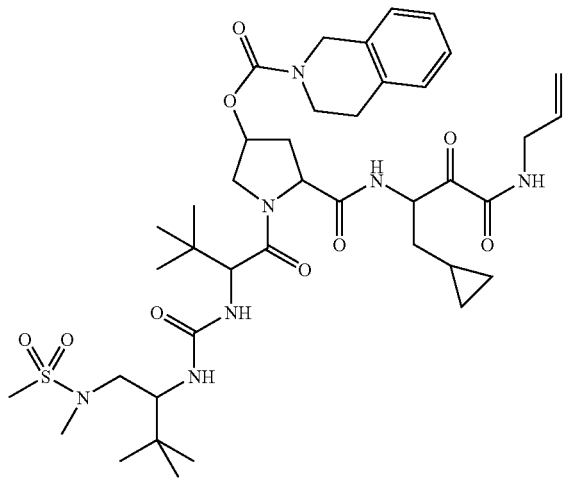
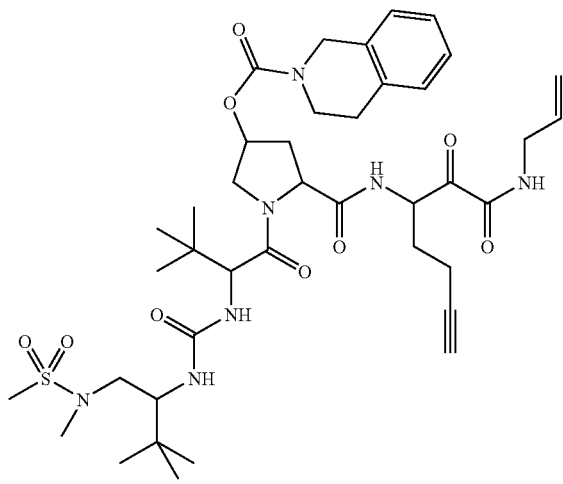
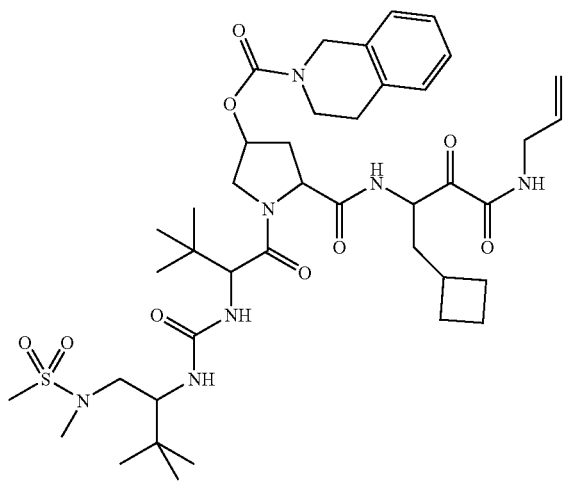

-continued
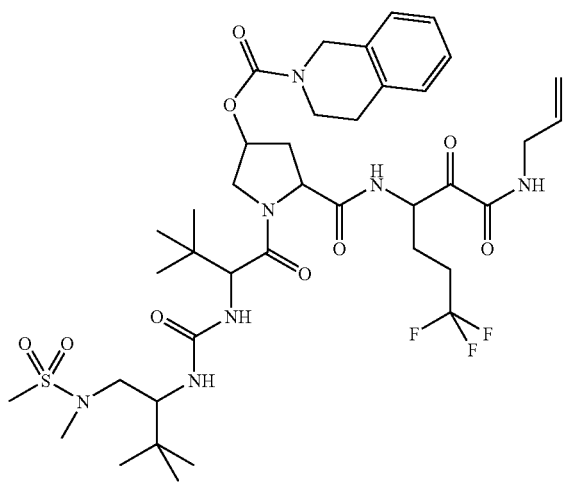
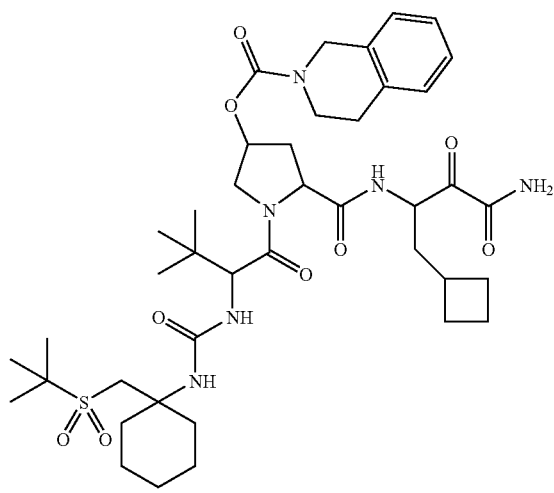
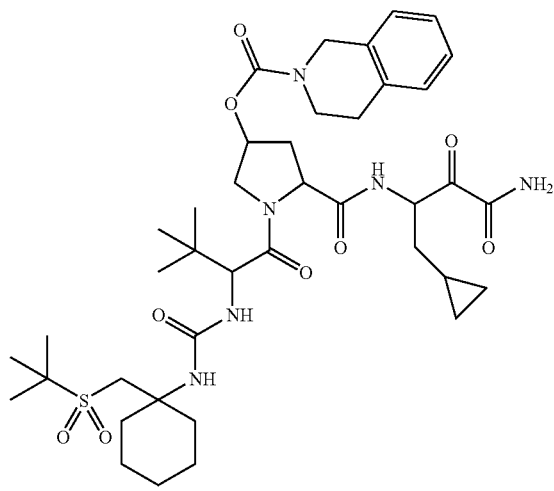

-continued
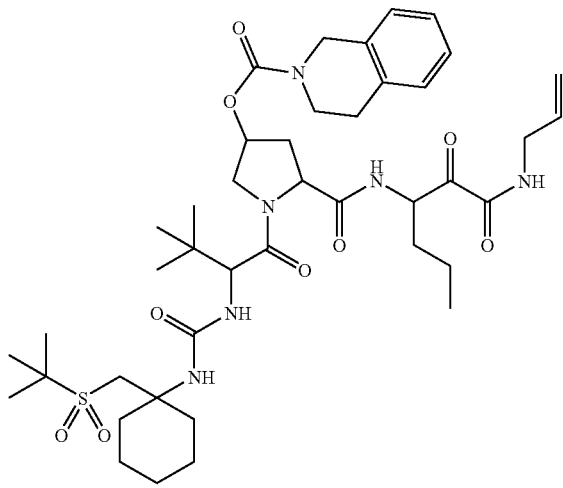
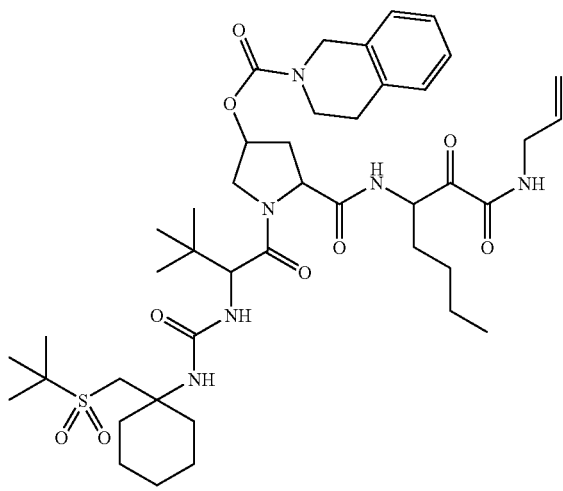
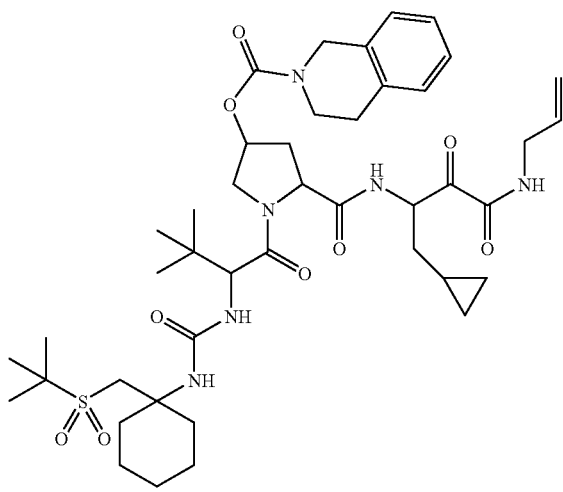

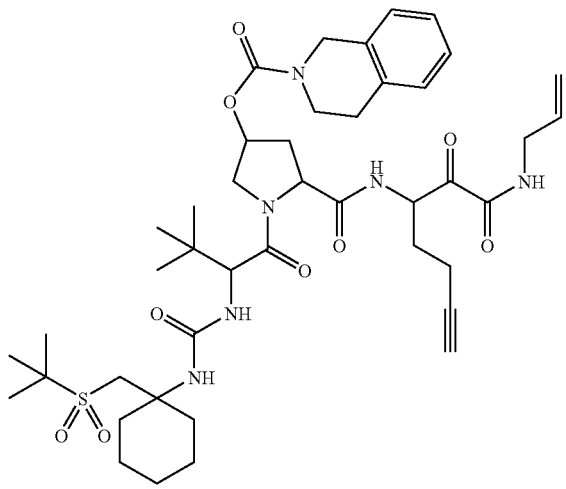
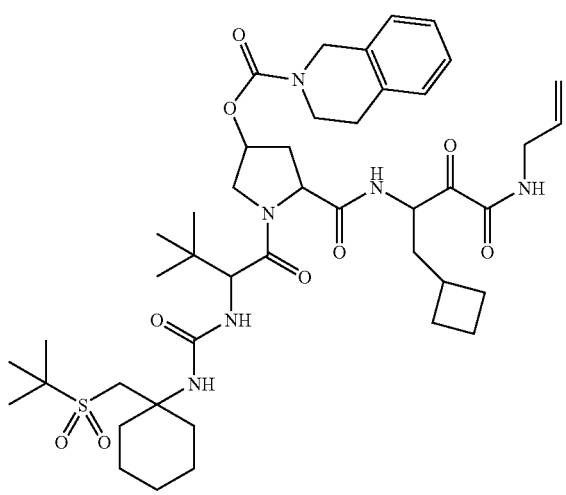
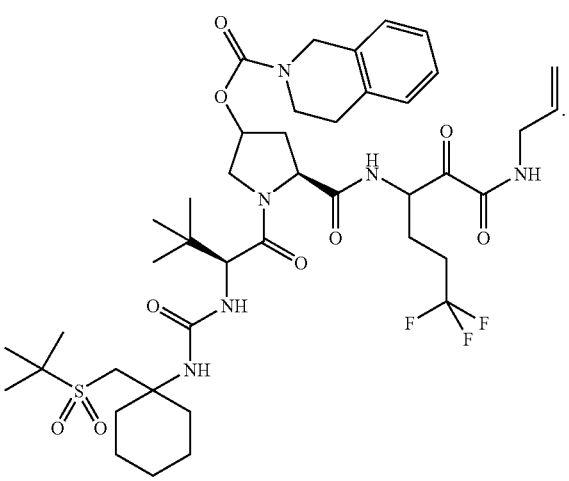

22. A compound, or enantiomers, stereoisomers, rotamers, tautomers, and racemates of said compound, or a pharmaceutically acceptable salt or solvate of said compound, said compound being selected from the compounds of structures listed below:
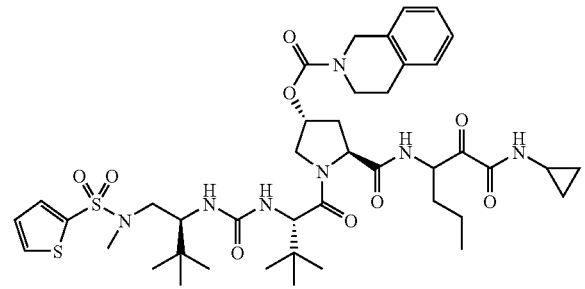
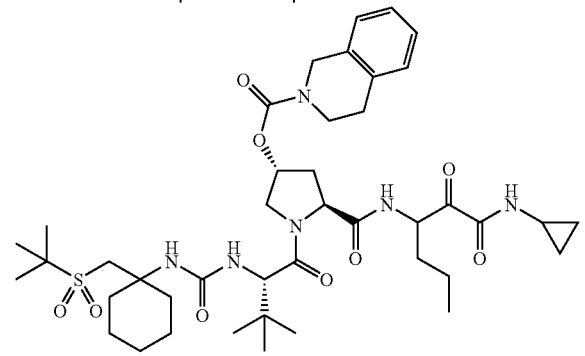
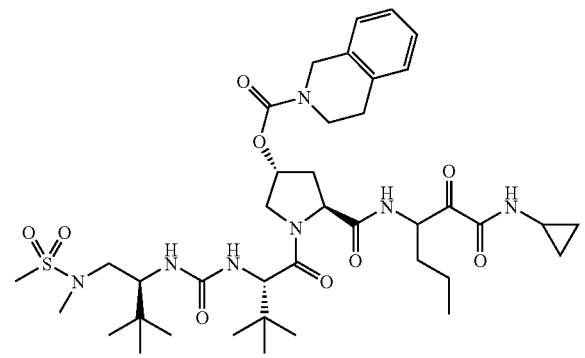
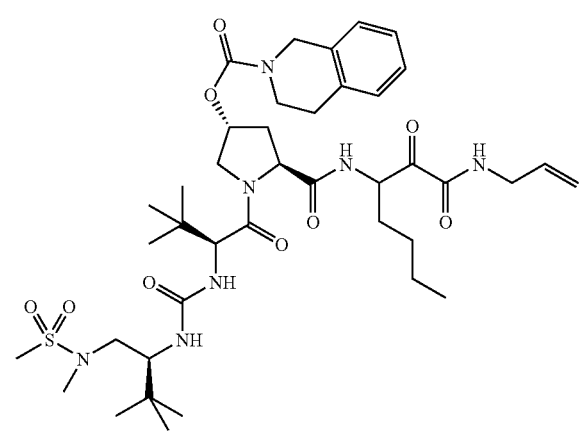
-continued
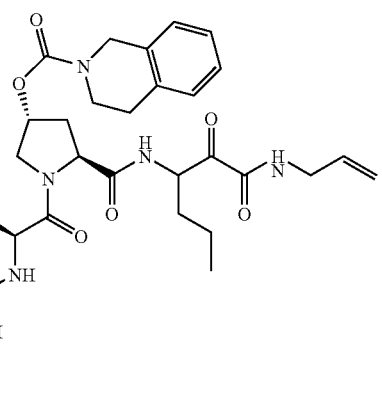
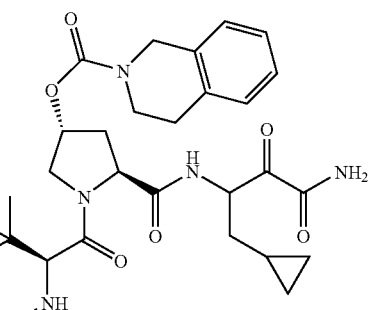
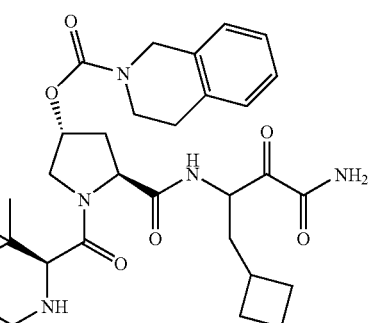

237
-continued
238
-continued
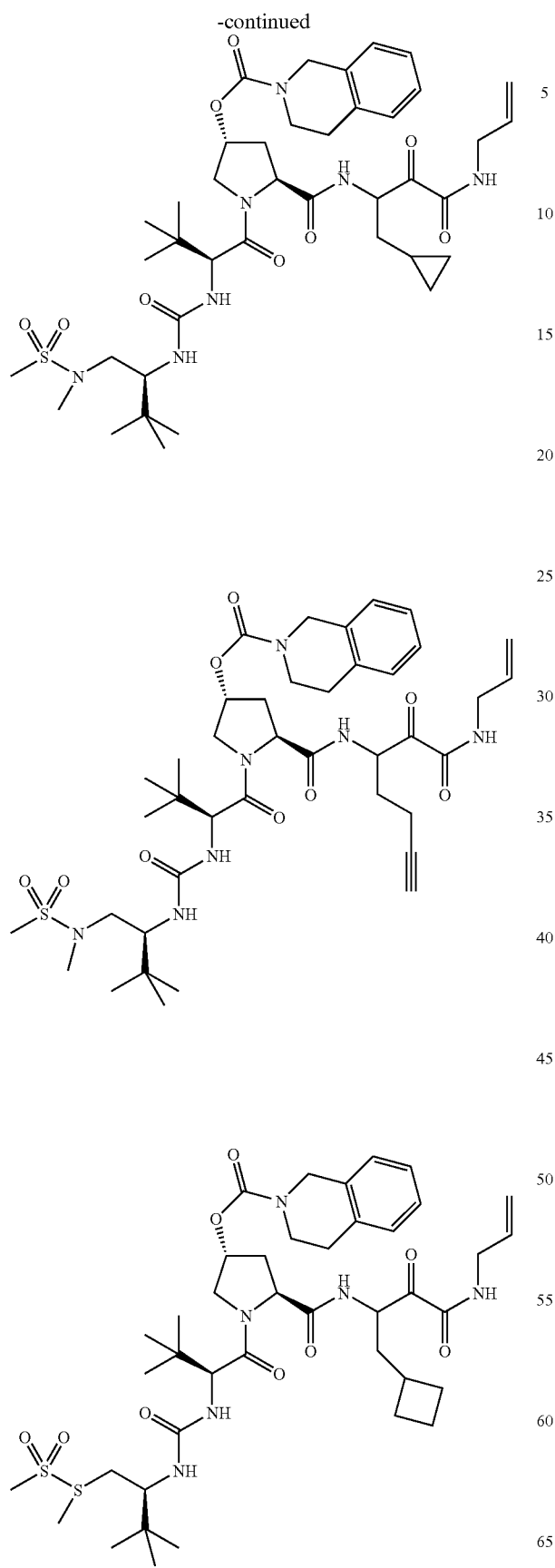

239
-continued
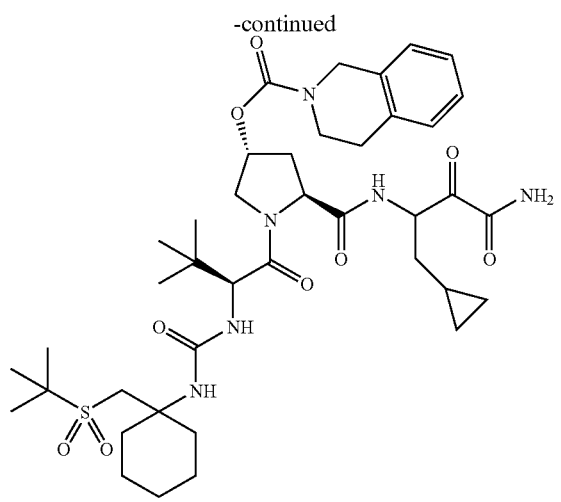
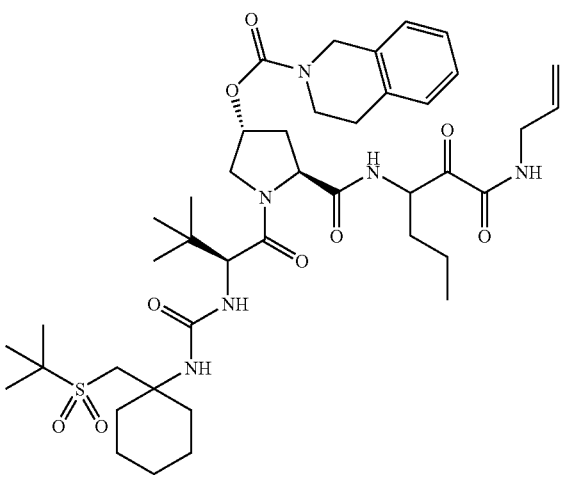
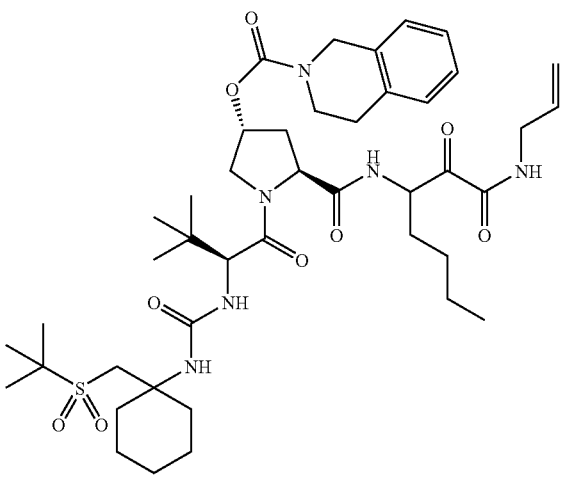
240
-continued
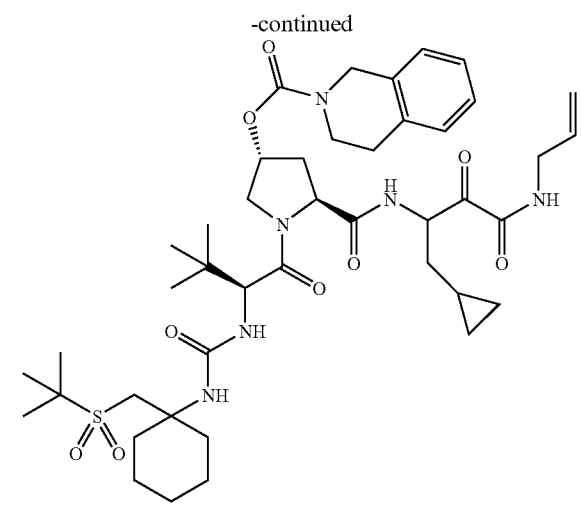
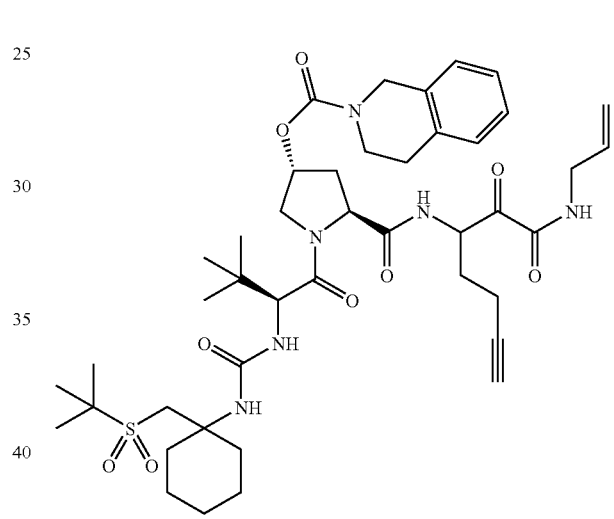
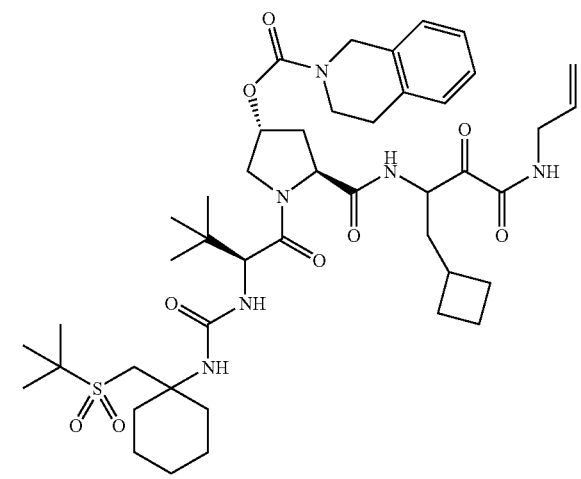

-continued

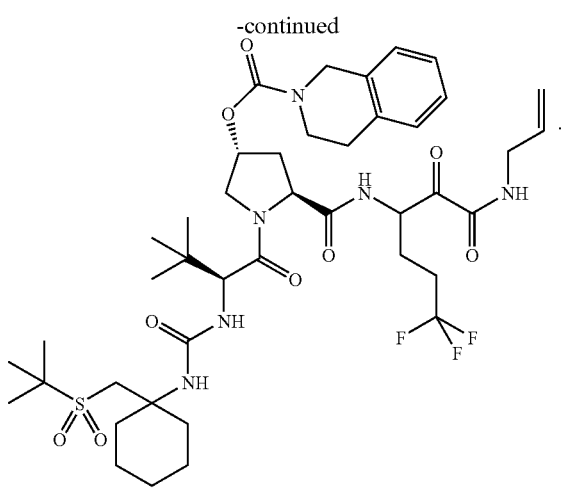

23. A pharmaceutical composition, said composition comprising therapeutically effective amount of one or more compounds in claim 21 and a pharmaceutically acceptable carrier.

24. The pharmaceutical composition of claim 23, additionally containing at least one antiviral agent.

25. The pharmaceutical composition of claim 24, additionally containing at least one interferon or PEG-interferon alpha conjugate.

26. The pharmaceutical composition of claim 25, wherein said at least one antiviral agent is ribavirin and said at least one interferon is α-interferon.

* * * * *